US007968577B2

(12) United States Patent
Yang et al.

(10) Patent No.: US 7,968,577 B2
(45) Date of Patent: Jun. 28, 2011

(54) MODULATORS OF GLUCOCORTICOID RECEPTOR, AP-1, AND/OR NF-κB ACTIVITY AND USE THEREOF

(75) Inventors: Bingwei Vera Yang, Belle Mead, NJ (US); Lidia M. Doweyko, Long Valley, NJ (US); Wayne Vaccaro, Yardley, PA (US); Tram N. Huynh, Pennington, NJ (US); David R. Tortolani, Skillman, NJ (US); T. G. Murali Dhar, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 53 days.

(21) Appl. No.: 12/513,187

(22) PCT Filed: Oct. 31, 2007

(86) PCT No.: PCT/US2007/083094
§ 371 (c)(1),
(2), (4) Date: May 1, 2009

(87) PCT Pub. No.: WO2008/057862
PCT Pub. Date: May 15, 2008

(65) Prior Publication Data
US 2010/0063051 A1    Mar. 11, 2010

Related U.S. Application Data

(60) Provisional application No. 60/855,950, filed on Nov. 1, 2006.

(51) Int. Cl.
| A61K 31/5377 | (2006.01) |
| A61K 31/5375 | (2006.01) |
| A61K 31/505 | (2006.01) |
| A61K 31/50 | (2006.01) |
| A61K 31/4965 | (2006.01) |
| A61K 31/496 | (2006.01) |
| A61K 31/4709 | (2006.01) |
| A61K 31/454 | (2006.01) |
| A61K 31/4439 | (2006.01) |
| A61K 31/433 | (2006.01) |
| A61K 31/426 | (2006.01) |
| A61K 31/427 | (2006.01) |
| A61K 31/428 | (2006.01) |
| A61K 31/421 | (2006.01) |
| A61K 31/4168 | (2006.01) |
| A61K 31/415 | (2006.01) |
| A61K 31/165 | (2006.01) |
| C07D 417/04 | (2006.01) |
| C07D 417/12 | (2006.01) |
| C07D 277/46 | (2006.01) |
| C07D 285/135 | (2006.01) |
| C07D 263/48 | (2006.01) |
| C07D 241/20 | (2006.01) |
| C07D 239/42 | (2006.01) |
| C07D 233/88 | (2006.01) |
| C07D 231/44 | (2006.01) |

(52) U.S. Cl. .................. 514/371; 514/367; 514/254.02; 514/353; 514/236.2; 514/236.8; 514/255.06; 514/256; 514/398; 514/377; 514/404; 514/314; 514/622; 514/352; 514/342; 514/361; 514/254.03; 544/133; 544/134; 544/131; 544/329; 544/336; 544/367; 544/369; 546/233; 546/221; 546/309; 546/270.7; 548/195; 548/163; 548/139; 548/140; 548/332.1; 548/233; 548/372.5; 564/174

(58) Field of Classification Search ............... 514/371, 514/367, 254.02, 353, 236.2, 236.8, 255.06, 514/256, 398, 377, 404, 314, 622, 352, 342, 514/361, 254.03; 544/133, 134, 131, 329, 544/336, 367, 369; 546/233, 221, 309, 270.7; 548/195, 163, 139, 233, 372.5; 564/174
See application file for complete search history.

(56) References Cited

U.S. PATENT DOCUMENTS

| 2004/0082568 A1 | 4/2004 | Yang | |
| 2005/0004164 A1* | 1/2005 | Caggiano et al. | 514/310 |

FOREIGN PATENT DOCUMENTS

| JP | 8-231516 | 9/1996 |
| WO | WO 03/059899 | 7/2003 |
| WO | WO 2004/005261 | 1/2004 |
| WO | WO 2005/003098 | 1/2005 |
| WO | WO2008/021926 | 2/2008 |
| WO | WO2008/057856 | 5/2008 |
| WO | WO2008/057859 | 5/2008 |
| WO | WO2008/057867 | 5/2008 |

OTHER PUBLICATIONS

CAplus Registry entry for Registry No. 500534-63-4 (entered STN on Mar. 25, 2003).*
Butke et al. J. Org. Chem. 1978, 43, 954-960.*
Sheridan, J. Chem. Inf. Comput. Sci., vol. 42, 2002, 103-108.*
Baldwin, Jr., A.S., "The transcription factor NF-κB and human disease", The Journal of Clinical Investigation, vol. 107, No. 1, pp. 3-6 (2001).
Burke, J.R., "Targeting IκB kinase for the treatment of inflammatory and other disorders", Current Opinion in Drug Discovery & Development, vol. 6, No. 5, pp. 720-728 (2003).
Caldenhoven, E. et al., "Negative Cross-Talk between ReIA and the Glucocorticoid Receptor: A Possible Mechanism for the Antiinflammatory Action of Glucocorticoids", Molecular Endocrinology, vol. 9, No. 4, pp. 401-412 (1995).
Chakravarti, D. et al., "Role of CBP/P300 in nuclear receptor signalling", Nature, vol. 383, pp. 99-103 (1996).
Diamond, M.I. et al., "Transcription Factor Interactions: Selectors of Positive or Negative Regulation from a Single DNA Element", Science, vol. 249, pp. 1266-1272 (1990).
Firestein, G.S. et al., "Signal Transduction and Transcription Factors in Rheumatic Disease", Arthritis & Rheumatism, vol. 42, No. 4, pp. 609-621 (1999).
Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).
Kamei, Y. et al., "A CBP Integrator Complex Mediates Transcriptional Activation and AP-1 Inhibition by Nuclear Receptors", Cell, vol. 85, pp. 403-414 (1996).
Manning, A.M., et al., "Targeting JNK for Therapeutic Benefit: from Junk to Gold?", Nature, vol. 2, pp. 554-565 (2003).
Miesfeld, R. et al., "Characterization of a steroid hormone receptor gene and mRNA in wild-type and mutant cells", Nature, vol. 312, pp. 779-781 (1984).

Peltz, G., "Transcription factors in immune-mediated disease", Current Opinion in Biotechnology, vol. 8, pp. 467-473 (1997).

Reichardt, H.M. et al., "DNA Binding of the Glucocorticoid Receptor is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Weinberger, C. et al., "Domain structure of human glucocorticoid receptor and its relationship to the v-erb-A oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

* cited by examiner

*Primary Examiner* — Joseph R Kosack
*Assistant Examiner* — Matthew P Coughlin
(74) *Attorney, Agent, or Firm* — Burton Rodney; Laurelee A. Duncan

(57) ABSTRACT

Novel non-steroidal compounds are provided which are useful in treating diseases associated with modulation of the glucocorticoid receptor, AP-1, and/or NF-κB activity including inflammatory and immune diseases, obesity and diabetes having the structure of formula (I) an enantiomer, diastereomer, tautomer, solvate (e.g. a hydrate), or a pharmaceutically-acceptable salt, thereof, wherein: M is selected from alkyl, substituted alkyl, cycloalkyl, aryl, heterocyclo, and heteroaryl, provided that if M is alkyl then $R_6$ and $R_7$ taken together with the carbon atom to which they are both attached are selected from a group other than cycloalkyl; Q is selected from (i) hydrogen, $C_1$-$C_4$ alkyl, and substituted $C_1$-$C_4$ alkyl; or (ii) Q and $R_6$ are combined with the carbon atoms to which they are attached to form a 3- to 6-membered cycloalkyl; or (iii) Q and $M_aM$ are combined with the carbon atom(s) to which they are attached to form a 3- to 7-membered ring containing 1-2 heteroatoms which are independently selected from the group consisting of O, S, $SO_2$, and N which ring may be optionally substituted with 0-2 $R_5$ groups or carbonyl; Z is selected from cycloalkyl, heterocyclo, aryl, or heteroaryl; and $M_a$, $Z_a$, $R_1$, $R_2$, $R_3$, $R_4$, $R_6$, $R_7$, and $R_{22}$ are as defined herein. Also provided are pharmaceutical compositions and methods of treating metabolic and inflammatory- or immune-associated diseases or disorders using said compounds.

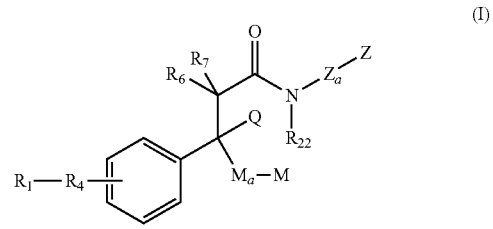

16 Claims, No Drawings

MODULATORS OF GLUCOCORTICOID RECEPTOR, AP-1, AND/OR NF-κB ACTIVITY AND USE THEREOF

This application claims the benefit of priority from U.S. provisional application Ser. No. 60/855,950 filed Nov. 1, 2006, which is incorporated herein by reference.

FIELD OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides pharmaceutical compositions and combinations thereof and methods for using such compounds and compositions to treat these and related diseases or disorders.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation,* 107, 3 (2001); Firestein, G. S., and Manning, A. M., *Arthritis and Rheumatism,* 42, 609 (1999); and Peltz, G., *Curr. Opin. in Biotech.* 8, 467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. and Davis, R. J., *Nature Rev. Drug Disc.*, V. 2, 554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK has been shown to be efficacious in animal models of inflammatory disease. See Burke, J. R., *Curr. Opin. Drug Discov. Devel.,* September; 6(5), 720-8, (2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science,* 228, 740-742 (1985); Weinberger et al., *Nature,* 318, 670-672 (1986) and for results in rats see Miesfeld, R., *Nature,* 312, 779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell,* 62, 1189 (1990); Yang-Yen, H. F. et al., *Cell,* 62, 1205 (1990); Diamond, M. I. et al., *Science* 249, 1266 (1990); and Caldenhoven, E. et al., *Mol. Endocrinol.,* 9, 401 (1995). Other mechanisms such as sequestration of co-activators by GR have also been proposed. See Kamei, Y. et al., *Cell,* 85, 403 (1996); and Chakravarti, D. et al., *Nature,* 383, 99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell,* 93, 531 (1998) and Reichardt, H. M., *EMBO J.,* 20, 7168 (2001).

Compounds that modulate AP-1 and NF-κB activity would be in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents, however their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, AP-1, and/or NF-κB activity and thus are useful in treating diseases or disorders including metabolic and inflammatory or immune associated diseases or disorders. The present invention also provides compositions thereof and methods for using such compounds and compositions to treat these and related diseases or disorders.

In accordance with one aspect of the invention, compounds are provided having the structure of formula (I)

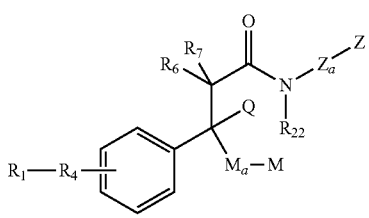

or an enantiomer, diastereomer, tautomer, prodrug, solvate (e.g. a hydrate), or a pharmaceutically-acceptable salt thereof (especially an enantiomer, diastereomer, or a pharmaceutically acceptable salt therefore), wherein:

M is selected from alkyl, substituted alkyl, cycloalkyl, aryl, heterocyclo, and heteroaryl, provided that if M is alkyl then $R_6$ and $R_7$ taken together with the carbon atom to which they are both attached are selected from a group other than cycloalkyl;

$M_a$ is a linker between C and M and is selected from a bond and $C_1$-$C_3$ alkylene;

Q is selected from
(i) hydrogen, $C_1$-$C_4$ alkyl, and substituted $C_1$-$C_4$ alkyl; or
(ii) Q and $R_6$ are combined with the carbon atoms to which they are attached to form a 3- to 6-membered cycloalkyl; or
(iii) Q and M are combined with the carbon atom(s) to which they are attached to form a 3- to 7-membered ring containing 1-2 heteroatoms which are independently selected from the group consisting of O, S, $SO_2$, and N which ring may be optionally substituted with 0-2 $R_5$ groups or carbonyl;

Z is selected from cycloalkyl, heterocyclo, aryl, or heteroaryl;

$Z_a$ is a linker between N and Z and is selected from a bond and $C_1$-$C_3$ alkylene;

$R_1$, $R_2$, $R_3$, and $R_4$ at each occurrence are independently selected from hydrogen, halogen, alkyl, substituted alkyl, alkenyl, substituted alkenyl, alkynyl, substituted alkynyl, nitro, cyano, —$OR_{10}$, —$SR_{10}$ —$NR_{10}R_{11}$, —C(=O)$R_{10}$, —$CO_2R_{10}$, —C(=O)$NR_{10}R_{11}$, —O—C(=O)$R_{10}$, —$NR_{10}$C(=O)$NR_{10}R_{11}$, —$NR_{10}$C(=O)$R_{11}$, —$NR_{10}$C(=O)$OR_{11}$, —$NR_{10}$C(S)$OR_{11}$, —S(=O)$_p$$R_{12}$, —$NR_{10}SO_pR_{12}$, —$SO_pNR_{10}R_{11}$, cycloalkyl, heterocyclo, aryl, and heteroaryl;

$R_5$ at each occurrence is independently selected from hydrogen, halogen, alkyl, substituted alkyl, alkenyl, substituted alkenyl, alkynyl, substituted alkynyl, nitro, cyano, —$OR_{13}$, —$NR_{13}R_{14}$, —C(=O)$R_{13}$, —$CO_2R_{13}$, —C(=O)$NR_{13}R_{14}$, —O—C(=O)$R_{13}$, —$NR_{13}$C(=O)$R_{14}$, —$NR_{13}$C(=O)$OR_{14}$, —$NR_{13}$C(S)$OR_{14}$, —S(=O)$_p$$R_{15}$, —$NR_{13}SO_2R_{15}$, —$SO_2NR_{13}R_{14}$, cycloalkyl, heterocyclo, aryl, or heteroaryl;

$R_6$ is selected from alkyl, substituted alkyl, alkenyl, substituted alkenyl, alkynyl, substituted alkynyl, —C(=O)$R_{17}$, —$CO_2R_{17}$, —C(=O)$NR_{16}R_{17}$, cycloalkyl, heterocyclo, and heteroaryl, provided that the point of attachment occurs at a carbon atom on the heterocyclo or heteroaryl;

$R_7$ is selected from halogen, alkyl, substituted alkyl, alkenyl, substituted alkenyl, alkynyl, substituted alkynyl, nitro, cyano, —$OR_{19}$, —$SR_{19}$, —$NR_{19}R_{20}$, —C(=O)$R_{19}$, —$CO_2R_{19}$, —C(=O)$NR_{19}R_{20}$, —O—C(=O)$R_{19}$, —$NR_{19}$C(=O)$R_{20}$, —$NR_{19}$C(=O)$OR_{20}$, —$NR_{19}$C(=S)$OR_{20}$, —S(=O)$_p$$R_{21}$, —$NR_{19}SO_2R_{21}$, —$SO_2NR_{19}R_{20}$, cycloalkyl, heterocyclo, aryl, and heteroaryl, provided that if $R_7$ is OH then the other of $R_6$ is other than substituted alkyl;

or $R_6$ and $R_7$ are taken together with the carbon to which they are attached to form a cycloalkyl, or heterocyclo group;

$R_8$, $R_9$, $R_{10}$, $R_{11}$, $R_{13}$, $R_{14}$, $R_{16}$, $R_{17}$, $R_{19}$, and $R_{20}$ at each occurrence are independently selected from
(i) hydrogen, alkyl, substituted alkyl, alkenyl, substituted alkenyl, alkynyl, substituted alkynyl, cycloalkyl, aryl, heteroaryl, and heterocyclo; or
(ii) $R_{10}$ is taken together with $R_{11}$, and/or $R_{13}$ is taken together with $R_{14}$; and/or $R_{16}$ is taken together with $R_{17}$; and/or $R_{19}$ is taken together with $R_{20}$ to form a 4- to 7-membered heteroaryl or heterocyclo ring;

$R_{12}$, $R_{15}$, and $R_{21}$ are independently selected from alkyl, substituted alkyl, alkenyl, substituted alkenyl, alkynyl, substituted alkynyl, cycloalkyl, aryl, heteroaryl, or heterocyclo;

$R_{22}$ is selected from hydrogen, alkyl, substituted alkyl, C(=O)alkyl, $CO_2$(alkyl), $SO_2$alkyl, alkoxy, amino, substituted amino, aryl, heteroaryl, heterocyclo, and cycloalkyl; and p is 1 or 2.

It is preferred that in compounds of formula (I) that $R_1$, $R_2$, $R_3$, and $R_4$ are independently selected from (i) hydrogen, halogen, cyano, $CF_3$, $C_{1-6}$alkyl, CH(OH)$R_{10}$, $C_{2-4}$alkenyl, $C_{2-4}$alkynyl, $OR_{10}$, $CO_2R_{10}$, $SR_{10}$, $SO_2R_{12}$, C(O)$R_{10}$, C(O)$NR_{10}R_{11}$, $SO_2NR_{10}R_{11}$, NHC(O)$R_{11}$, NHC(O)$NR_{10}R_{11}$, NHC(O)$_2R_{11}$, NHS(O)$_2R_{12}$, and $NR_{10}R_{11}$; and/or (ii) $C_{0-3}$alkylene substituted by an optionally substituted group selected from phenyl and a 5- to 7-membered heterocyclo or heteroaryl;

$R_{10}$ and $R_{11}$ at each occurrence are independently selected from (i) hydrogen, substituted $C_{1-6}$alkyl, and $C_{1-6}$alkyl; and/or (ii) $C_{0-3}$alkylene substituted by an optionally substituted group selected from $C_{3-7}$cycloalkyl, phenyl, naphthyl, and a 5- to 7-membered heterocyclo or heteroaryl; and/or (iii) $R_{10}$ is taken together with $R_{11}$ and the nitrogen atom to which they are both attached to form an optionally substituted 5- to 6-membered heteroaryl or heterocyclo; and $R_{12}$ at each occurrence is selected from $C_{1-6}$alkyl and $C_{0-3}$alkylene substituted by an optionally substituted group selected from $C_{3-7}$cycloalkyl, heterocyclo, aryl, and heteroaryl.

It is also preferred that in compounds of formula (I)

Q is hydrogen or alkyl;

M is alkyl, aryl, cycloalkyl, heteroaryl, arylalkyl, heterocyclo, alkylarylalkyl, alkylaryl, or haloaryl; and $R_6$ is selected from $C_{1-4}$alkyl, $C_{1-4}$substituted alkyl, and $C_{3-7}$cycloalkyl;

$R_7$ is selected from $C_{1-4}$alkyl, $C_{1-4}$substituted alkyl, nitro, cyano, $C_{1-4}$alkoxy, and $C_{3-7}$cycloalkyl;

or $R_6$ and $R_7$ are taken together with the carbon to which they are attached to form a $C_{3-7}$cycloalkyl group;

or Q and $R_6$ together with the carbon atoms to which they are attached are combined to form

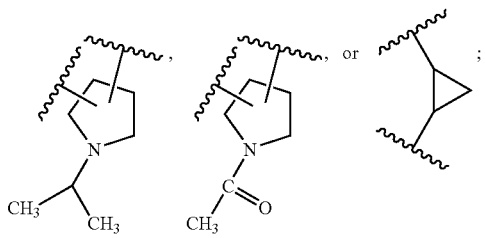

or Q and $M_a$-M together with the atom to which they are both attached are combined to form

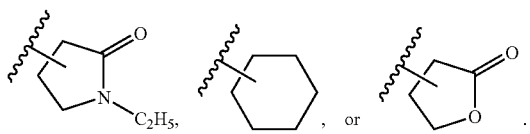

More preferred compounds of formula (I) are those in which
$M_a$ is a bond;
M is selected from $C_{1-6}$alkyl or aryl; and
Q is hydrogen or $C_{1-4}$alkyl;
or Q and $R_6$ together with the carbon atoms to which they are attached can be combined to form

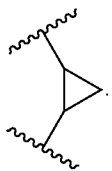

Other preferred compounds of formula (I) are those in which
$Z_a$ is a bond;
Z is $C_{3-6}$cycloalkyl or a 5- to 7-membered heterocyclo or heteroaryl, each group substituted with one to three groups, $R'''$, $R''$, and/or $R°$;
$R'''$, $R''$, and $R°$ are independently selected from
(i) hydrogen, halogen, alkyl, substituted alkyl, alkenyl, substituted alkenyl, alkynyl, substituted alkynyl, nitro, cyano, $OR_{23}$, $SR_{23}$, —C(=$NOR_{23}$)$CO_2R_{24}$, $NR_{23}R_{24}$, —$CO_tR_{23}$, C(=O)$NR_{23}R_{24}$, —O—C(=O)$R_{23}$, $NR_{23}$C(=O)$R_{24}$, $NR_{23}$C(=O)$OR_{24}$, $NR_{23}$C(=S)$OR_{24}$, S(=O)$_tR_{25}$, $NR_{23}$SO$_tR_{25}$, SO$_tNR_{23}R_{24}$, cycloalkyl, heterocyclo, aryl, or heteroaryl; or
(ii) two of $R'''$, $R''$, and/or $R°$ located on adjacent atoms together with the atoms to which they are attached may combine to form an optionally substituted fused cycloalkyl, aryl, heteroaryl, or heterocyclo ring;
$R_{23a}$, $R_{23}$ and $R_{24}$ at each occurrence are independently selected from (i) hydrogen, alkyl, substituted alkyl, —C(=O)alkyl, —$CO_2$(alkyl), alkenyl, substituted alkenyl, alkynyl, substituted alkynyl, amino, substituted amino, aryl, heteroaryl, heterocyclo, and cycloalkyl; or (ii) $R_{23}$ and $R_{24}$ together with the atom(s) to which they are attached form a heteroaryl or heterocyclo ring;
$R_{25}$ is selected from alkyl, substituted alkyl, alkenyl, substituted alkenyl, alkynyl, substituted alkynyl, alkoxy, amino, substituted amino, heteroaryl, heterocyclo, cycloalkyl, and aryl; and t is 1 or 2.

More preferred compounds of formula (I) are those in which

Z is selected from thiazolyl, benzothiazolyl, tetrahydrobenzothiazolyl, pyridyl, pyrimidinyl, pyrazinyl, imidazolyl, oxazolyl, pyrazolyl, thiadiazolyl, cyclopropyl, cyclobutyl, cyclopentyl, or morpholinyl, each group substituted by one to two groups, $R'''$ and/or $R''$;

$R'''$ and $R''$ are independently selected from (i) hydrogen, halogen, nitro, cyano, alkyl, substituted alkyl, —$NR_{23}R_{24}$, —$CO_2R_{23}$, —C(=O)$R_{23}$, —C(O)N($R_{23}$)($R_{24}$), —C(=$NOR_{23}$)$CO_2R_{24}$, $OR_{23}$, cycloalkyl, aryl, heterocyclo or heteroaryl; (more preferably $R'''$ and $R''$ at each occurrence are independently selected from (i) hydrogen, fluoro, chloro, bromo, $C_{1-4}$alkyl, trifluoromethyl, nitro, —(CH$_2$)$_{0-2}$CO$_2$C$_{1-4}$alkyl, —C(=NOC$_{1-4}$alkyl)CO$_2$C$_{1-4}$ alkyl, —C(=NOH)CO$_2$C$_{1-4}$alkyl, $C_{1-4}$alkoxy, and/or (ii) $C_{0-3}$alkylene substituted by an optionally substituted ring selected from phenyl, napthyl, a 5- to 7-membered heterocyclo or heteroaryl, and a 7- to 11-membered bicyclic heterocyclo or heteroaryl ring)

or $R'''$ and $R''$ together with the atoms to which they are attached combine to form an optionally substituted fused 5- or 6-membered cycloalkyl, aryl, heteroaryl, or heterocyclo ring.

Yet other preferred compounds of formula (I) are those in which

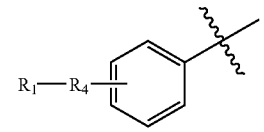

is selected from

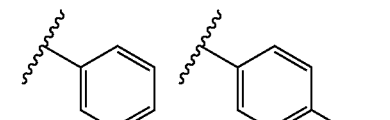

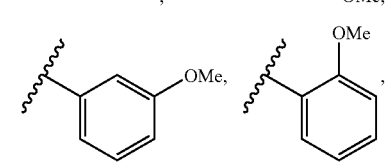

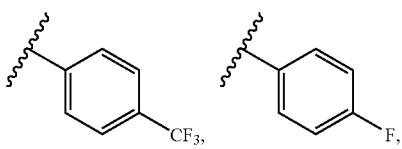

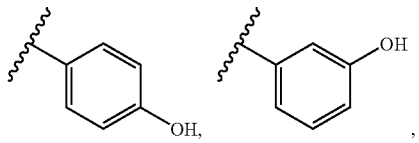

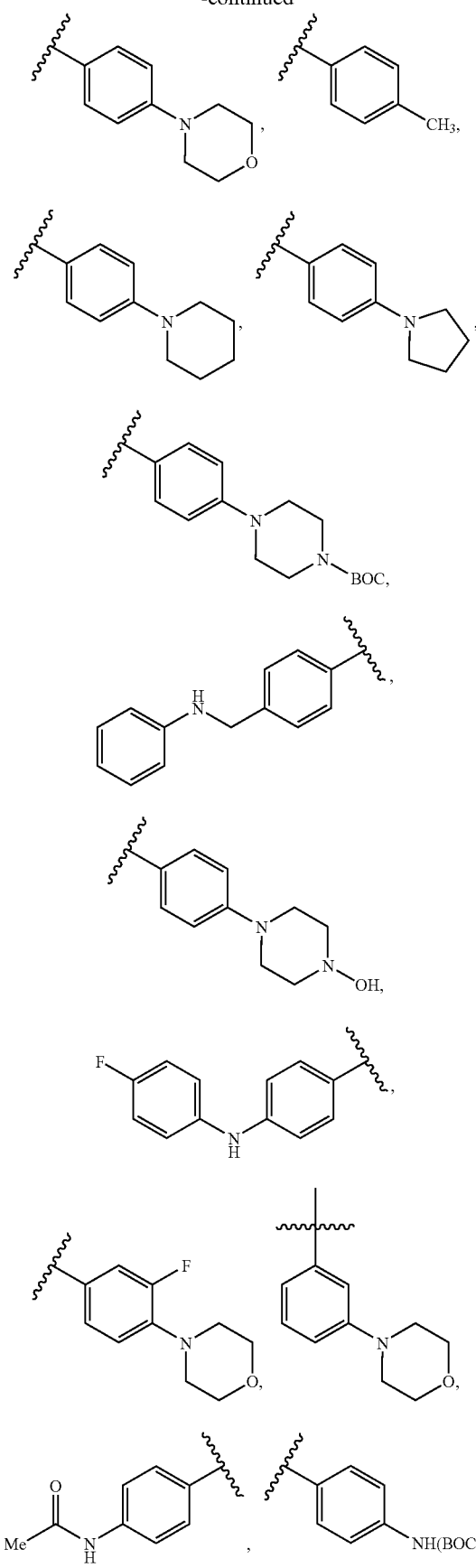
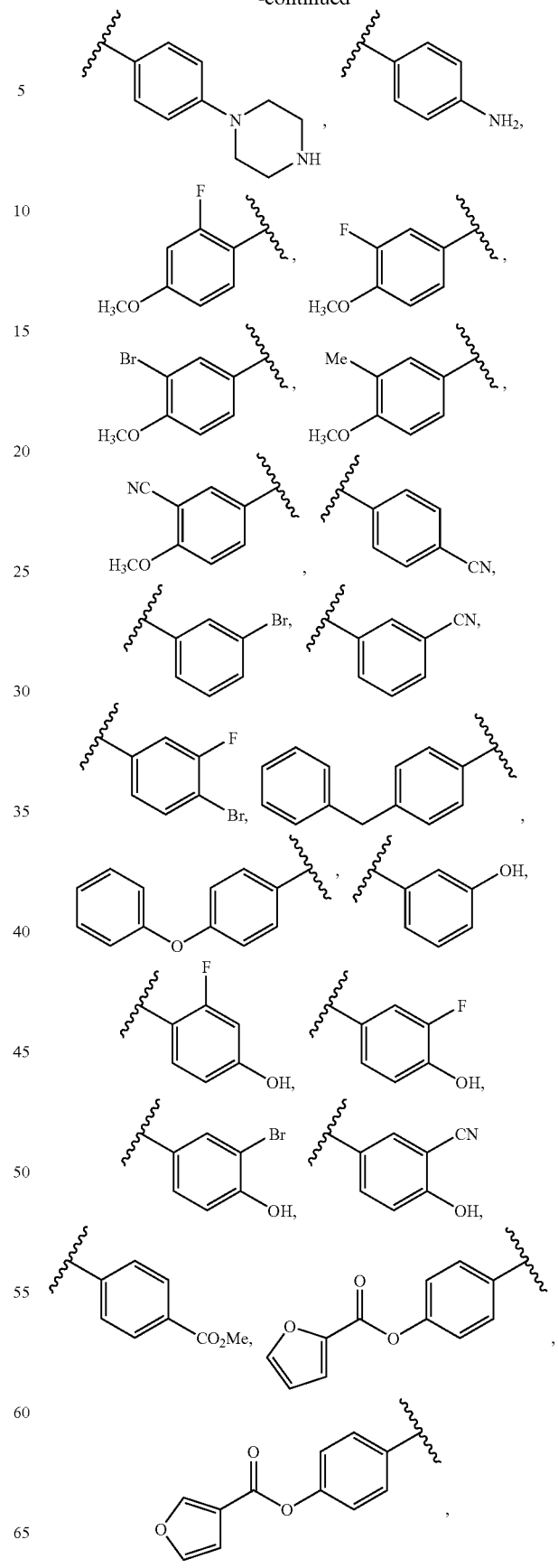

-continued
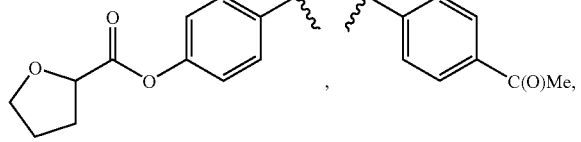
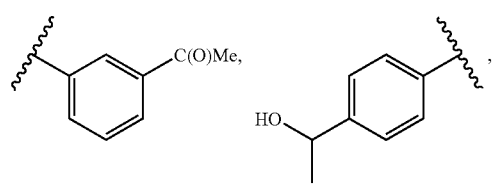
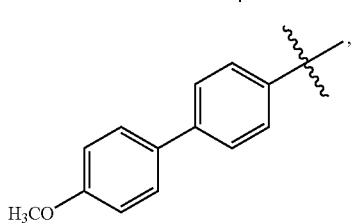
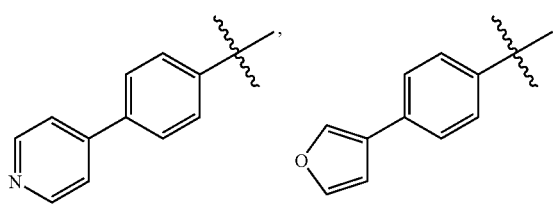
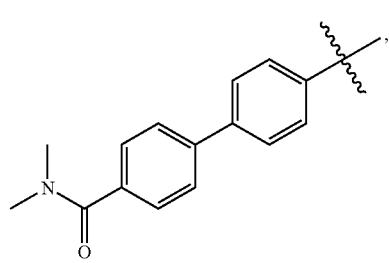
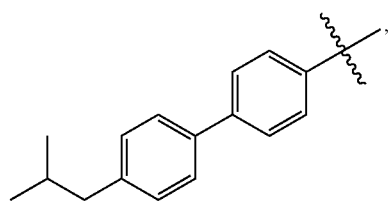
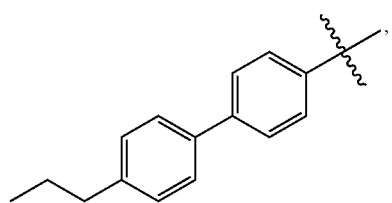
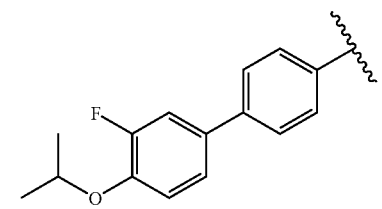
-continued
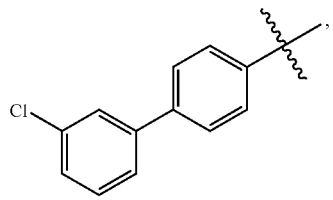
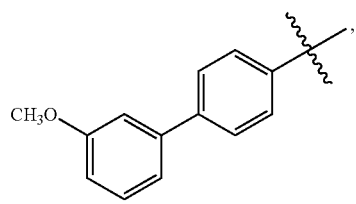
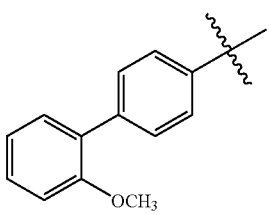
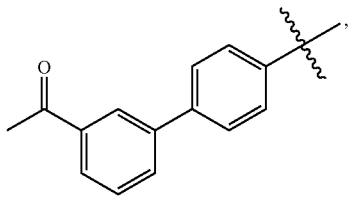
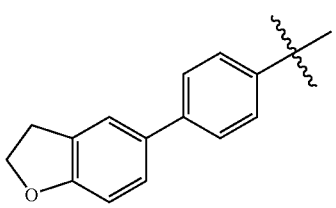
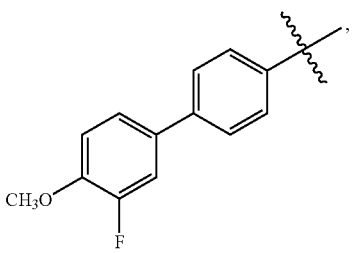
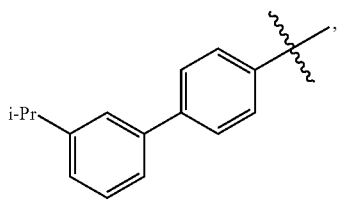
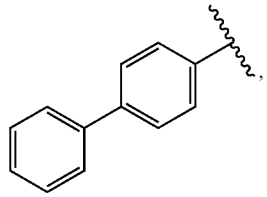

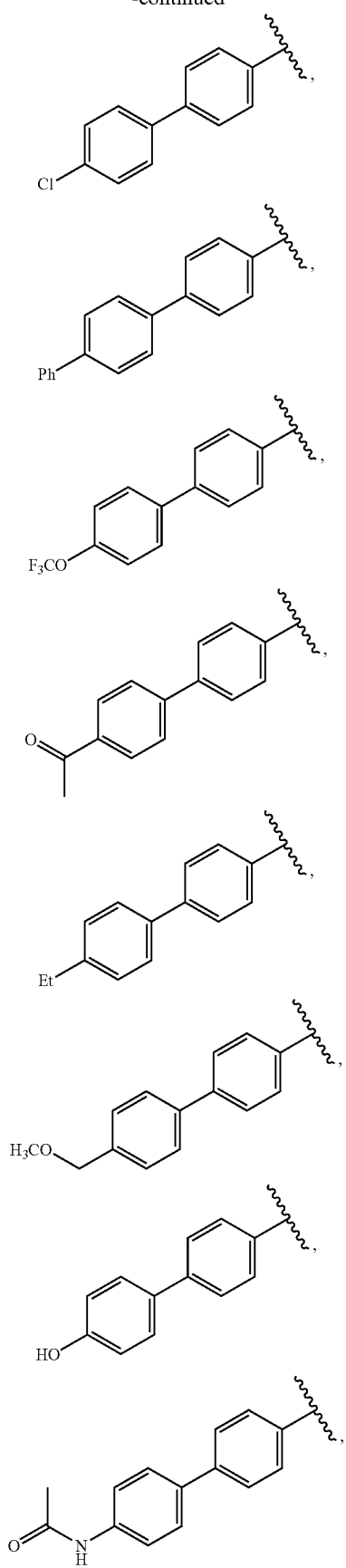
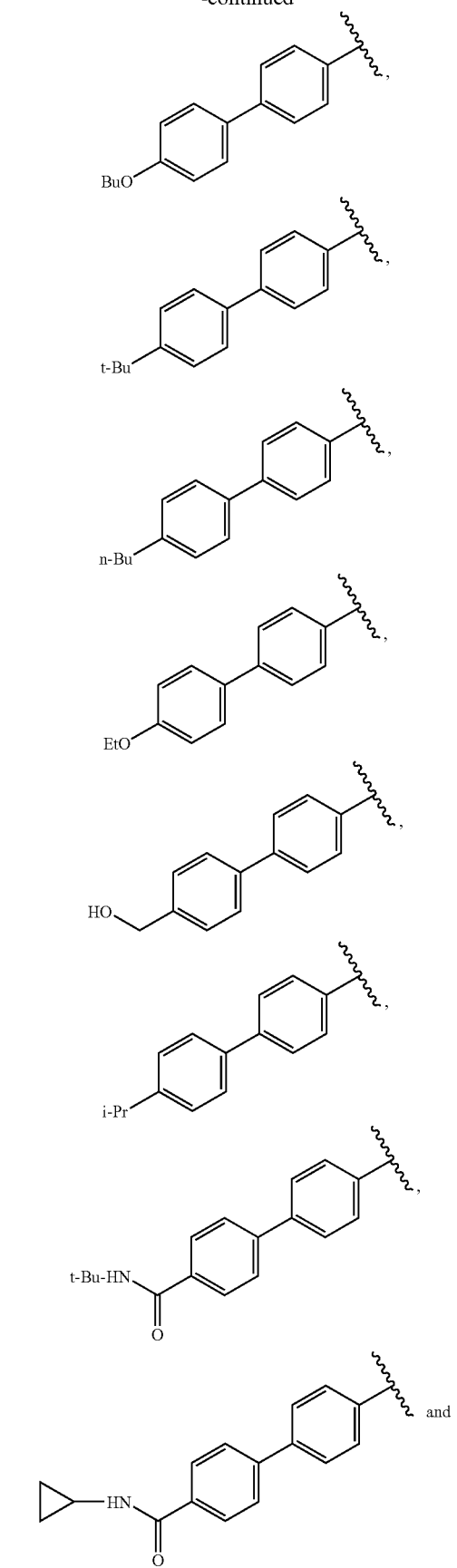

-continued
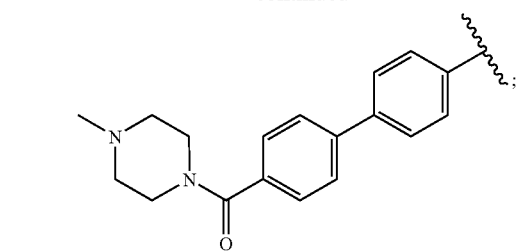
—Z$_a$Z is
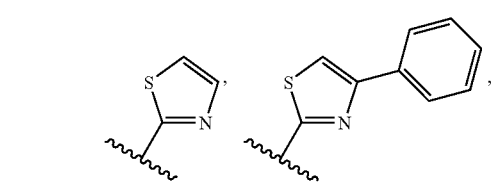
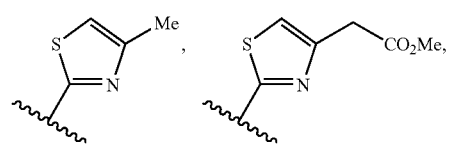
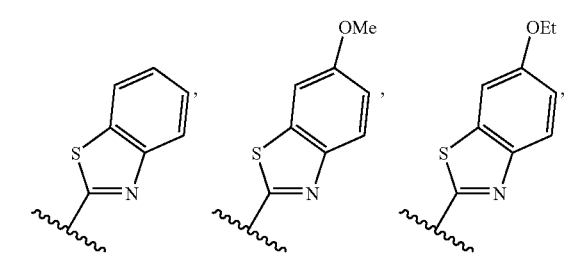
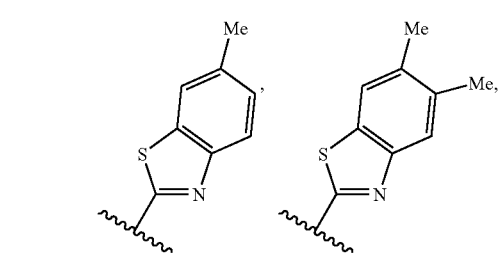
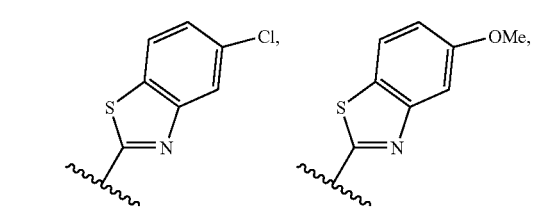
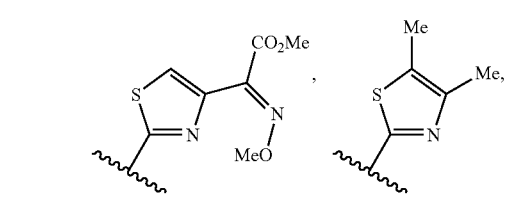
-continued
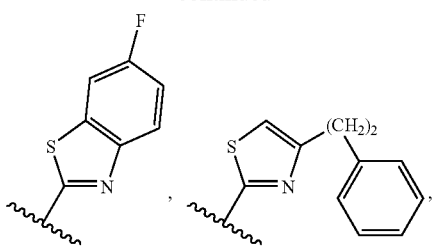
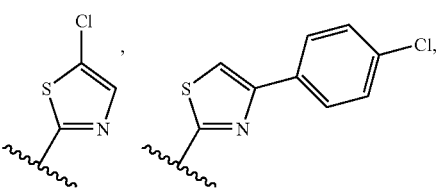
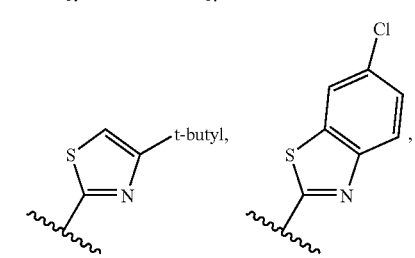
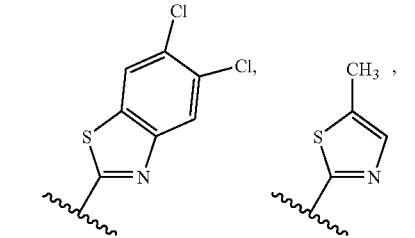
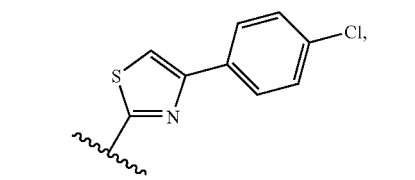
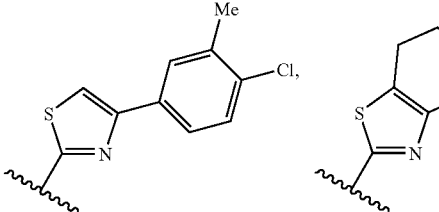
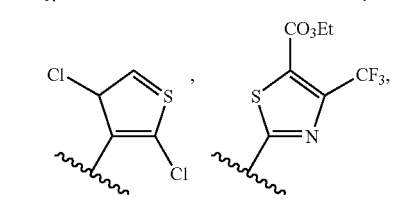
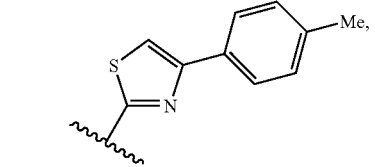

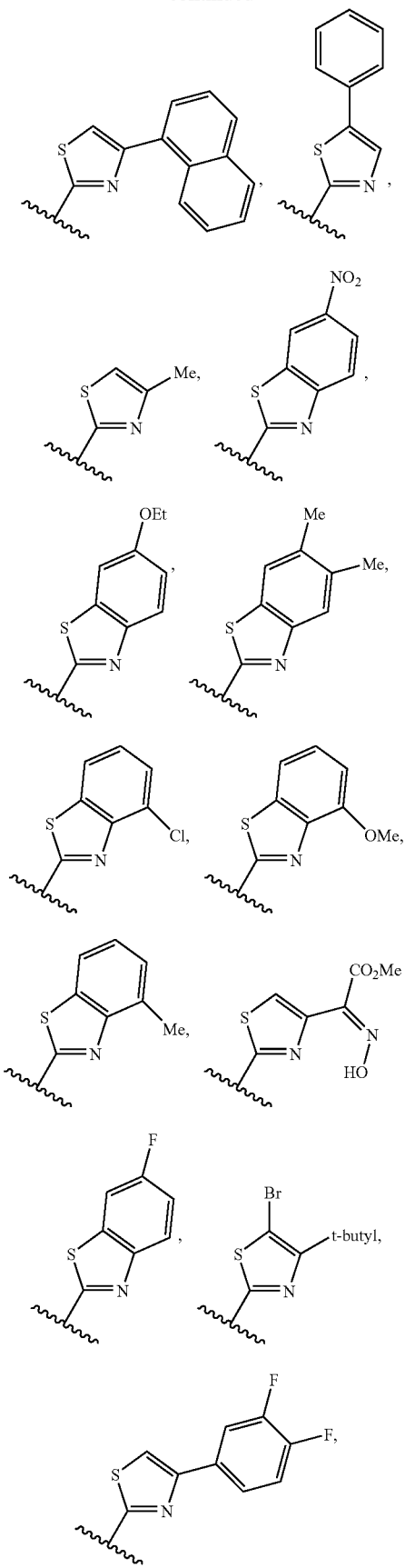
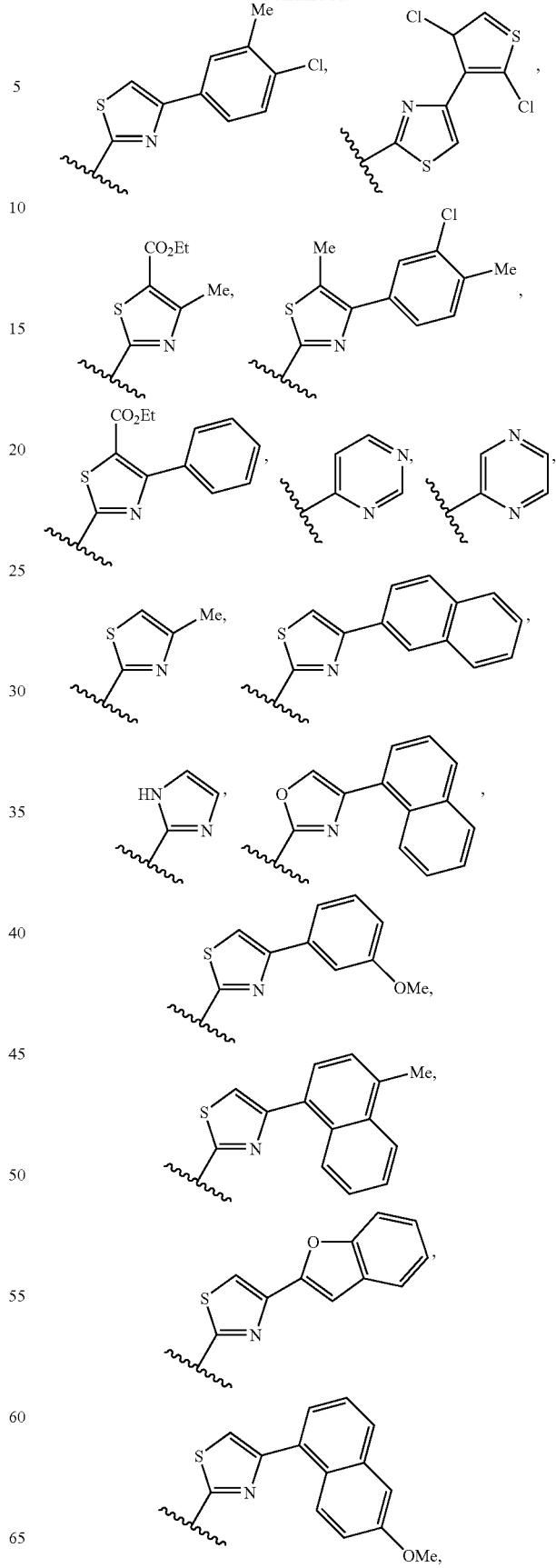

-continued
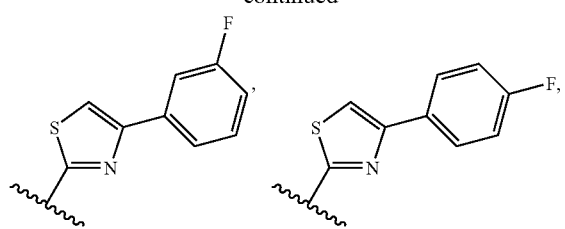
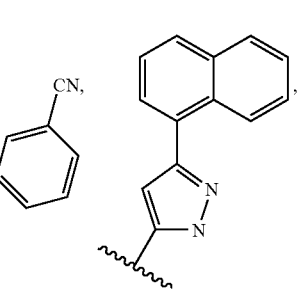
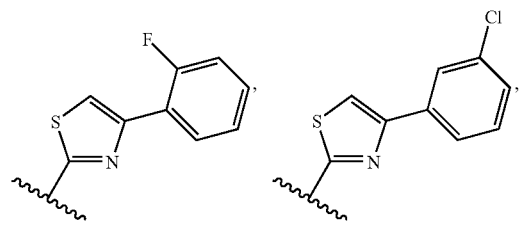
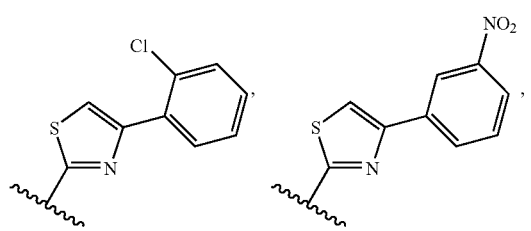
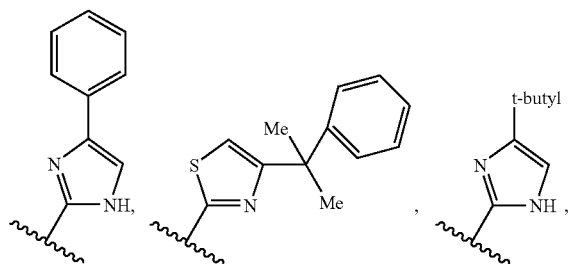
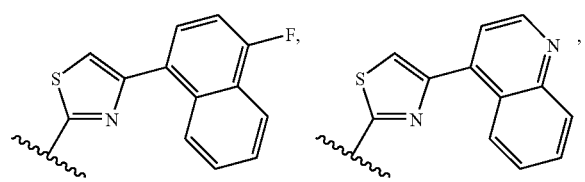
-continued
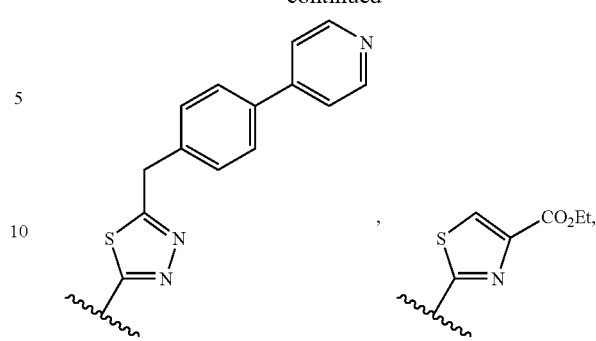
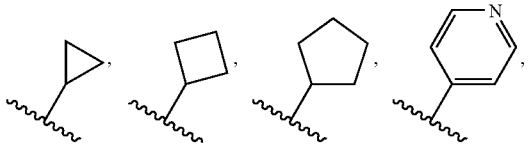
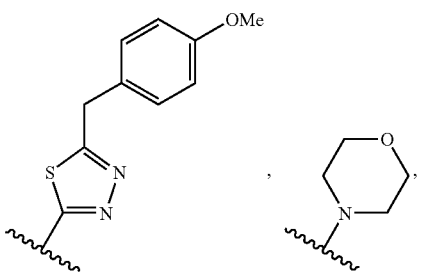
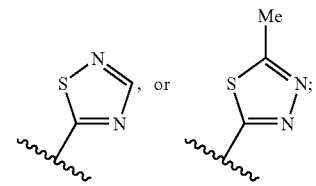
$-M_aM$ is
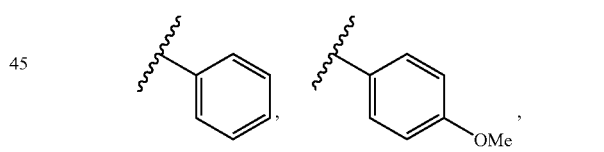
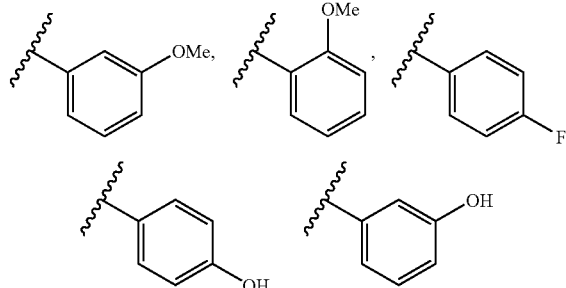
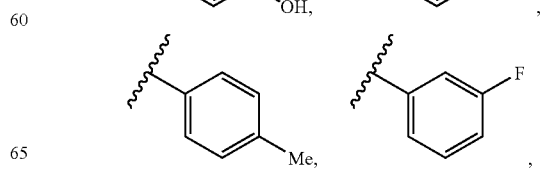

-continued

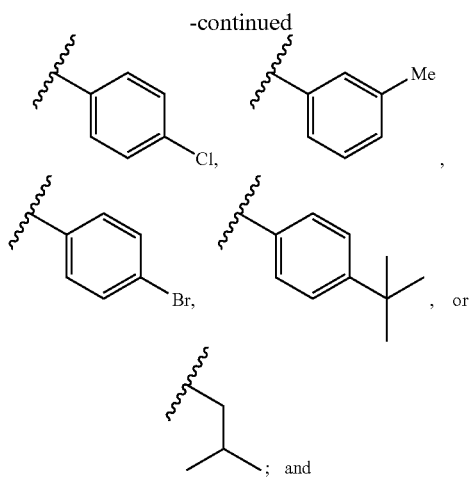

Q is H or $CH_3$;

or Q and $R^6$ together with the carbon atoms to which they are attached can be combined to form

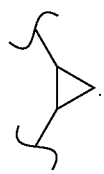

Alternatively preferred compounds within the scope of formula (I) are those having formula (Ia):

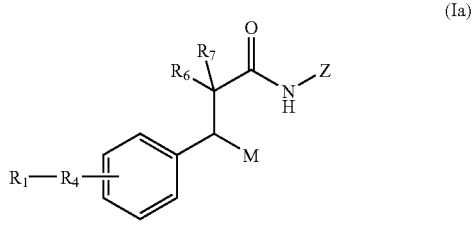

or an enantiomer, diastereomer, tautomer, prodrug, solvate (e.g. a hydrate), or a pharmaceutically-acceptable salt thereof (especially an enantiomer, diastereomer, or a pharmaceutically acceptable salt therefore), wherein:

M is

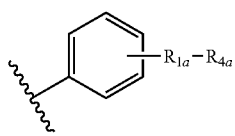

or $C_{1-6}$alkyl;

Z is selected from thiazolyl, benzothiazolyl, tetrahydrobenzothiazolyl, pyridyl, pyrimidinyl, pyrazinyl, imidazolyl, oxazolyl, pyrazolyl, thiadiazolyl, or morpholinyl, each group substituted by one to two groups, $R'''$ and/or $R''$;

$R'''$ and $R''$ are independently selected from hydrogen, halogen, nitro, cyano, alkyl, substituted alkyl, —$NR_{23}R_{24}$, —$CO_2R_{23}$, —$C(=O)R_{23}$, —$C(O)N(R_{23})(R_{24})$, —$C(=NOR_{23a})CO_2R_{24}$, $OR_{23}$; cycloalkyl, aryl, heterocyclo and heteroaryl; (preferably $R'''$ and $R''$ at each occurrence are independently selected from (i) hydrogen, fluoro, chloro, bromo, $C_{1-4}$alkyl, trifluoroalkyl, nitro, —$(CH_2)_{0-2}CO_2C_{1-4}$alkyl, —$C(=NOC_{1-4}$alkyl$)CO_2C_{1-4}$alkyl, —$C(=NOH)CO_2C_{1-4}$alkyl, $C_{1-4}$alkoxy, and/or (ii) $C_{0-3}$alkylene substituted by an optionally substituted ring selected from phenyl, napthyl, a 5- to 7-membered heterocyclo or heteroaryl, and a 7- to 11-membered bicyclic heterocyclo or heteroaryl ring)

or $R'''$ and $R''$ together with the atoms to which they are attached combine to form an optionally substituted fused 5- or 6-membered cycloalkyl, aryl, heteroaryl, or heterocyclo ring;

$R_1$, $R_2$, $R_3$, $R_4$, $R_{1a}$, $R_{2a}$, $R_{3a}$, and/or $R_{4a}$ are independently selected from (i) hydrogen, halogen, cyano, $CF_3$, $C_{1-6}$alkyl, $CH(OH)R_{10}$, $C_{2-4}$alkenyl, $C_{2-4}$alkynyl, $OR_{10}$, $CO_2R_{10}$, $SR_{10}$, $SO_pR_{12}$, $C(O)R_{10}$, $C(O)NR_{10}R_{11}$, $SO_pNR_{10}R_{11}$, $NHC(O)R_{11}$, $NHC(O)NR_{10}R_{11}$, $NHC(O)_2R_{11}$, $NHS(O)_pR_{12}$, and $NR_{10}R_{11}$; and/or (ii) $C_{0-3}$alkylene substituted by an optionally substituted group selected from phenyl and a 5- to 7-membered heterocyclo or heteroaryl;

$R_6$ is selected from $C_{1-6}$alkyl, $C_{1-4}$substituted alkyl, and $C_{3-7}$cycloalkyl;

$R_7$ is selected from $C_{1-4}$alkyl, $C_{1-4}$substituted alkyl, nitro, cyano, $C_{1-4}$alkoxy, and $C_{3-7}$cycloalkyl;

or $R_6$ and $R_7$ are taken together with the carbon to which they are attached to form a $C_{3-7}$cycloalkyl group;

$R_{10}$ and $R_{11}$ at each occurrence are independently selected from (i) hydrogen, substituted $C_{1-6}$alkyl, and $C_{1-6}$alkyl; and/or (ii) $C_{0-3}$alkylene substituted by an optionally substituted group selected from $C_{3-7}$cycloalkyl, phenyl, naphthyl, and a 5- to 7-membered heterocyclo or heteroaryl; and/or (iii) $R_{10}$ is taken together with $R_{11}$ and the nitrogen atom to which they are both attached to form an optionally substituted 5- to 6-membered heteroaryl or heterocyclo;

$R_{12}$ at each occurrence is selected from $C_{1-6}$alkyl and $C_{0-3}$alkylene substituted by an optionally substituted group selected from $C_{3-7}$cycloalkyl, heterocyclo, aryl, and heteroaryl;

$R_{23a}$, $R_{23}$, and $R_{24}$ at each occurrence are independently selected from (i) hydrogen, alkyl, substituted alkyl, —$C(=O)$alkyl, —$CO_2$(alkyl), alkenyl, substituted alkenyl, alkynyl, substituted alkynyl, amino, substituted amino, aryl, heteroaryl, heterocyclo, and cycloalkyl, or (ii) $R_{23}$ and $R_{24}$ are combined with the nitrogen atom to which they are both attached to form a heteroaryl or heterocyclo ring; and t and p at each occurrence are independently 1 or 2.

More preferred compounds within the scope of formula (Ia) are those in which $R_1$, $R_2$, $R_3$, and $R_4$, are independently selected from (i) hydrogen, methyl, ethyl, t-butyl, fluoro, chloro, bromo, hydroxy, cyano, $CF_3$, $CH(OH)C_{1-4}$alkyl, $CH_2OH$, $C_{2-4}$ alkenyl, $C_{1-4}$alkoxy, $C_{2-4}$ alkynyl, $CO_2Me$, $C(O)N(C_{1-4}$alkyl$)_2$, $SO_2NR_{10}R_{11}$, $NH_2$, and $NHC(O)_{1-2}C_{1-4}$ alkyl; and/or (ii) $NH(CH_2)_{0-1}C(O)$phenyl, —$CO_2$furyl, —$CO_2$tetrahydrofuryl, phenoxy, —$(CH_2)_{0-2}$-phenyl, —$NH(CH_2)_{0-1}C(O)$phenyl, morpholinyl, pyrrolidinyl, piperazinyl, pyridinyl, and furyl, wherein the ring of said group is substituted by one to two groups selected from hydrogen, —$C(O)$-4-morpholinyl, —$C(O)N(C_{1-4}$alkyl$)_2$, —$C(O)NH(C_{1-4}$alkyl$)$, $NH_2$, $C_{1-4}$alkoxy, halogen, $C_{1-6}$alkyl, BOC, hydroxy, OCF$_3$, C(O)(C$_{1-4}$alkyl), CH$_2$OH, C(O)-4-methyl-1-piperazinyl, and CH$_2$O(C$_{1-4}$alkyl); and $R_{1a}$, $R_{2a}$, $R_{3a}$, and/or $R_{4a}$ are independently selected from hydrogen, halogen, hydroxy, C$_{1-4}$alkoxy, C$_{1-6}$alkyl, and cyano.

Other more preferred compounds within the scope of formula (Ia) are those wherein:

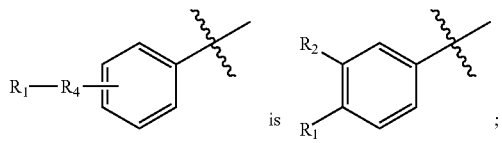

is $R_1$ is selected from hydrogen, C$_{1-4}$alkyl, C$_{1-4}$alkoxy, hydroxy, CO$_2$C$_{1-4}$alkyl, —CO$_2$(2-furyl), —CO$_2$(3-furyl), —CO$_2$(2-tetrahydrofuryl), N-morpholinyl; and phenyl substituted in the 4-position by one to two groups selected from hydrogen, —C(O)-4-morpholinyl, —C(O)N(C$_{1-4}$alkyl)$_2$, —C(O)NH(C$_{1-4}$alkyl), NH$_2$, C$_{1-4}$alkoxy, halogen, C$_{1-6}$alkyl, BOC, hydroxy, OCF$_3$, C(O)(C$_{1-4}$alkyl), CH$_2$OH, C(O)-4-methyl-1-piperazinyl, and CH$_2$O(C$_{1-4}$alkyl); and $R_2$ is selected from hydrogen, C$_{1-4}$alkyl, halogen, hydroxy, and cyano.

Still more preferred compounds in the scope of formula (Ia) are those in which

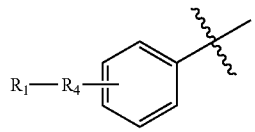

is selected from

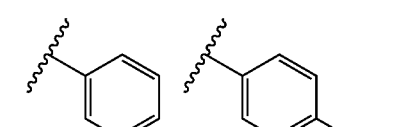

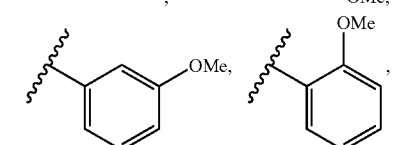

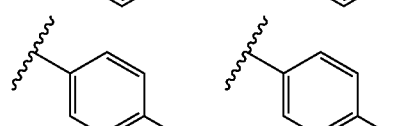

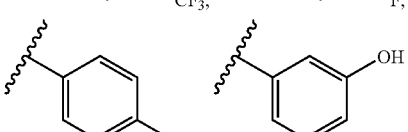

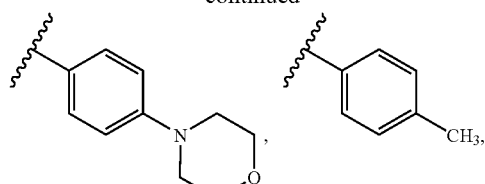

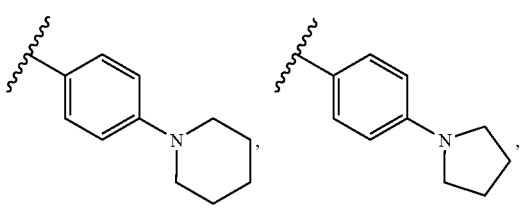

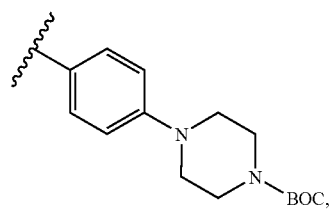

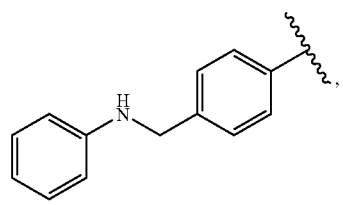

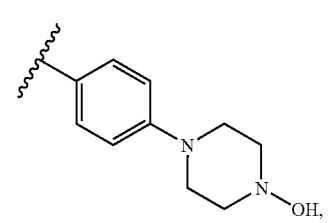

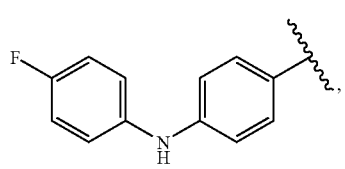

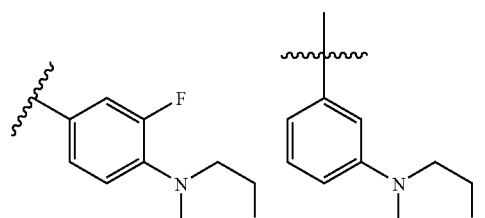

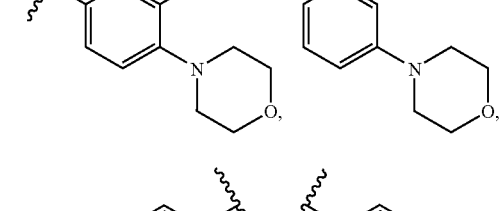

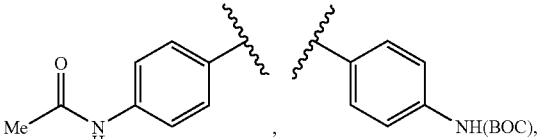

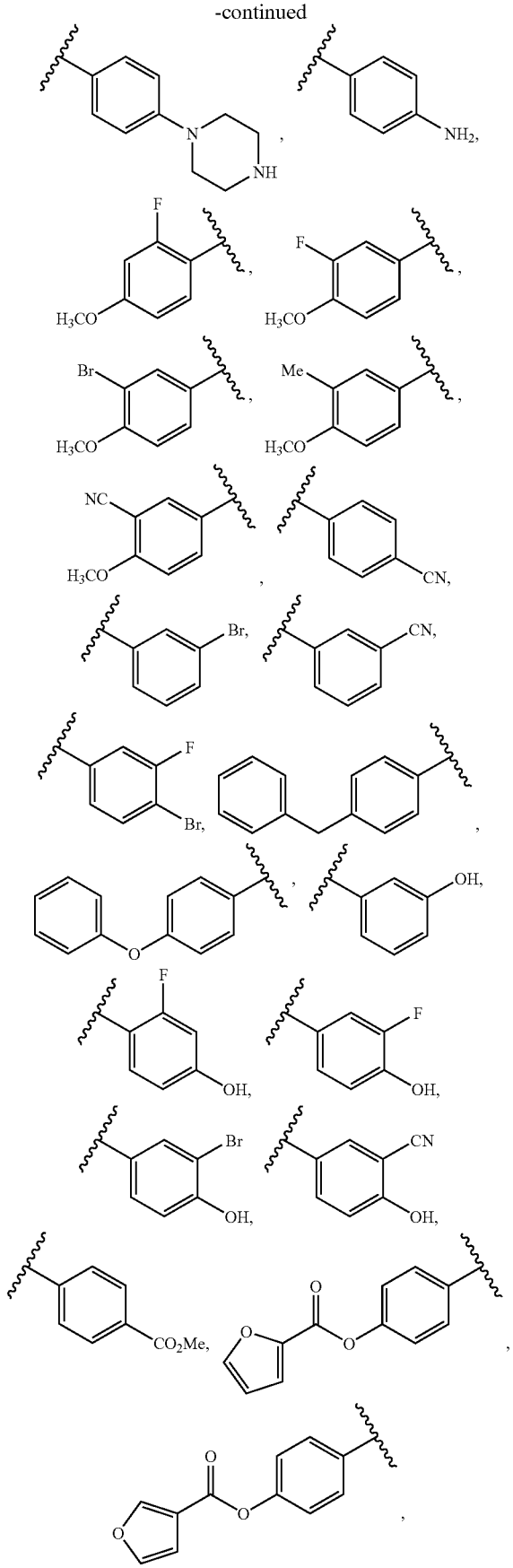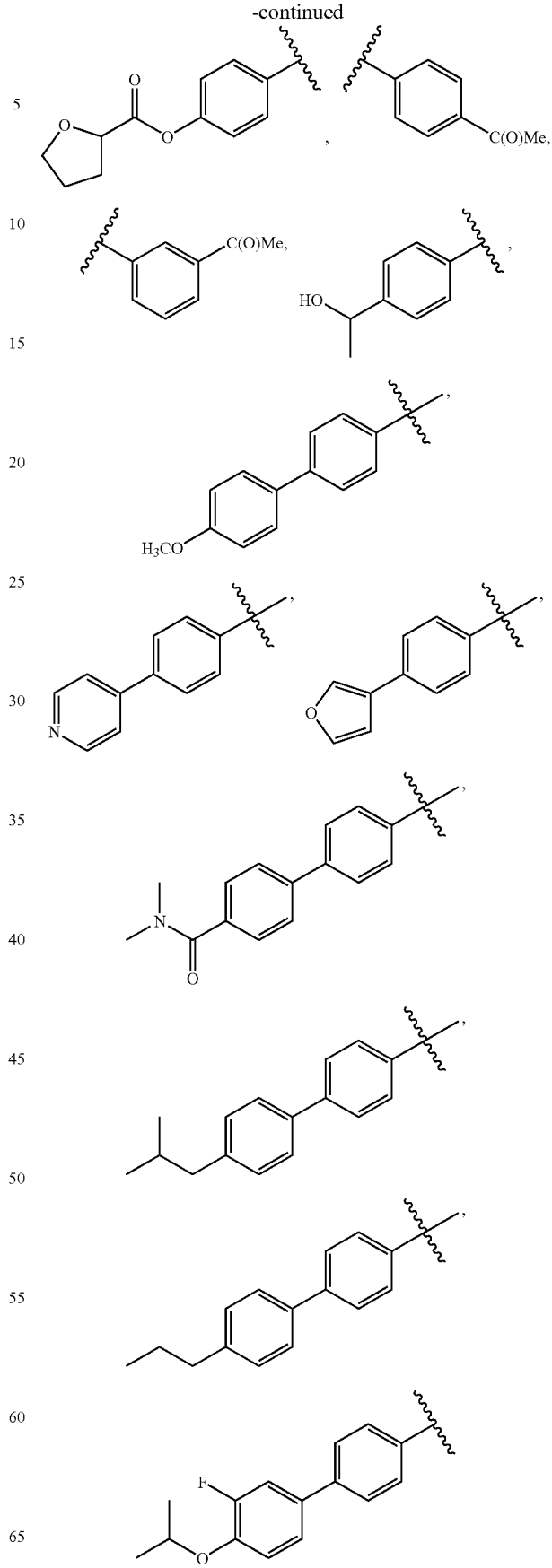

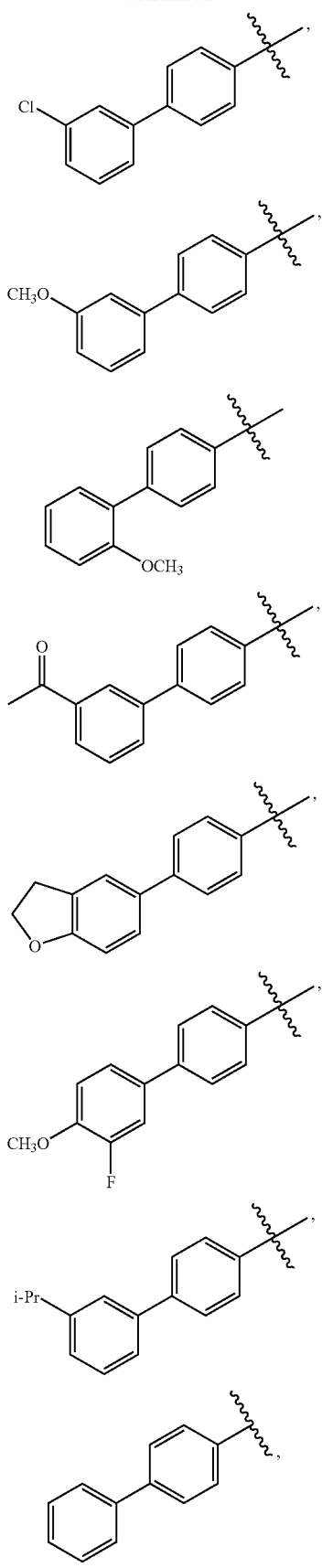
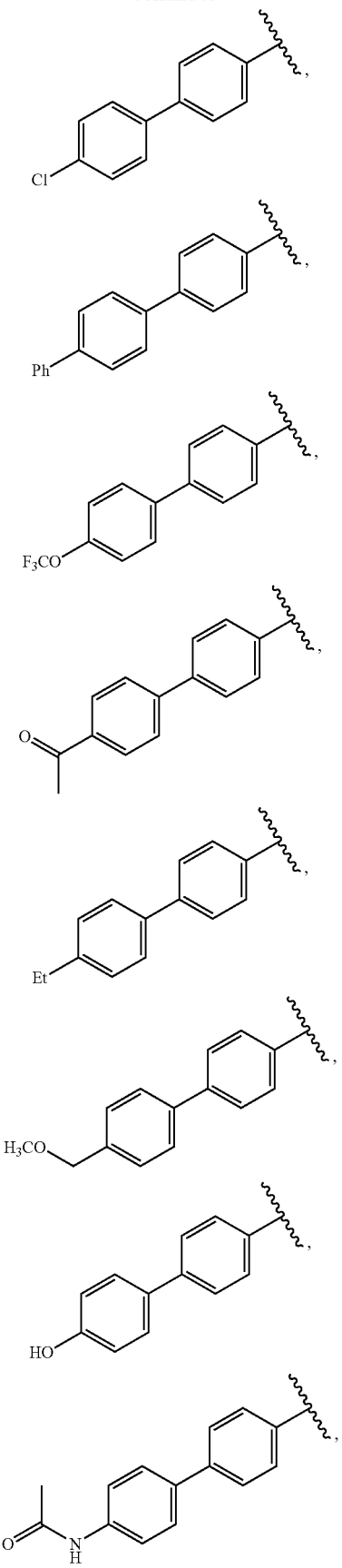

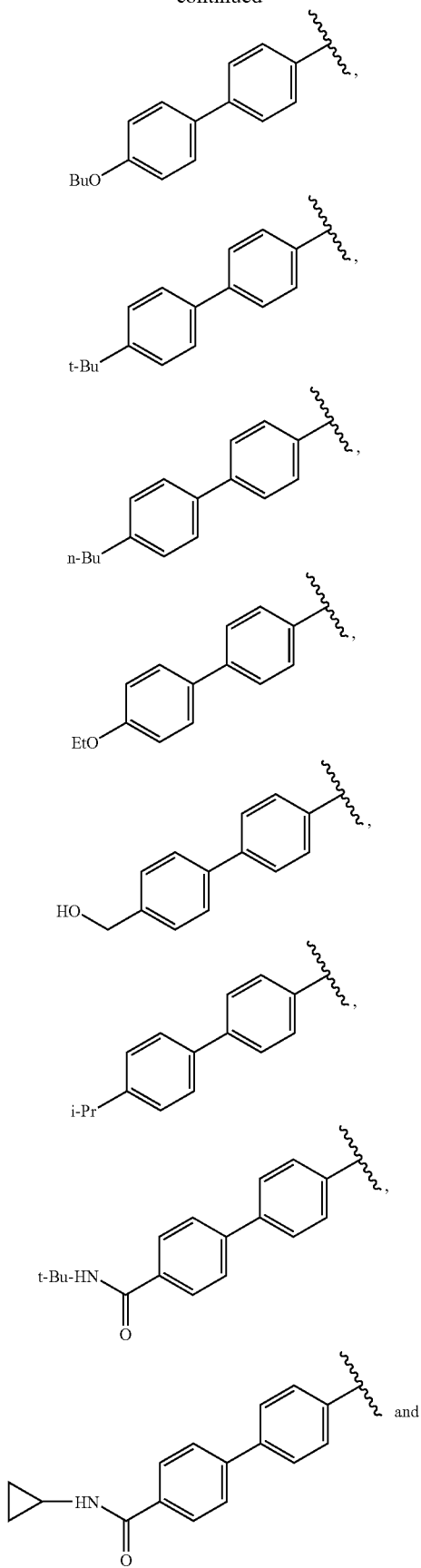

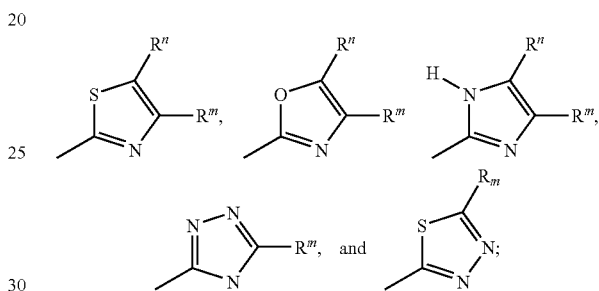

Other preferred compounds within the scope of formula (Ia) are those in which M is isobutyl, phenyl or phenyl substituted with $C_{1-4}$alkyl, $C_{1-4}$alkoxy, halogen, hydroxy, or morpholinyl.

Still other preferred compounds within the scope of formula (Ia) are those in which Z is selected from

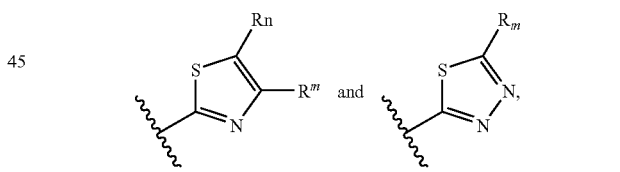

$R^m$ and $R^n$ are independently selected from (i) hydrogen, fluoro, chloro, bromo, $C_{1-4}$alkyl, trifluoroalkyl, nitro, —$(CH_2)_{0-2}CO_2R_{23}$, —$C(=NOR_{23a})CO_2R_{24}$, and $C_{1-4}$alkoxy, or (ii) $C_{0-3}$alkylene substituted by an optionally substituted ring selected from phenyl, napthyl, a 5- to 7-membered heterocyclo or heteroaryl, and a 7- to 11-membered bicyclic heterocyclo or heteroaryl ring.

Even more preferred are those compounds of formula (Ia) in which Z is selected from

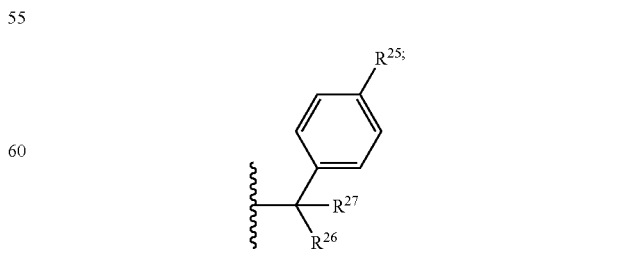

particularly those compounds in which $R^m$ is hydrogen, $C_{1-4}$alkyl, —$CO_2R_{23}$, —$C(O)N(R_{23})(R_{24})$, or (more preferably $R^m$ is selected from hydrogen, —$CO_2(C_{1-4}$alkyl), —$C(O)N(C_{1-4}$alkyl)($C_{1-4}$alkyl), and

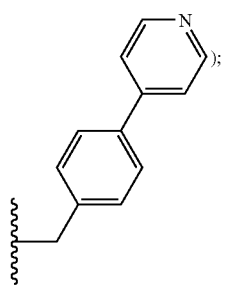

R" is hydrogen or $C_{1-4}$alkyl, —$CO_2(C_{1-4}$alkyl), phenyl, or halogen (more preferably R" is hydrogen, methyl, $CO_2Et$, unsubstituted phenyl, Cl, or Br);

$R_{23}$ and $R_{24}$ at each occurrence are independently selected from (i) hydrogen and $C_{1-4}$alkyl; or (ii) $R_{23}$ and $R_{24}$ together with the nitrogen atom to which they are attached form an optionally substituted 5- to 7-membered heterocyclo;

$R^{25}$ is $C_{1-4}$alkoxy; halogen, pyrimidinyl, isoxazolyl, pyrazolyl, or pyridinyl, each group optionally substituted by morpholinyl, $C_{1-4}$alkoxy, or $C_{1-4}$alkyl; and $R^{26}$ and $R^{27}$ are independently hydrogen, halogen, or hydroxy; or $R^{26}$ and $R^{27}$ combine to form =O.

Other preferred compounds within the scope of formulae (I) and (Ia) are those wherein $R^6$ and $R^7$ are independently selected from $C_{1-4}$alkyl, particularly where $R^6$ and $R^7$ are both methyl.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements (including individual variable definitions) of an embodiment are meant to be combined with any and all other elements from any of the embodiments to describe additional embodiments. The present invention also provides a pharmaceutical composition comprising a compound of formula (I), or an enantiomer, diastereomer, or a pharmaceutically-acceptable salt, and a pharmaceutically acceptable carrier therefore.

Other embodiments of the present invention include a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder, wherein the disease or disorder is selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease.

In still another embodiment, the present invention provides a method of treating endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, a disease associated with the expression product of a gene whose transcription is stimulated or repressed by glucocorticoid receptors, or a disease associated with AP-1- and/or NFκB-induced transcription, or a disease associated with AP-1 and/or NF-κB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Other embodiments of the present invention are a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder wherein the disease or disorder is selected from a metabolic disease or an inflammatory or immune disease comprising the administration to a patient in need of treatment, a therapeutically effective amount of a compound of formula (I).

More preferred embodiments of the present invention provide a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder wherein the disease or disorder is selected from a metabolic disease wherein the disease is a metabolic disease selected from Type I diabetes, Type II diabetes, juvenile diabetes, and obesity.

Other preferred embodiments of the present invention include a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder, wherein the disease or disorder is an inflammatory or immune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis, eczema, seborrhoea, pulmonary inflammation, eye uveitis, hepatitis, Graves' disease, Hashimoto's thyroiditis, autoimmune thyroiditis, Behcet's or Sjorgen's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia greata, autoimmune alopecia, autoimmune hypopituitarism, Guillain-Barre syndrome, alveolitis, contact hypersensitivity, delayed-type hypersensitivity, contact dermatitis, urticaria, skin allergies, respiratory allergies, hayfever, gluten-sensitive enteropathy, osteoarthritis, acute pancreatitis, chronic pancreatitis, acute respiratory distress syndrome, Sezary's syndrome, restenosis, stenosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, sepsis, and chronic obstructive pulmonary disease.

Especially preferred embodiments provide a method of treating a disease or disorder comprising administering to a patient in need of treatment a therapeutically effective amount of a compound of formula (I), a compound of formula (I) for use in treating a disease or disorder, and use of a compound of formula (I) in the manufacture of a medicament for treating a disease or disorder where the disease or disorder is selected from transplant rejection, rheumatoid arthritis, psoriatic arthritis, multiple sclerosis, asthma, inflammatory bowel disease, systemic lupus erythematosis, and psoriasis.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB- (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κB (particularly AP-1), such as inflammatory and immune disorders, cancer and tumor disorders, such as solid tumors, lymphomas and leukemia, and fungal infections such as mycosis fungoides.

In still another embodiment, the present invention provides a pharmaceutical combination comprising one or more compounds of Formula (I) and an immunosuppressant, an anti-cancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fabric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

Even more preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, N,N-2344, L895645, YM-440, R-119702, AJ9677, repaglinide, nateglinide, KAD1129, AR-HO39242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2, 2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary adrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger, et al., *Science*, 228:740-742 (1985), and in Weinberger, et al., *Nature*, 318:670-672 (1986); rat glucocorticoid receptor as disclosed in Miesfeld, R., *Nature*, 312:779-781 (1985); mouse glucocortoid receptor as disclosed in Danielson, M. et al., *EMBO J.*, 5:2513; sheep glucocorticoid receptor as disclosed in Yang, K. et al., *J. Mol. Endocrinol.*, 8:173-180 (1992); marmoset glucocortoid receptor as disclosed in Brandon, D. D. et al., *J. Mol. Endocrinol.* 7:89-96 (1991); and human GR-beta as disclosed in Hollenberg, S. M. et al., *Nature*, 318:635 (1985); Bamberger, C. M. et al., *J. Clin Invest.*, 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders;

cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjorgen's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitelige (depigmentation of the skin), alopecia greata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), urticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and atherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in the schemes of this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Additionally, the various steps in the synthesis may be performed in an alternate sequence in order to give the desired compound or compounds. Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

Compounds of formula (I) of the invention are prepared as described in the schemes and examples below. Various groups including M, $M_a$, Z, $Z_a$, $R_1$-$R_4$, $R_6$, $R_7$ correspond to those described above.

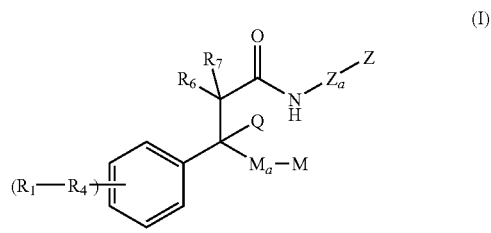

(I)

Scheme I

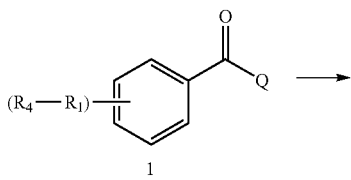

-continued

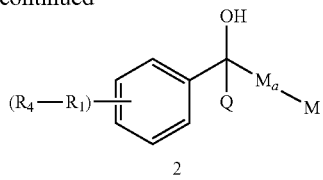

Compounds of formula 2 are constructed by the addition of an organometallic compound $M_aM$-"metal", where "metal"=MgBr, MgCl or Li, prepared from the corresponding bromide or chloride, to the compound of formula 1 by one of the methods well known to those skilled in the art.

Scheme II

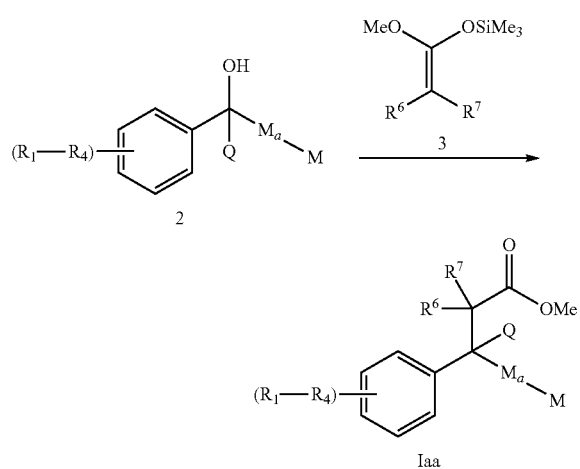

A compound of formula 2 is reacted with a compound of formula 3 in the presence of a Lewis acid such as $TiCl_4$ or $SnCl_4$, in an appropriate solvent such as dichloromethane, 1,2-dichloroethan or THF, at temperatures ranging from −78° C. to room temperature to form compound of formula Iaa. The ($R_1$-$R_4$) groups in Iaa may also be further elaborated.

Scheme III

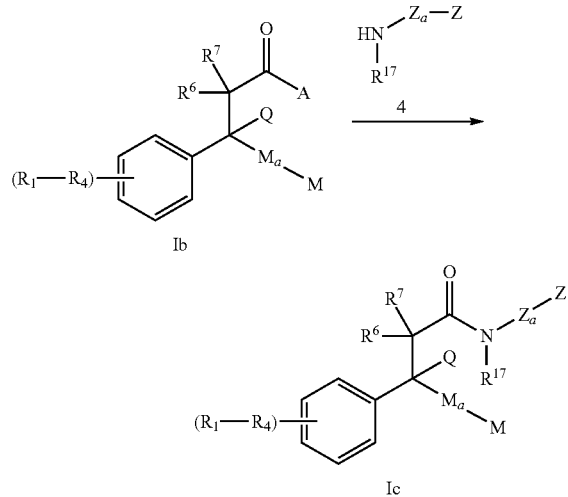

A compound of formula Ib, Where A=OH, Cl, F or O-alkyl can be reacted with an amine of formula 4 by one of the many methods of amidation well known to those skilled in the art (such as treatment of compound of formula Ib where A=OH, in a suitable solvent such as acetonitrile with 1-[3-(dimethylamino)propyl]-3-ethylcarbodiimide hydrochloride (EDC), 1-hydroxy-7-azabenzotriazole, triethylamine and amine 4) to provide compound of formula Ic of the invention. The ($R_1$-$R_4$) groups in Ic may also be further elaborated.

Scheme IV

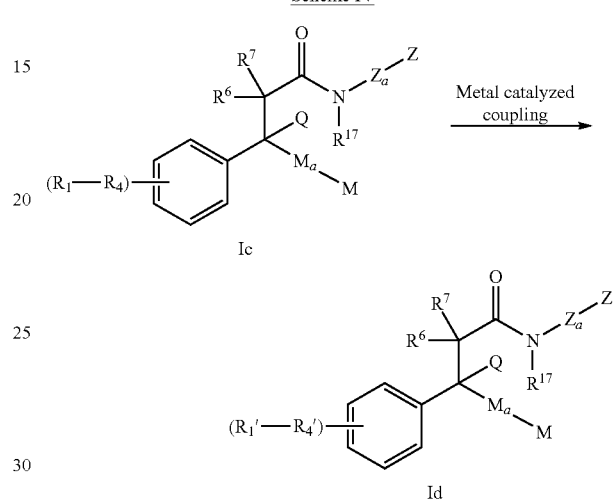

A compound of formula Ic, where at least one of $R_1$, $R_2$, $R_3$, or $R_4$ is a halogen atom (I, Br and Cl) or OTf (triflate), undergoes a metal (such as palladium) catalyzed coupling reaction with an organometallic compound (such as organoboron or organostannic compound) using one of the methods well known to those skilled in the art to provide a compound of formula Id where at least one of the $R_1$', $R_2$', $R_3$', or $R_4$' groups is selected from aryl, alkyl, —C(=O)$R_{10}$, or —CO$_2R_{10}$.

Scheme V

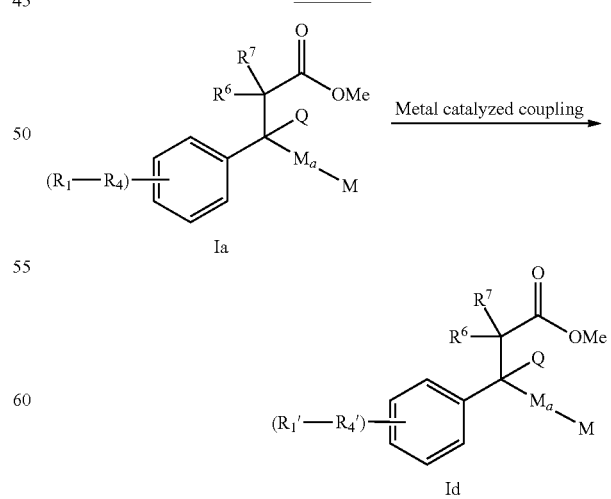

A compound of formula Iaa, where at least one of $R_1$, $R_2$, $R_3$, or $R_4$ is halogen atom (I, Br and Cl) or OTf (triflate), can undergo metal (such as palladium) catalyzed coupling reaction with an amine ($HNR_{10}R_{11}$) or Aryl-OH using one of the methods well known to those skilled in the art (such as the procedures described by S. Buchwald in *Acc. Chem. Res.* 1998, 31, 805 and *J. Org. Chem.* 2000, 65, 1158) to provide a compound of formula Id where at least one of the $R_1'$, $R_2'$, $R_3'$, or $R_4'$ groups is selected from $NR_{10}R_{11}$ or O-Aryl.

Scheme VI

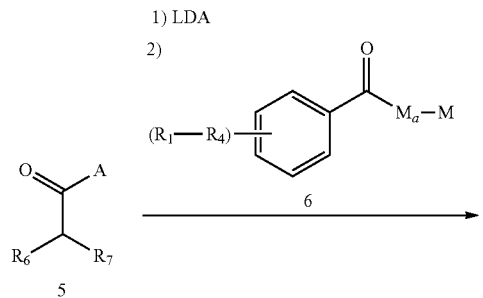

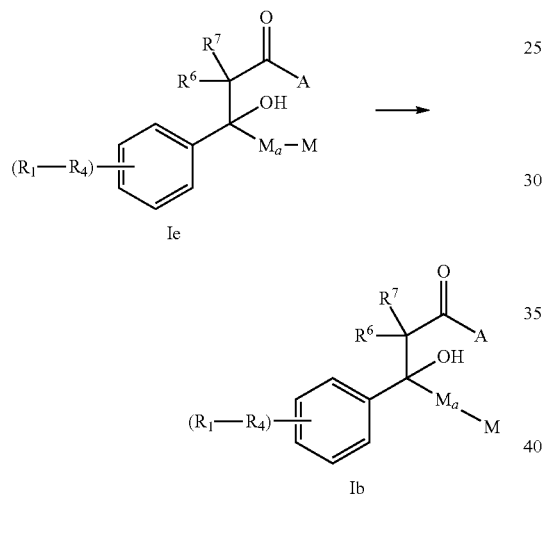

A compound of formula 5 where A is OH or OR etc., when treated with a base such as LDA followed by reaction with a compound of formula 6, provides a compound of formula Ie in a similar manner as described by R. Burkett, *J. Org. Chem.*, 36, 1149, (1971). Treatment of compounds of formula Ie with a suitable reducing agent such as triethylsilane provides compounds of formula Ib (A=OR or OH) in a similar manner as described by M. Orfanopoulous, *Synthetic Commun.*, 18, 833, (1988).

Scheme VII

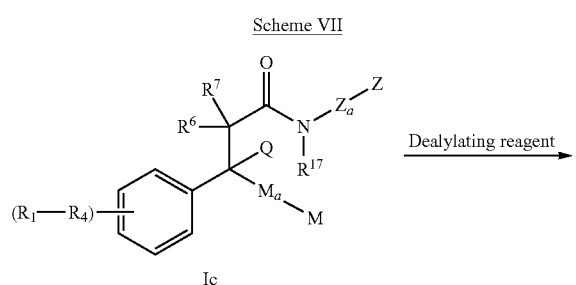

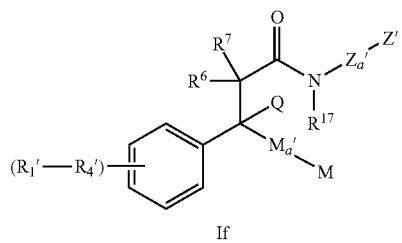

A compound of formula Ic, where the $M_a$-M or $Z_a$—Z groups have one or more arylalkylether groups, or at least one of the $R_1$, $R_2$, $R_3$, or $R_4$ is an alkylether group, can be treated with a dealkylating agent such as boron tribromide, sodium methyl sulfide or one of the other well known dealkylating agents to provide the corresponding phenol of formula If. The resultant phenol may be further elaborated by methods known to those of skill in the art.

Scheme VIII

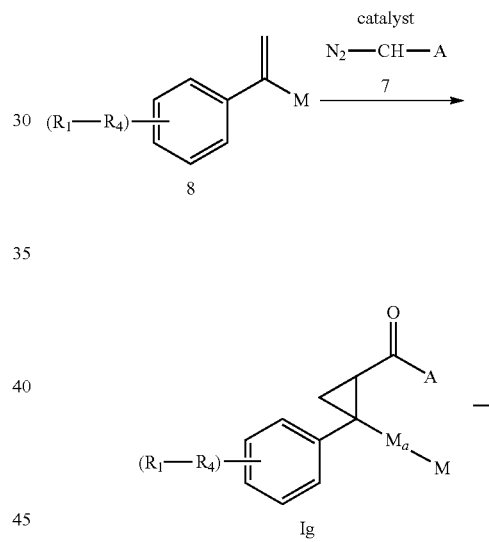

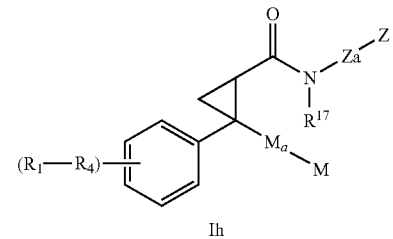

A compound of formula 8, when reacted with a diazo compound of formula 7 and a catalyst such as rhodium (II) acetate dimmer, provides a compound of formula Ig (A=OEt) that can be converted to a compound of formula Ig (A=OH) followed by conversion to a compound of formula Ih in a similar manner to Scheme III.

Scheme IX

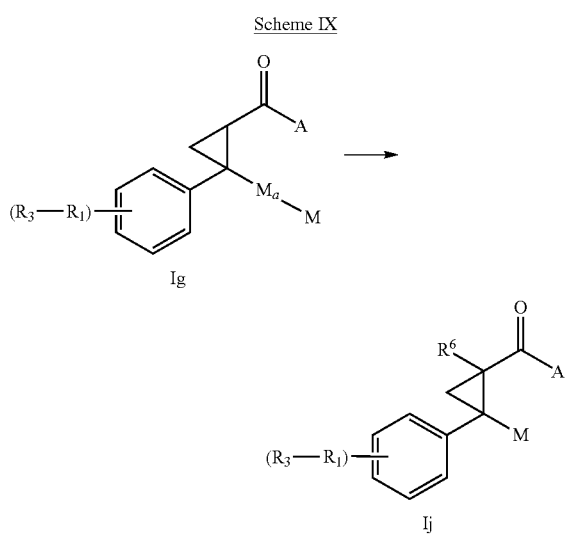

A compound of formula Ig, where A is OH or O-alkyl, is treated with a suitable base such as LDA and an appropriate $R^6$-Lg, where Lg is a leaving group, such as methyl iodide affords a compound of formula Ij. The $R^6$ group may be further elaborated by methods known to those of skill in the art.

It should be understood that protecting groups may be utilized as appropriate throughout synthetic Schemes described above. Common protecting groups for amine-containing heterocycles are ureas, sulfonamides, carbamates, and alkyl groups (such as benzyl). The judicious use of protecting groups is known to one skilled in the art and is described in Greene and Wuts "Protecting Groups in Organic Synthesis 3rd Ed. ©1999.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" refers to straight or branched chain hydrocarbon groups having 1 to 12 carbon atoms, preferably 1 to 6 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$ alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$) hydroxyalkyl includes hydroxy, hydroxymethyl and hydroxyethyl.

The term "substituted alkyl" refers to an alkyl group as defined above having one, two, or three substituents selected from the group consisting of halo (e.g., trifluoromethyl), alkenyl, substituted alkenyl, alkynyl, nitro, cyano, oxo (=O), $OR_a$, $SR_a$, (=S), —$NR_aR_b$, —N(alkyl)$_3^+$, —$NR_aSO_2$, —$NR_aSO_2R_c$, —$SO_2R_c$, —$SO_2NR_aR_b$, —$SO_2NR_aC(=O)$ $R_b$, $SO_3H$, —$PO(OH)_2$, —$OC(O)R_a$, —$C(=O)R_a$, —$CO_2R_a$, —$C(=O)NR_aR_b$, —$C(=O)(C_{1-4}$alkylene) $NR_aR_b$, —$C(=O)NR_a(SO_2)R_b$, —$CO_2(C_{1-4}$alkylene) $NR_aR_b$, —$NR_aC(=O)R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, $CO_2H$, $CO_2$(alkyl), $C_{3-7}$cycloalkyl, phenyl, benzyl, phenylethyl, napthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being selected from the group consisting of ($C_{1-6}$)alkyl, ($C_{2-6}$)alkenyl, hydroxy, halogen, cyano, nitro, =O (as valence allows), $CF_3$, $O(C_{1-6}$alkyl), $OCF_3$, $C(=O)H$, $C(=O)(C_{1-6}$alkyl), $CO_2H$, $CO_2(C_{1-6}$alkyl), $NHCO_2(C_{1-6}$ alkyl), —$S(C_{1-6}$alkyl), —$NH_2$, $NH(C_{1-6}$alkyl), $N(C_{1-6}$ alkyl)$_2$, $N(CH_3)_3^+$, $SO_2(C_{1-6}$alkyl), $C(=O)(C_{1-4}$alkylene) $NH_2$, $C(=O)(C_{1-4}$alkylene)NH(alkyl), $C(=O)(C_{1-4}$alkylene)N($C_{1-4}$alkyl)$_2$, $C_{3-7}$cycloalkyl, phenyl, benzyl, phenylethyl, phenyloxy, benzyloxy, napthyl, a four to seven membered heterocyclo or cycloalkyl, or a five to six membered heteroaryl. When a substituted alkyl is substituted with an aryl (including, for example, phenyl and napthyl), heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

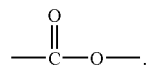

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl(Co)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., {—$CH_2$—}$_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO$_2$—, —NH—, and —NHSO$_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—(CH$_2$)$_{1-5}$NH—CH$_2$—, —O—(CH$_2$)$_{1-5}$S(=O)—CH$_2$—, —NHSO$_2$—CH$_2$—, —CH$_2$—NH—, and so forth. Preferably, a heteroalkylene does not have two adjacent atoms simultaneously selected from —O— and —S—. When a subscript is used with the term heteroalkylene, e.g., as in C$_{2-3}$ heteroalkylene, the subscript refers to the number of carbon atoms in the group in addition to heteroatoms. Thus, for example, a C$_{1-2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or A$_1$-Q-A$_2$-R$_h$, wherein A$_1$ is a bond, C$_{1-2}$alkylene, or C$_{2-3}$ alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; A$_2$ is a bond, C$_{1-3}$alkylene, C$_{2-3}$alkenylene, —C$_{1-4}$alkylene-NR$_d$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein said A$_2$ alkylene groups are branched or straight chain and optionally substituted as defined herein for substituted alkylene; R$_h$ is hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that for a substituted heteroalkylene R$_h$ is not hydrogen when A$_1$, Q and A$_2$ are each bonds. When R$_h$ is aryl, heteroaryl, cycloalkyl, or heterocyclo, these rings are, in turn, optionally substituted with one to three groups as defined below in the definitions for these terms.

The term "alkoxy" refers to an oxygen atom substituted by alkyl or substituted alkyl, as defined herein. For example, the term "alkoxy" or includes the group —O—C$_{1-6}$ alkyl.

The term "alkylthio" refers to a sulfur atom that is substituted by an alkyl or substituted alkyl group as defined herein. For example, the term "thioalkyl" includes the group —S—C$_{1-6}$ alkyl, and so forth.

The term "alkylamino" refers to an amino group substituted with an alkyl group or substituted alkyl group as defined above. For example, the term "alkylamino" includes the group —NR—C$_{1-12}$alkyl. (where R is preferably hydrogen but may include alkyl or substituted alkyl as defined above.)

When a subscript is used with reference to an alkoxy, thioalkyl or aminoalkyl, the subscript refers to the number of carbon atoms that the group may contain in addition to heteroatoms. Thus, for example, monovalent C$_{1-2}$-aminoalkyl includes the groups —CH$_2$—N(CH$_3$)$_2$, and —(CH$_2$)$_2$—NH$_2$. A lower aminoalkyl comprises an aminoalkyl having one to four carbon atoms. The term (C$_{1-4}$alkyl)$_{0-2}$-amino includes the groups NH$_2$, —NH(C$_{1-4}$alkyl), and —N(C$_{1-4}$alkyl)$_2$. "Amino" refers to the group NH$_2$. A "substituted amino" refers to an amino group substituted as described above for the nitrogen atom of a heteroalkylene chain and includes, for example, the terms alkylamino and acylamino (—NR$_d$C(O)R$_e$).

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—C$_{1-12}$alkyl, whereas a bivalent alkoxy includes groups such as —O—C$_{1-12}$alkylene-.

It should be understood that the selections for all groups, including for examples, alkoxy, thioalkyl, and aminoalkyl, will be made by one skilled in the field to provide stable compounds. Thus, for example, in compounds of formula (I), when G is attached to a nitrogen atom (N*) of ring A and is selected from an alkoxy or alkylthio group, the alkoxy and alkylthio groups will have at least one carbon atom bonded directly to ring A (at N*), with the oxygen or sulfur atoms being at least one atom away from said nitrogen atom.

The term "carbonyl" refers to a bivalent carbonyl group —C(=O)—. When the term "carbonyl" is used together with another group, such as in "heterocyclocarbonyl", this conjunction defines with more specificity at least one of the substituents that the substituted carbonyl will contain. For example, "heterocyclocarbonyl" refers to a carbonyl group as defined above where at least one of the substituents is an heterocyclo, such as morpholinyl.

The term "acyl" refers to a carbonyl group linked to an organic radical, more particularly, the group C(=O)R$_e$. The group R$_e$ can be selected from alkyl, alkenyl, alkynyl, aminoalkyl, substituted alkyl (i.e. substituted alkylene), substituted alkenyl, substituted alkynyl, cycloalkyl, heterocyclo, aryl, or heteroaryl, as defined herein. When R$_e$ is aryl, heteroaryl, cycloalkyl, or heterocyclo, these rings are, in turn, optionally substituted with one to three groups as defined below in the definitions for these terms.

The term "alkoxycarbonyl" refers to a carboxy group

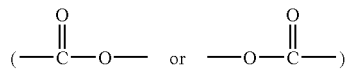

linked to an organic radical (CO$_2$R$_e$), as well as the bivalent groups —CO$_2$—, —CO$_2$R$_e$— which are linked to organic radicals in compounds of formula (I), wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.) Accordingly, in compounds of formula (I), when it is recited that G can be "alkoxycarbonyl," this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "carboxamide", "carboxamidyl", or "carboxamido" refers to the group —NR$_d$C(=O)R$_e$, wherein the groups R$_d$ and R$_e$ are defined as recited above in the definitions for heteroalkyl, alkoxycarbonyl and acyl. For example, the group

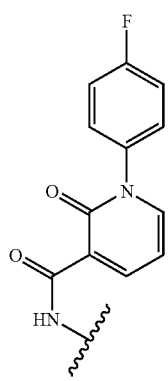

is a carboxamido group where $R_e$ is a substituted heterocyclo according to the definitions herein.

The term "amide", "amidyl", or "amido" refers to the group —C(=O)NR$_a$R$_b$, wherein the groups $R_a$ and $R_b$ are defined as recited above in the definition for substituted alkyl groups.

The term "urea" refers to the group —NR$_d$C(=O)NR$_a$R$_b$, wherein the groups $R_a$, $R_b$, and $R_d$ are defined as recited above in the definition for substituted alkyl groups. Additionally, the urea group may be bivalent, in which case one of the groups $R_a$ and $R_b$ will be a bond. Thus, in compounds of formula (I), when it is stated that G may be urea, it can mean that G is a group —NR$_d$(C(=O)NR$_a$— where appropriate.

The term "sulfonyl" refers to a sulphoxide group linked to an organic radical in compounds of formula (I), more particularly, the monovalent group —S(O)$_2$—R$_e$. Additionally, the sulfonyl group may be bivalent, in which case R$_e$ is a bond. Accordingly, in compounds of formula (I), when it is recited that G can be "sulfonyl," it can mean that G is a group —S(O) where appropriate. The group $R_e$ is selected from those recited above for acyl and alkoxycarbonyl groups, with the exception that $R_e$ is not hydrogen.

The terms "sulfonamide", "sulfonamidyl", or "sulfonamido" refers to the group —S(O)$_2$NR$_a$R$_b$, wherein $R_a$ and $R_b$ are as defined above for substituted alkyl groups.

The term "cycloalkyl" refers to fully saturated and partially unsaturated hydrocarbon rings (and therefore includes hydrocarbon rings also known as "cycloalkenyl rings") of 3 to 9, preferably 3 to 7 carbon atoms. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$alkyl, (C$_{2-4}$)alkenyl, (C$_{2-4}$)alkynyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3^+$, SO$_2$(C$_{1-4}$alkyl), C(=O)(C$_{1-4}$alkylene)NH$_2$, C(=O)(C$_{1-4}$alkylene)NH(alkyl), C(=O)(C$_{1-4}$alkylene)N(C$_{1-4}$alkyl)$_2$ and/or phenyl optionally substituted with any of the preceding groups. As valence allows, if said further ring is cycloalkyl or heterocyclo it is additionally optionally substituted with =O (oxo).

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems,

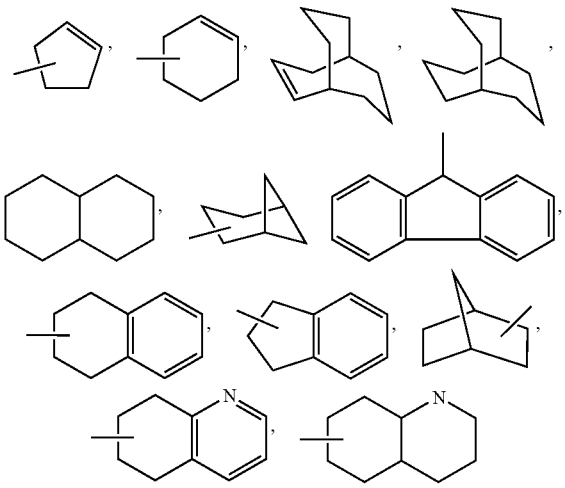

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "aryl" refers to phenyl, biphenyl, fluorenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), SO$_3$H, —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein $R_a$, $R_b$ and $R_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}$alkyl$)$, $OCF_3$, $C(=O)H$, $C(=O)(C_{1-4}$alkyl$)$, $CO_2H$, $CO_2(C_{1-4}$alkyl$)$, $NHCO_2(C_{1-4}$alkyl$)$, $-S(C_{1-4}$alkyl$)$, $-NH_2$, $NH(C_{1-4}$alkyl$)$, $N(C_{1-4}$alkyl$)_2$, $N(C_{1-4}$alkyl$)_3^+$, $SO_2(C_{1-4}$alkyl$)$, $C(=O)(C_{1-4}$alkylene$)NH_2$, $C(=O)(C_{1-4}$alkylene$)NH($alkyl$)$, $C(=O)(C_{1-4}$alkylene$)N(C_{1-4}$alkyl$)_2$ and/or phenyl optionally substituted with any of the preceding groups. As valence allows, if said further ring is cycloalkyl or heterocyclo it is additionally optionally substituted with $=O$ (oxo).

Thus, examples of aryl groups include:

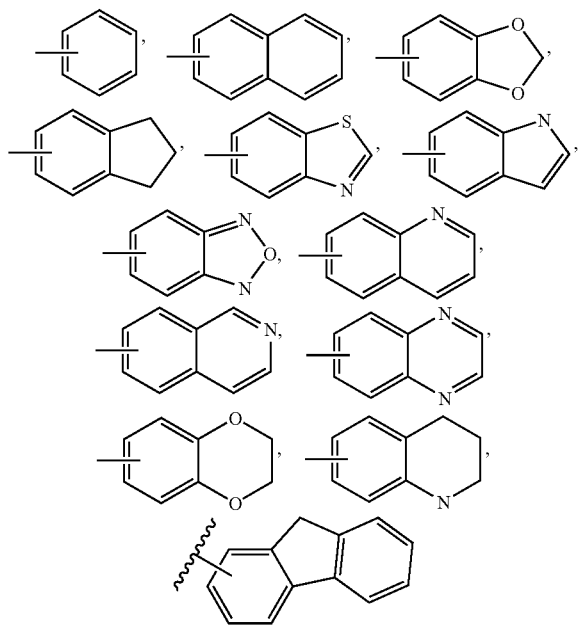

(fluorenyl) and the like, which optionally may be substituted at any available carbon or nitrogen atom. A preferred aryl group is optionally-substituted phenyl.

The terms "heterocycloalkyl", "heterocyclo" or "heterocyclic" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo $(=O)$, $OR_a$, $SR_a$, $(=S)$, $-NR_aR_b$, $-N($alkyl$)_3^+$, $-NR_aSO_2$, $-NR_aSO_2R_c$, $-SO_2R_c$, $-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}$alkylene$)NR_aR_b$, $-C(=O)NR_a(SO_2)R_b$, $-CO_2(C_{1-4}$alkylene$)NR_aR_b$, $-NR_aC(=O)R_b$, $-NR_aCO_2R_b$, $-NR_a(C_{1-4}$alkylene$)CO_2R_b$, $=N-OH$, $=N-O$-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of $(C_{1-4})$alkyl, $(C_{2-4})$alkenyl, $(C_{2-4})$alkynyl, halogen, hydroxy, cyano, nitro, $CF_3$, $O(C_{1-4}$alkyl$)$, $OCF_3$, $C(=O)H$, $C(=O)(C_{1-4}$alkyl$)$, $CO_2H$, $CO_2(C_{1-4}$alkyl$)$, $NHCO_2(C_{1-4}$alkyl$)$, $-S(C_{1-4}$alkyl$)$, $-NH_2$, $NH(C_{1-4}$alkyl$)$, $N(C_{1-4}$alkyl$)_2$, $N(C_{1-4}$alkyl$)_3^+$, $SO_2(C_{1-4}$alkyl$)$, $C(=O)(C_{1-4}$alkylene$)NH_2$, $C(=O)(C_{1-4}$alkylene$)NH($alkyl$)$, $C(=O)(C_{1-4}$alkylene$)N(C_{1-4}$alkyl$)_2$ and/or phenyl optionally substituted with any of the preceding groups. As valence allows, if said further ring is cycloalkyl or heterocyclo it is additionally optionally substituted with $=O$ (oxo).

Monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolidinyl, 2-oxazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Heterocyclo groups in compounds of formula (I) include

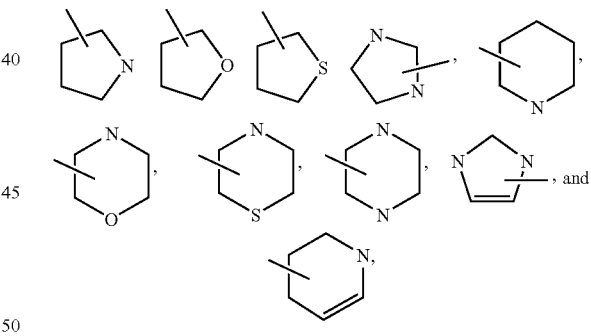

, and which optionally may be substituted.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (═S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(═O)$ $R_b$, $SO_3H$, —$PO(OH)_2$, —$C(═O)R_a$, —$CO_2R_a$, —$C(═O)$ $NR_aR_b$, —$C(═O)(C_{1-4}alkylene)NR_aR_b$, —$C(═O)NR_a$ $(SO_2)R_b$, —$CO_2(C_{1-4}alkylene)NR_aR_b$, —$NR_aC(═O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of ($C_{1-4}$alkyl, ($C_{2-4}$) alkenyl, ($C_{2-4}$)alkynyl, halogen, hydroxy, cyano, nitro, $CF_3$, $O(C_{1-4}alkyl)$, $OCF_3$, $C(═O)H$, $C(═O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $SO_2(C_{1-4}alkyl)$, $C(═O)(C_{1-4}alkylene)NH_2$, $C(═O)(C_{1-4}alkylene)NH$ (alkyl), $C(═O)(C_{1-4}alkylene)N(C_{1-4}alkyl)_2$ and/or phenyl optionally substituted with any of the preceding groups. As valence allows, if said further ring is cycloalkyl or heterocyclo it is additionally optionally substituted with ═O (oxo).

Monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrolinyl, acridinyl, phenanthridinyl, xanthenyl and the like.

In compounds of formula (I), preferred heteroaryl groups include

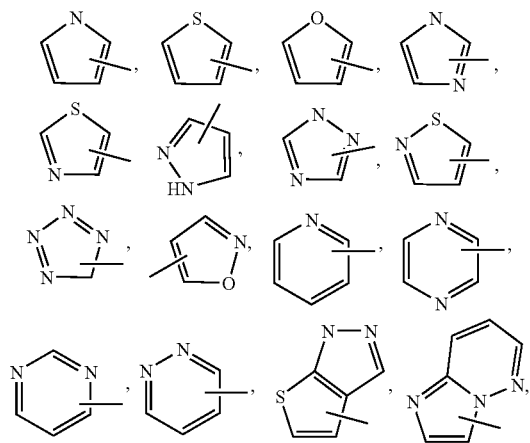

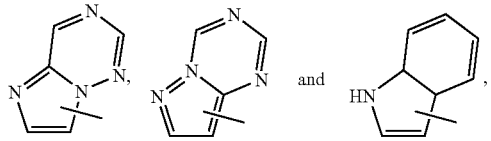

and the like, which optionally may be substituted at any available carbon or nitrogen atom. Aromatic rings may also be designated by an unbroken circle in the ring.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl,) unless otherwise specifically indicated the reference is intended to include rings having 0 to 3, preferably 0-2, substituents selected from those recited above for the aryl, cycloalkyl, heterocyclo and/ or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

When the term "optionally substituted" is used herein to refer to a ring or group, the ring or group may be substituted or unsubstituted.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) can form salts which are also within the scope of this invention. Unless otherwise indicated, reference to an inventive compound is understood to include reference to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates (e.g. hydrates) of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound of formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$ alkylbenzyl, 4-methoxybenzyl, indanyl, phthalyl, methoxymethyl, $C_{1-6}$ alkanoyloxy-$C_{1-6}$ alkyl, e.g. acetoxymethyl, pivaloyloxymethyl or propionyloxymethyl, $C_{1-6}$ alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers or diastereomers as starting materials. When enantiomeric or diastereomeric products are prepared, they can be separated by conventional methods for example, chromatographic or fractional crystallization.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, antiobesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula (I) of the invention include cyclosporins, for example cyclosporin A, mycophenolate, interferon-beta, deoxyspergolin, FK-506 or Ant.-IL-2.

The anti-cancer agents which may be optionally employed in combination with compounds of formula (I) of the invention include azathiprine, 5-fluorouracil, cyclophosphamide, cisplatin, methotrexate, thiotepa, carboplatin, and the like.

The anti-viral agents which may be optionally employed in combination with compounds of formula (I) of the invention include abacavir, aciclovir, ganciclovir, zidanocin, vidarabine, and the like.

The anti-inflammatory agents which may be optionally employed in combination with compounds of formula (I) of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti- CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-kappa B function, such as deoxyspergualin (DSG).

The anti-fungal agents which may be optionally employed in combination with compounds of formula (I) of the invention include fluconazole, miconazole, amphotericin B, and the like.

The antibiotics which may be optionally employed in combination with compounds of formula (I) of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula (I) of the invention include methotrexate, leflunomide, FK506 (tacrolimus, Prograf), The hypolipidemic agent or lipid-lowering agent or lipid modulating agents which may be optionally employed in combination with the compounds of formula (I) of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

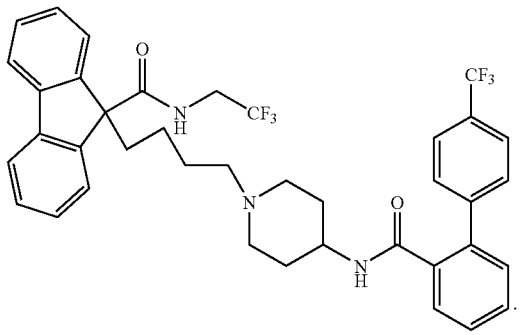

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., J. Med. Chem., Vol. 31, No. 10, pp. 1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, Vol. 2, pp. 1-40 (1996).

In addition, other squalene synthetase inhibitors suitable for use herein include the terpenoid pyrophosphates disclosed by P. Ortiz de Montellano et al., J. Med. Chem., 1977, 20, 243-249, the farnesyl diphosphate analog A and presqualene pyrophosphate (PSQ-PP) analogs as disclosed by Corey and Volante, J. Am. Chem. Soc., 98, 1291-1293 (1976), phosphinylphosphonates reported by McClard, R. W. et al., J. Am. Chem. Soc., 1987, 109, 5544 (1987), and cyclopropanes reported by Capson, T. L., PhD dissertation, Dept. Med. Chem. U. of Utah, Abstract, Table of Contents, pp. 16, 17, 40-43, 48-51, Summary (June, 1987).

Other hypolipidemic agents suitable for use herein include, but are not limited to, fibric acid derivatives, such as fenofibrate, gemfibrozil, clofibrate, benzafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, Drugs of the Future, 24, 9-15 (1999), (Avasimibe); "The ACAT inhibitor, Cl-1011 is effective in the prevention and regression of aortic fatty streak area in hamsters", Nicolosi et al., *Atherosclerosis* (Shannon, Irel). 137 (1), 77-85 (1998), "The pharmacological profile of FCE 27677: a novel ACAT inhibitor with potent hypolipidemic activity mediated by selective suppression of the hepatic secretion of ApoB100-containing lipoprotein", Ghiselli, Giancarlo, *Cardiovasc. Drug Rev.* (1998), 16(1), 16-30; "RP 73163: a bioavailable alkylsulfinyl-diphenylimidazole ACAT inhibitor", Smith, C., et al, *Bioorg. Med. Chem. Lett.* 6(1), 47-50 (1996); "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., *Inflammation: Mediators Pathways* 173-98 (1995), Publisher: CRC, Boca Raton, Fla.; "ACAT inhibitors: potential anti-atherosclerotic agents", Sliskovic et al, *Curr. Med. Chem.* 1(3), 204-25 1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl) methyl]ureas with enhanced hypocholesterolemic activity", Stout et al, *Chemtracts: Org. Chem.* 8(6), 359-62 (1995), or TS-962 (acetamide, N-[2,6-bis(1-methylethyl)phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis* 115, 45-63 (1995) and *J. Med. Chem.* 41, 973 (1998).

The hypolipidemic agent may be an ileal $Na^+$/bile acid cotransporter inhibitor such as disclosed in *Drugs of the Future*, 24, 425-430 (1999).

The lipid-modulating agent may be a cholesteryl ester transfer protein (CETP) inhibitor such as Pfizer's CP 529,414 (torcetrapib) (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physician's Desk Reference and/or in the patents set out above.

The compounds of formula (I) of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", *Brit. J. Pharmacology* 120, 1199-1206 (1997), and Cornicelli et al, "15-Lipoxygenase and its Inhibition: A Novel Therapeutic Target for Vascular Disease", *Current Pharmaceutical Design*, 5, 11-20 (1999).

The compounds of formula (I) and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula (I) may be 1, 2, 3 or more antidiabetic agents or antihyperglycemic agents including insulin secretagogues or insulin sensitizers, or other antidiabetic agents preferably having a mechanism of action different from the compounds of formula (I) of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), N,N-2344 (balaglitazone) (Dr. Reddy/NN), or YM-440 ((Z)-1,4-bis-4-[(3,5-dioxo-1,2,4-oxadiazolidine-2-yl-methyl)] phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1-36) amide, GLP-1 (7-36) amide, GLP-1 (7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physicians' Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physicians' Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2,4-dioxo-5-thiazolidinyl)methyl]-2-methoxy-N-[[4-(trifluoromethyl)phenyl]methyl]- (Kyorin Merck) as well as those disclosed by Murakami et al, "A Novel Insulin Sensitizer Acts As a Coligand for Peroxisome Proliferation-Activated Receptor Alpha (PPAR alpha) and PPAR gamma Effect on PPAR alpha Activation on Abnormal Lipid Metabolism in Liver of Zucker Fatty Rats", *Diabetes* 47, 1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), saxagliptin (preferred), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, *Biochemistry,* 38(36), 11597-11603, (1999), TSL-225 (tryptophyl-1,2,3,4-tetrahydro-isoquinoline-3-carboxylic acid (disclosed by Yamada et al, *Bioorg. & Med. Chem. Lett.* 8 1537-1540 (1998), 2-cyanopyrrolidides and 4-cyanopyrrolidides as disclosed by Ashworth et al, *Bioorg. & Med. Chem. Lett.*, Vol. 6, No. 22, pp 1163-1166 and 2745-2748 (1996) employing dosages as set out in the above references.

The meglitinide which may optionally be employed in combination with the compound of formula (I) of the invention may be repaglinide, nateglinide (Novartis) or KAD1229 (mitiglinide) (PF/Kissei), with repaglinide being preferred.

The compound of formula (I) will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula (I) may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula (I) may be AJ9677 (rafabegron) (Takeda/Dainippon), L750355 (benzenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of formula (I) may be orlistat or ATL-962 (Alizyme), with orlistat being preferred.

The serotonin (and dopamine) reuptake inhibitor which may be optionally employed in combination with a compound of formula (I) may be sibutramine, topiramate (Johnson & Johnson) or axokine (Regeneron), with sibutramine and topiramate being preferred.

The thyroid receptor agonist which may be optionally employed in combination with a compound of formula (I) may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula (I) may be dexamphetamine, phentermine, phenylpropanolamine or mazindol, with dexamphetamine being preferred.

The various anti-obesity agents described above may be employed in the same dosage form with the compound of formula (I) or in different dosage forms, in dosages and regimens as generally known in the art or in the PDR.

The antihypertensive agents which may be employed in combination with the compound of formula (I) of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in *Clin. Exp. Pharmacol. Physiol.* 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxycarbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechsst) disclosed in Euro. Patent No. 79-022 and *Curr. Ther. Res.* 40:74 (1986); Ru 44570 (Hoechst) disclosed in *Arzneimittelforschung* 34:1254 (1985), cilazapril (Hoffman-LaRoche) disclosed in *J. Cardiovasc. Pharmacol.* 9:39 (1987); R 31-2201 (Hoffman-LaRoche) disclosed in *FEBS Lett.* 165:201 (1984); lisinopril (Merck), indalapril (delapril) disclosed in U.S. Pat. No. 4,385,051; indolapril (Schering) disclosed in *J. Cardiovasc. Pharmacol.* 5:643, 655 (1983), spirapril (Schering) disclosed in *Acta. Pharmacol. Toxicol.* 59 (Supp. 5):173 (1986); perindopril (Servier) disclosed in *Eur. J. Clin. Pharmacol.* 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1, 2,3,4-tetrahydro-6,7-dimethoxy-3-isoquinolinecarboxylic acid HCl) disclosed in *Pharmacologist* 26:243, 266 (1984), WY-44221 (Wyeth) disclosed in *J. Med. Chem.* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366, 973, 5,225,401, 4,722,810, 5,223,516, 4,749,688, U.S. Pat. No. 5,552,397, U.S. Pat. No. 5,504,080, U.S. Pat. No. 5,612, 359,U.S. Pat. No. 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat ([S—(R*,R*)]-hexahydro-6-[(2-mercapto-1-oxo-3-phenylpropyl)amino]-2, 2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula (I) include hydrochlorothiazide, torasemide, furosemide, spironolactono, and indapamide.

Antiplatelet agents which may be employed in combination with compounds of formula (I) of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula (I) of the invention include parathyroid hormone or bisphosphonates, such as MK-217 (alendronate) (Fosamax®).

Dosages employed for the above drugs will be as set out in the Physicians' Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 0.5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of formula (I) of the invention are glucocorticoid receptor modulators as shown either by their ability to bind glucocorticoid receptors in GR binding assays, or by their ability to inhibit AP-1 activity as indicated in cellular transrespressional assays, and cause none to minimal transactivation as indicated in cellular transcriptional assays.

Compounds of the invention, including the compounds described in the examples hereof, have been tested in at least one of the assay(s) described below and have glucocorticoid receptor (GR)/Dexamethasone (Dex) inhibition activity (>25% at 10 µM) and/or AP-1 inhibition activity (EC50 less than 15 µM).

Identical and/or similar assays are described in U.S. application Ser. No. 10/621,807, filed Jul. 17, 2003 which is incorporated in its entirety herein by reference.

Assays

Glucocorticoid Receptor Binding Assay (I)[a]

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e. Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 µM dexamethasone and expressed as % relative binding activity with dexamethasone being 100% and no inhibition is 0%. Test compounds were analyzed in the concentration range from 8.5 E-05 µM to 5 µM.

Glucocorticoid Receptor Binding Assay (II)[b]

In order to measure the binding of compounds on the glucocorticoid receptor a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of test compound. After one hour at room temperature, the fluorescence polarization (FP) of the samples were measured. The FP of a mixture of receptor, fluorescent probe (i.e. Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 2.4 nM to 40 microMolar.

Site I binding assays for any NHR (Nuclear Hormone Receptor) are conducted similarly to the above. An appropriate cell lysate or purified NHR is used as the source of the NHR. The fluorescent probe and unlabeled competitor are appropriate for the specific NHR, i.e. are ligands for the specific NHR.

Cellular Transrepressional Assay

To measure the ability of test molecules to inhibit AP-1 induced transcriptional activity we utilized an A549 cell which was stably transfected with a plasmid containing 7× AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K., et al., *J. Biol. Chem.*, December 29; 270(52):31315-20 (1995) may be used.

The cellular transrepressional assays described above may be used to measure transrepression by any NHR. One of skill in the art will understand that assays may require the addition of components, such as a stimulus (eg. PMA, lipopolysaccharide, TNF-α, etc) which will induce transcription mediated by AP-1 or NF-κB.

Additionally, AR mediated transrepression may be measured by the assay described in Palvimo J J, et al. *J. Biol. Chem.*, September 27; 271(39):24151-6 (1996), and PR mediated transrepression may be measured by the assay described in Kalkhoven E., et al. *J. Biol. Chem.*, March 15; 271(11):6217-24 (1996).

Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diaststereoselectivity of transformations, providing enantio-enriched products upon cleavage of the chiral auxiliary.

Abbreviations

The following abbreviations are employed in the following Preparations and Examples:
BOC=tert-butoxycarbonyl
bp=boiling point
Bu=butyl
DMAP=4-dimethylaminopyridine
DIPEA or DIEA=N,N-diisopropylethylamine
DME=1,2-dimethoxyethane
DMF=dimethyl formamide
EDCI=1-3-dimethylaminopropyl)-3-ethylcarbodiimide
Et=ethyl
$Et_2O$=diethyl ether
HOBT=1-hydroxybenzotriazole
EtOAc=ethyl acetate
EtOH=ethanol
g=gram(s)
l=liter
mCPBA—meta chloro perbenzoic acid
Me=methyl
MeCN=acetonitrile
MeOH=methanol
NMP=1-methyl-2-pyrrolidinone
Pr=propyl
PS=polystyrene
TEA=triethylamine
TFA=trifluoroacetic acid
mg=milligram(s)
ml or mL=milliliter
μl=microliter
mmol=millimole
μmol=micromole
mol=mole
mp=melting point
RT=room temperature
HPLC=high pressure liquid chromatography
LC/MS=liquid chromatography/mass spectrometry Preparations The preparations described below were used for the synthesis of reagents that were not obtained from commercial sources.

Analytical HPLC Method Employed in Characterization of Examples

Analytical HPLC was performed on Shimadzu SCL10A liquid chromatographs using the following methods:

Method A: Column: YMC Combiscreen ODS-A, 4.6×50 mm, Mobile phase: 10-90% aq $CH_3OH/0.2\%$ $H_3PO_4$, 4.0 min. gradient with 1.0 min. hold, Flow rate: 4 ml/min, 220 nm detection wavelength.

Method B: Column: XETRRA C-18 4.6×50 mm., Mobile Phase: 10-90% aq $CH_3OH/0.2\%$ $H_3PO_4$, 4.0 min. gradient with 1 min. hold, Flow rate: 4.0 mL/min. 220 nm detection wavelength.

Method C: Column: Phenomenex Synergi C-18 4.6×50 mm, Mobile phase: 10-90% aq $CH_3OH/0.2\%$ $H_3PO_4$, 4.0 min. gradient with 1 min. hold, Flow rate: 4.0 mL/min, 220 nm detection wavelength.

Method D: Column: Shimadzu VP-0DS; C-18 Ballistic 4.6×50 mm., Mobile phase: 10-90% aq $CH_3OH/0.2\%$ $H_3PO_4$, 4.0 min. gradient with 1 min. hold, Flow rate: 4.0 mL/min, 220 nm detection wavelength.

Preparation 1

1-Methyl-2,2-diphenyl-cyclopropanecarboxylic acid

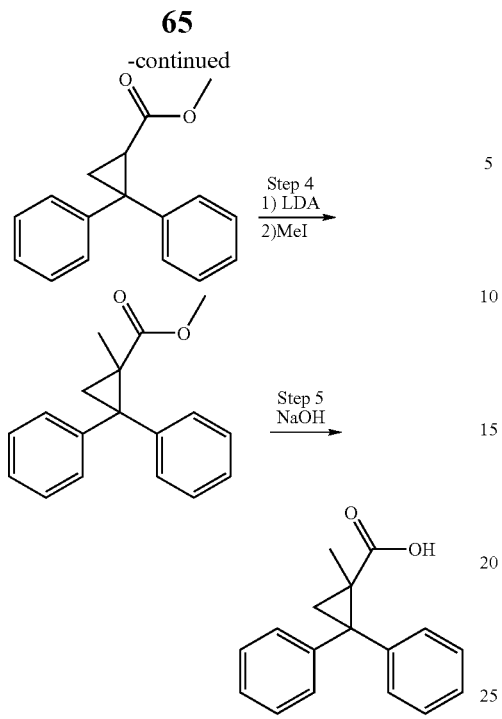

Step 1

To a solution of 1,1-diphenylethylene (27.91 mmol, 5.03 g) in dichloromethane (3.5 mL) was added rhodium (II) acetate dimer (0.13 mmol, 57 mg). Ethyl diazoacetate (5.58 mmol, 0.64 mL) in dichloromethane (3.5 mL) was then added over 8 hours by syringe pump. After 16 hours the reaction mixture was concentrated in vacuo and the residue chromatographed on silica gel (eluted with 5% ethyl acetate in hexane) to give 1.50 g (Y: 100%) of the product of step 1. MS (E+) m/z: 376 (MH+). Product is contaminated with diethyl fumarate and diethyl maleate. Impurities will be removed in the next step.

Step 2

To a solution of the product of step 1 (5.58 mmol, 1.48 g) in EtOH (10 mL) was added sodium hydroxide (3.0 mL of 19N NaOH). After 2 hours at RT the reaction mixture was quenched with 1N HCl (30 mL) and extracted with dichloromethane (3×30 mL). The organic phases were dried over $Na_2SO_4$ and concentrated in vacuo to give 1.13 g (Y: 85%) of the product of step 2.

Step 3

To a solution the product of step 2 (4.83 mmol, 1.15 g) in THF (8.0 mL) and methanol (4.0 mL) is added (trimethylsilyl)diazomethane (19.42 mmol, 9.71 mL of a 2 M solution in hexanes). After 0.5 h at RT the reaction mixture was concentrated in vacuo to give 1.17 g (Y: 96%) of the product of step 3.

Step 4

To a solution of the product of step 3 (2.20 mmol, 555 mg) in THF (7.0 mL) at −78° C. was added lithium diisopropylamide (2.75 mmol, 1.38 ml of a 2 M solution in heptane/THF/ethyl benzene) dropwise. After 1 hour, iodomethane (6.60 mmol, 1.0 g) was added. The mixture was allowed to warm to RT, quenched with 1N HCl (30 mL) and extracted with dichloromethane (3×30 mL). The organic phases were dried over $Na_2SO_4$ and concentrated in vacuo to give 470 mg (Y: 80%) of the product of step 4.

Step 5

To a solution of the product of step 4 (1.77 mmol, 470 mg) in MeOH (10 mL) was added sodium hydroxide (2.0 mL of 10N NaOH). After 16 hours at 70° C. the reaction mixture was quenched with 1N HCl (30 mL) and extracted with dichloromethane (3×30 mL). The organic phases were dried over $Na_2SO_4$ and concentrated in vacuo to give 400 mg (Y: 90%) of the title compound of 1.

Preparation 2

2,2-Dimethyl-3,3-diphenyl-propionic acid 2a

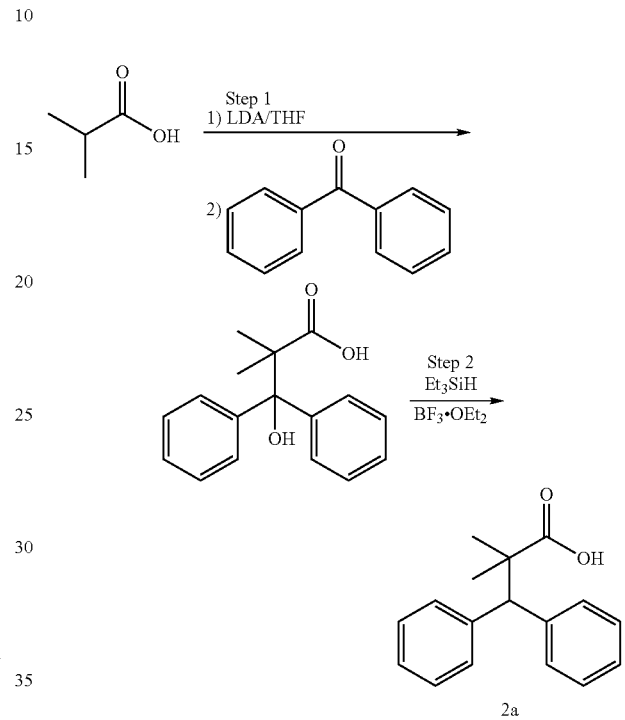

Reference: R. Burkett, G. W. Moersch, *J. Org. Chem.*, 36, 1149 (1971); M. Orfanopoulos, I. Smounou, *Synthetic Commun.*, 18, 833 (1988).

Step 1

To a solution of lithium dipropylamide (LDA, 22.6 mL, 45.2 mmol, 2.0 equi.) in THF (10 mL) at 0° C. was added dropwise a solution of isobutyric acid (2.10 mL, 22.6 mmol, 1.0 equi.) in THF (10 mL) in 15 minutes. The reaction solution was stirred at 0° C. for 30 minutes, then heated to 60° C. for 2 hours. The reaction solution was recooled to 0° C. and a solution of benzophenone (4.12 g, 22.6 mmol, 1.0 equi.) in THF (10 mL) was added in dropwise in 30 minutes. The reaction solution was then allowed to warm to room temperature and stirred at room temperature for 18 hours. The reaction was quenched with hydrochloric acid (1N). The aqueous phase was extracted with ethyl acetate (3×). The combined organic phases were then extracted with sodium hydroxide (1N, 3×). The basic phases were acidified with hydrochloric acid (1N), and the product extracted with ethyl acetate (3×). The crude product mixture was purified by flash chromatography (10% ethyl acetate in hexane) to yield 2.3 g (56%) of the product of step 1: MS (m/z 268, (M−H)+); $^1$H NMR ($CDCl_3$) δ 7.22-7.32 (m, 10H), 1.30 (s, 6H).

Step 2

To a solution of the product of step 1 (2.3 g, 8.5 mmol, 1.0 equi.) in dichloromethane (10 mL) at 0° C., was added triethylsilane (2.7 mL, 17.0 mmol, 2 equi.), followed by boron trifluoride diethyl etherate (2.15 mL, 17 mmol, 2.0 equi.). The solution was stirred at 0° C. for 2 hours and then quenched with saturated sodium carbonate solution. The aqueous phase was acidified with hydrochloric acid (1N), and the product acid extracted with ethyl acetate (3×). Re-crystallization of the crude product mixture with ethyl acetate and hexane, yielded 1.95 g (90%) of the title compound of 2: MS (m/z 253, (M−H)+); 1H NMR (CDCl3) δ 7.22-7.32 (m, 10H), 4.44 (s, 1H), 1.30 (s, 6H).

According to the procedure described above, the acids of formula (2b)-(2e) were prepared from the corresponding 3 to 6-membered cycloalkane-carboxylic acids.

| Preparation | Structure |
|---|---|
| 2b | (cyclopropane-1,1-diyl with CO2H and CH(Ph)2) |
| 2c | (cyclobutane-1,1-diyl with CO2H and CH(Ph)2) |
| 2d | (cyclopentane-1,1-diyl with CO2H and CH(Ph)2) |
| 2e | (cyclohexane-1,1-diyl with CO2H and CH(Ph)2) |

Preparation 3

4-[1-(4-Fluoro)napthyl]aminothiazole 3a

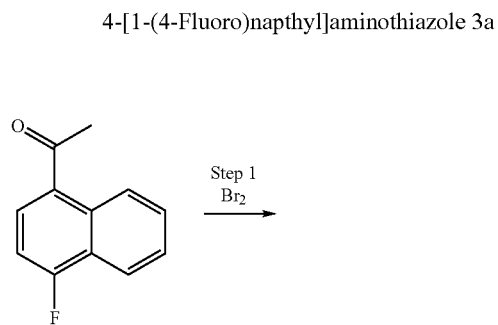

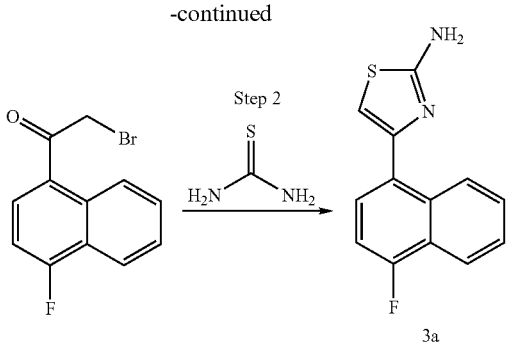

Step 1

To a solution of 4'-fluoro-1'-acetonaphthone (28.69 mmol, 5.4 g) in 1,4-dioxane (18.0 mL) at 0° C. was added bromine (35.13 mmol, 5.61 g). After 3 hours at room temperature the reaction mixture was concentrated in vacuo to give 7.66 g (Y: 100%) of the product of step 1.

Step 2

To a solution of the product of step 1 (28.69 mmol, 7.66 g) in ethyl alcohol (20 mL) at room temperature was added thiourea (36.13 mmol, 2.75 g). After 1 hour at room temperature a precipitate formed. To the reaction mixture was added water (100 mL) and the solid was collected by vacuum filtration. The solid was then washed with water (3×100 mL) and dichloromethane (3×100 mL). The solid was then dried in vacuo to give 5.5 g (Y: 75%) of the title compound of 3a. MS (E+) m/z: 245 (MH+).

In a similar manner the following compounds were prepared from the corresponding ketone.

| Preparation | Structure |
|---|---|
| 3b | 2-amino-4-(3-methoxyphenyl)thiazole |
| 3c | 2-amino-4-(3-fluorophenyl)thiazole |
| 3d | 2-amino-4-(4-fluorophenyl)thiazole |
| 3e | 2-amino-4-(2-fluorophenyl)thiazole |
| 3f | 2-amino-4-(2-nitrophenyl)thiazole |

| Preparation | Structure |
|---|---|
| 3g | 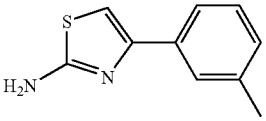 |
| 3h | 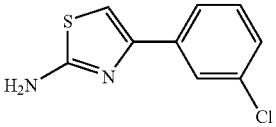 |
| 3i | 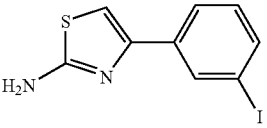 |
| 3j | 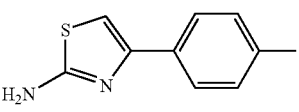 |
| 3k | 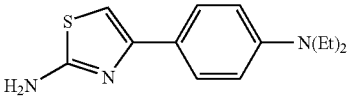 |
| 3l | 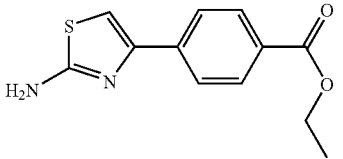 |
| 3m | 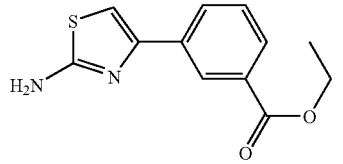 |
| 3n | 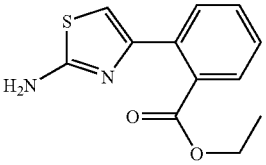 |
| 3o | 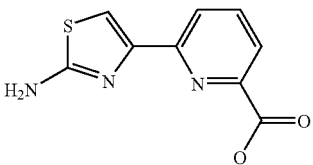 |
| 3o | 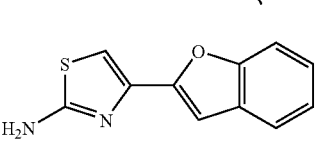 |
| Preparation | Structure |
|---|---|
| 3p | 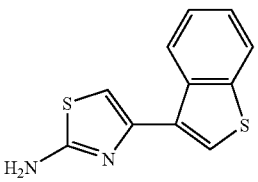 |
| 3q | 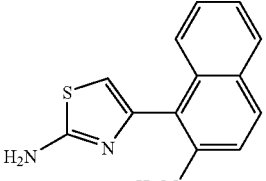 |
| 3r |  |
| 3s | 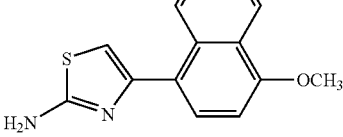 |
| 3t | 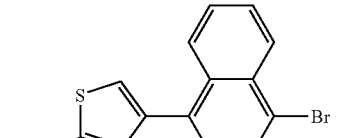 |
| 3v | 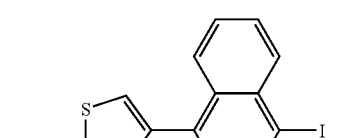 |
Preparation 4
4-[1-(6-Methoxy)napthyl]-3-aminothiazole 4a
Step 1
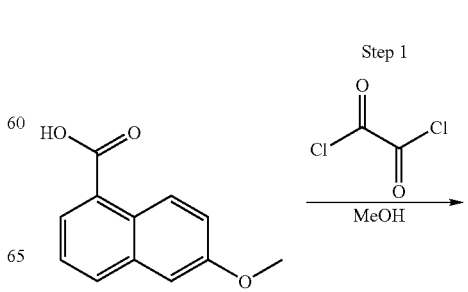

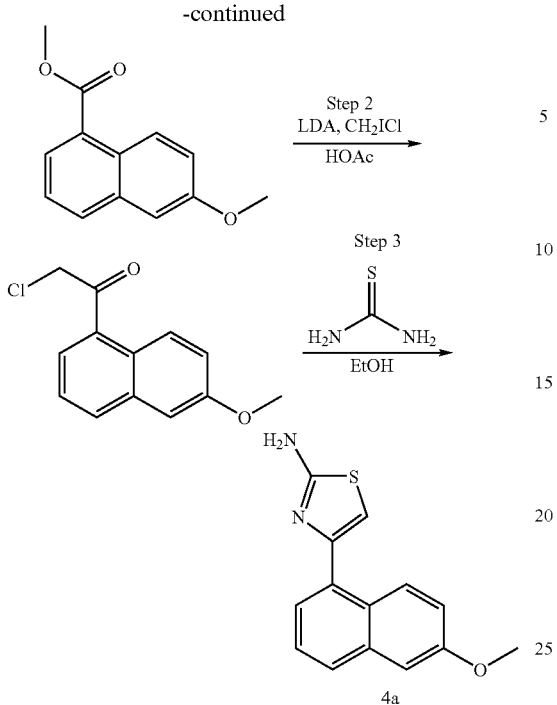

Reference
Step 2: P. Chen, P. T. Cheng, S. H. Spergel, R. Zahler, X. Wang, J. Thottathi, J. C. Barrish, R. P. Polniaszek, *Tetrahedron Letters*, 38, 3175 (1997).

Step 1

To a solution of 6-methoxy-1-naphthoic acid (0.5 g, 2.47 mmol, 1.0 equi.) in dichloromethane (10 mL) at room temperature was added a solution of oxalyl chloride (2M in dichloromethane, 2.5 mL, 5.0 mmol, 2 equi.). The solution was stirred at room temperature for 2 hours, and the excess oxalyl chloride removed in vacuo. The residue was dissolved in methanol and stirred at room temperature for 18 hours. The solvent was removed in vacuo, yielding 0.45 g (84%) of the product of step 1: LC/MS (m/z 217, (M–H)$^+$); $^1$H NMR (CDCl$_3$) δ 8.82 (d, 1H), 8.03 (dd, 1H), 7.90 (d, 1H), 7.44 (t, 1H), 7.26 (dd, 1H), 7.16 (s, 1H), 4.02 (s, 3H), 3.95 (s, 3H).

Step 2

To a solution of the product of step 1 (0.238 g, 1.1 mmol, 1.0 equi.) and chloroiodomethane (0.32 mL, 4.4 mmol, 4 equi.) in THF (5 mL) was added a solution of LDA (2M, 2.2 mL, 4.0 equi.) in THF (10 mL) dropwise in 30 minutes, while keeping the solution temperature at –78° C. The reaction solution was stirred at –78° C. for 10 minutes. A solution of acetic acid (1.5 mL) in THF (10 mL) was added in dropwise in 10 minutes. After stirring for an additional 10 minutes at –78° C., the solution was quenched with ethyl acetate and saturated sodium chloride solution. The organic phase was washed with saturated sodium bisulfate, saturated sodium chloride, dried with sodium sulfate and concentrated in vacuo. The residue was purified by flash chromatography (10% ethyl acetate in hexane) to yield the 0.23 g (90%) of the product of step 2: LC/MS (m/z 235, (M+H)$^+$); $^1$H NMR (CDCl$_3$) δ 8.82 (d, 1H), 8.03 (dd, 1H), 7.90 (d, 1H), 7.44 (t, 1H), 7.26 (dd, 1H), 7.16 (s, 1H), 4.80 (s, 2H), 3.95 (s, 3H).

Step 3

To a solution of the product of step 2 (0.23 g, 1.0 mmol, 1.0 equi.) in ethanol (5 mL) at room temperature was added thiourea (90 mg, 1.2 mmol, 1.2 equi.). The reaction solution was stirred at room temperature for 2 hours, after which a yellow precipitate was formed. The reaction was quenched by addition of water and ethyl acetate. The aqueous phase was extracted with ethyl acetate (3×). The combined organic phases were dried with sodium sulfate and concentrated in vacuo to yield 200 mg (78%) of the title compound 6a: LC/MS (m/z 235, (M+H)$^+$); $^1$H NMR (CDCl$_3$) δ 8.1 (d, 1H), 7.9 (m, 1H), 7.43 (m, 2H), 7.25 (m, 1H), 7.10 (dd, 1H), 6.65 (s, 1H), 3.95 (s, 3H).

In a similar manner the following compounds were prepared.

| Preparation | Structure |
|---|---|
| 4b | 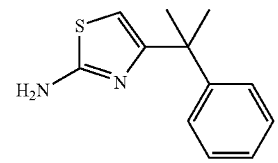 |
| 4c | 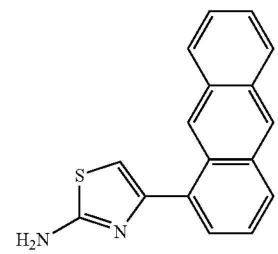 |

Preparation 5

4-(3-Pyridyl)-2-aminothiazole 5a

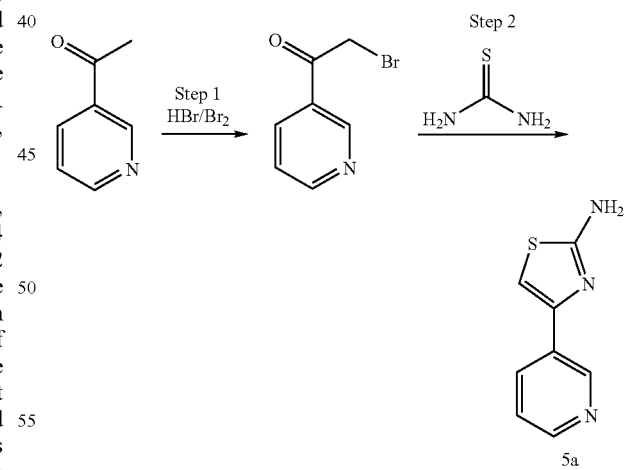

Step 1

To a solution of 3-acetylpyridine (20.0 mmol, 2.42 g) in 48% HBr (10.0 mL) was added bromine (20.0 mmol, 3.2 g) in 48% HBr (4.0 mL). The reaction mixture was heated to 65° C. for one hour and then stirred at RT for an additional hour. The reaction mixture was then quenched with ice and filtered. The solid was then washed with acetone (2×10 mL) and diethyl ether (2×10 mL). The solid was then dried in vacuo to give 3.70 g (Y: 83%) of the product of step 1.

Step 2

To a solution of the product of step 1 (6.10 mmol, 1.22 g) in ethyl alcohol (10 mL) at room temperature was added thiourea (7.32 mmol, 560 mg). After 1 hour at room temperature the reaction mixture was quenched with water (30 mL) and washed with dichloromethane (3×100 mL). The aqueous layer was then purified by cation exchange chromatography to give 600 mg (Y: 56%) of the title compound 5a. MS (E+) m/z: 178 (MH$^+$).

In a similar manner the following compounds were prepared.

| Preparation | Structure |
|---|---|
| 5b | (2-amino-4-(pyridin-4-yl)thiazole) |
| 5c | (2-amino-4-(pyridin-2-yl)thiazole) |
| 5d | (2-amino-4-(quinolin-4-yl)thiazole) |

Preparation 6

4-(1-Isoquinolinyl)-2-aminothiazole 6

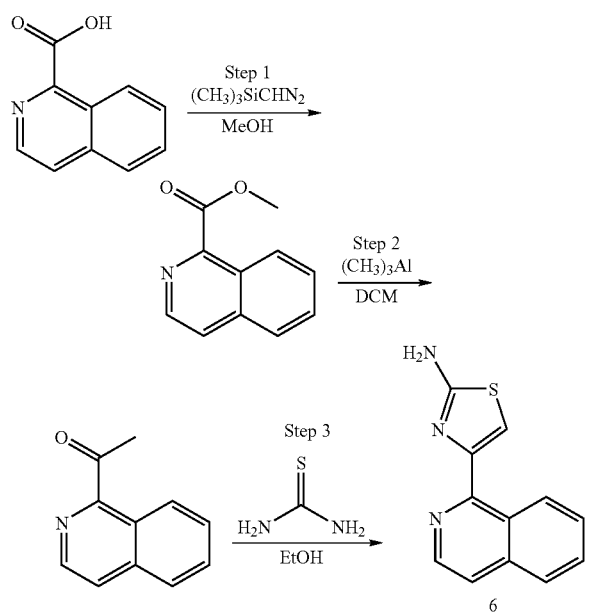

Step 1

To a solution of 1-isoquinolinecarboxylic acid (11.55 mmol, 2.0 g) in THF (20.0 mL) and methanol (10.0 mL) is added trimethylsilyldiazomethane (69.3 mmol, 32.0 mL of a 2 M solution in hexanes). After 2 h at RT the reaction mixture was concentrated in vacuo to give 1.17 g (Y: 99%) of the product of step 1. MS (E+) m/z: 188 (MH$^+$).

Step 2

To a solution of the product of step 1 (10.69 mmol, 2.0 g) in dichloromethane (100.0 mL) was added trimethylaluminum (32.88 mmol, 16.44 mL of a 2.0 M solution in toluene) at −78° C. After the addition was complete the reaction was allowed to warm to 0° C. The reaction mixture was then quenched with water (30 mL) and extracted with dichloromethane (3×30 mL). The organic phases were concentrated in vacuo and the residue chromatographed on silica gel (eluted with 10% ethyl acetate in hexanes) to give 930 mg (Y: 51%) of the product of step 2. MS (E+) m/z: 172 (MH$^+$).

Step 3

The product of step 2 was converted to the title compound 6 as described in preparation 8. MS (E+) m/z: 228 (MH$^+$).

Preparation 7

4-[1-(4-Fluoro)napthyl]aminoimidazole 7a

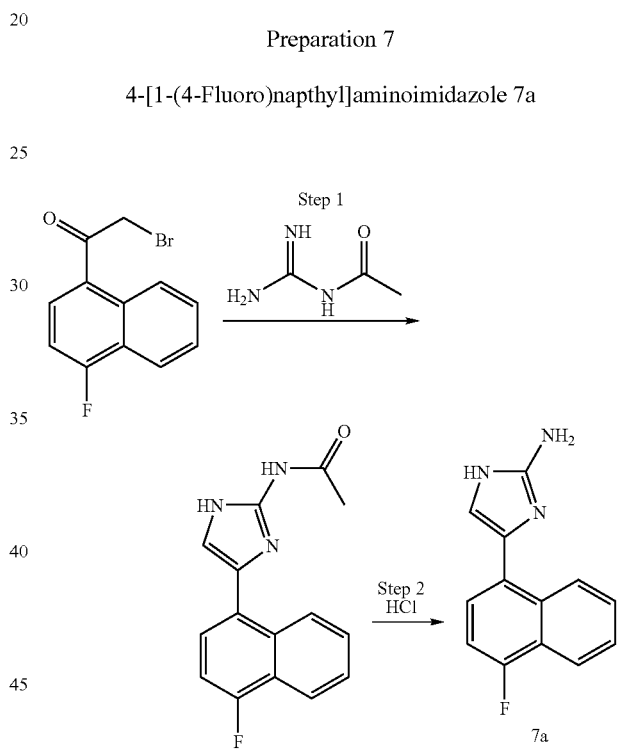

Step 1

To a solution of the product of preparation 1, step 1 (18.73 mmol, 5.0 g) in DMF (15 mL) at room temperature was added 1-acetylguanidine (57.43 mmol, 5.80 g). After 5 hours at room temperature, the reaction mixture was diluted with water (100 mL) and extracted with ethyl acetate (3×100 mL). The organic phases were concentrated in vacuo and the residue chromatographed on silica gel (eluted with 5% methanol in dichloromethane) to give 2.0 g (Y: 39%) of the product of step 1. MS (E+) m/z: 270 (MH$^+$).

Step 2

To a solution of the product of step 1 (7.43 mmol, 2.0 g) in methanol (17 mL) was added water (8.5 mL) and 12 N HCl (12.0 mL). After 1 hour at reflux the reaction mixture was concentrated in vacuo to approximately 15 mL. The resulting solution was then purified and neutralized by cation exchange SPE to give 1.66 g (Y: 99%) of the title compound 7a. MS (E+) m/z: 228 (MH$^+$).

In a similar manner the following compounds were prepared from the corresponding ketones.

| Preparation | Structure |
|---|---|
| 7b | 4-methylnaphthyl-2-aminoimidazole |
| 7c | 4-phenyl-2-aminoimidazole |
| 7d | 4-tert-butyl-2-aminoimidazole |
| 7e | 4-(1-naphthyl)-2-aminoimidazole |
| 7f | 4-(4-fluoronaphthyl)-2-aminoimidazole |
| 7e | 4-(6-methoxynaphthyl)-2-aminoimidazole |

Preparation 8

4-(1-Napthyl)aminooxazole 8

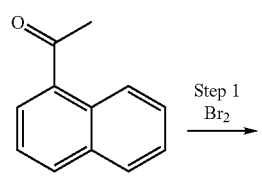

Step 1

To a solution of 1-acetonaphthone (29.38 mmol, 5.0 g) in glacial acetic acid (10.0 mL) at RT was added bromine (30.06 mmol, 4.80 g) in glacial acetic acid (5.0 mL). After 5 minutes the reaction mixture was poured onto crushed ice and extracted with dichloromethane to give 7.31 g (Y: 100%) of the product of step 1. MS (E+) m/z: 250 (MH$^+$).

Step 2

To a solution of the product of step 1 (5.50 mmol, 1.37 g) in ethyl alcohol (10 mL) was added urea (27.50 mmol, 1.65 g). After 2 hours at reflux the reaction mixture was concentrated in vacuo and the residue chromatographed on silica gel (eluted with 30% ethyl acetate in hexane) to give 100 mg (Y: 9%) of the title compound 8. MS (E+) m/z: 211 (MH$^+$).

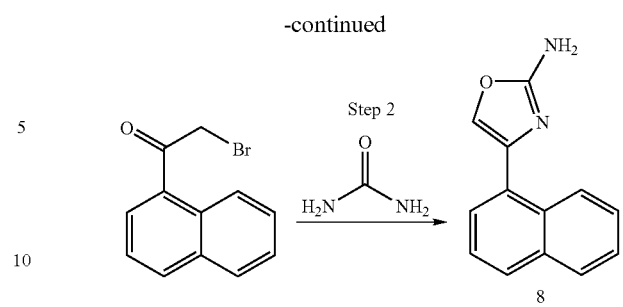

Preparation 9

5-(1-Napthyl)-3-aminoisoxazole 9

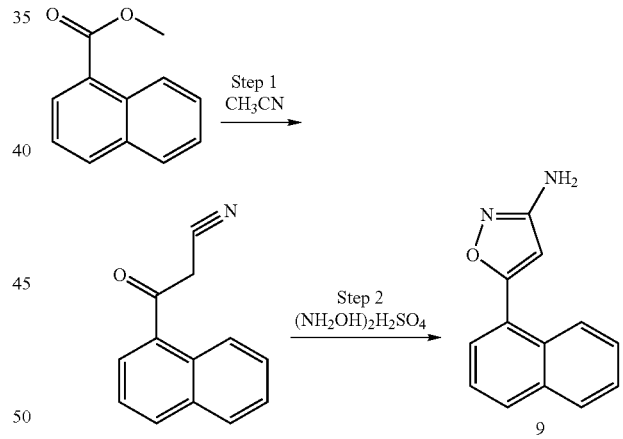

Step 1

To a solution of acetonitrile (12.18 mmol, 0.50 g) in THF (10.0 mL) was added 60% sodium hydride (24.36 mmol, 0.975 g), followed by 1-naphthoic acid methyl ester (12.18 mmol, 2.27 g). After 2 hours at 70° C. the reaction mixture was quenched with an excess of 1N HCl and extracted with dichloromethane (3×30 mL). The organic phases were concentrated in vacuo and the residue was chromatographed on silica gel (eluted with 33% ethyl acetate in hexane) to give 1.80 g (Y: 76%) of the product of step 1. MS (E+) m/z: 196 (MH$^+$).

Step 2

Hydroxylamine sulfate (1.61 mmol, 264 mg) was added to a stirred solution of the product of step 1 (2.94 mmol, 573 mg) and NaOH (3.53 mmol, 141 mg) in 50% aq. EtOH (6.0 mL).

The mixture was heated at 80° C. for 5 hours and then stirred at RT for 14 hours. The reaction mixture was quenched with an excess of 1N HCl, washed with dichloromethane (3×50 mL), neutralized with saturated sodium bicarbonate solution and extracted with dichloromethane (3×50 mL). The organic extracts were combined, dried over $Na_2SO_4$ and concentrated under vacuo to give 237 mg (Y: 38%) of the title compound 9. MS (E+) m/z: 211 (MH$^+$).

Preparation 10

5-(1-Napthyl)-3-aminopyrazole 10

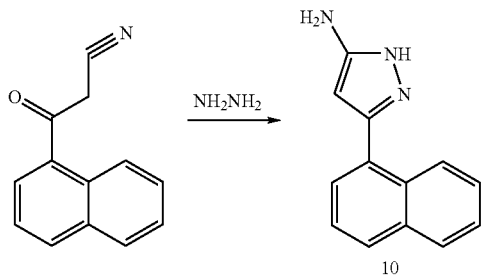

To a solution of the product of preparation 4, step 1 (2.70 mmol, 527 mg) in EtOH (5.0 mL) was added hydrazine (2.70 mmol, 85 mg). The resulting mixture was refluxed for 2 h, cooled, diluted with 1N HCl, washed with dichloromethane (3×50 mL), neutralized with saturated sodium bicarbonate solution and extracted with dichloromethane (3×50 mL). The organic extracts were combined, dried over $Na_2SO_4$ and concentrated under vacuum to give 280 mg (Y: 51%) of the title compound 10. MS (E+) m/z: 210 (MH$^+$).

Preparation 11

5-(1-Napthyl)-2-aminopyridine 11a

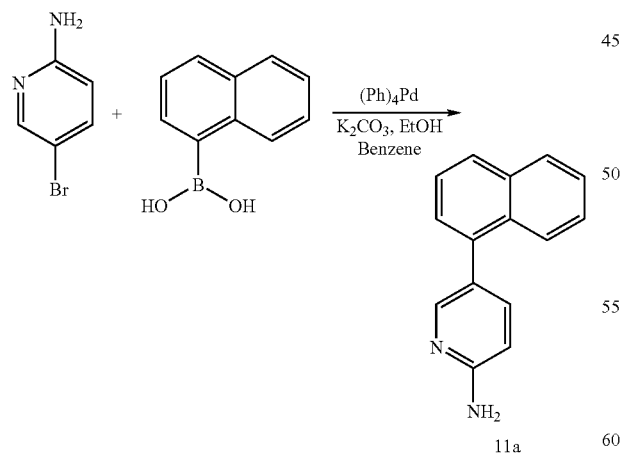

Potassium carbonate (5.19 mmol, 717 mg) in water (2.5 mL) and tetrakis(triphenylphosphine)palladium(0) (0.04 mol %, 80 mg) in ethyl alcohol (2.5 mL) were added to 2-amino-5-bromopyridine (1.73 mmol, 299 mg) and 1-naphthaleneboronic acid (2.60 mmol, 446 mg) in benzene (10.0 mL). After 2 hours at 90° C. the reaction mixture was quenched with water (30 mL) and extracted with dichloromethane (3×30 mL). The organic phases were concentrated in vacuo and the residue chromatographed on silica gel (eluted with 50% ethyl acetate in hexanes) to give 260 mg (Y: 68%) of the title compound 11a. MS (E+) m/z: 381 (MH$^+$).

In a similar manner the following compounds were prepared.

| Preparation | Structure |
|---|---|
| 11b | 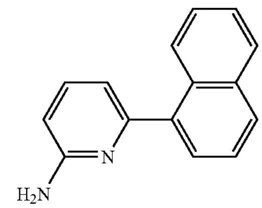 |
| 11c | 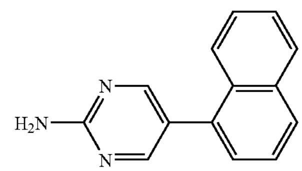 |

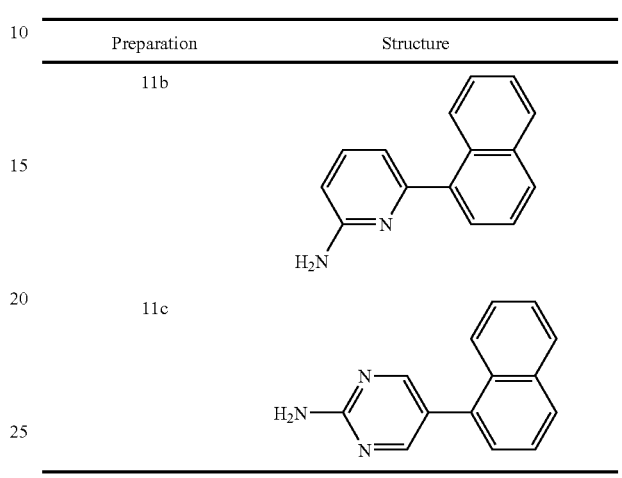

Preparation 12

4-(2,3-Dihydro-benzo[1,4]dioxin-5-yl)-thiazol-2-ylamine

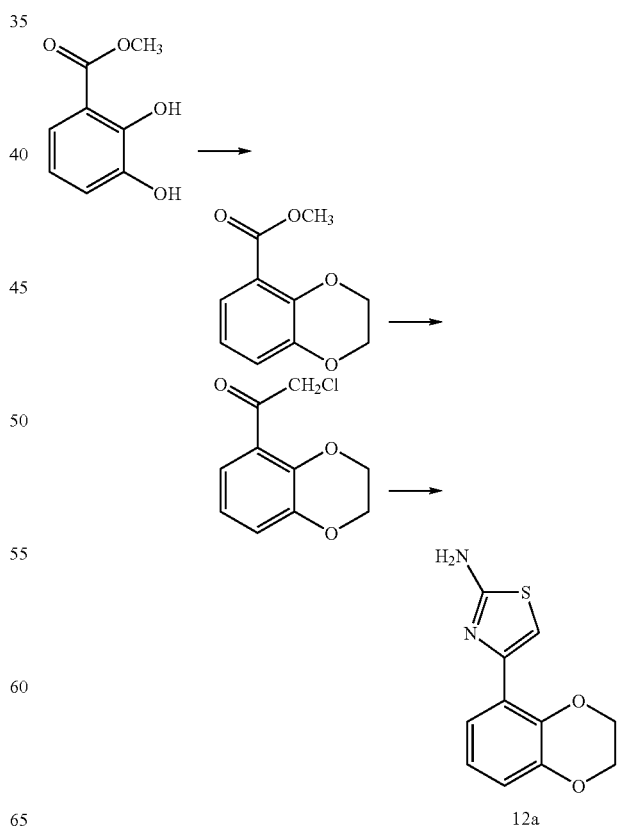

Step 1: 2,3-Dihydro-benzo[1,4]dioxine-5-carboxylic acid methyl ester

A suspension of 2,3-Dihydroxy-benzoic acid methyl ester (336 mg, 2 mmol) and cesium carbonate (1.56 g, 4.8 mmol) in DMF was stirred at room temperature for 0.5 h. 1,2-Dibromoethane (0.224 ml, 2.6 mmol) was added to the DMF solution. The mixture was stirred at 80 C for 4 h, and then diluted with ethyl acetate. The organic layer was washed with water and brine, dried over anhydrous MgSO4, filtered and concentrated in vacuo to give the crude product. It was chromatographed on silica gel with EtOAc/hexane (20%-40%) as eluent to afford 2,3-dihydro-benzo[1,4]dioxine-5-carboxylic acid methyl ester as a white solid. (223 mg, 1.14 mmol, 57.4% yield).

Step 2: 4-(2,3-Dihydro-benzo[1,4]dioxin-5-yl)-thiazol-2-ylamine (Ref. *Tetrahedron Lett,* 1997, 3173-78)

To a mixture of 2,3-dihydro-benzo[1,4]dioxine-5-carboxylic acid methyl ester (100 mg, 0.515 mmol) and chloroiodomethane (0.075 ml, 1.03 mmol) in 1 ml of THF was added a solution of LDA in THF (2M, 0.57 ml, 1.13 mmol) dropwise at −78 C over 15 min. The reaction mixture was stirred at −78 C for 10 min. A solution of acetic acid (0.75 ml) in THF (5 ml) was added dropwise over 5 min at −78 C. The resulting solution was stirred at the same temperature for additional 10 min. and was then partitioned between ethyl acetate and water. The organic layer was washed with aqueous sodium bicarbonate, brine, dried over MgSO4 and concentrated in vacuo to give the crude 2-chloro-1-(2,3-dihydro-benzo[1,4]dioxin-5-yl)-ethanone as a light brown liquid. The crude product was dissolved in EtOH (1.5 ml). Thiourea (76 mg, 1 mmol) was added followed by addition of TEA (0.14 ml, 1 mmol). The solution was heated at 80 C for 6 h. After removal of ethanol, the reaction mixture was taken into ethyl acetate and aqueous sodium bicarbonate. The organic layer was washed with 0.5 N HCl. After separation, the aqueous layer was adjusted to pH 9 with sodium carbonate, and extracted with ethyl acetate. The ethyl acetate solution was washed with brine, dried over MgSO4 and concentrated to give 4-(2,3-dihydro-benzo[1,4]dioxin-5-yl)-thiazol-2-ylamine as a brown solid, 37 mg (0.16 mmol, 31% yield). $^1$H NMR (CDCl$_3$) δ 7.46 (dd, 1H), 7.04 (s, 1H), 6.75-6.83 (m, 2H), 5.33 (br s, 2H), 4.23-4.34 (m, 4H); LC/MS m/z 235 (M+H)$^+$.

4-Benzo[1,3]dioxol-4-yl-thiazol-2-ylamine 12b, was prepared in a similar manner.

| Compound | Structure |
|---|---|
| 12b | 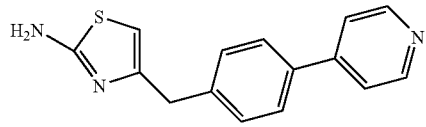 | mL of 48% HBr was added a solution of bromine (40 g, 217 mmol) in 50 mL of acetic acid. After 4 hr, acetone (150 mL) was added and the reaction mixture was stirred for 3 d. The reaction was concentrated by rotary evaporator, diluted with brine, and extracted 2×DCM. The DCM extracts were dried over MgSO$_4$. The solution was filtered, concentrated by rotary evaporator, and chromatographed on SiO$_2$ using DCM to give 20.8 g (98%) of a dark oil 4a. $^1$H-NMR (400 MHz, CDCl$_3$): δ 7.49 (d, 2H), 7.12 (d, 2H), 3.94 (s, 2H), 3.92 (s, 2H).

(b) To a solution of 4a (116 mmol) in 200 mL of EtOH was added thiourea (9.0 g, 118 mmol) all at once. The reaction was heated at reflux for 4 hr. The reaction was concentrated by rotary evaporator and the crude residue was dissolved in EtOAc and extracted 3×1N HCl. The aqueous extracts were basified with 1N NaOH and then extracted 2× EtOAC. EtOAc extracts were dried over MgSO$_4$, and solid was triturated in 10% hexanes in EtOAc. Solid was collected and dried in vacuo to give 18 g (57%) of pure 6b. MS found: (M+H)+= 270.

(c) Charged a flask with 4b (8.07 g, 30 mmol), 4-pyridineboronic acid (6.1 g, 50 mmol), tetrakis(triphenylphosphine)palladium(0) (3.5 g, 3.0 mmol), 30 mL of 2M K$_2$CO$_3$, and 200 mL of DMF. The reaction mixture was degassed by bubbling nitrogen through for 15 min then heated at 100° C. overnight. The reaction mixture was diluted in EtOAc and extracted 3×1N HCl. The aqueous extracts were basified with 1N NaOH and then allowed to stand in refrigerator for 2 hr. Solid was collected and dried in vacuo to give 5.4 g (68%) of pure 4c. MS found: (M+H)+=268.

Preparation 14

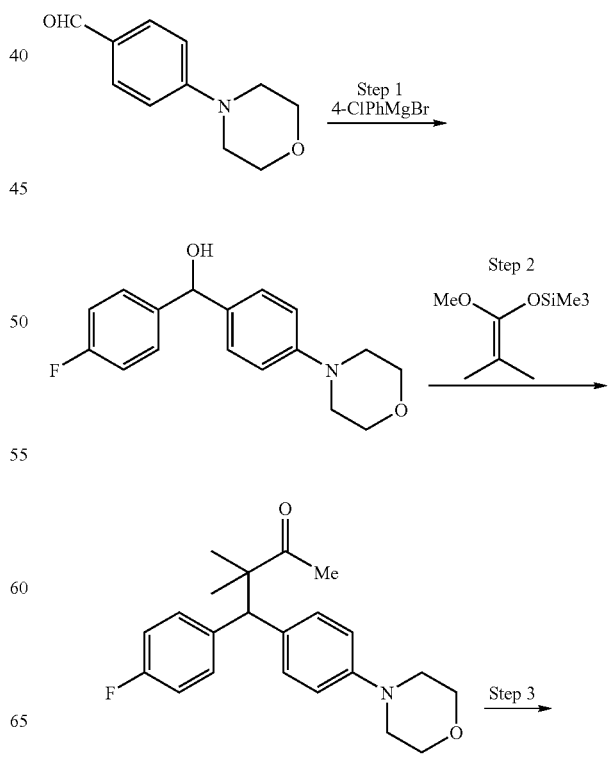

Preparation 13

(a) To a solution of commercially available 4-bromophenylacetone (25 g, 117 mmol) in 30 mL of acetic acid and 15

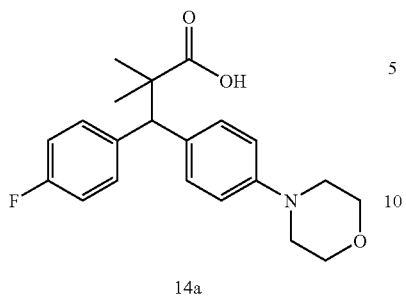

14a

Step 1

To a solution of 4-fluorophenyl)magnesium bromide (1M in THF, 10.6 ml. 10.6 mmol) at 0° C. was added a solution of 4-morpholinobenzaldehyde (1 g, 5.233 mmol) in THF (10 ml) dropwise. After being stirred at 0° C. for 10 minutes and room temperature for 4 hours, the reaction mixture was poured onto an iced aqueous NH$_4$Cl. The solution was extracted with ethyl acetate. The organic layer was washed with brine, dried over MgSO$_4$ and concentrated to give (4-chlorophenyl)(4-morpholinophenyl)methanol as a pinkish white solid (1.49 g, 99 yield). HPLC (Column: Shimadzu VP-ODS, C-18 Ballistic; 10-90% aq CH$_3$OH/0.1% H$_3$PO$_4$, same for compounds hereafter unless noted) Rt: 2.117 min.

Step 2

To a solution of (5-bromo-thiophen-2-yl)-(4-fluoro-phenyl)-methanol (2.23 mmol) and (1-methoxy-2-methyl-propenyloxy)-trimethyl-silane (2.26 ml, 11.5 mmol) in dichloromethane (6 ml) at 0° C. was added a solution of titanium tetrachloride in dichloromethane (1M solution, 4.9 ml, 4.9 mmol) slowly. After being stirred at 0° C. for 10 minutes and room temperature for 5 hours, to the reaction mixture was added water. After stirring for 10 min., the solution was adjust to pH 6 with sodium carbonate power, and was extracted with ethyl acetate. The organic layer was washed, dried (MgSO$_4$) and concentrated to give methyl 3-(4-fluorophenyl)-2,2-dimethyl-3-(4-morpholinophenyl) propanoate as pinkish white solid (607 mg, 71% yield). LC/MS (m/z) 372.4 [(M+23)$^+$]; HPLC Rt: 3.35 min.

Step 3

To a solution of methyl 3-(4-fluorophenyl)-2,2-dimethyl-3-(4-morpholinophenyl) propanoate (480 mg, 1.29 mmol) in MeOH (6 ml) and DMSO (6 ml) was added a 40% aqueous solution of potassium hydroxide (5 ml). The reaction mixture was heated at 79° C. for 20 hours. After removal of methanol and THF, the solution was adjusted to pH 2 and was extracted with ethyl ether. The ether layer was washed, dried and evaporated to give 3-(4-fluorophenyl)-2,2-dimethyl-3-(4-morpholinophenyl)propanoic acid (14a) as a viscous oil (470 mg, 100% yield). HPLC Rt: 3.035 min. LC/MS (m/z) 358.37 [(M+1)$^+$].

In a similar manner, the acids of formula (14b-14f) were prepared from 4-morpholinobenzaldehyde and phenylmagnesium bromide or the corresponding substituted phenylmagnesium bromide via a 3-step procedure as described above.

| Preparation | Structure |
|---|---|
| 14b | 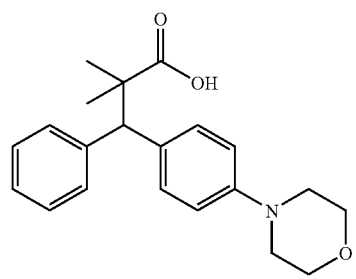 |
| 14c | 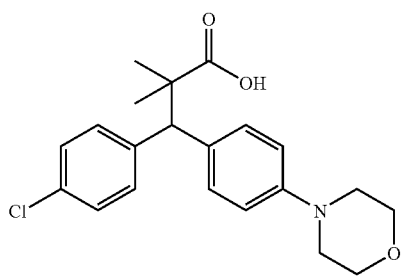 |
| 14d | 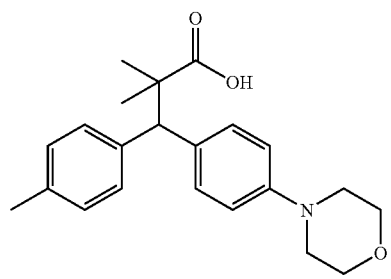 |
| 14e | 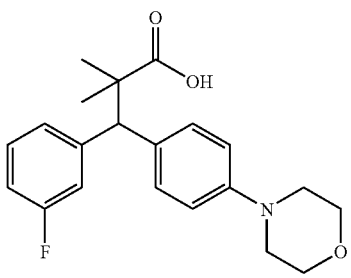 |
| 14f | 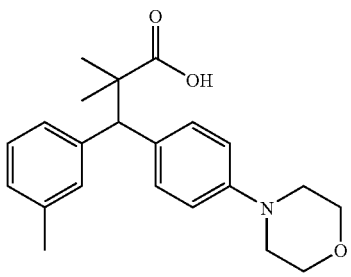 |

Preparation 15

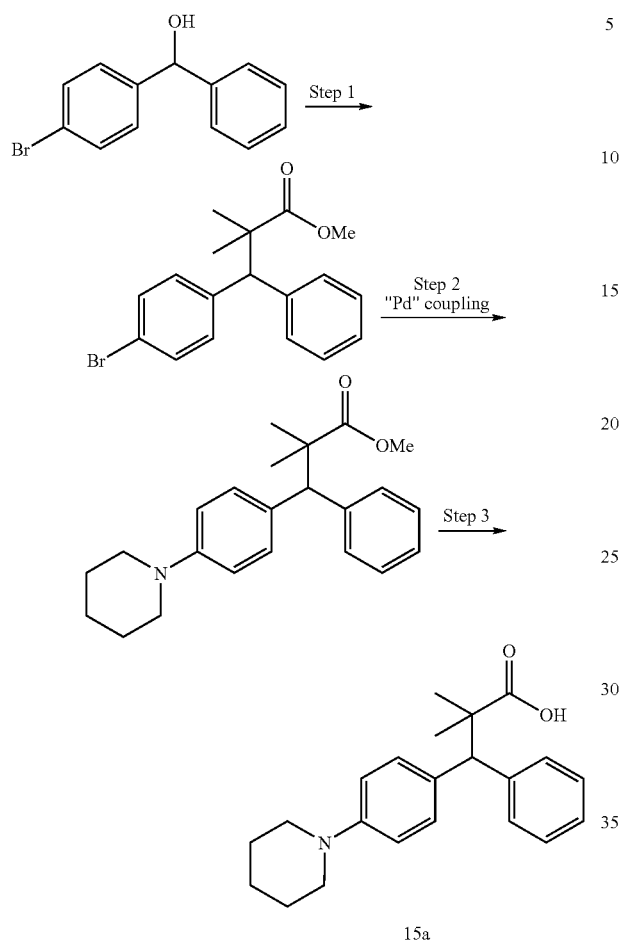

15a

Step 1

In a similar manner to Preparation 14, Step 2, the reaction of (4-bromophenyl)(phenyl)methanol (10 g, 38 mmol), and (1-methoxy-2-methylprop-1-enyloxy)trimethylsilane (23.2 g, 133 mmol) in the presence of titanium tetrachloride (1M in DCM, 42 ml. 41.8 mmol) afforded methyl 3-(4-bromophenyl)-2,2-dimethyl-3-phenylpropanoate (13 g, 99% yield). LC/MS (m/z) 347.05, 349 [(M+1)$^+$]; HPLC Rt: 4.18 min.

Step 2

A mixture of methyl 3-(4-bromophenyl)-2,2-dimethyl-3-phenylpropanoate (250 mg, 0.72 mmol), piperidine (3 mL), palladium acetate (32 mg, 0.144 mmol), 2-(di-tert-butylphosphino)-biphenyl (87 mg, 0.29 mmol), and sodium tert-butoxide (166 mg, 1.73 mmol) in toluene (5 ml) was heated at 80° C. for 1.5 h. The reaction mixture was cooled to room temperature, the solid was removed by filtration, and the filtrate was concentrated in vacuo. The crude product was purified by silica gel flash chromatography using 10% ethyl acetate in hexanes to give methyl 2,2-dimethyl-3-phenyl-3-(4-(piperidin-1-yl)phenyl)propanoate as a white solid (207 mg, 82%). LC/MS (m/z) 352.24 [(M+H)$^+$]; HPLC Rt: 2.448 min.

Step 3

In a similar manner to Preparation 14, Step 3, the basic hydrolysis of methyl 2,2-dimethyl-3-phenyl-3-(4-(piperidin-1-yl)phenyl)propanoate (99 mg, 0.281 mmol) afforded 2,2-dimethyl-3-phenyl-3-(4-(piperidin-1-yl)phenyl)propanoic acid (15a) as a white solid (84 mg, 89% yield). LC/MS (m/z) 338.29 [(M+H)$^+$]; HPLC Rt: 2.29 min.

According to the procedures described above, the acids of formula (15b-15f) were prepared via the Buchwald coupling reaction of methyl 3-(4-bromophenyl)-2,2-dimethyl-3-phenylpropanoate, the product of Preparation 15, Step 1, with the appropriate amines followed by the basic hydrolysis.

| Preparation | Structure |
|---|---|
| 15b | 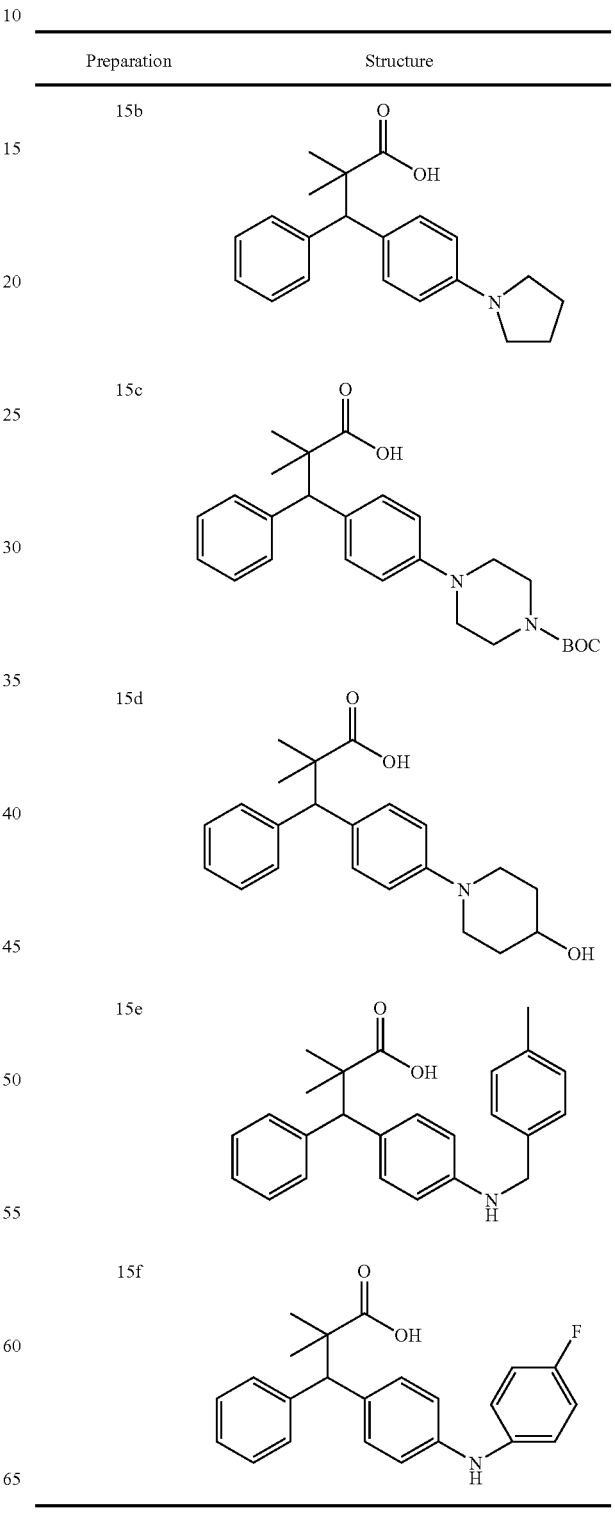 |
| 15c | 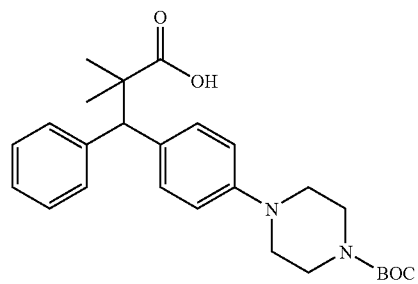 |
| 15d | 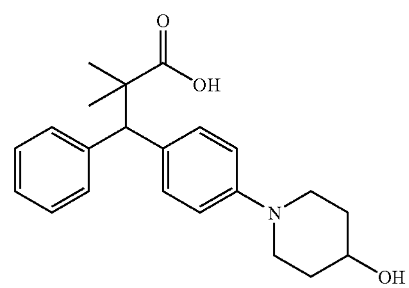 |
| 15e | 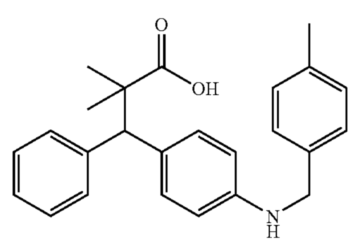 |
| 15f | 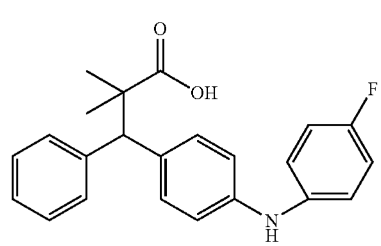 |

Preparation 16

In a similar manner to Preparation 15, the acids of formula (16a) to (16c) were prepared via the Buchwald coupling reaction of morpholine with the corresponding esters, prepared from (3-bromophenyl)-(phenyl)methanol, (4-bromo-3-fluorophenyl)-(phenyl)methanol or 1-(4-morpholinophenyl)-1-phenylethanol respectively, followed by the basic hydrolysis.

| Preparation | Structure |
| --- | --- |
| 16a | 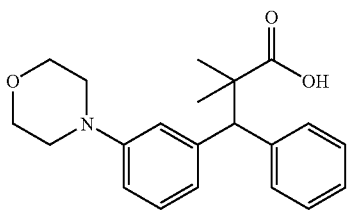 |
| 16b | 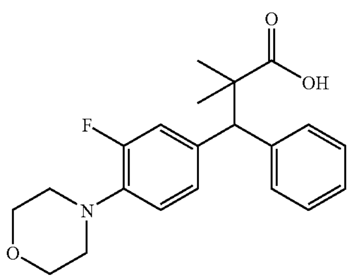 |
| 16c | 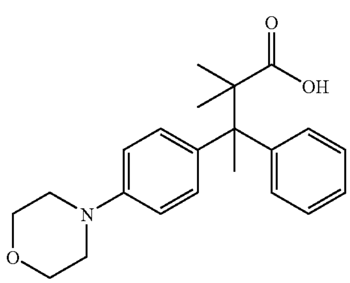 |

Preparation 17

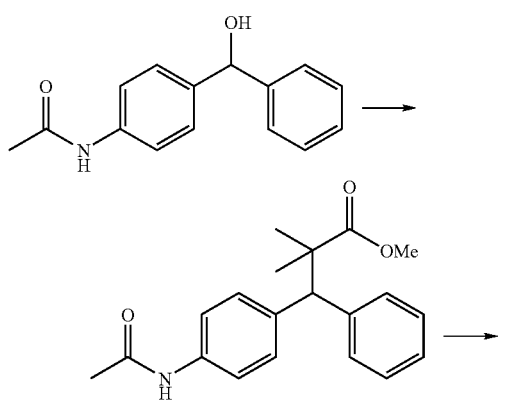

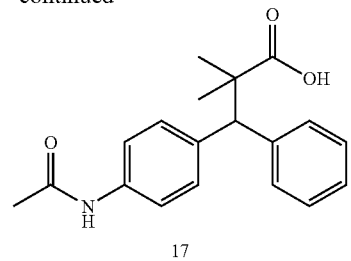

17

In a similar manner to Preparation 14 Step 2, the reaction of N-(4-(hydroxy(phenyl)methyl)phenyl)acetamide (227 mg, 0.942 mmol) and (1-methoxy-2-methyl-propenyloxy)-trimethyl-silane in the presence of titanium tetrachloride in DCM afforded methyl 3-(4-acetamidophenyl)-2,2-dimethyl-3-phenyl propanoate (281 mg, 91% yield). The methyl ester (184 mg, 0.566 mmol) was treated with potassium trimethylsiloxide (362 mg, 2.828 mmol) in THF (5.5 ml) and DMSO (0.55 ml) at room temperature for 4 days. After removal of THF, the reaction mixture was taken into water and extracted with ethyl ether/hexane (1:1). The organic extract was washed (brine), dried (MgSO$_4$) and concentrated to give the acid of formula (17) as a viscous oil (58 mg). LC/MS (m/z) 312 [(M+1)$^+$]; HPLC Rt: 3.083 min.

The aqueous layer was adjusted to pH 2 with 6N HCl followed by extraction with ethyl acetate. The organic layer, after aqueous work up, afforded an off-white solid (150 mg) containing the acid of formula (17) and its corresponding methyl ester at a ratio of 75/25.

Preparation 18

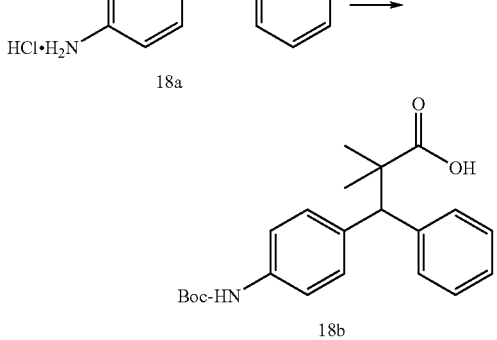

90 mg of the acid of formula (17) (containing 25% of its corresponding methyl ester) was dissolved in dioxane (6 ml)

and 6N HCl (6 ml). The reaction mixture was heated at 100° C. overnight and evaporated to give 3-(4-aminophenyl)-2,2-dimethyl-3-phenylpropanoic acid (18a) as a brown liquid. The acid (18a) was taken into dioxane. The solution was adjusted to pH 9 with 1N aqueous NaOH and cooled to 0° C. Di-tert-butyl dicarbonate (196 mg, 0.9 mmol) was added. The reaction mixture was allowed to warm to room temperature overnight. The reaction mixture was taken into ethyl acetate and water. The organic extract was washed, dried and concentrated. The crude product was purified by silica gel flash chromatography using 10% ethyl acetate in hexanes to afford the acid of formula (18b) as a colorless glass (49.5 mg). LC/MS (m/z) 392.17 [(M+23)$^+$]; HPLC Rt: 4.010 min.

Preparation 19

The acid of formula (14b) was resolved into its corresponding enantiomers using chiral supercritical fluid chromatography (SFC) with the following conditions, Column: Chiralcel OJ 30×250 mm, 10 um, Mobil Phase: Hexane/EtOH/meOH=60:20:20 with 0.1% TFA, Flowrate: 20 mL/min, Detection: UV (274 nm). Analytical HPLC conditions, Column: Chiralpak OJ 4.6×250 mm; 10 um, Mobile phase: 60% (1:1 MeOH/EtOH)/40% heptanes with 0.1% TFA, Temperature: ambient, Flow rate: 1 mL/min, Detection: UV (245 & 220 nm). Retention Time (min) First eluting enantiomer, 9.08 (>99.9% ee); Second eluting enantiomer, 10.94 (>99% ee). The first peak to elute under the preparative (SFC) conditions described above also eluted first under the aforementioned analytical chiral LC conditions A sample of the first-eluting enantiomer (19a) was co-crystallized with (+)-β-methylphenethylamine in acetonitrile. An X-ray crystal structure determination of the crystalline material thus obtained proved (19a) to be of (R) absolute stereochemistry.

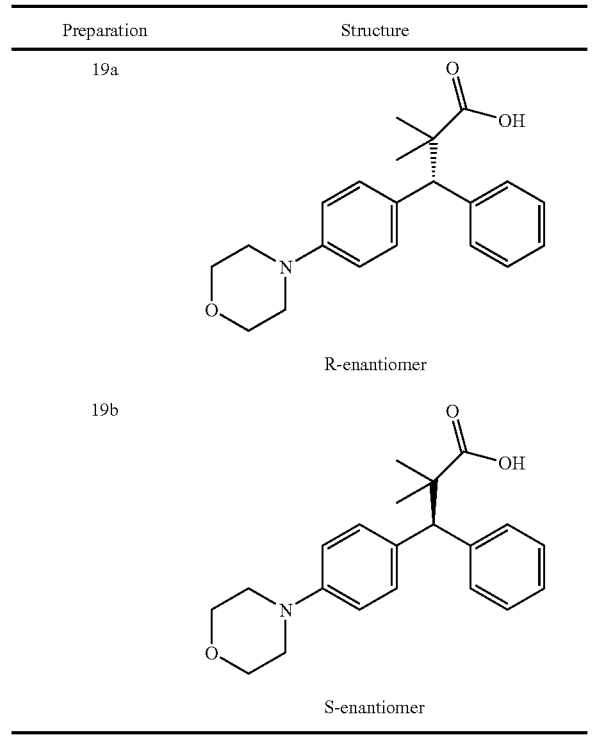

Preparation 20

In a similar manner to Preparation 2, the acid of formula (20a) was were prepared from (4-methoxyphenyl)-(phenyl)methanone via a 2-step procedure as described therein. LC/MS ESI (m/z) 283.28 [(M−1)$^+$]; HPLC Rt: 3.598 min.

The acid of formula (20a) was resolved into its corresponding enantiomers using chiral supercritical fluid chromatography (SFC) with the following conditions, Column: Chiralpak®-AD, 3×25 cm, Mobil Phase: CO2/MeOH/TFA=85:15:0.1, Flow rate: 60 mL/min, Detection: UV (220 nm). Analytical HPLC conditions, Column: Chiralcel OJ 4.6×250 mm; 10 um, Mobile phase: 1:1 MeOH/EtOH with 0.1% TFA, Temperature: ambient, Flow rate: 1 mL/min, Detection: UV (254 & 220 nm). Retention Time (min) First eluting enantiomer, 7.82 (>99% ee); Second eluting enantiomer, 8.84 (>99% ee).

The first peak to elute under the preparative (SFC) conditions described above also eluted first under the aforementioned analytical chiral LC conditions.

A sample of the second-eluting enantiomer (20c) was co-crystallized with (S)-(−)β-methylphenethylamine in acetonitrile. An X-ray crystal structure determination of the crystalline material thus obtained proved (20c) to be of (R) absolute stereochemistry. The first-eluting enantiomer (20b) was thus deduced to be of (S) absolute stereochemistry.

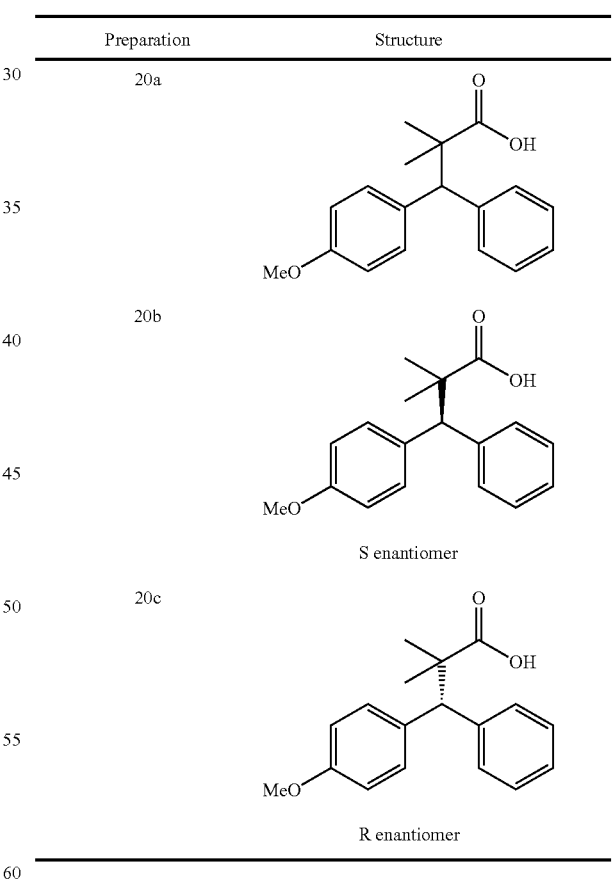

Preparation 21

In a similar manner to Preparation 14, the acids of formula (21a), (21b) and (21c) were prepared from the corresponding aldehydes and phenylmagnesium bromide via a 3-step procedure as described therein.

The acid of formula (21a) was resolved into its corresponding enantiomers using chiral supercritical fluid chromatography (SFC) with the following conditions, Column: Chiralcel®-OJ, 3×25 cm, Mobil Phase: CO2/MeOH=85/15, Flowrate: 65 mL/min, Detection: UV (220 nm). Analytical HPLC conditions, Column: Chiralcel OJ 4.6×250 mm; 10 um, Mobile phase: 20% (1:1 MeOH/EtOH)/80% heptanes with 0.1% TFA, Temperature: ambient, Flow rate: 1 mL/min, Detection: UV (254 & 220 nm). Retention Time (min): First eluting enantiomer (21d), 11.07 (>99.9% ee); Second eluting enantiomer (21e), 18.65 (>99.9% ee).

The first peak to elute under the preparative (SFC) conditions described above also eluted first under the aforementioned analytical chiral LC conditions.

| Preparation | Structure |
|---|---|
| 21a | 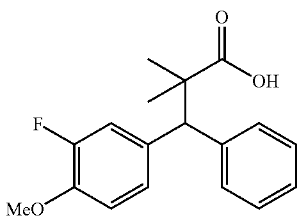 |
| 21b | 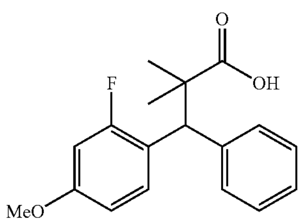 |
| 21c | 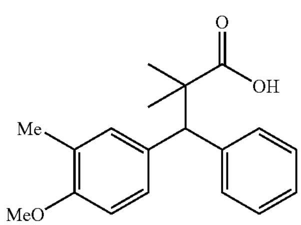 |
| 21d | Isomer A |
| 21e | Isomer B |

Preparation 22

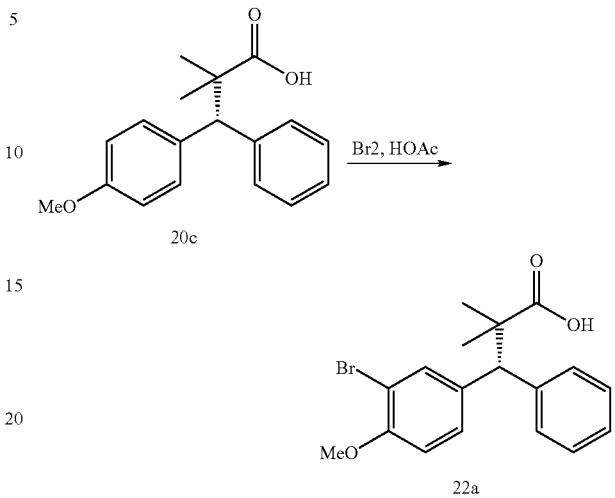

To a suspension of the acid of formula (20c) (1 g, 3.52 mmol) and NaOAc (433 mg, 5.28 mmol) in acetic acid (20 ml) was added bromine (0.271 ml, 5.28 mmol) drop wise at room temperature. After stirring for 3 h, the reaction mixture was poured into 10% aqueous sodium hydrosulfite ($Na_2S_2O_4$) solution. The solution was adjusted to pH 7 with concentrated ammonium hydroxide, and extracted with ethyl ether. The organic extract was washed, dried and concentrated to afford the acid of formula (22a) as a white solid (1.239 g, 96.9% yield). LC/MS (m/z) 363.3 [(M+1)$^+$]; HPLC Rt: 3.696 min.

In a similar manner, the acid of formula (22b) was prepared from acid of formula (20b) as described above.

| Preparation | Structure |
|---|---|
| 23b | (S-isomer) |

Preparation 23

In a similar manner to Preparation 2, the acid of formula (23a) was were prepared from (4-bromophenyl)-(phenyl)methanone via a 2-step procedure as described therein. LC/MS ESI (m/z) 331, 333 [M−1]; HPLC Rt: 3.848 min.

The acid of formula (21a) was resolved into its corresponding enantiomers using chiral supercritical fluid chromatography (SFC) with the following conditions, Column: Chiralcel®-OJ, 30×250 mm, Mobil Phase: CO2/MeOH=90:10, Flow rate: 60 mL/min, Detection: UV (220 nm). Analytical HPLC conditions, Column: Chiralcel OJ 4.6×250 mm; 10 um, Mobile phase: 10% (1:1 MeOH/EtOH)/90% heptanes, Temperature: ambient, Flowrate: 1 mL/min, Detection: UV (254 & 220 nm). Retention Time (min): First eluting enantiomer (23b), 7.91 (>99% ee); Second eluting enantiomer (23c), 11.11 (95% ee).

The first peak to elute under the preparative (SFC) conditions described above also eluted first under the aforementioned analytical chiral LC conditions.

| Preparation | Structure |
|---|---|
| 23a | (structure: 2-methyl-2-(phenyl(4-bromophenyl)methyl)propanoic acid) |
| 23b | (structure, Isomer A) |
| 23c | (structure, Isomer B) |

Preparation 24

In a similar manner to Preparation 14, the acids of formula (24a) and (24b) were prepared from 4-morpholinobenzaldehyde or 4-bromobenzaldehyde with isobutylmagnesium bromide via a 3-step procedure as described therein.

| Preparation | Structure |
|---|---|
| 24a | (structure with morpholine) |
| 24b | (structure with Br) |

EXAMPLES

Example 1

1-Methyl-2,2-diphenyl-cyclopropanecarboxylic acid thiazol-2-ylamide (Reaction scheme: Preparation 1 → 1) Oxalyl Chloride, 2) H$_2$N-thiazole → product)

To a solution of the product of Preparation 1 (1.59 mmol, 400 mg) in dichloromethane (5.0 mL) is added oxalyl chloride (2.0 mmol, 1.0 mL of a 2 N solution in dichloromethane) and DMF (2 drops). After 1 hour at RT the reaction mixture is concentrated in vacuo and then redissolved in dichloromethane (5.0 mL). To the resulting mixture is then added triethylamine (2.0 mmol, 0.20 mL) and 2-aminothiazole (2.0 mmol, 200 mg). After 1 hour the reaction mixture is quenched with 1N HCl, extracted with dichloromethane (3×30 mL), and washed with saturated sodium bicarbonate solution (3×30 mL). The combined organic phases are concentrated under vacuo and the residue chromatographed on silica gel (eluted with 33% ethyl acetate in hexane) to give 367 mg (Y: 69%) of the title compound of Example 1. MS (E+) m/z: 335 (MH$^+$).

Examples 2 to 31

In a similar manner to Example 1, Examples 2 to 31 were prepared via the coupling reactions of the acids of Preparation 1 with the appropriate amines (Compounds are racemic unless noted)

| Example No. | Name | Structure | MS [m/z (M + H)] |
|---|---|---|---|
| 2 | 1-methyl-2,2-diphenyl-N-1,3-thiazol-2-ylcyclopropanecarboxamide | 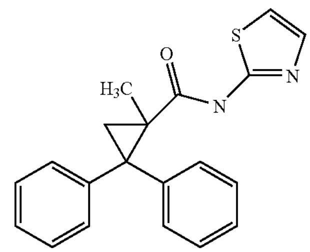 | 334.44 |
| 3 | 1-methyl-2,2-diphenyl-N-(4-phenyl-1,3-thiazol-2-yl)cyclopropanecarboxamide | 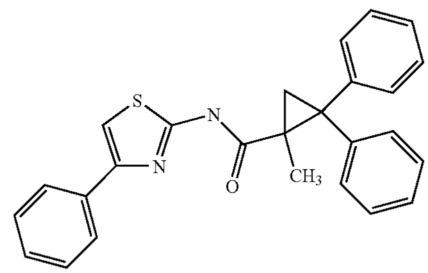 | 410.5 |
| 4 | 1-methyl-N-(4-methyl-1,3-thiazol-2-yl)-2,2-diphenylcyclopropanecarboxamide | 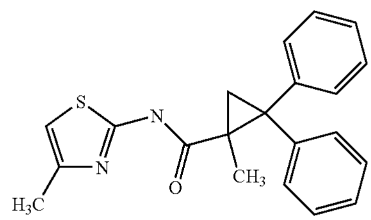 | 348.5 |
| 5 | ethyl (2-(((1-methyl-2,2-diphenylcyclopropyl)carbonyl)amino)-1,3-thiazol-4-yl)acetate | 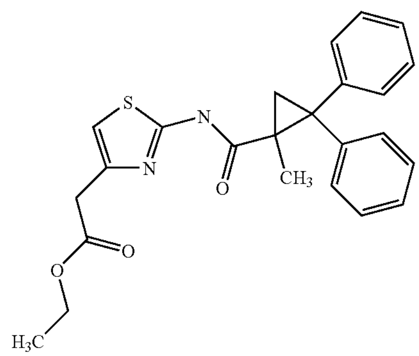 | 420.5 |
| 6 | N-1,3-benzothiazol-2-yl-1-methyl-2,2-diphenylcyclopropanecarboxamide | 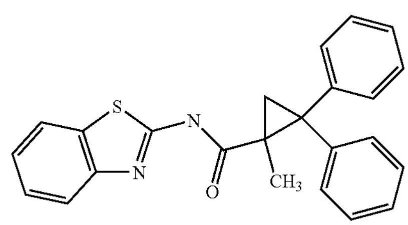 | 384.5 |
| 7 | 1-methyl-N-(6-(methyloxy)-1,3-benzothiazol-2-yl)-2,2-diphenylcyclopropanecarboxamide | 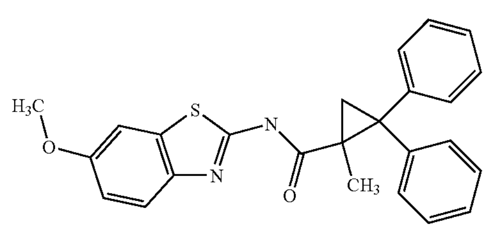 | 414.5 |

-continued

| Example No. | Name | Structure | MS [m/z (M + H)] |
|---|---|---|---|
| 8 | N-(6-(ethyloxy)-1,3-benzothiazol-2-yl)-1-methyl-2,2-diphenylcyclopropanecarboxamide | 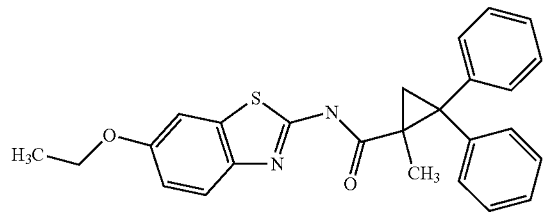 | 428.6 |
| 9 | 1-methyl-N-(6-methyl-1,3-benzothiazol-2-yl)-2,2-diphenylcyclopropanecarboxamide | 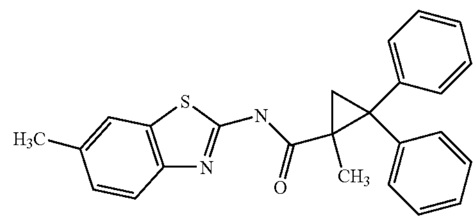 | 398.5 |
| 10 | N-(5,6-dimethyl-1,3-benzothiazol-2-yl)-1-methyl-2,2-diphenylcyclopropanecarboxamide | 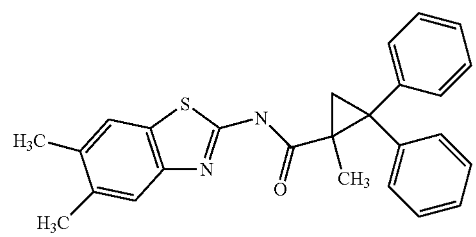 | 412.6 |
| 11 | N-(4-chloro-1,3-benzothiazol-2-yl)-1-methyl-2,2-diphenylcyclopropanecarboxamide | 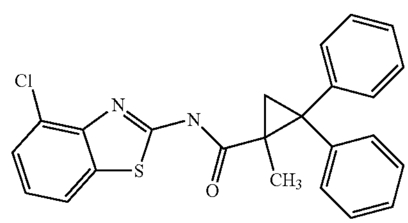 | 419 |
| 12 | 1-methyl-N-(4-(methyloxy)-1,3-benzothiazol-2-yl)-2,2-diphenylcyclopropanecarboxamide | 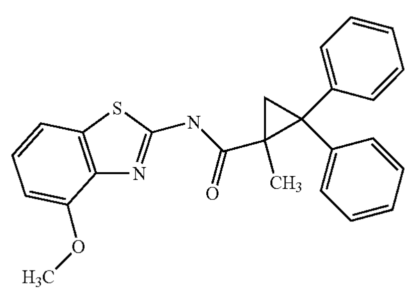 | 414.5 |
| 13 | 1-methyl-N-(4-methyl-1,3-benzothiazol-2-yl)-2,2-diphenylcyclopropanecarboxamide | 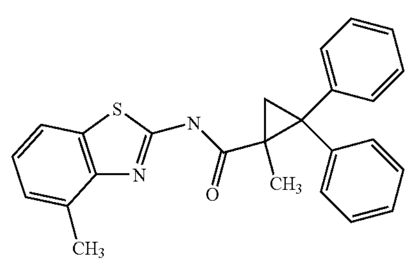 | 398.5 |

-continued

| Example No. | Name | Structure | MS [m/z (M + H)] |
|---|---|---|---|
| 14 | ethyl (2E)-(2-(((1-methyl-2,2-diphenylcyclopropyl)carbonyl)amino)-1,3-thiazol-4-yl)((methyloxy)imino)ethanoate | 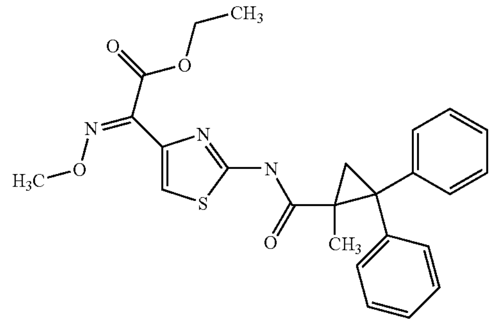 | 463.6 |
| 15 | N-(4,5-dimethyl-1,3-thiazol-2-yl)-1-methyl-2,2-diphenylcyclopropanecarboxamide | 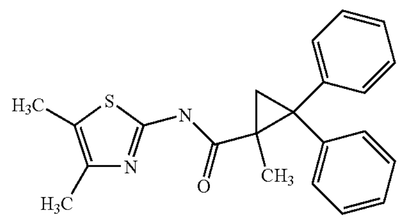 | 362.5 |
| 16 | N-(6-fluoro-1,3-benzothiazol-2-yl)-1-methyl-2,2-diphenylcyclopropanecarboxamide | 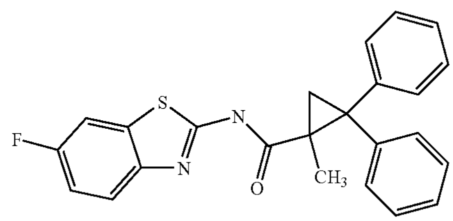 | 402.5 |
| 17 | 1-methyl-2,2-diphenyl-N-(4-(2-phenylethyl)-1,3-thiazol-2-yl)cyclopropanecarboxamide | 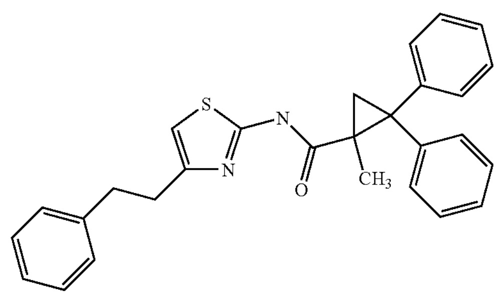 | 438.6 |
| 18 | N-(5-chloro-1,3-thiazol-2-yl)-1-methyl-2,2-diphenylcyclopropanecarboxamide | 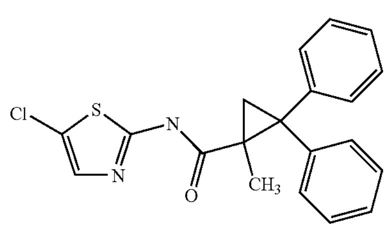 | 368.9 |
| 19 | N-(4-(4-chlorophenyl)-1,3-thiazol-2-yl)-1-methyl-2,2-diphenylcyclopropanecarboxamide | 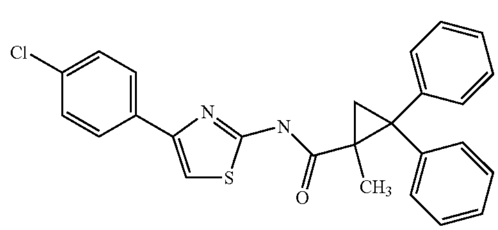 | 445 |

-continued

| Example No. | Name | Structure | MS [m/z (M + H)] |
|---|---|---|---|
| 20 | N-(4-(1,1-dimethylethyl)-1,3-thiazol-2-yl)-1-methyl-2,2-diphenylcyclopropanecarboxamide | 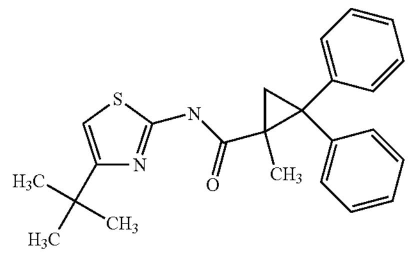 | 390.6 |
| 21 | N-(6-chloro-1,3-benzothiazol-2-yl)-1-methyl-2,2-diphenylcyclopropanecarboxamide | 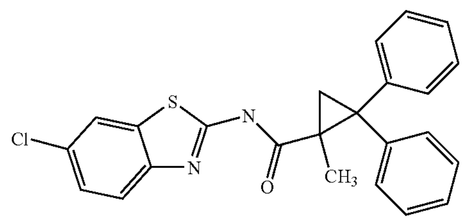 | 419 |
| 22 | N-(5,6-dichloro-1,3-benzothiazol-2-yl)-1-methyl-2,2-diphenylcyclopropanecarboxamide | 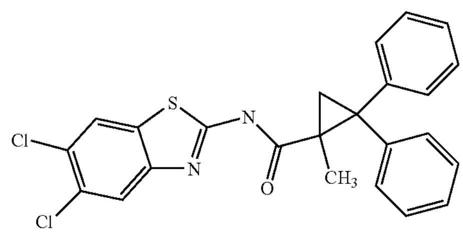 | 453.4 |
| 23 | 1-methyl-N-(5-methyl-1,3-thiazol-2-yl)-2,2-diphenylcyclopropanecarboxamide | 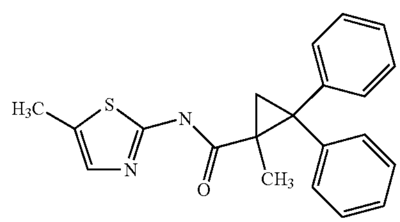 | 348.5 |
| 24 | N-(4-(4-chloro-3-methylphenyl)-1,3-thiazol-2-yl)-1-methyl-2,2-diphenylcyclopropanecarboxamide | 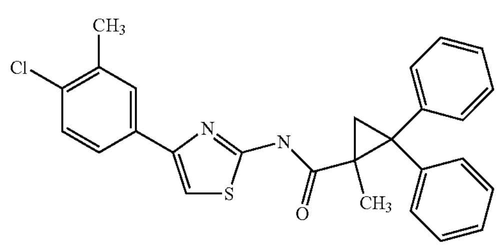 | 459 |
| 25 | 1-methyl-2,2-diphenyl-N-(4,5,6,7-tetrahydro-1,3-benzothiazol-2-yl)cyclopropanecarboxamide | 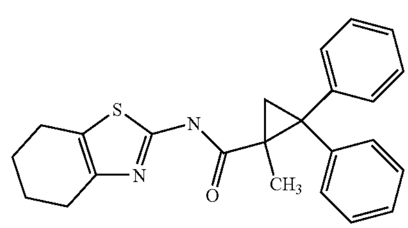 | 388.5 |

| Example No. | Name | Structure | MS [m/z (M + H)] |
|---|---|---|---|
| 26 | N-(4-(2,5-dichloro-3-thienyl)-1,3-thiazol-2-yl)-1-methyl-2,2-diphenylcyclopropanecarboxamide | 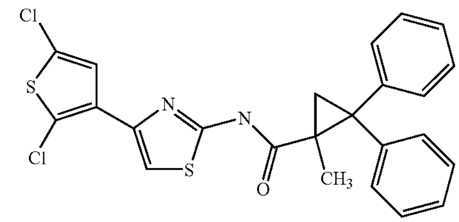 | 485.5 |
| 27 | ethyl 4-methyl-2-(((1-methyl-2,2-diphenylcyclopropyl)carbonyl)amino)-1,3-thiazole-5-carboxylate | 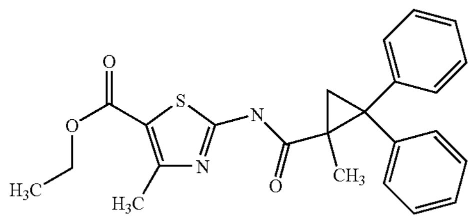 | 420.5 |
| 28 | ethyl 2-(((1-methyl-2,2-diphenylcyclopropyl)carbonyl)amino)-4-(trifluoromethyl)-1,3-thiazole-5-carboxylate | 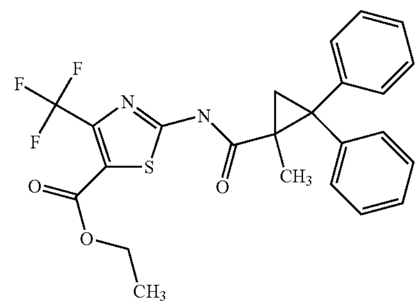 | 474.5 |
| 29 | 1-methyl-N-(4-(4-methylphenyl)-1,3-thiazol-2-yl)-2,2-diphenylcyclopropanecarboxamide | 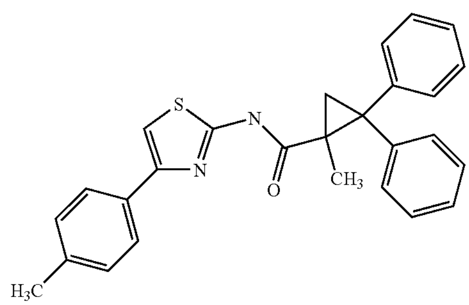 | 424.6 |
| 30 | 1-methyl-N-(4-(1-naphthalenyl)-1,3-thiazol-2-yl)-2,2-diphenylcyclopropanecarboxamide | 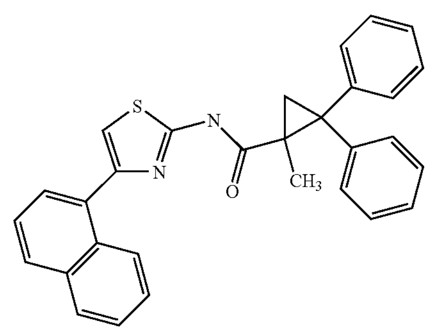 | 460.6 |

| Example No. | Name | Structure | MS [m/z (M + H)] |
|---|---|---|---|
| 31 | 1-methyl-2,2-diphenyl-N-(5-phenyl-1,3-thiazol-2-yl)cyclopropanecarboxamide | 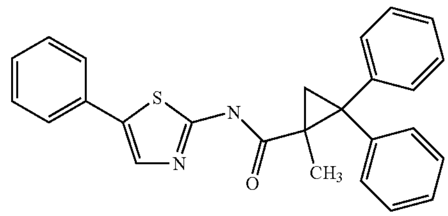 | 410.5 |

Example 32

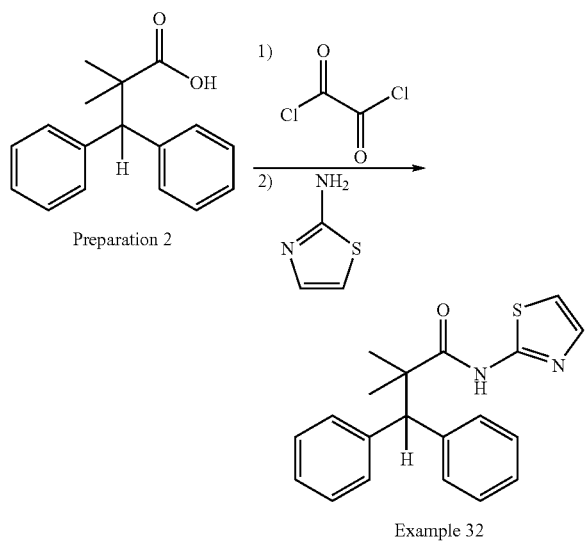

Preparation 2

Example 32

To a solution of the product of Preparation 2 (30 mg, 0.12 mmol, 1.0 equi.) in dichloromethane (5 mL) was added an oxalyl chloride solution in dichloromethane (2M, 0.1 mL, 0.2 mmol, 1.7 equi.) in dropwise. The solution was stirred at RT for 2 hours, after which the solvent was removed in vacuo. The acid chloride was redissolved in dichloromethane (5 mL) and a solution of 2-aminothiazole (17.7 mg, 0.17 mmol, 1.5 equi.) in dichloromethane (1 mL) added. The reaction solution was stirred at RT for 4 hours and then the solution was concentrated in vacuo. Purification of the crude product mixture by reversed phased PREP HPLC, followed by neutralization with cation exchange SPE, yielded 28.4 mg (72%) of the title compound of Example 32: LC/MS (m/z 337, (M+H)$^+$); $^1$H NMR (CDCl$_3$) 7.19-7.47 (m, 11H), 6.95 (s, 1H), 4.75 (s, 1H), 1.45 (s, 6H).

Examples 33 to 184

In a similar manner to Example 32, Examples 33 to 184 were prepared via the coupling reactions of acids of Preparations 2 or appropriate acids prepared from corresponding ketones according to the procedure described in preparation 2, with the appropriate amines (Compounds are racemic unless noted)

| Example No. | Name | Structure | MS [m/z (M + H)] |
|---|---|---|---|
| 33 | 2,2-dimethyl-3,3-diphenyl-N-1,3-thiazol-2-ylpropanamide | 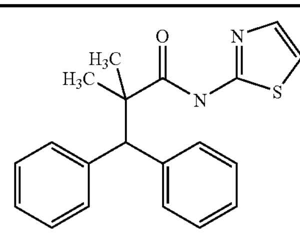 | 336.46 |
| 34 | 2,2-dimethyl-N-(4-methyl-1,3-thiazol-2-yl)-3,3-diphenylpropanamide | 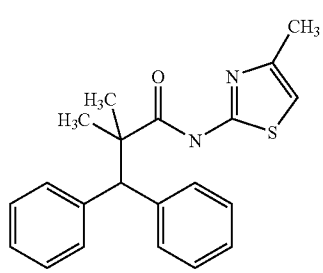 | 350.49 |

-continued

| Example No. | Name | Structure | MS [m/z (M + H)] |
|---|---|---|---|
| 35 | 2,2-dimethyl-N-(5-methyl-1,3-thiazol-2-yl)-3,3-diphenylpropanamide | 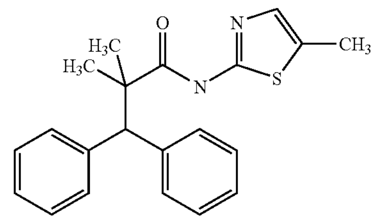 | 350.49 |
| 36 | 2,2-dimethyl-3,3-diphenyl-N-(4-phenyl-1,3-thiazol-2-yl)propanamide | 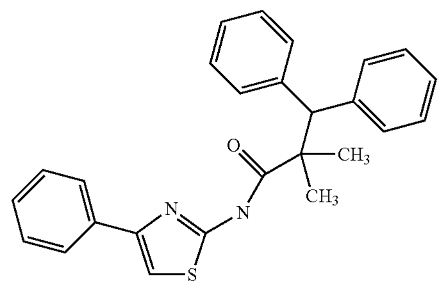 | 412.6 |
| 37 | ethyl (2-((2,2-dimethyl-3,3-diphenylpropanoyl)amino)-1,3-thiazol-4-yl)acetate | 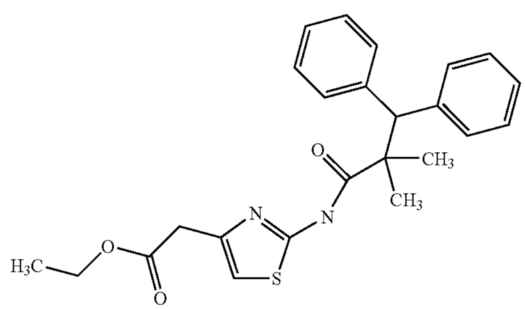 | 422.6 |
| 38 | N-1,3-benzothiazol-2-yl-2,2-dimethyl-3,3-diphenylpropanamide | 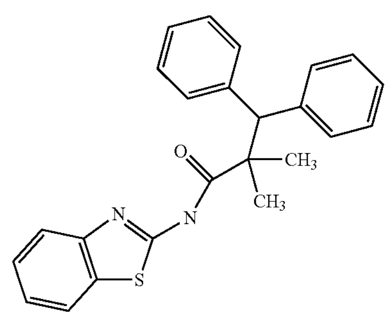 | 386.5 |
| 39 | 2,2-dimethyl-N-(6-nitro-1,3-benzothiazol-2-yl)-3,3-diphenylpropanamide | 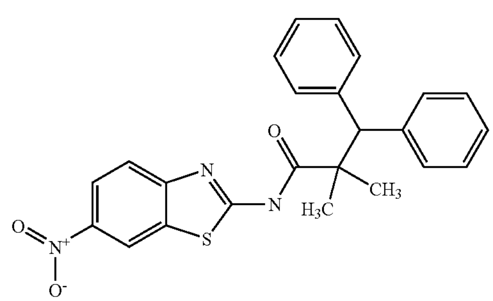 | 431.5 |

-continued
| Example No. | Name | Structure | MS [m/z (M + H)] |
|---|---|---|---|
| 40 | 2,2-dimethyl-N-(6-(methyloxy)-1,3-benzothiazol-2-yl)-3,3-diphenylpropanamide | 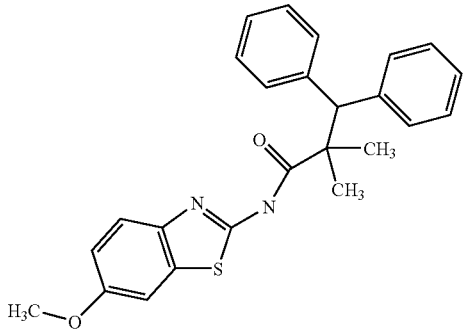 | 416.5 |
| 42 | N-(6-(ethyloxy)-1,3-benzothiazol-2-yl)-2,2-dimethyl-3,3-diphenylpropanamide | 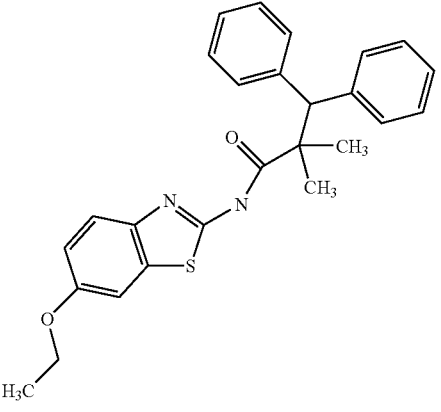 | 430.6 |
| 43 | 2,2-dimethyl-N-(6-methyl-1,3-benzothiazol-2-yl)-3,3-diphenylpropanamide | 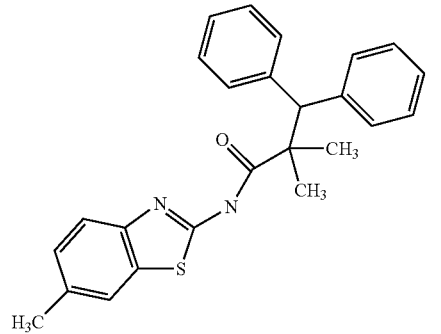 | 400.5 |
| 44 | N-(5,6-dimethyl-1,3-benzothiazol-2-yl)-2,2-dimethyl-3,3-diphenylpropanamide | 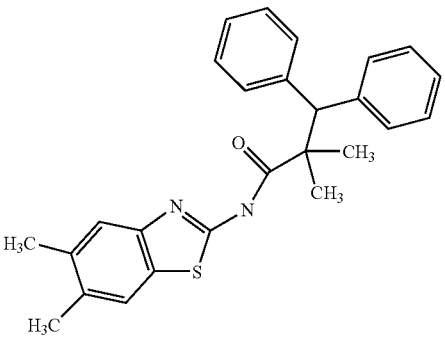 | 414.6 |

-continued

| Example No. | Name | Structure | MS [m/z (M + H)] |
|---|---|---|---|
| 45 | N-(4-chloro-1,3-benzothiazol-2-yl)-2,2-dimethyl-3,3-diphenylpropanamide | 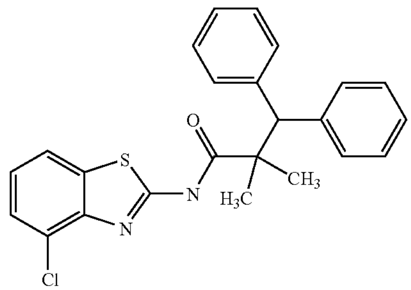 | 421 |
| 46 | 2,2-dimethyl-N-(4-(methyloxy)-1,3-benzothiazol-2-yl)-3,3-diphenylpropanamide | 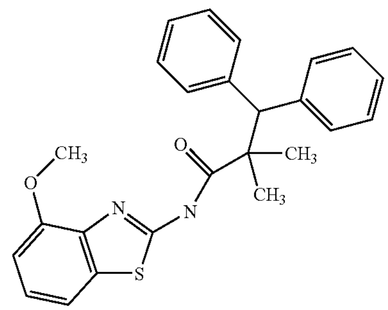 | 416.5 |
| 47 | 2,2-dimethyl-N-(4-methyl-1,3-benzothiazol-2-yl)-3,3-diphenylpropanamide | 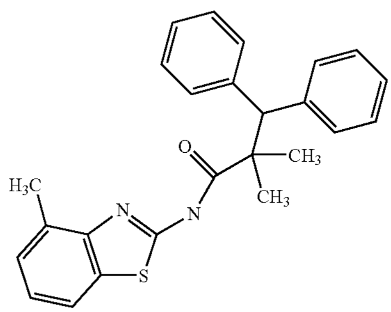 | 400.5 |
| 48 | ethyl (2E)-(2-((2,2-dimethyl-3,3-diphenylpropanoyl)amino)-1,3-thiazol-4-yl)(hydroxyimino)ethanoate | 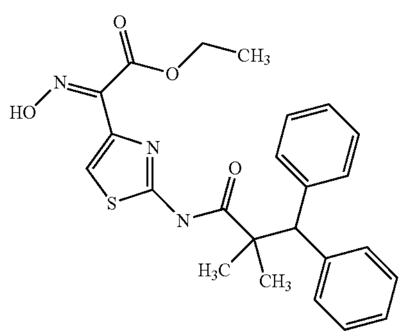 | 451.6 |
| 49 | ethyl (2E)-(2-((2,2-dimethyl-3,3-diphenylpropanoyl)amino)-1,3-thiazol-4-yl)((methyloxy)imino)ethanoate | 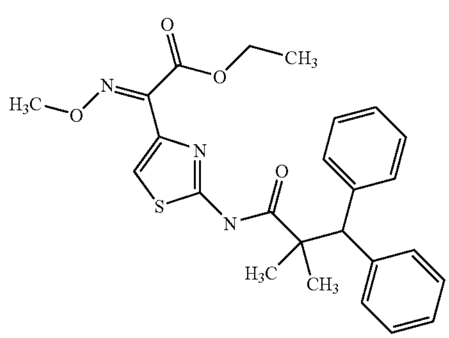 | 465.6 |

-continued

| Example No. | Name | Structure | MS [m/z (M + H)] |
|---|---|---|---|
| 50 | N-(6-fluoro-1,3-benzothiazol-2-yl)-2,2-dimethyl-3,3-diphenylpropanamide | 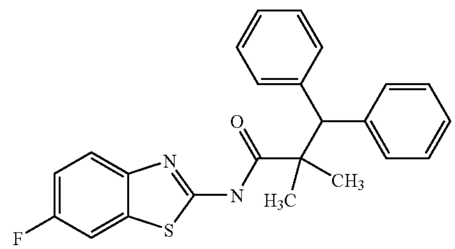 | 404.5 |
| 51 | 2,2-dimethyl-3,3-diphenyl-N-(4-(2-phenylethyl)-1,3-thiazol-2-yl)propanamide | 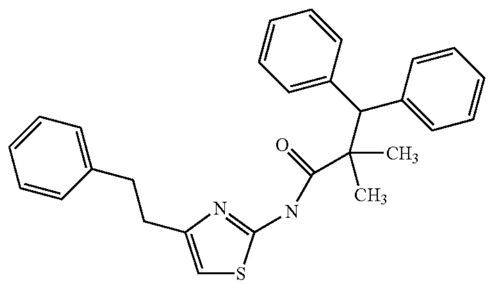 | 440.6 |
| 52 | N-(5-chloro-1,3-thiazol-2-yl)-2,2-dimethyl-3,3-diphenylpropanamide | 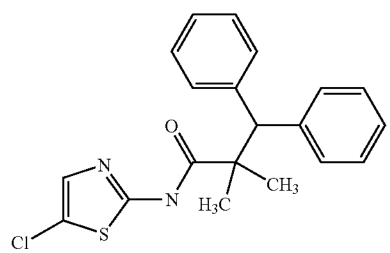 | 370.9 |
| 53 | N-(4-(4-chlorophenyl)-1,3-thiazol-2-yl)-2,2-dimethyl-3,3-diphenylpropanamide | 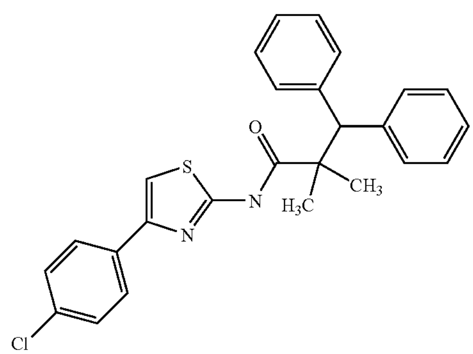 | 447 |
| 54 | N-(4-(1,1-dimethylethyl)-1,3-thiazol-2-yl)-2,2-dimethyl-3,3-diphenylpropanamide | 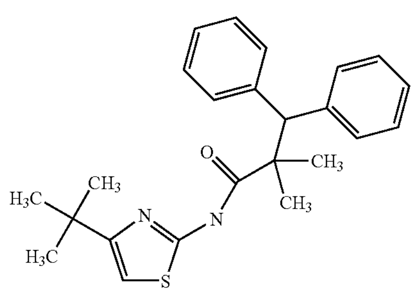 | 392.6 |

-continued
| Example No. | Name | Structure | MS [m/z (M + H)] |
|---|---|---|---|
| 55 | N-(5-bromo-4-(1,1-dimethylethyl)-1,3-thiazol-2-yl)-2,2-dimethyl-3,3-diphenylpropanamide | 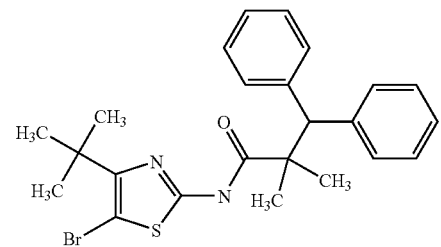 | 471.5 |
| 56 | N-(4-(3,4-difluorophenyl)-1,3-thiazol-2-yl)-2,2-dimethyl-3,3-diphenylpropanamide | 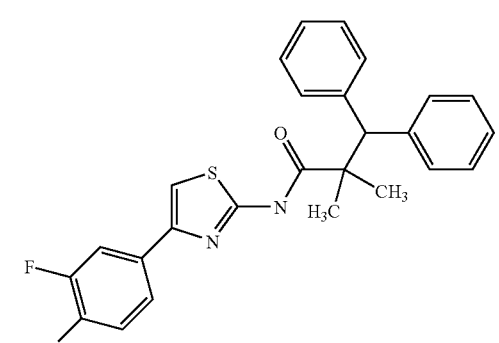 | 448.5 |
| 57 | N-(5,6-dichloro-1,3-benzothiazol-2-yl)-2,2-dimethyl-3,3-diphenylpropanamide | 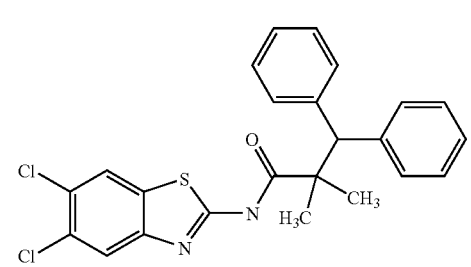 | 455.4 |
| 58 | N-(4-(4-chloro-3-methylphenyl)-1,3-thiazol-2-yl)-2,2-dimethyl-3,3-diphenylpropanamide | 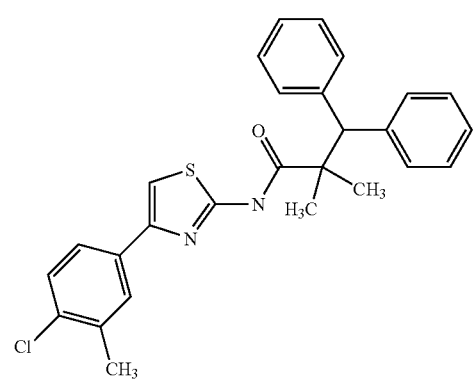 | 461 |

-continued
| Example No. | Name | Structure | MS [m/z (M + H)] |
|---|---|---|---|
| 59 | N-(4-(2,5-dichloro-3-thienyl)-1,3-thiazol-2-yl)-2,2-dimethyl-3,3-diphenylpropanamide | 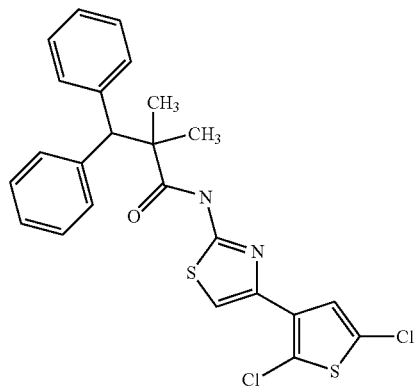 | 487.5 |
| 60 | ethyl 2-((2,2-dimethyl-3,3-diphenylpropanoyl)amino)-4-methyl-1,3-thiazole-5-carboxylate | 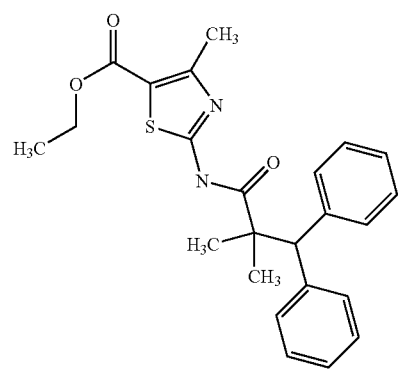 | 422.6 |
| 61 | ethyl 2-((2,2-dimethyl-3,3-diphenylpropanoyl)amino)-4-(trifluoromethyl)-1,3-thiazole-5-carboxylate | 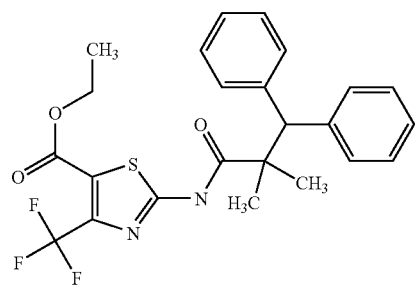 | 476.5 |
| 62 | 2,2-dimethyl-N-(4-(4-methylphenyl)-1,3-thiazol-2-yl)-3,3-diphenylpropanamide | 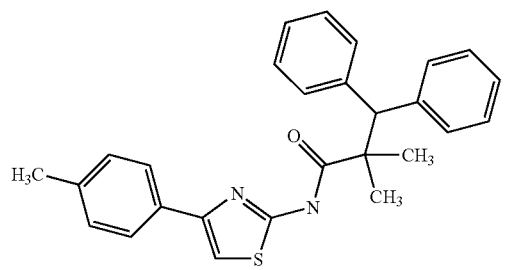 | 426.6 |

-continued
| Example No. | Name | Structure | MS [m/z (M + H)] |
|---|---|---|---|
| 63 | N-(4-(3-chloro-4-methylphenyl)-5-methyl-1,3-thiazol-2-yl)-2,2-dimethyl-3,3-diphenylpropanamide | 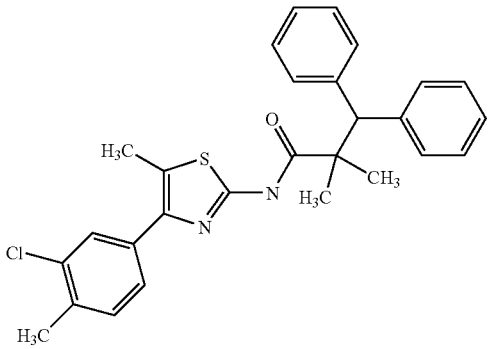 | 475.1 |
| 64 | 2,2-dimethyl-N-(4-(1-naphthalenyl)-1,3-thiazol-2-yl)-3,3-diphenylpropanamide | 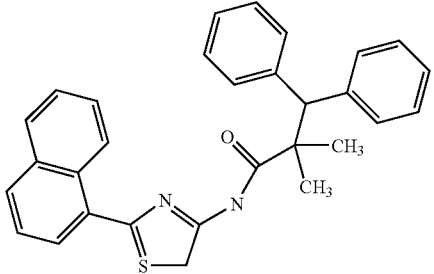 | 462.6 |
| 65 | 2,2-dimethyl-3,3-diphenyl-N-(5-phenyl-1,3-thiazol-2-yl)propanamide | 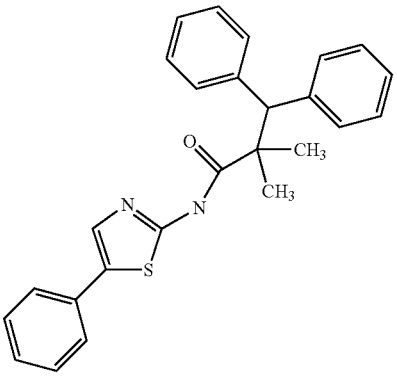 | 412.6 |
| 66 | ethyl 2-((2,2-dimethyl-3,3-diphenylpropanoyl)amino)-4-phenyl-1,3-thiazole-5-carboxylate | 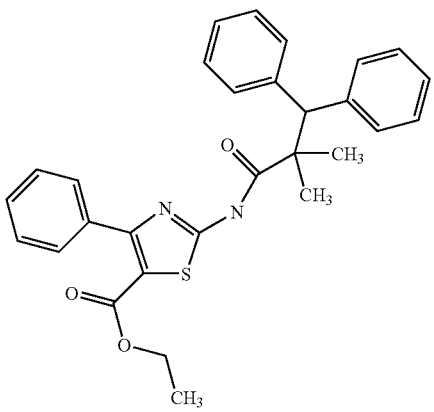 | 484.6 |

-continued

| Example No. | Name | Structure | MS [m/z (M + H)] |
|---|---|---|---|
| 67 | 2,2-dimethyl-3,3-diphenyl-N-4-pyrimidinylpropanamide | 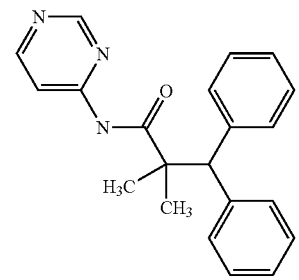 | 331.4 |
| 68 | 2,2-dimethyl-3,3-diphenyl-N-2-pyrazinylpropanamide | 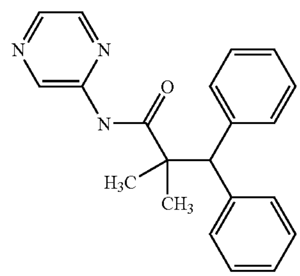 | 331.4 |
| 69 | 2,2-dimethyl-3,3-bis(4-(methyloxy)phenyl)-N-1,3-thiazol-2-ylpropanamide | 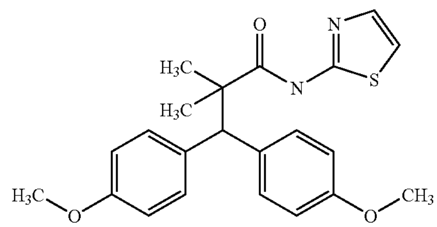 | 396.51 |
| 70 | 2,2-dimethyl-3,3-bis(4-(methyloxy)phenyl)-N-(5-methyl-1,3-thiazol-2-yl)propanamide | 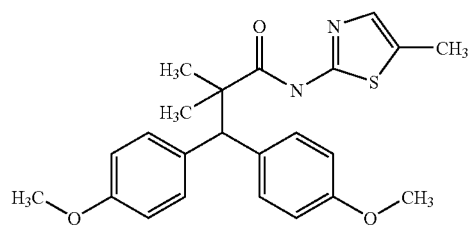 | 410.54 |
| 71 | 2,2-dimethyl-3,3-bis(4-(methyloxy)phenyl)-N-(4-methyl-1,3-thiazol-2-yl)propanamide | 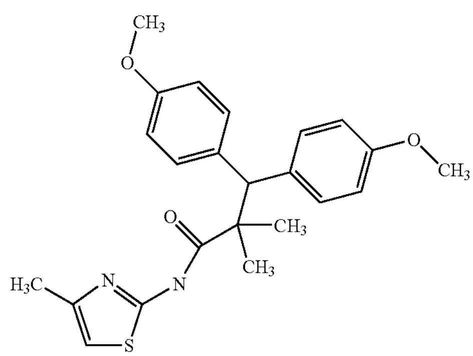 | 410.5 |

-continued

| Example No. | Name | Structure | MS [m/z (M + H)] |
|---|---|---|---|
| 72 | N-(4,5-dimethyl-1,3-thiazol-2-yl)-2,2-dimethyl-3,3-bis(4-(methyloxy)phenyl)propanamide | 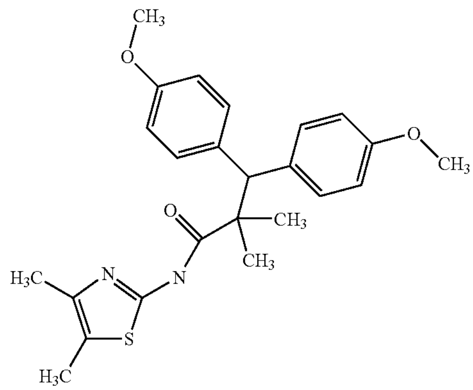 | 424.6 |
| 73 | 2,2-dimethyl-3,3-bis(4-(methyloxy)phenyl)-N-(4-phenyl-1,3-thiazol-2-yl)propanamide | 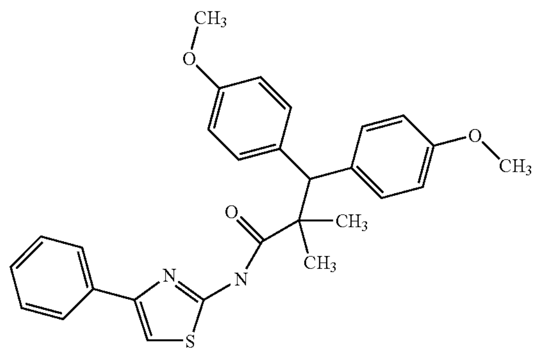 | 472.6 |
| 74 | N-(4-(1,1-dimethylethyl)-1,3-thiazol-2-yl)-2,2-dimethyl-3,3-bis(4-(methyloxy)phenyl)propanamide | 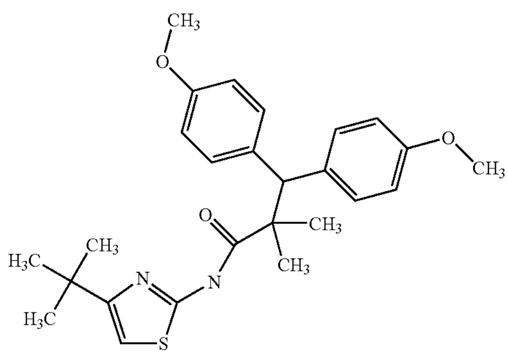 | 452.6 |
| 75 | 2,2-dimethyl-3,3-bis(4-(methyloxy)phenyl)-N-(4-(2-phenylethyl)-1,3-thiazol-2-yl)propanamide | 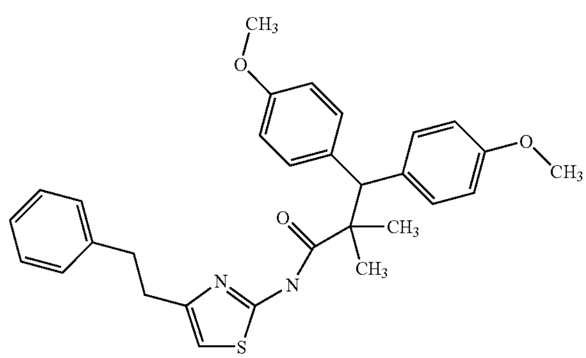 | 500.7 |

-continued

| Example No. | Name | Structure | MS [m/z (M + H)] |
|---|---|---|---|
| 76 | 2,2-dimethyl-3,3-bis(4-(methyloxy)phenyl)-N-(4-(1-naphthalenyl)-1,3-thiazol-2-yl)propanamide | 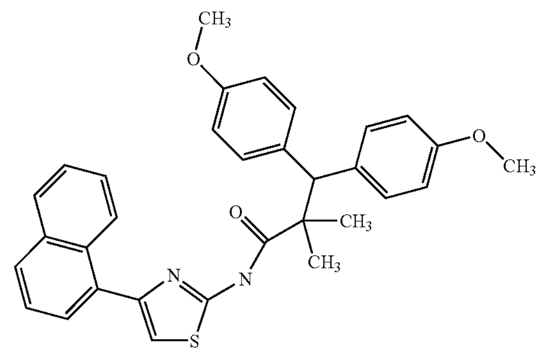 | 522.7 |
| 77 | ethyl 2-((2,2-dimethyl-3,3-bis(4-(methyloxy)phenyl)propanoyl)amino)-4-methyl-1,3-thiazole-5-carboxylate | 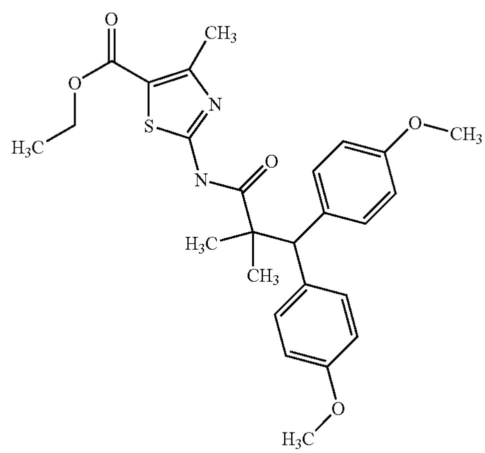 | 482.6 |
| 78 | N-1,3-benzothiazol-2-yl-2,2-dimethyl-3,3-bis(4-(methyloxy)phenyl)propanamide | 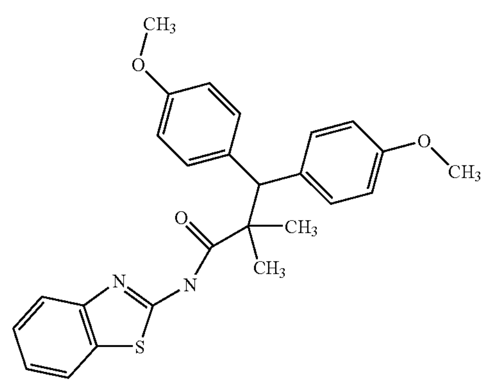 | 446.6 |
| 79 | N-(6-chloro-1,3-benzothiazol-2-yl)-2,2-dimethyl-3,3-bis(4-(methyloxy)phenyl)propanamide | 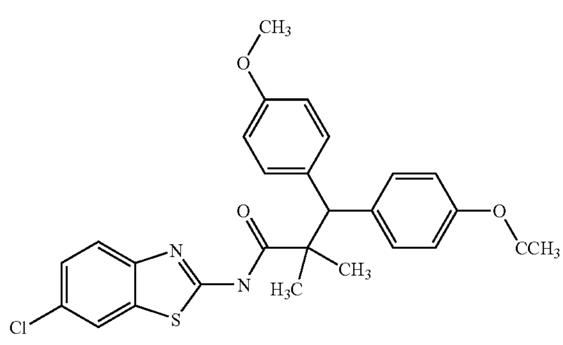 | 481 |

-continued

| Example No. | Name | Structure | MS [m/z (M + H)] |
|---|---|---|---|
| 80 | 2,2-dimethyl-3-(2-(methyloxy)phenyl)-3-phenyl-N-1,3-thiazol-2-ylpropanamide | 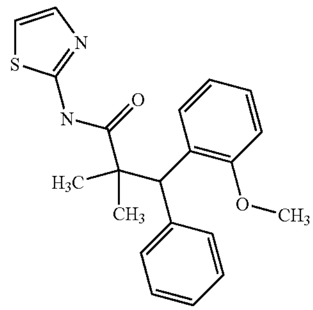 | 366.5 |
| 81 | 2,2-dimethyl-3-(2-(methyloxy)phenyl)-N-(4-methyl-1,3-thiazol-2-yl)-3-phenylpropanamide | 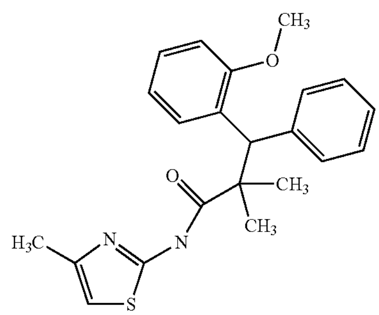 | 380.5 |
| 82 | 2,2-dimethyl-3-(2-(methyloxy)phenyl)-N-(5-methyl-1,3-thiazol-2-yl)-3-phenylpropanamide | 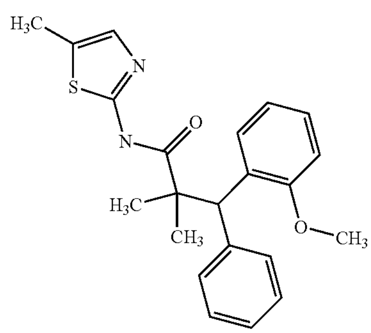 | 380.5 |
| 83 | N-(4,5-dimethyl-1,3-thiazol-2-yl)-2,2-dimethyl-3-(2-(methyloxy)phenyl)-3-phenylpropanamide | 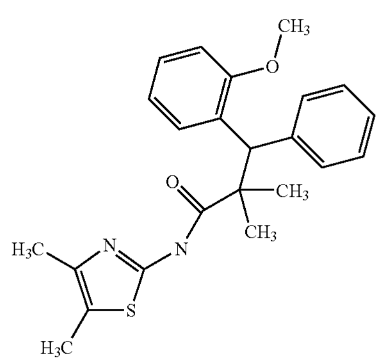 | 394.5 |

-continued

| Example No. | Name | Structure | MS [m/z (M + H)] |
|---|---|---|---|
| 84 | 2,2-dimethyl-3-(2-(methyloxy)phenyl)-3-phenyl-N-(4-phenyl-1,3-thiazol-2-yl)propanamide | 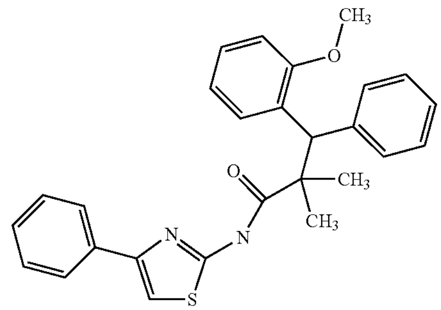 | 442.6 |
| 85 | N-(4-(1,1-dimethylethyl)-1,3-thiazol-2-yl)-2,2-dimethyl-3-(2-(methyloxy)phenyl)-3-phenylpropanamide | 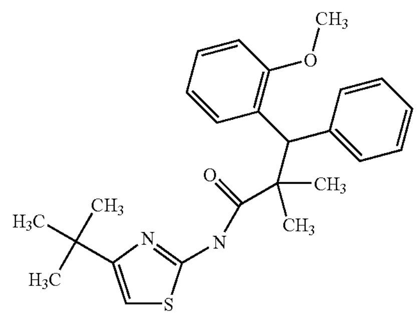 | 422.6 |
| 86 | 2,2-dimethyl-3-(2-(methyloxy)phenyl)-3-phenyl-N-(4-(2-phenylethyl)-1,3-thiazol-2-yl)propanamide | 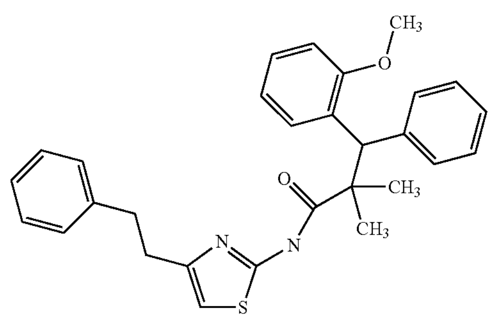 | 470.6 |
| 87 | 2,2-dimethyl-3-(2-(methyloxy)phenyl)-N-(4-(1-naphthalenyl)-1,3-thiazol-2-yl)-3-phenylpropanamide | 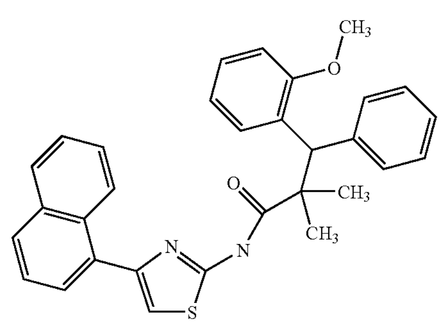 | 492.6 |

| Example No. | Name | Structure | MS [m/z (M + H)] |
|---|---|---|---|
| 88 | ethyl 2-((2,2-dimethyl-3-(2-(methyloxy)phenyl)-3-phenylpropanoyl)amino)-4-methyl-1,3-thiazole-5-carboxylate | 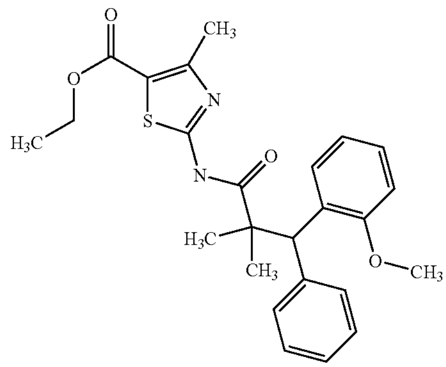 | 452.6 |
| 89 | N-1,3-benzothiazol-2-yl-2,2-dimethyl-3-(2-(methyloxy)phenyl)-3-phenylpropanamide | 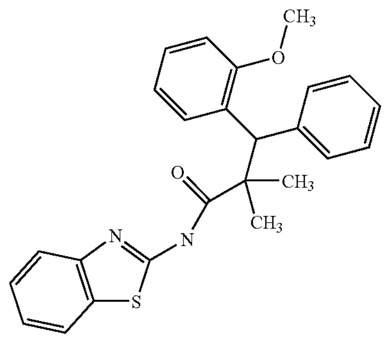 | 416.5 |
| 90 | N-(6-chloro-1,3-benzothiazol-2-yl)-2,2-dimethyl-3-(2-(methyloxy)phenyl)-3-phenylpropanamide | 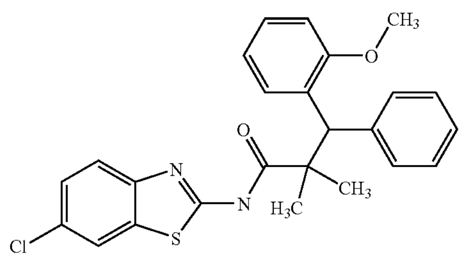 | 451 |
| 91 | 2,2-dimethyl-3-(3-(methyloxy)phenyl)-3-phenyl-N-1,3-thiazol-2-ylpropanamide | 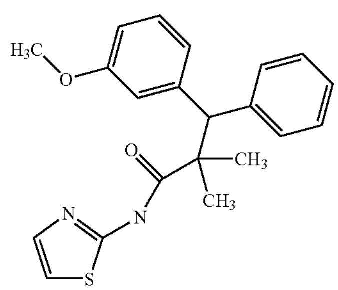 | 366.5 |
| 92 | 2,2-dimethyl-3-(3-(methyloxy)phenyl)-N-(4-methyl-1,3-thiazol-2-yl)-3-phenylpropanamide | 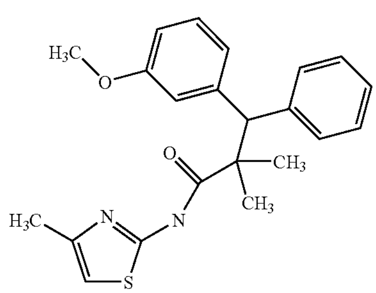 | 380.5 |

-continued

| Example No. | Name | Structure | MS [m/z (M + H)] |
|---|---|---|---|
| 93 | 2,2-dimethyl-3-(3-(methyloxy)phenyl)-N-(5-methyl-1,3-thiazol-2-yl)-3-phenylpropanamide | 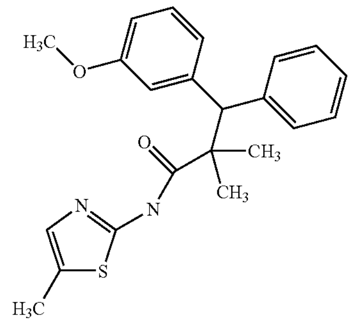 | 380.5 |
| 94 | N-(4,5-dimethyl-1,3-thiazol-2-yl)-2,2-dimethyl-3-(3-(methyloxy)phenyl)-3-phenylpropanamide | 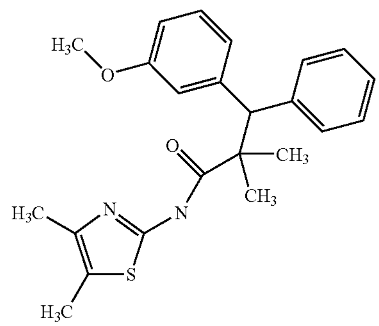 | 394.5 |
| 95 | 2,2-dimethyl-3-(3-(methyloxy)phenyl)-3-phenyl-N-(4-phenyl-1,3-thiaozl-2-yl)propanamide | 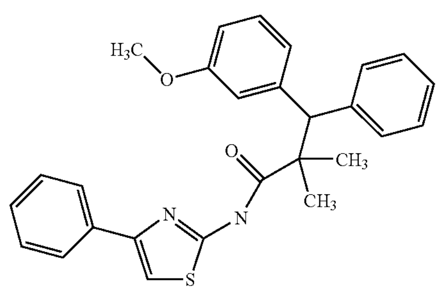 | 442.6 |
| 96 | N-(4-(1,1-dimethylethyl)-1,3-thiazol-2-yl)-2,2-dimethyl-3-(3-(methyloxy)phenyl)-3-phenylpropanamide | 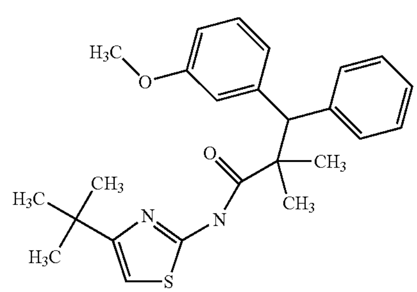 | 422.6 |
| 97 | 2,2-dimethyl-3-(3-(methyloxy)phenyl)-3-phenyl-N-(4-(2-phenylethyl)-,3-thiaozl-2-yl)propanamide | 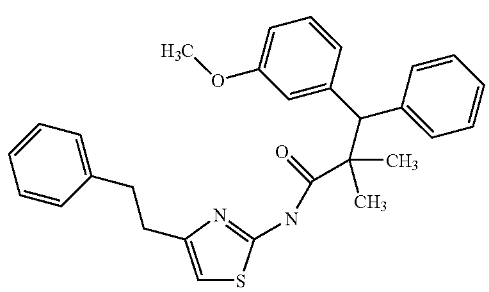 | 470.6 |

| Example No. | Name | Structure | MS [m/z (M + H)] |
|---|---|---|---|
| 98 | 2,2-dimethyl-3-(3-(methyloxy)phenyl)-N-(4-(2-naphthalenyl)-1,3-thiazol-2-yl)-3-phenylpropanamide | 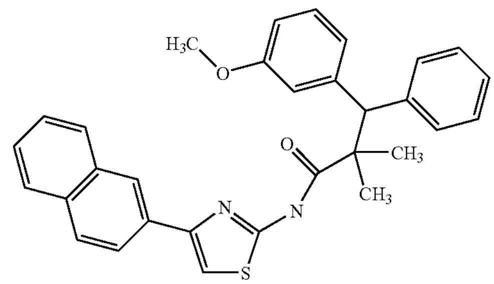 | 492.6 |
| 99 | 2,2-dimethyl-3-(3-(methyloxy)phenyl)-N-(4-(1-naphthalenyl)-1,3-thiazol-2-yl)-3-phenylpropanamide | 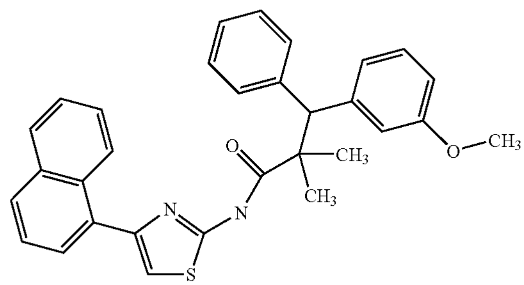 | 492.6 |
| 100 | ethyl 2-((2,2-dimethyl-3-(3-(methyloxy)phenyl)-3-phenylpropanoyl)amino)-4-methyl-1,3-thiazole-5-carboxylate | 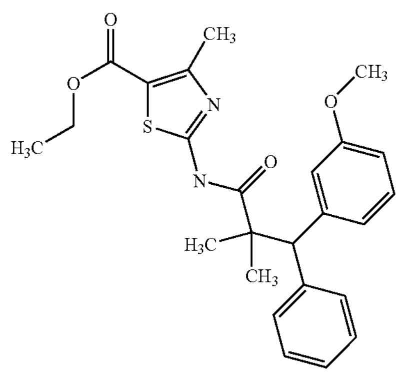 | 452.6 |
| 101 | N-1,3-benzothiazol-2-yl-2,2-dimethyl-3-(3-(methyloxy)phenyl)-3-phenylpropanamide | 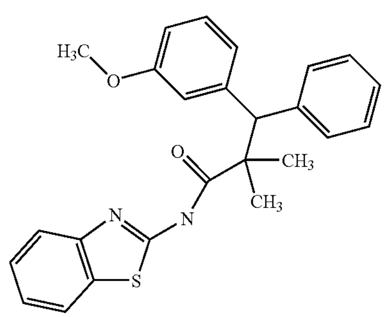 | 416.5 |
| 102 | N-(6-chloro-1,3-benzothiazol-2-yl)-2,2-dimethyl-3-(3-(methyloxy)phenyl)-3-phenylpropanamide | 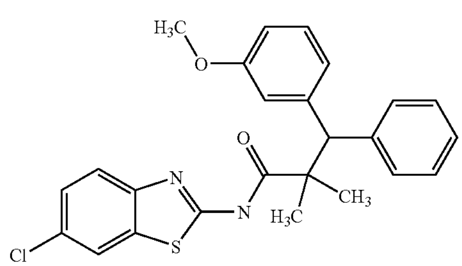 | 451 |

-continued

| Example No. | Name | Structure | MS [m/z (M + H)] |
|---|---|---|---|
| 103 | 2,2-dimethyl-3-(4-(methyloxy)phenyl)-3-phenyl-N-1,3-thiazol-2-ylpropanamide | 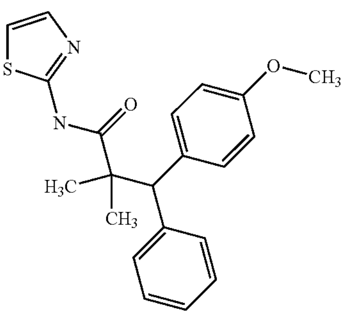 | 366.5 |
| 104 | 2,2-dimethyl-3-(4-(methyloxy)phenyl)-N-(4-methyl-1,3-thiazol-2-yl)-3-phenylpropanamide | 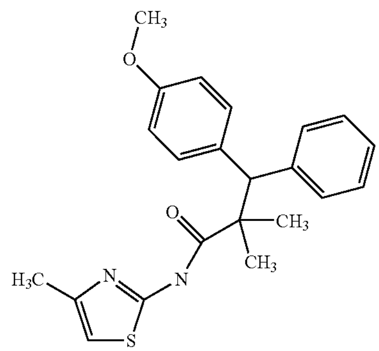 | 380.5 |
| 105 | 2,2-dimethyl-3-(4-(methyloxy)phenyl)-N-(5-methyl-1,3-thiazol-2-yl)-3-phenylpropanamide | 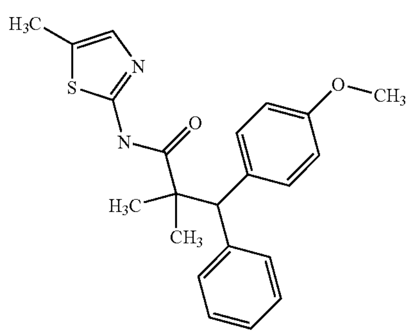 | 380.5 |
| 106 | N-(4,5-dimethyl-1,3-thiazol-2-yl)-2,2-dimethyl-3-(4-(methyloxy)phenyl)-3-phenylpropanamide | 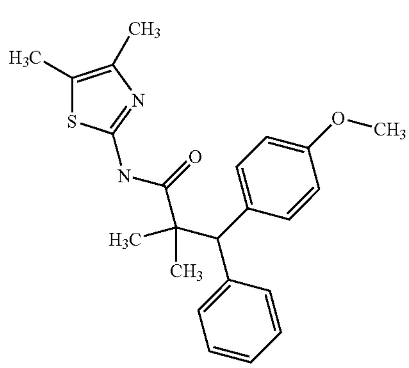 | 394.5 |

| Example No. | Name | Structure | MS [m/z (M + H)] |
|---|---|---|---|
| 107 | 2,2-dimethyl-3-(4-(methyloxy)phenyl)-3-phenyl-N-(4-phenyl-1,3-thiaozl-2-yl)propanamide | 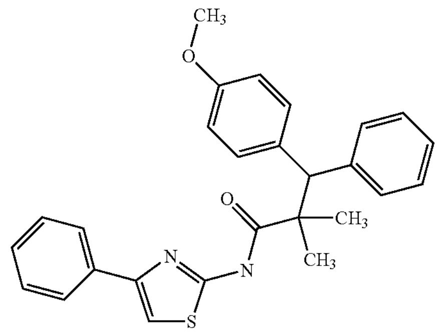 | 442.6 |
| 108 | N-(4-(1,1-dimethylethyl)-1,3-thiazol-2-yl)-2,2-dimethyl-3-(4-(methyloxy)phenyl)-3-phenylpropanamide | 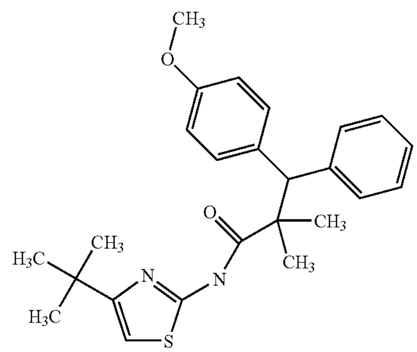 | 422.6 |
| 109 | 2,2-dimethyl-3-(4-(methyloxy)phenyl)-3-phenyl-N-(4-(2-phenylethyl)-1,3-thiazol-2-yl)propanamide | 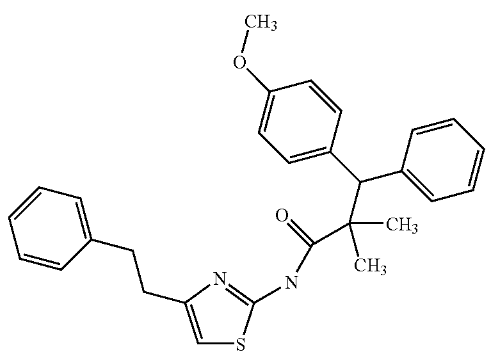 | 470.6 |
| 110 | 2,2-dimethyl-3-(4-(methyloxy)phenyl)-N-(4-(2-naphthalenyl)-1,3-thiazol-2-yl)-3-phenylpropanamide | 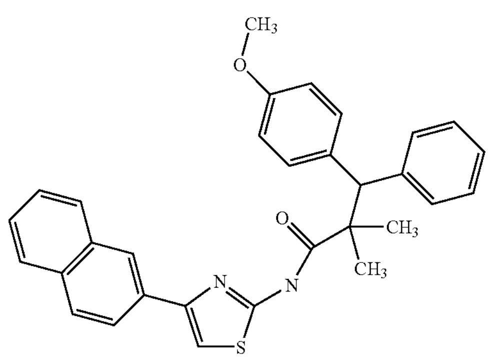 | 492.6 |

| Example No. | Name | Structure | MS [m/z (M + H)] |
|---|---|---|---|
| 111 | 2,2-dimethyl-3-(4-(methyloxy)phenyl)-N-(4-(1-naphthalenyl)-1,3-thiazol-2-yl)-3-phenylpropanamide | 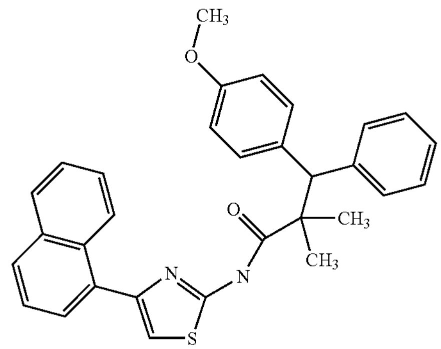 | 492.6 |
| 112 | ethyl 2-((2,2-dimethyl-3-(4-(methyloxy)phenyl)-3-phenylpropanoyl)amino)-4-methyl-1,3-thiazole-5-carboxylate | 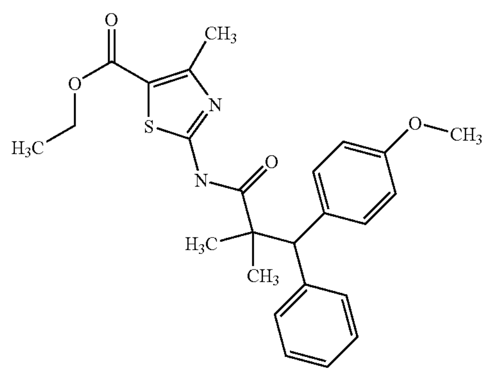 | 452.6 |
| 113 | N-1,3-benzothiazol-2-yl-2,2-dimethyl-3-(4-(methyloxy)phenyl)-3-phenylpropanamide | 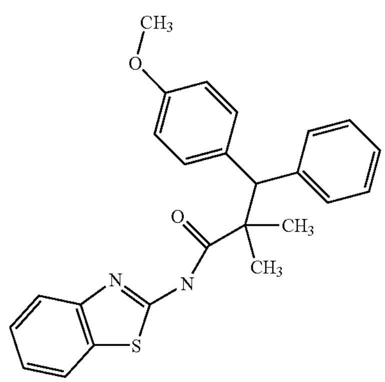 | 416.5 |
| 114 | N-(6-chloro-1,3-benzothiazol-2-yl)-2,2-dimethyl-3-(4-(methyloxy)phenyl)-3-phenylpropanamide | 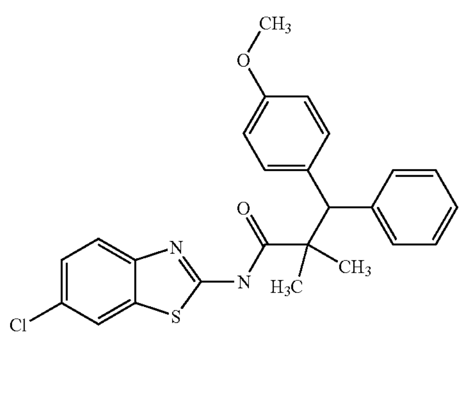 | 451 |

-continued

| Example No. | Name | Structure | MS [m/z (M + H)] |
|---|---|---|---|
| 116 | 2,2-dimethyl-3-phenyl-N-1,3-thiazol-2-yl-3-(4-(trifluoromethyl)phenyl)propanamide | 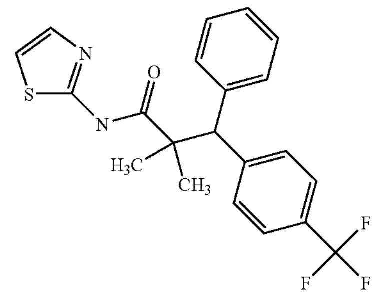 | 404.5 |
| 117 | 2,2-dimethyl-N-(4-methyl-1,3-thiazol-2-yl)-3-phenyl-3-(4-(trifluoromethyl)phenyl)propanamide | 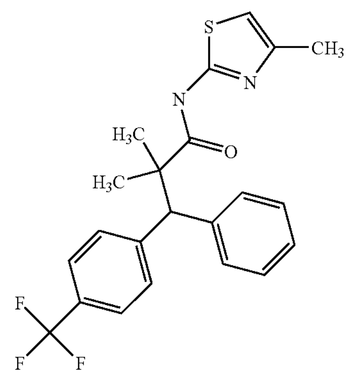 | 418.5 |
| 118 | 2,2-dimethyl-N-(5-methyl-1,3-thiazol-2-yl)-3-phenyl-3-(4-(trifluoromethyl)phenyl)propanamide | 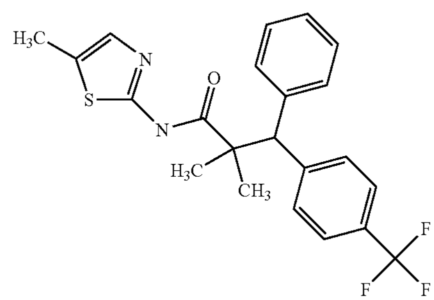 | 418.5 |
| 119 | N-(4,5-dimethyl-1,3-thiazol-2-yl)-2,2-dimethyl-3-phenyl-3-(4-(trifluoromethyl)phenyl)propanamide | 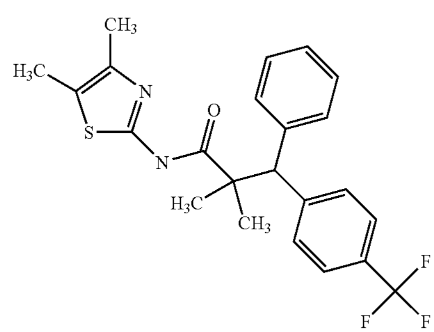 | 432.5 |

-continued

| Example No. | Name | Structure | MS [m/z (M + H)] |
|---|---|---|---|
| 120 | 2,2-dimethyl-3-phenyl-N-(4-phenyl-1,3-thiazol-2-yl)-3-(4-(trifluoromethyl)phenyl)propanamide | 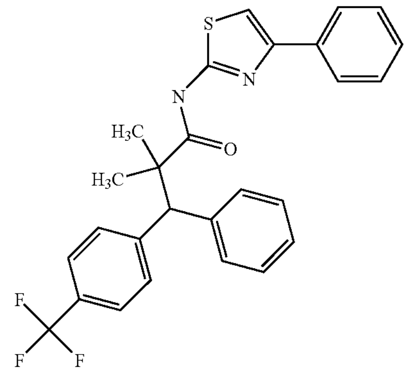 | 480.6 |
| 121 | N-(4-(1,1-dimethylethyl)-1,3-thiazol-2-yl)-2,2-dimethyl-3-phenyl-3-(4-(trifluoromethyl)phenyl)propanamide | 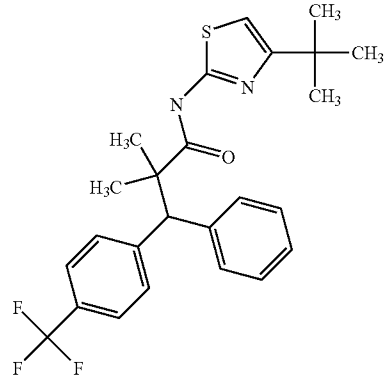 | 460.6 |
| 122 | 2,2-dimethyl-3-phenyl-N-(4-(2-phenylethyl)-1,3-thiazol-2-yl)-3-(4-(trifluoromethyl)phenyl)propanamide | 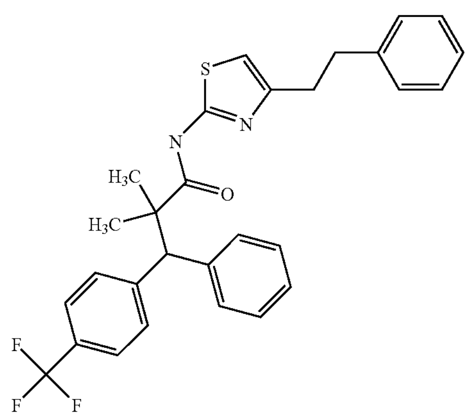 | 508.6 |
| 123 | 2,2-dimethyl-N-(4-(2-naphthalenyl)-1,3-thiazol-2-yl)-3-phenyl-3-(4-(trifluoromethyl)phenyl)propanamide | 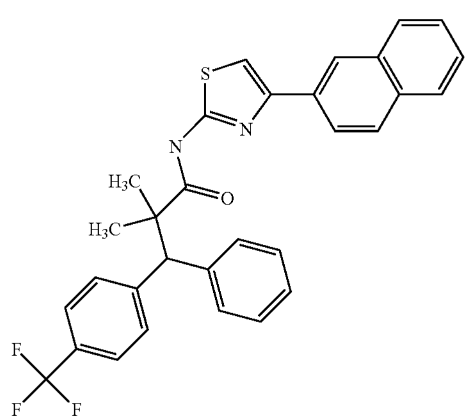 | 530.6 |

-continued

| Example No. | Name | Structure | MS [m/z (M + H)] |
|---|---|---|---|
| 124 | 2,2-dimethyl-N-(4-(1-naphthalenyl)-1,3-thiazol-2-yl)-3-phenyl-3-(4-(trifluoromethyl)phenyl)propanamide | 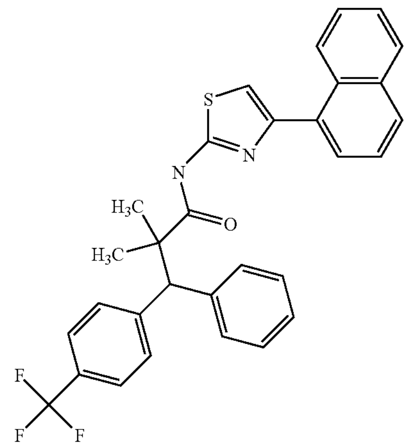 | 530.6 |
| 125 | ethyl 2-((2,2-dimethyl-3-phenyl-3-(4-(trifluoromethyl)phenyl)propanoyl)amino)-4-methyl-1,3-thiazole-5-carboxylate | 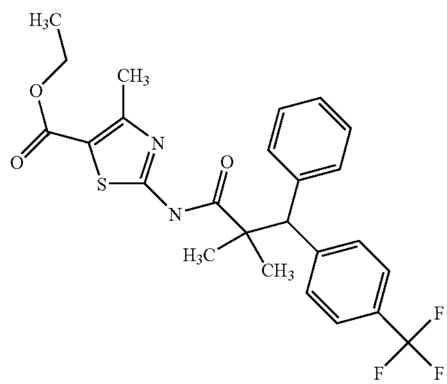 | 490.5 |
| 126 | N-1,3-benzothiazol-2-yl-2,2-dimethyl-3-phenyl-3-(4-(trifluoromethyl)phenyl)propanamide | 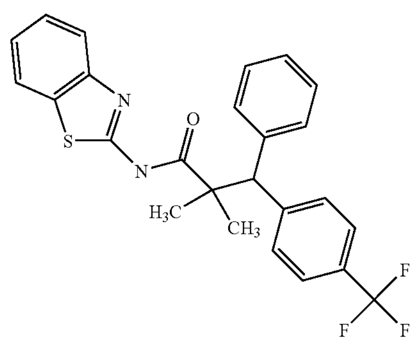 | 454.5 |
| 127 | N-(6-chloro-1,3-benzothiazol-2-yl)-2,2-dimethyl-3-phenyl-3-(4-(trifluoromethyl)phenyl)propanamide | 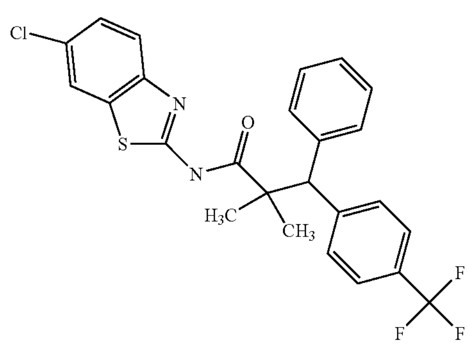 | 489 |

-continued

| Example No. | Name | Structure | MS [m/z (M + H)] |
|---|---|---|---|
| 128 | 3,3-bis(4-fluorophenyl)-2,2-dimethyl-N-1,3-thiazol-2-ylpropanamide | 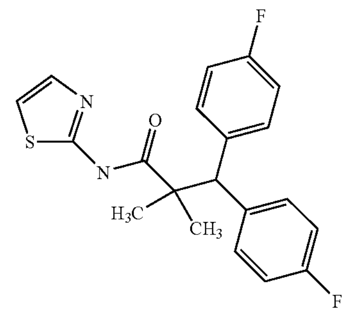 | 372.4 |
| 129 | 3,3-bis(4-fluorophenyl)-2,2-dimethyl-N-(4-methyl-1,3-thiazol-2-yl)propanamide | 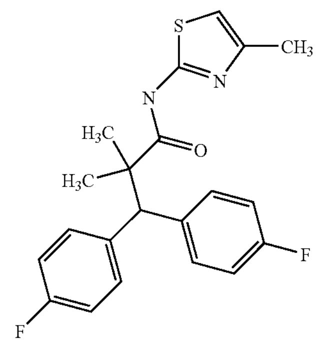 | 386.5 |
| 130 | 3,3-bis(4-fluorophenyl)-2,2-dimethyl-N-(5-methyl-1,3-thiazol-2-yl)propanamide | 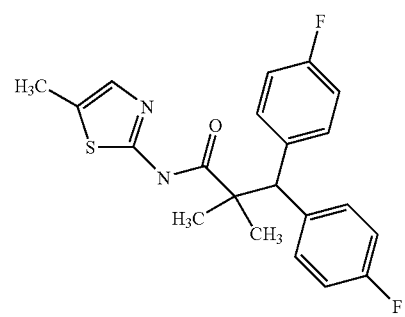 | 386.5 |
| 131 | N-(4,5-dimethyl-1,3-thiazol-2-yl)-3,3-bis(4-fluorophenyl)-2,2-dimethylpropanamide | 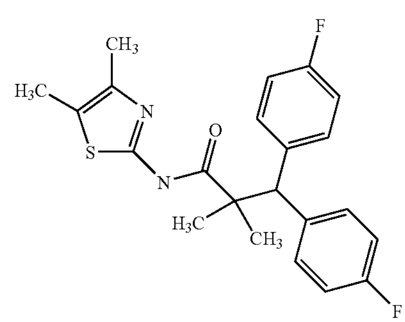 | 400.5 |

-continued

| Example No. | Name | Structure | MS [m/z (M + H)] |
|---|---|---|---|
| 132 | 3,3-bis(4-fluorophenyl)-2,2-dimethyl-N-(4-phenyl-1,3-thiazol-2-yl)propanamide | 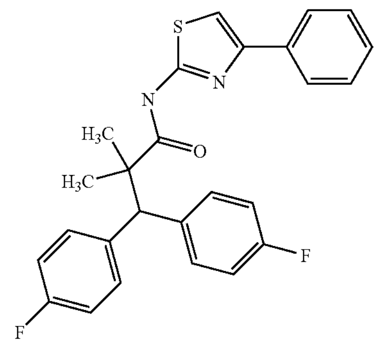 | 448.5 |
| 133 | N-(4-(1,1-dimethylethyl)-1,3-thiazol-2-yl)-3,3-bis(4-fluorophenyl)-2,2-dimethylpropanamide | 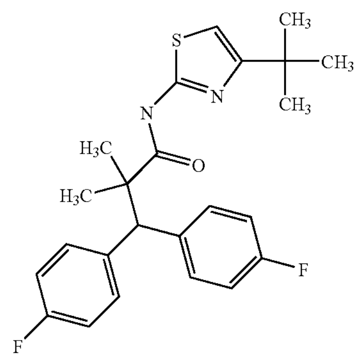 | 428.5 |
| 134 | 3,3-bis(4-fluorophenyl)-2,2-dimethyl-N-(4-(2-naphthalenyl)-1,3-thiazol-2-yl)propanamide | 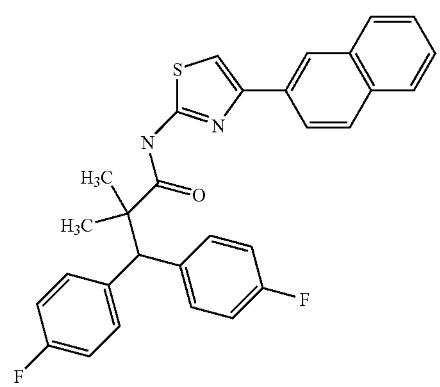 | 498.6 |
| 135 | 3,3-bis(4-fluorophenyl)-2,2-dimethyl-N-(4-(1-naphthalenyl)-1,3-thiazol-2-yl)propanamide | 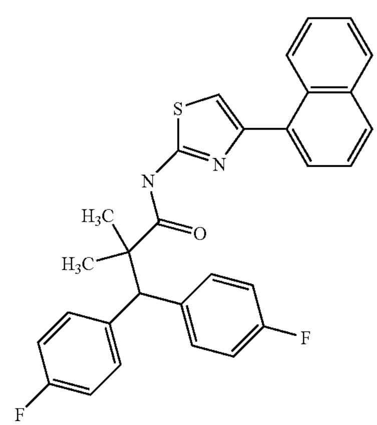 | 498.6 |

-continued

| Example No. | Name | Structure | MS [m/z (M + H)] |
|---|---|---|---|
| 136 | ethyl 2-((3,3-bis(4-fluorophenyl)-2,2-dimethylpropanoyl)amino)-4-methyl-1,3-thiazole-5-carboxylate | 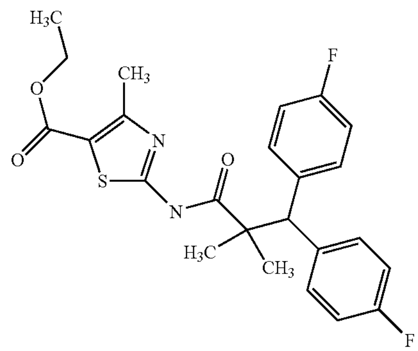 | 458.5 |
| 137 | N-1,3-benzothiazol-2-yl-3,3-bis(4-fluorophenyl)-2,2-dimethylpropanamide | 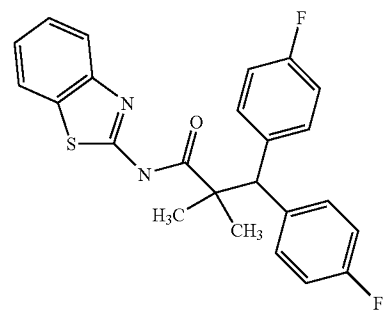 | 422.5 |
| 138 | N-(6-chloro-1,3-benzothiazol-2-yl)-3,3-bis(4-fluorophenyl)-2,2-dimethylpropanamide | 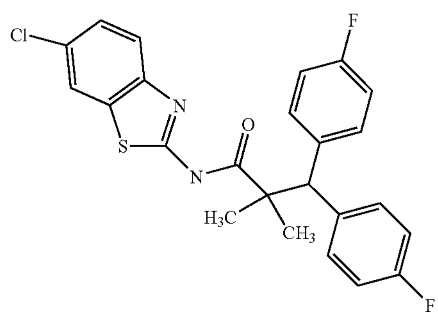 | 456.9 |
| 139 | 3,3-bis(4-fluorophenyl)-N-1H-imidazol-2-yl-2,2-dimethylpropanamide | 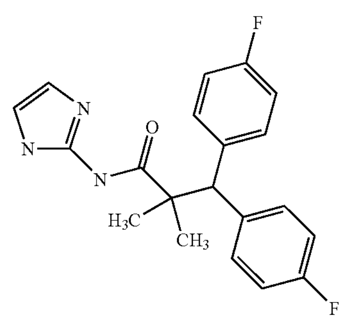 | 355.4 |
| 140 | 1-(diphenylmethyl)-N-1,3-thiazol-2-ylcyclopropanecarboxamide | 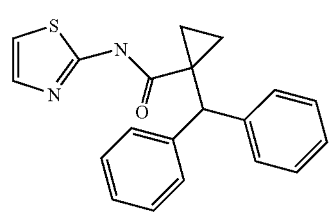 | 334.4 |

-continued

| Example No. | Name | Structure | MS [m/z (M + H)] |
|---|---|---|---|
| 141 | 1-(diphenylmethyl)-N-(4-methyl-1,3-thiazol-2-yl)cyclopropanecarboxamide | 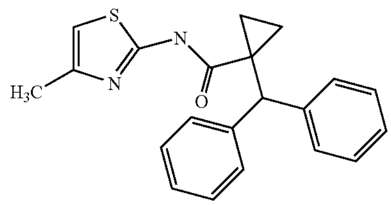 | 348.5 |
| 142 | 1-(diphenylmethyl)-N-(5-methyl-1,3-thiazol-2-yl)cyclopropanecarboxamide | 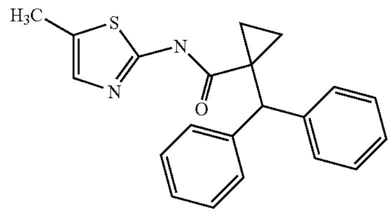 | 348.5 |
| 143 | 1-(diphenylmethyl)-N-(4-phenyl-1,3-thiazol-2-yl)cyclopropanecarboxamide | 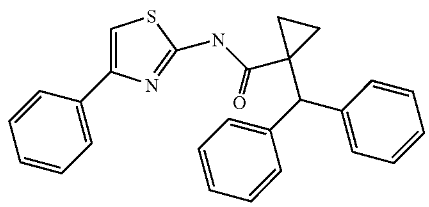 | 410.5 |
| 144 | N-(4-(1,1-dimethylethyl)-1,3-thiazol-2-yl)-1-(diphenylmethyl)cyclopropanecarboxamide | 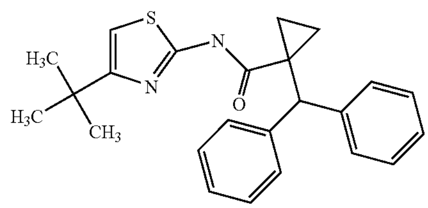 | 390.6 |
| 145 | 1-(diphenylmethyl)-N-(4-(2-phenylethyl)-1,3-thiazol-2-yl)cyclopropanecarboxamide | 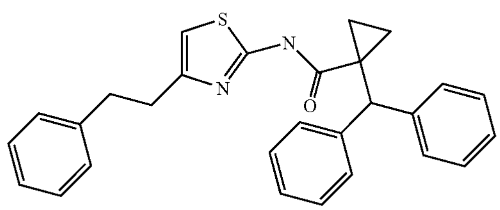 | 438.6 |
| 146 | 1-(diphenylmethyl)-N-(4-(2-naphthalenyl)-1,3-thiazol-2-yl)cyclopropanecarboxamide | 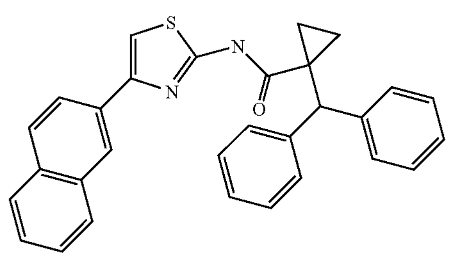 | 460.6 |
| 147 | 1-(diphenylmethyl)-N-(4-(1-naphthalenyl)-1,3-thiazol-2-yl)cyclopropanecarboxamide | 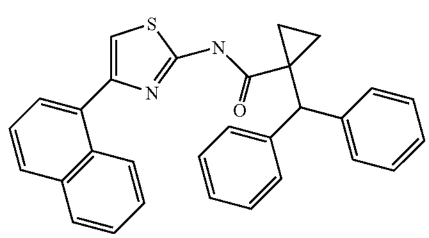 | 460.6 |

-continued

| Example No. | Name | Structure | MS [m/z (M + H)] |
|---|---|---|---|
| 148 | N-1,3-benzothiazol-2-yl-1-(diphenylmethyl)cyclopropanecarboxamide | 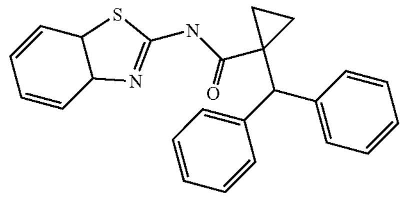 | 384.5 |
| 149 | 1-(diphenylmethyl)-N-1H-imidaozl-2-ylcyclopropanecarboxamide | 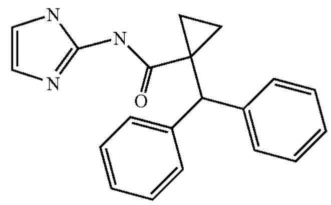 | 317.4 |
| 150 | 1-(diphenylmethyl)-N-(4-(1-naphthalenyl)-1,3-thiazol-2-yl)cyclopentanecarboxamide | 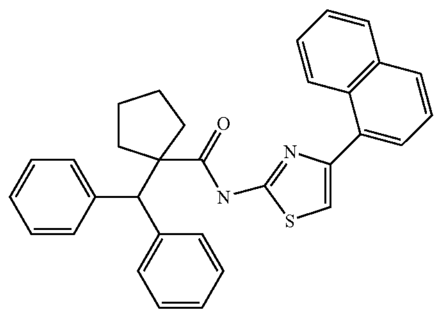 | 488.66 |
| 151 | N-(4-(1,1-dimethylethyl)-1,3-thiazol-2-yl)-1-(diphenylmethyl)cyclopentanecarboxamide | 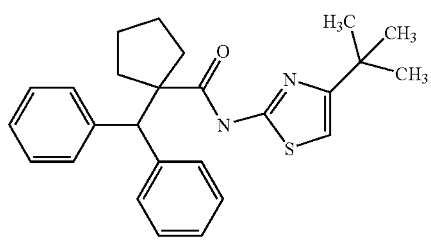 | 418.61 |
| 152 | 2,2-dimethyl-N-(4-(1-naphthalenyl)-1,3-oxazol-2-yl)-3,3-diphenylpropanamide | 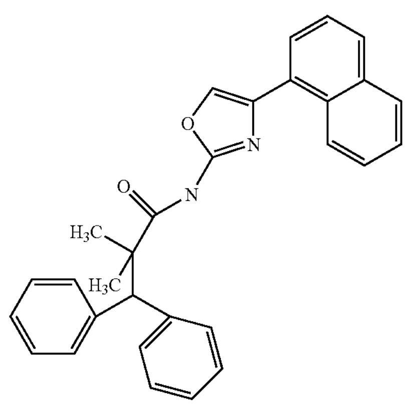 | 446.55 |
| 153 | 1-(diphenylmethyl)-N-1,3-thiazol-2-ylcyclobutanecarboxamide | 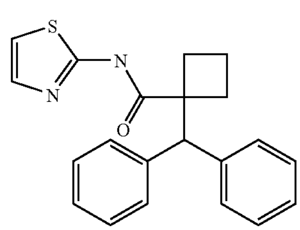 | 348.5 |

| Example No. | Name | Structure | MS [m/z (M + H)] |
|---|---|---|---|
| 154 | N-(4-(1,1-dimethylethyl)-1,3-thiazol-2-yl)-1-(diphenylmethyl)cyclobutanecarboxamide | 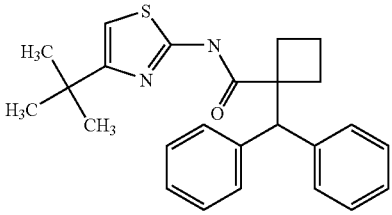 | 404.6 |
| 155 | 1-(diphenylmethyl)-N-(4-(1-naphthalenyl)-1,3-thiazol-2-yl)cyclobutanecarboxamide | 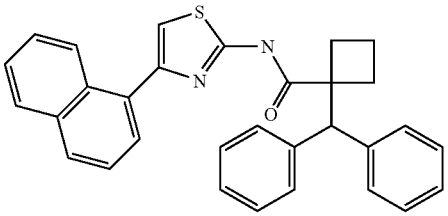 | 474.6 |
| 156 | 1-(diphenylmethyl)-N-1,3-thiazol-2-ylcyclohexanecarboxamide | 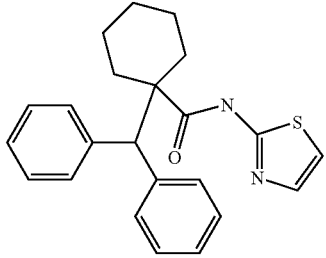 | 376.5 |
| 157 | N-(4-(1,1-dimethylethyl)-1,3-thiazol-2-yl)-1-(diphenylmethyl)cyclohexanecarboxamide | 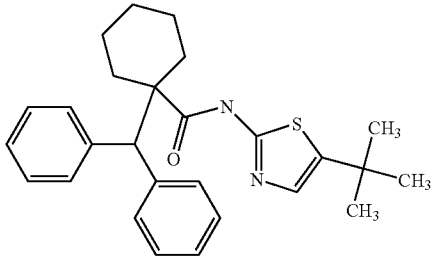 | 432.6 |
| 158 | 1-(diphenylmethyl)-N-(4-(1-naphthalenyl)-1,3-thiazol-2-yl)cyclohexanecarboxamide | 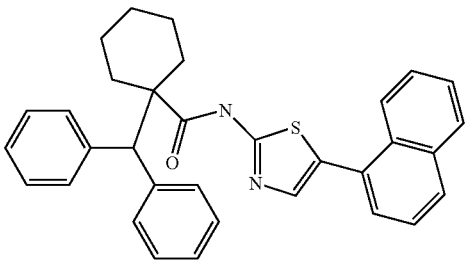 | 502.7 |
| 159 | 2-(diphenylmethyl)-2-ethyl-N-1,3-thiaozl-2-ylbutanamide | 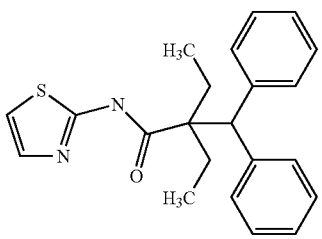 | 364.5 |

-continued

| Example No. | Name | Structure | MS [m/z (M + H)] |
|---|---|---|---|
| 160 | N-(4-(1,1-dimethylethyl)-1,3-thiazol-2-yl)-2-(diphenylmethyl)-2-ethylbutanamide | 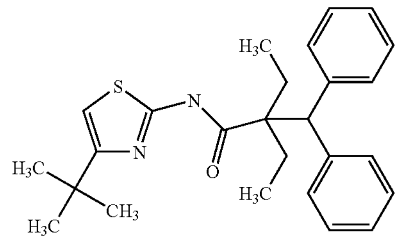 | 420.6 |
| 161 | 2-(diphenylmethyl)-2-ethyl-N-(4-(1-naphthalenyl)-1,3-thiazol-2-yl)butanamide | 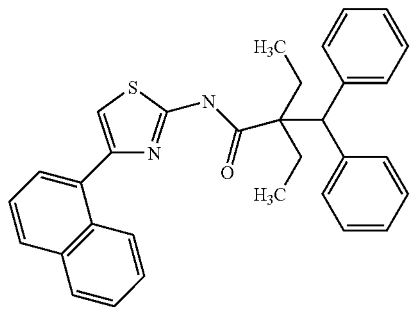 | 490.7 |
| 162 | 1-(diphenylmethyl)-N-1,3-thiazol-2-ylcyclopentanecarboxamide | 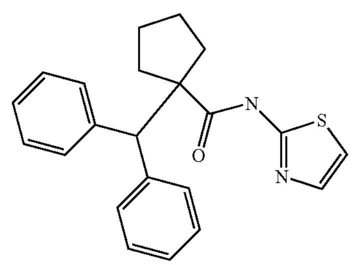 | 362.5 |
| 163 | 2,2-dimethyl-N-(4-(3-(methyloxy)phenyl)-1,3-thiazol-2-yl)-3,3-diphenylpropanamide | 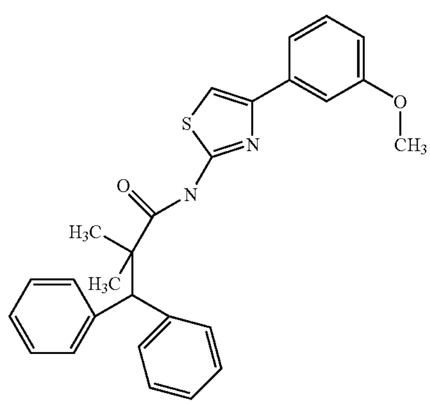 | 442.58 |

-continued

| Example No. | Name | Structure | MS [m/z (M + H)] |
|---|---|---|---|
| 164 | 2,2-dimethyl-N-(4-(4-methyl-1-naphthalenyl)-1,3-thiazol-2-yl)-3,3-diphenylpropanamide | 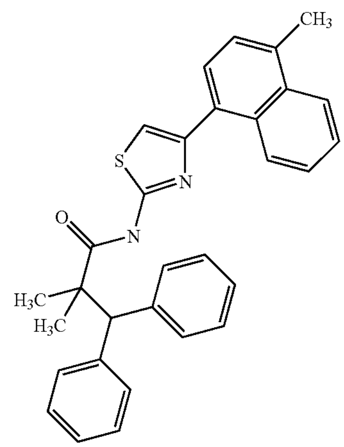 | 476.65 |
| 165 | N-(4-(1-benzofuran-2-yl)-1,3-thiazol-2-yl)-2,2-dimethyl-3,3-diphenylpropanamide | 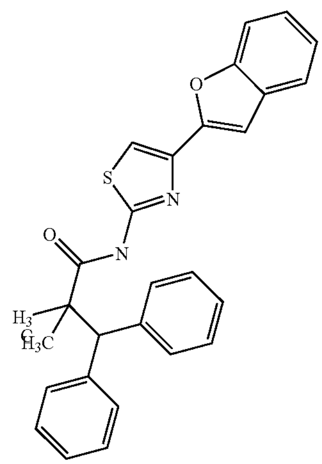 | 452.58 |
| 166 | 2,2-dimethyl-N-(4-(6-(methyloxy)-1-naphthalenyl)-1,3-thiazol-2-yl)-3,3-diphenylpropanamide | 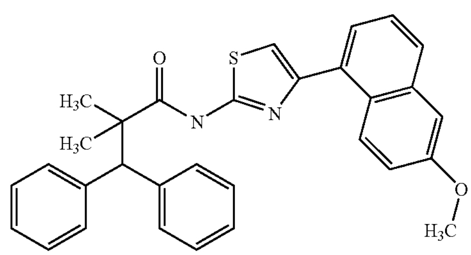 | 492.65 |
| 167 | N-(4-(3-fluorophenyl)-1,3-thiazol-2-yl)-2,2-dimethyl-3,3-diphenylpropanamide | 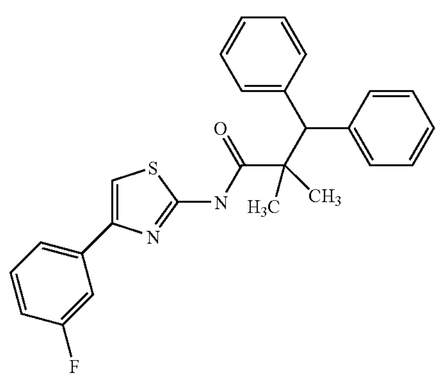 | 430.6 |

-continued

| Example No. | Name | Structure | MS [m/z (M + H)] |
|---|---|---|---|
| 168 | N-(4-(4-fluorophenyl)-1,3-thiazol-2-yl)-2,2-dimethyl-3,3-diphenylpropanamide | 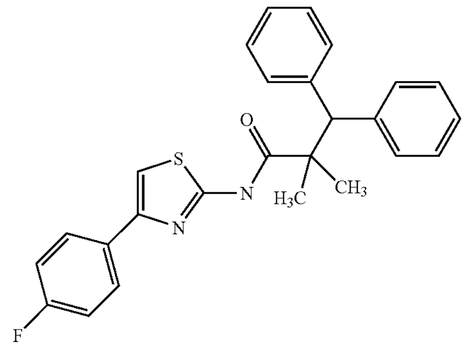 | 430.6 |
| 169 | 2,2-dimethyl-N-(4-(2-nitrophenyl)-1,3-thiazol-2-yl)-3,3-diphenylpropanamide | 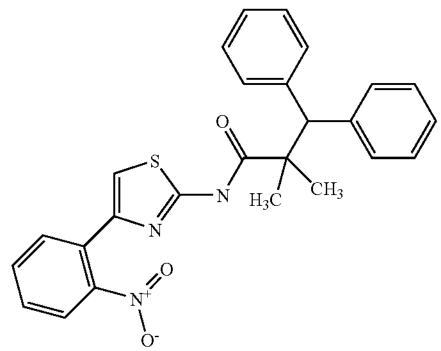 | 457.6 |
| 170 | 2,2-dimethyl-N-(4-(3-methylphenyl)-1,3-thiazol-2-yl)-3,3-diphenylpropanamide | 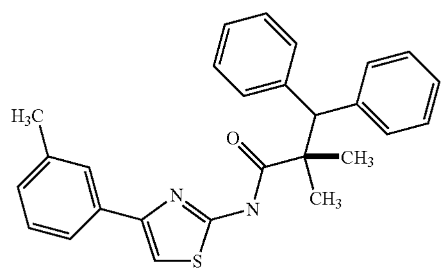 | 426.6 |
| 171 | 2,2-dimethyl-N-(3-(1-naphthalenyl)-1H-pyrazol-5-yl)-3,3-diphenylpropanamide | 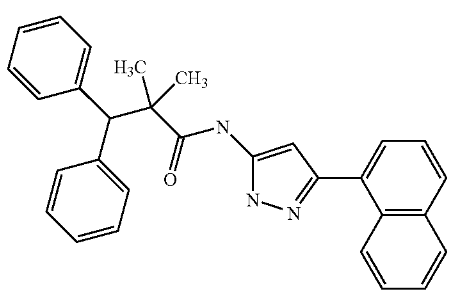 | 445.6 |
| 172 | N-(4-(2-fluorophenyl)-1,3-thiazol-2-yl)-2,2-dimethyl-3,3-diphenylpropanamide | 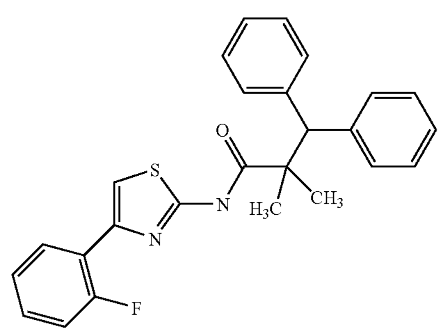 | 430.6 |

-continued

| Example No. | Name | Structure | MS [m/z (M + H)] |
|---|---|---|---|
| 173 | N-(4-(3-chlorophenyl)-1,3-thiazol-2-yl)-2,2-dimethyl-3,3-diphenylpropanamide | 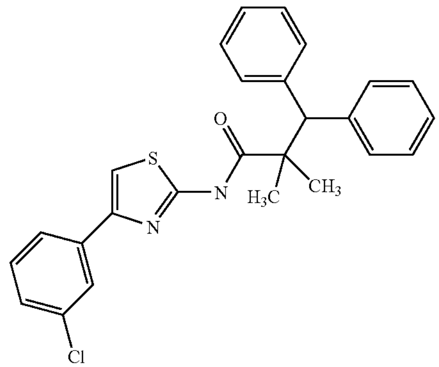 | 447 |
| 174 | N-(4-(2-chlorophenyl)-1,3-thiazol-2-yl)-2,2-dimethyl-3,3-diphenylpropanamide | 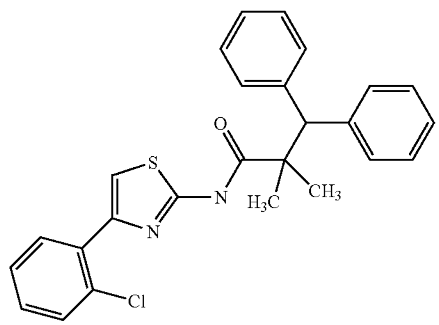 | 447 |
| 175 | 2,2-dimethyl-N-(4-(3-nitrophenyl)-1,3-thiazol-2-yl)-3,3-diphenylpropanamide | 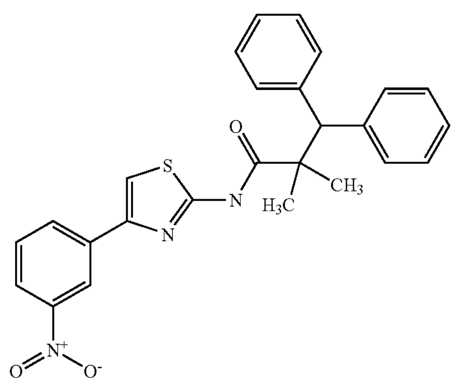 | 457.6 |
| 176 | 2-(diphenylmethyl)-2-methyl-N-1,3-thiazol-2-ylbutanamide | 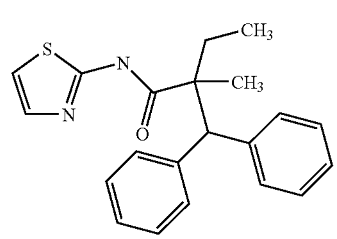 | 350.5 |
| 177 | N-(4-(1,1-dimethylethyl)-1,3-thiazol-2-yl)-2-(diphenylmethyl)-2-methylbutanamide | 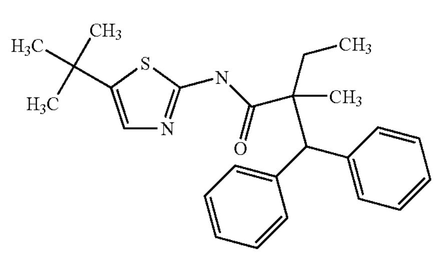 | 406.6 |

| Example No. | Name | Structure | MS [m/z (M + H)] |
|---|---|---|---|
| 178 | 2-(diphenylmethyl)-2-methyl-N-(4-(1-naphthalenyl)-1,3-thiazol-2-yl)butanamide | 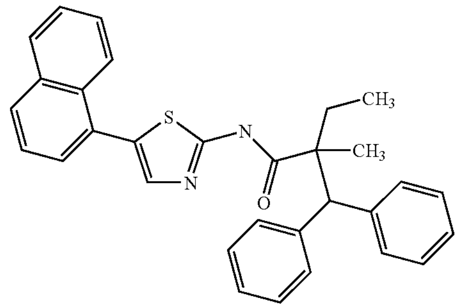 | 476.6 |
| 180 | 2,2-dimethyl-3,3-diphenyl-N-(4-phenyl-1H-imidazol-2-yl)propanamide | 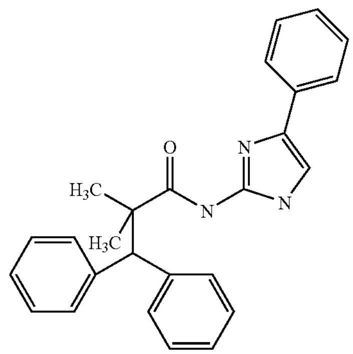 | 395.51 |
| 181 | 2,2-dimethyl-N-(4-(1-methyl-1-phenylethyl)-1,3-thiazol-2-yl)-3,3-diphenylpropanamide | 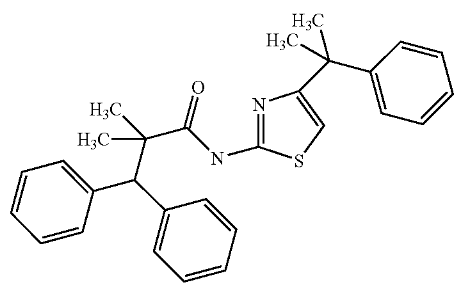 | 454.64 |
| 182 | N-(4-(1,1-dimethylethyl)-1H-imidaozl-2-yl)-2,2-dimethyl-3,3-diphenylpropanamide | 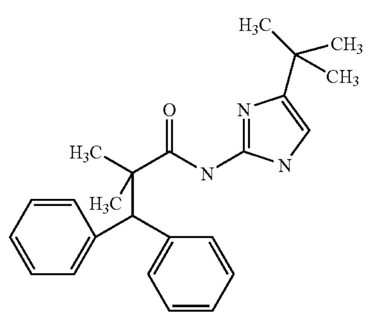 | 375.52 |
| 183 | N-(4-(4-fluoro-1-naphthalenyl)-1,3-thiazol-2-yl)-2,2-dimethyl-3,3-diphenylpropanamide | 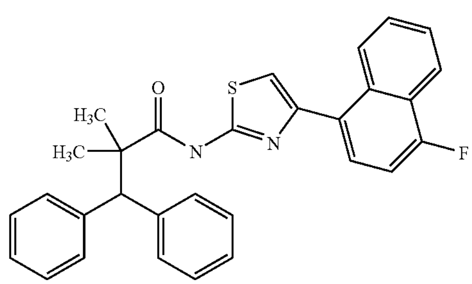 | 480.61 |

| Example No. | Name | Structure | MS [m/z (M + H)] |
|---|---|---|---|
| 184 | 2,2-dimethyl-3,3-diphenyl-N-(4-(4-quinolinyl)-1,3-thiazol-2-yl)propanamide | 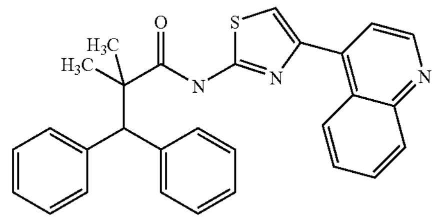 | 463.61 |

Example 185

3,3-Bis-(4-hydroxy-phenyl)-2,2-dimethyl-N-(5-methyl-thiazol-2-yl)-propionamide

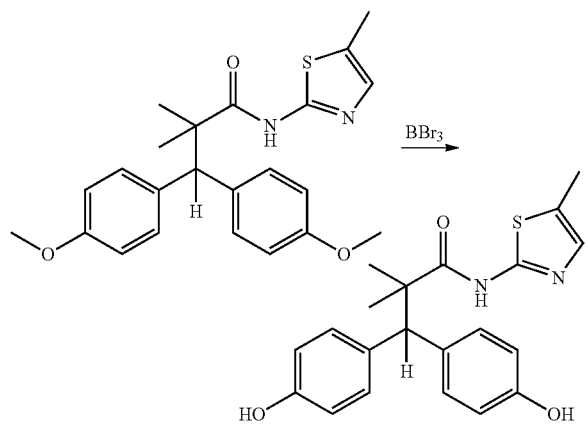

To a solution of Example 70 (20.5 mg, 0.05 mmol, 1.0 equi.) in dichloromethane (5 mL) at 0° C., was added a solution of boron tribromide in dichloromethane (1M, 0.25 mL, 0.25 mmol, 5 equi.). The reaction solution was stirred at 0° C. for 2 hours, then quenched with methanol. The crude product mixture was purified by reversed phased PREP HPLC, followed by neutralization with cation exchange SPE, to yield 8.1 mg (42%) of the title compound of Example 185: LC/MS (m/z 383, (M+H)$^+$); $^1$H NMR (CDCl$_3$) δ 7.07 (m, 4H), 6.55 (m, 4H), 4.26 (s, 1H), 2.24 (s, 3H), 1.21 (s, 6H).

Examples 186 to 221

In a similar manner to the Example 185, the following examples were prepared from the corresponding methoxyphenyl analogs.

| Example No. | Name | Structure | MS [m/z (M + H)] |
|---|---|---|---|
| 186 | 3,3-bis(4-hydroxyphenyl)-2,2-dimethyl-N-1,3-thiazol-2-ylpropanamide | 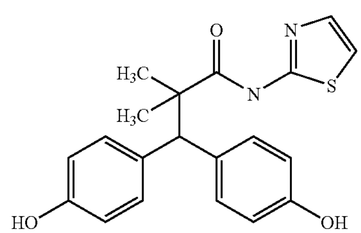 | 368.46 |
| 187 | 3,3-bis(4-hydroxyphenyl)-2,2-dimethyl-N-(5-methyl-1,3-thiazol-2-yl)propanamide | 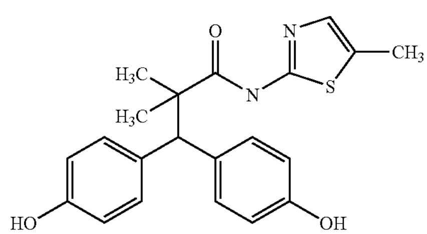 | 382.49 |

-continued

| Example No. | Name | Structure | MS [m/z (M + H)] |
|---|---|---|---|
| 188 | 3,3-bis(4-hydroxyphenyl)-2,2-dimethyl-N-(4-methyl-1,3-thiazol-2-yl)propanamide | 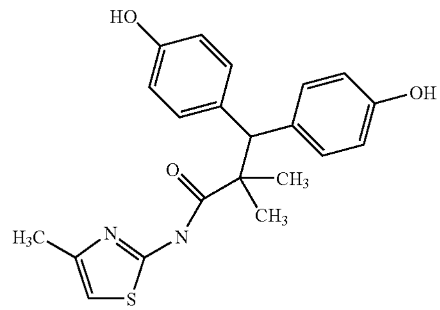 | 382.5 |
| 189 | N-(4,5-dimethyl-1,3-thiazol-2-yl)-3,3-bis(4-hydroxyphenyl)-2,2-dimethylpropanamide | 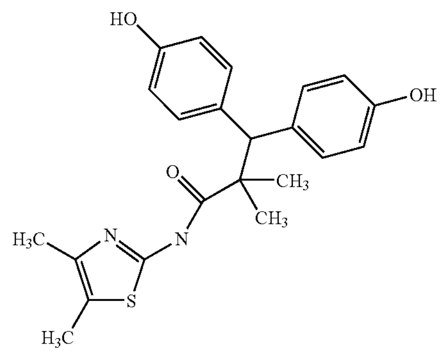 | 396.5 |
| 190 | 3,3-bis(4-hydroxyphenyl)-2,2-dimethyl-N-(4-phenyl-1,3-thiazol-2-yl)propanamide | 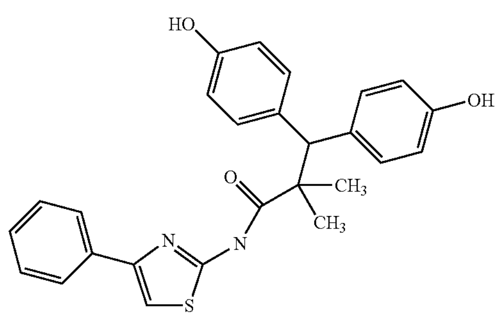 | 444.6 |
| 191 | N-(4-(1,1-dimethylethyl)-1,3-thiazol-2-yl)-3,3-bis(4-hydroyxphenyl)-2,2-dimethylpropanamide | 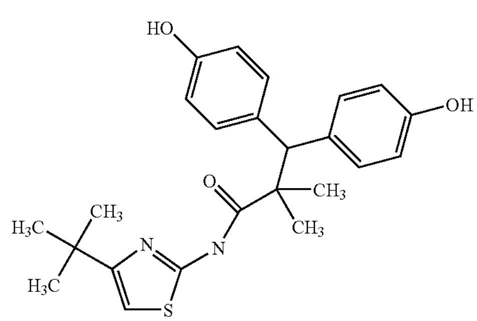 | 424.6 |

-continued

| Example No. | Name | Structure | MS [m/z (M + H)] |
|---|---|---|---|
| 192 | 3,3-bis(4-hydroxyphenyl)-2,2-dimethyl-N-(4-(2-phenylethyl)-1,3-thiazol-2-yl)propanamide | 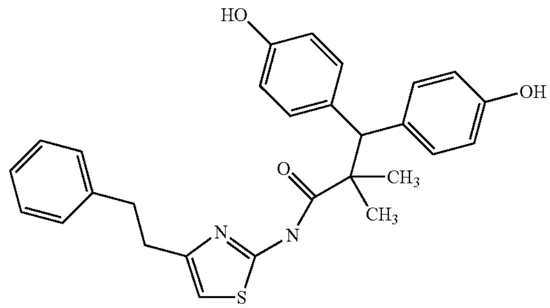 | 472.6 |
| 193 | 3,3-bis(4-hydroxyphenyl)-2,2-dimethyl-N-(4-(1-naphthalenyl)-1,3-thiazol-2-yl)propanamide | 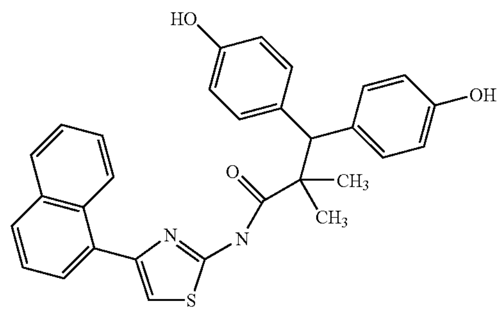 | 494.6 |
| 194 | ethyl 2-((3,3-bis(4-hydroxyphenyl)-2,2-dimethylpropanoyl)amino)-4-methyl-1,3-thiazole-5-carboxylate | 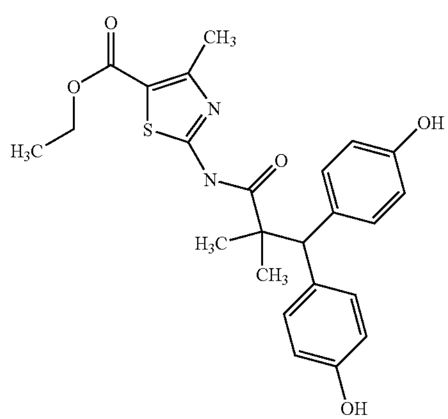 | 454.5 |
| 195 | N-1,3-benzothiazol-2-yl-3,3-bis(4-hydroxyphenyl)-2,2-dimethylpropanamide | 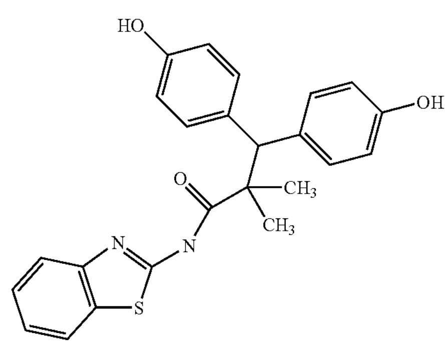 | 418.5 |

-continued

| Example No. | Name | Structure | MS [m/z (M + H)] |
|---|---|---|---|
| 196 | N-(6-chloro-1,3-benzothiazol-2-yl)-3,3-bis(4-hydorxyphenyl)-2,2-dimethylpropanamide | 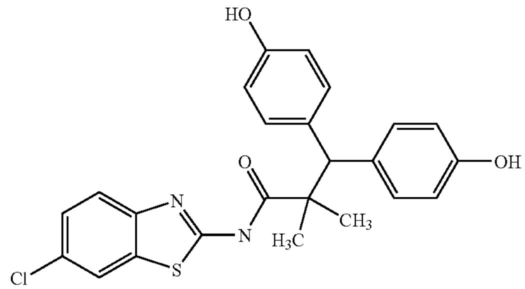 | 453 |
| 197 | 3-(3-hydroxyphenyl)-2,2-dimethyl-3-phenyl-N-1,3-thiazol-2-ylpropanamide | 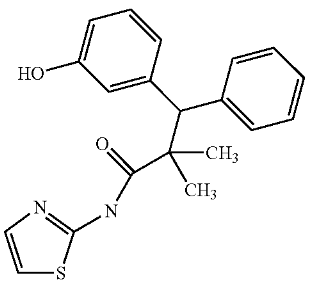 | 352.5 |
| 198 | 3-(3-hydroxyphenyl)-2,2-dimethyl-N-(4-methyl-1,3-thiazol-2-yl)-3-phenylpropanamide | 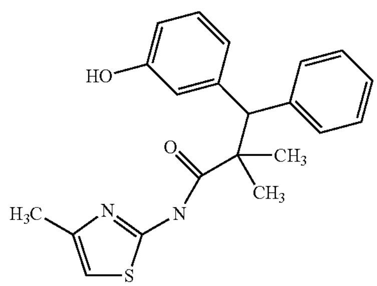 | 366.5 |
| 199 | 3-(3-hydroxyphenyl)-2,2-dimethyl-N-(5-methyl-1,3-thiazol-2-yl)-3-phenylpropanamide | 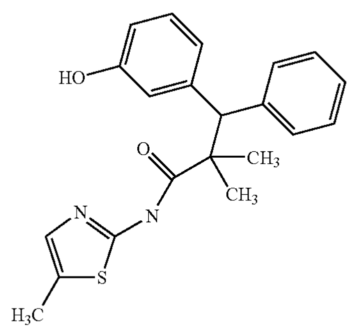 | 366.5 |
| 200 | N-(4,5-dimethyl-1,3-thiazol-2-yl)-3-(3-hydroxyphenyl)-2,2-dimethyl-3-phenylpropanamide | 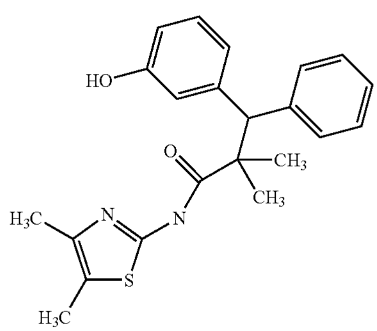 | 380.5 |

-continued

| Example No. | Name | Structure | MS [m/z (M + H)] |
|---|---|---|---|
| 201 | 3-(3-hydroxyphenyl)-2,2-dimethyl-3-phenyl-N-(4-phenyl-1,3-thiazol-2-yl)propanamide | 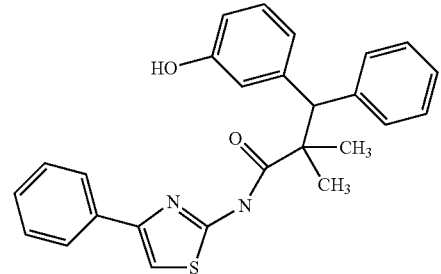 | 428.6 |
| 202 | N-(4-(1,1-dimethylethyl)-1,3-thiazol-2-yl)-3-(3-hydroxyphenyl)-2,2-dimethyl-3-phenylpropanamide | 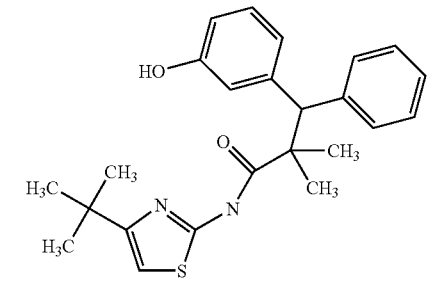 | 408.6 |
| 203 | 3-(3-hydroxyphenyl)-2,2-dimethyl-3-phenyl-N-(4-(2-phenylethyl)-1,3-thiazol-2-yl)propanamide | 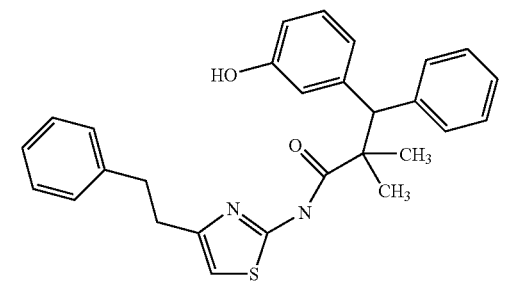 | 456.6 |
| 204 | 3-(3-hydroxyphenyl)-2,2-dimethyl-N-(4-2-naphthalenyl)-1,3-thiazol-2-yl)-3-phenylpropanamide | 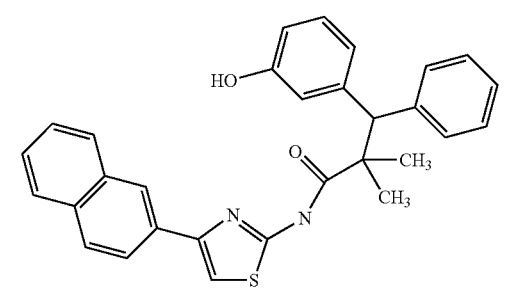 | 478.6 |
| 205 | 3-(3-hydroxyphenyl)-2,2-dimethyl-N(4-(1-naphthalenyl)-1,3-thiazol-2-yl)-3-phenylpropanamide | 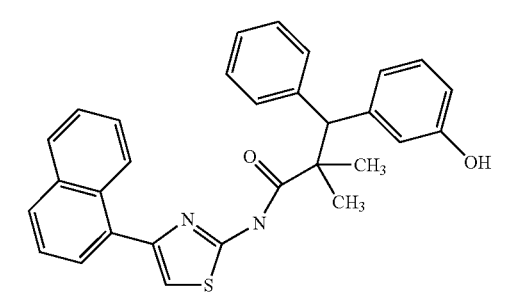 | 478.6 |

-continued

| Example No. | Name | Structure | MS [m/z (M + H)] |
|---|---|---|---|
| 206 | ethyl 2-((3-(3-hydroxyphenyl)-2,2-dimethyl-3-phenylpropanoyl)amino)-4-methyl-1,3-thiazole-5-carboxylate | 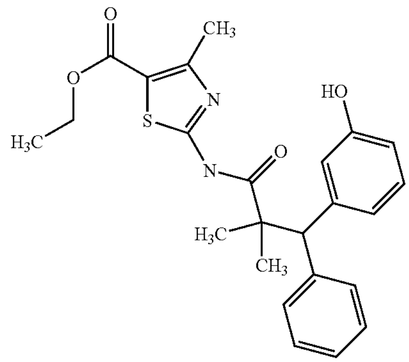 | 438.5 |
| 207 | N-1,3-benzothiazol-2-yl-3-(3-hydroxyphenyl)-2,2-dimethyl-3-phenylpropanamide | 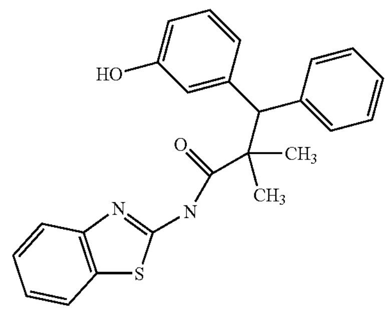 | 402.5 |
| 208 | N-(6-chloro-1,3-benzothiazol-2-yl)-3-(3-hydroxyphenyl)-2,2-dimethyl-3-phenylpropanamide | 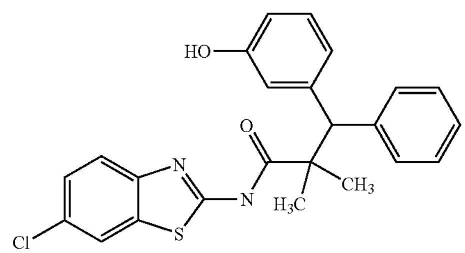 | 437 |
| 209 | 3-(4-hydroxyphenyl)-2,2-dimethyl-3-phenyl-N-1,3-thiazol-2-ylpropanamide | 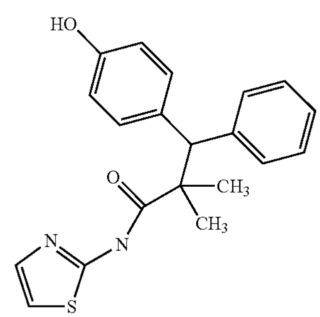 | 352.5 |
| 210 | 3-(4-hydroxyphenyl)-2,2-dimethyl-N-(4-methyl-1,3-thiazol-2-yl)-3-phenylpropanamide | 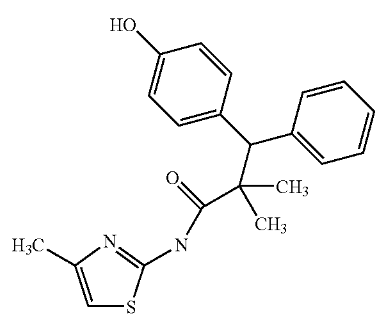 | 366.5 |

-continued
| Example No. | Name | Structure | MS [m/z (M + H)] |
|---|---|---|---|
| 211 | 3-(4-hydroxyphenyl)-2,2-dimethyl-N-(5-methyl-1,3-thiazol-2-yl)-3-phenylpropanamide | 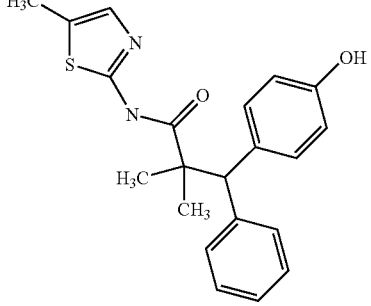 | 366.5 |
| 212 | N-(4,5-dimethyl-1,3-thiaozl-2-yl)-3-(4-hydroxyphenyl)-2,2-dimethyl-3-phenylpropanamide | 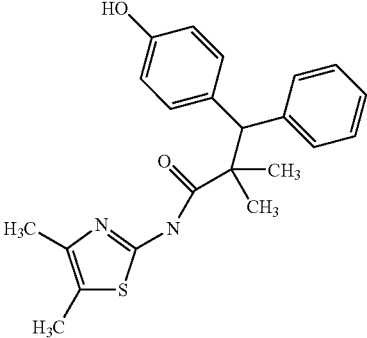 | 380.5 |
| 213 | 3-(4-hydroxyphenyl)-2,2-dimethyl-3-phenyl-N-(4-phenyl-1,3-thiazol-2-yl)propanamide | 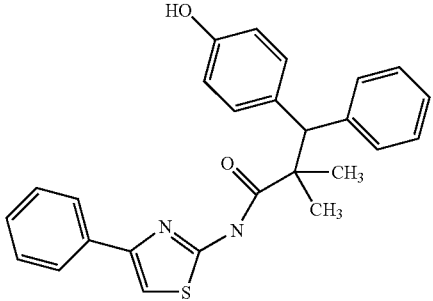 | 428.6 |
| 214 | N-(4-(1,1-dimethylethyl)-1,3-thiazol-2-yl)-3-(4-hydroxyphenyl)-2,2-dimethyl-3-phenylpropanamide | 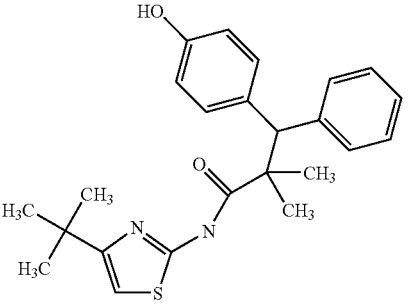 | 408.6 |

-continued
| Example No. | Name | Structure | MS [m/z (M + H)] |
|---|---|---|---|
| 215 | 3-(4-hydroxyphenyl)-2,2-dimethyl-3-phenyl-N-(4-(2-phenylethyl)-1,3-thiazol-2-yl)propanamide | 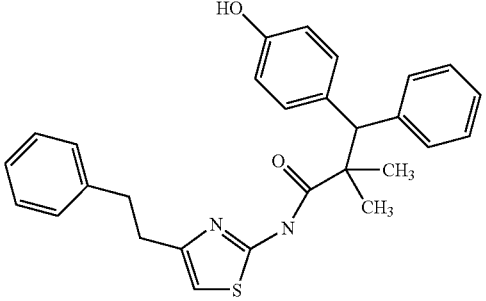 | 456.6 |
| 216 | 3-(4-hydroxyphenyl)-2,2-dimethyl-N-(4-(2-naphthalenyl)-1,3-thiazol-2-yl)-3-phenylpropanamide | 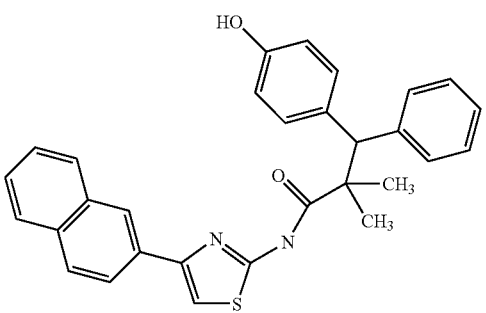 | 478.6 |
| 217 | 3-(4-hydroxyphenyl)-2,2-dimethyl-N-(4-(1-naphthalenyl)-1,3-thiazol-2-yl)-3-phenylpropanamide | 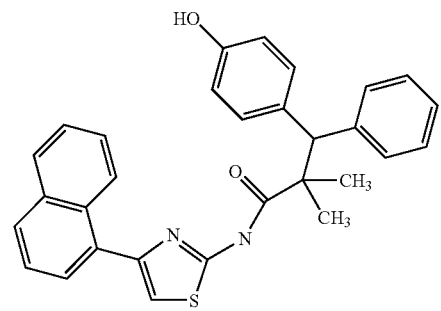 | 478.6 |
| 218 | ethyl 2-((3-(4-hydroxyphenyl)-2,2-dimethyl-3-phenylpropanoyl)amino)-4-methyl-1,3-thiazole-5-carboxylate | 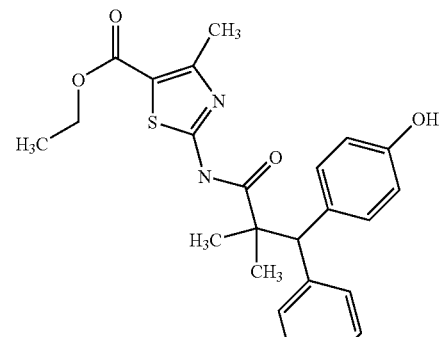 | 438.5 |

| Example No. | Name | Structure | MS [m/z (M + H)] |
|---|---|---|---|
| 219 | N-1,3-benzothiazol-2-yl-3-(4-hydroxyphenyl)-2,2-dimethyl-3-phenylpropanamide | 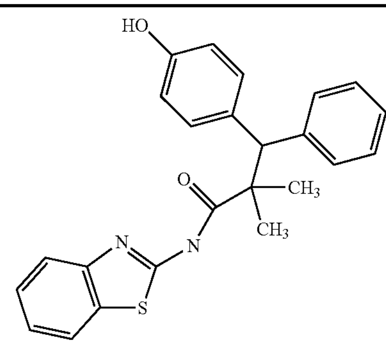 | 402.5 |
| 220 | N-(6-chloro-1,3-benzothiazol-2-yl)-3-(4-hydroxyphenyl)-2,2-dimethyl-3-phenylpropanamide | 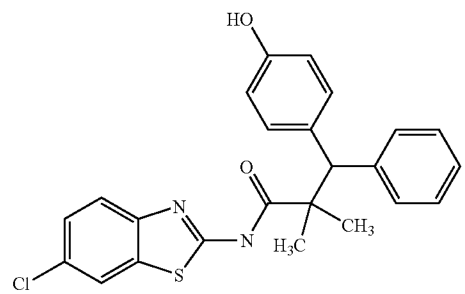 | 437 |
| 221 | N-(4-(6-hydroxy-1-naphthalenyl)-1,3-thiazol-2-yl)-2,2-dimethyl-3,3-diphenylpropanamide | 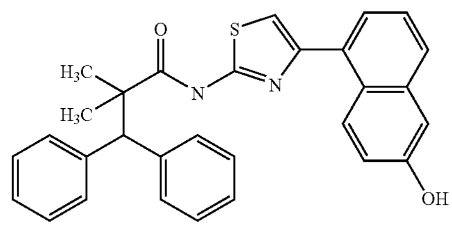 | 478.62 |

Example 222

3-(4-Fluorophenyl)-2,2-dimethyl-3-(4-(4-morpholinyl)phenyl)-N-1,3-thiazol-2-ylpropanamide

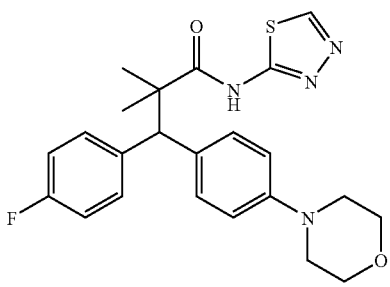

To a solution of the acid of Preparation 14a (51 mg, 0.142 mmol) in CH3CN (3 mL) were added 1-[3-(dimethylamino)propyl]-3-ethylcarbodiimide hydrochloride (EDC) (48.3 mg, 0.213 mmol) and 1-hydroxy-7-benzotriazole (HOBt) (34 mg, 0.213 mmol). After stirring for 5 minutes, to the solution were added 4-(4-methyl-naphthalen-1-yl)-thiazol-2-ylamine (50.4 mg, 0.426 mmol) and diisopropylethyl amine (0.742 ml, 0.426 mmol). The reaction was heated at 75° C. for 12 hours. The reaction mixture was filtered, and purified by preparative HPLC to give the title compound of Example 222 as a white solid (36 mg, 58% yield). LC/MS (m/z) 440.17 [(M+H)$^+$]; HPLC Rt: 3.12 min. $^1$H NMR (400 MHz, CDCl$_3$): δ 7.34 (1H, m), 7.18-7.26 (5H, m), 6.79-6.93 (4H, m), 4.42 (1H, s), 3.78 (4H, m), 3.06 (4H, m), 1.34 (6H, s). LC/MS (m/z) 440.17 [(M+H)$^+$]; HPLC Rt: 3.120 min.

Examples 223 to 235

In a similar manner to Example 222, Examples 223 to 235 were prepared via the amidation reactions of acids of Preparations (14b) to (14f) with the appropriate amines (Compounds are racemic unless noted)

| Example No. | Name | Structure | MS [m/z (M + H)] | HPLC Rt: minute |
|---|---|---|---|---|
| 223 | 2,2-dimethyl-3-(4-(4-morpholinyl)phenyl)-3-phenyl-N-(4-((4-(4-pyridinyl)phenyl)methyl)-1,3-thiazol-2-yl)propanamide | 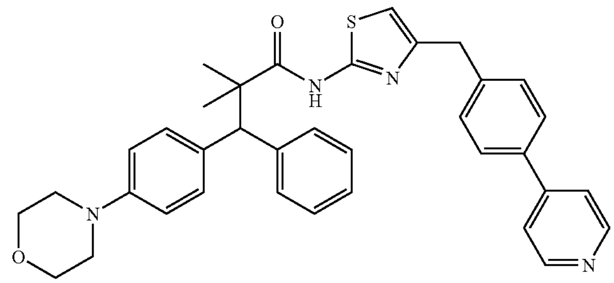 | 589.41 | 3.08 |
| 224 | 2,2-dimethyl-3-(4-(4-morpholinyl)phenyl)-3-phenyl-N-1,3-thiazol-2-ylpropanamide | 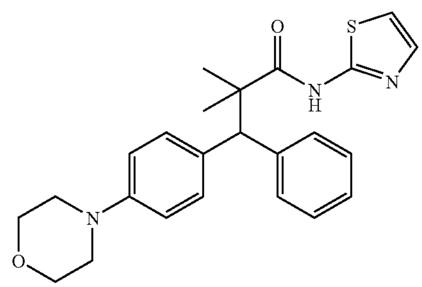 | 422.10 | 3.32 |
| 225 | 2,2-dimethyl-3-(4-(4-morpholinyl)phenyl)-3-phenyl-N-1,3,4-thiadiazol-2-ylpropanamide | 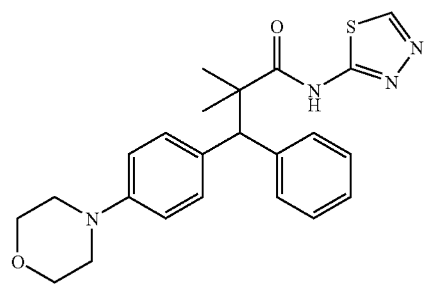 | 423.10 | 2.98 |
| 226 | 2,2-dimethyl-3-(4-methylphenyl)-3-(4-(4-morpholinyl)phenyl)-N-1,3,4-thiadiazol-2-ylpropanamide | 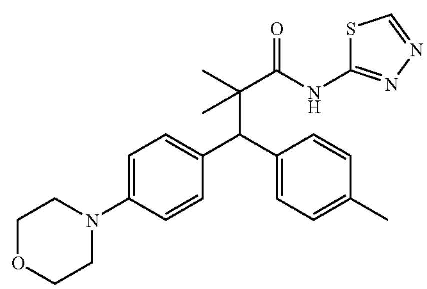 | 437.40 | 3.18 |
| 227 | 2,2-dimethyl-3-(4-methylphenyl)-3-(4-(4-morpholinyl)phenyl)-N-1,3-thiazol-2-ylpropanamide | 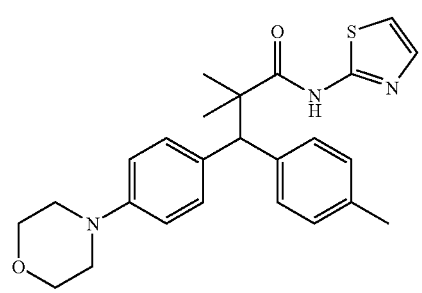 | 436.36 | 3.32 |

-continued

| Example No. | Name | Structure | MS [m/z (M + H)] | HPLC Rt: minute |
|---|---|---|---|---|
| 228 | 3-(3-fluorophenyl)-2,2-dimethyl-3-(4-(4-morpholinyl)phenyl)-N-1,3-thiazol-2-ylpropanamide | 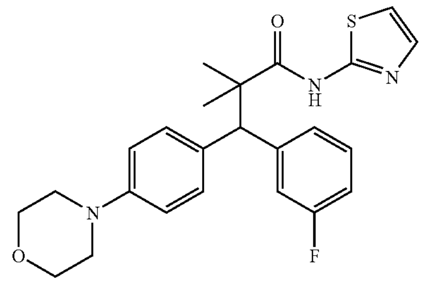 | 440.41 | 3.15 |
| 229 | 3-(3-fluorophenyl)-2,2-dimethyl-3-(4-(4-morpholinyl)phenyl)-N-1,3,4-thiadiazol-2-ylpropanamide | 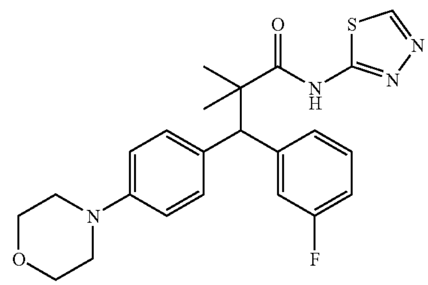 | 441.40 | 2.99 |
| 230 | 3-(4-fluorophenyl)-2,2-dimethyl-3-(4-(4-morpholinyl)phenyl)-N-1,3-thiazol-2-ylpropanamide | 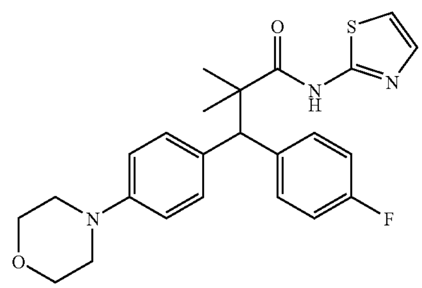 | 440.17 | 3.12 |
| 231 | 3-(4-fluorophenyl)-2,2-dimethyl-3-(4-(4-morpholinyl)phenyl)-N-1,3,4-thiadiazol-2-ylpropanamide | 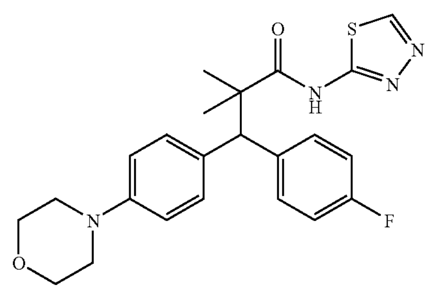 | 441.40 | 2.94 |
| 232 | 3-(4-chlorophenyl)-2,2-dimethyl-3-(4-(4-morpholinyl)phenyl)-N-1,3-thiazol-2-ylpropanamide | 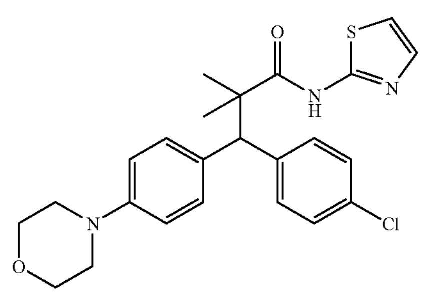 | 456.33 | 3.44 |

| Example No. | Name | Structure | MS [m/z (M + H)] | HPLC Rt: minute |
|---|---|---|---|---|
| 233 | 3-(4-chlorophenyl)-2,2-dimethyl-3-(4-(4-morpholinyl)phenyl)-N-1,3,4-thiadiazol-2-ylpropanamide | 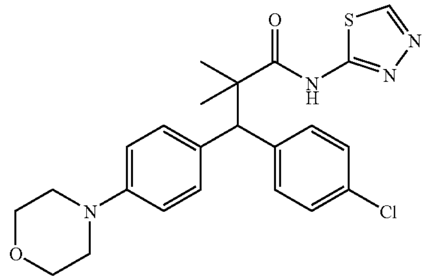 | 457.31 | 3.30 |
| 234 | 2,2-dimethyl-3-(3-methylphenyl)-3-(4-(4-morpholinyl)phenyl)-N-1,3-thiazol-2-ylpropanamide | 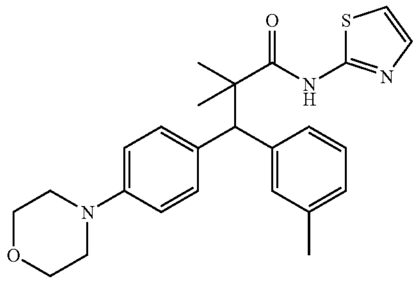 | 436.34 | 3.24 |
| 235 | 2,2-dimethyl-3-(3-methylphenyl)-3-(4-(4-morpholinyl)phenyl)-N-1,3,4-thiadiazol-2-ylpropanamide | 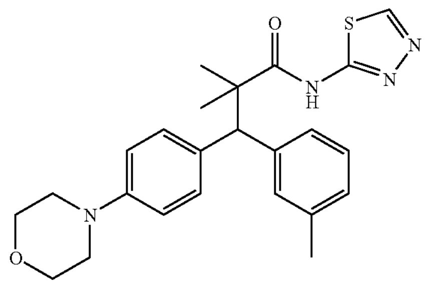 | 437.32 | 3.05 |

Examples 236 to 249

In a similar manner to Example 222, Examples 236 to 249 were prepared via the amidation reactions of acids of Preparations (15a) to (15f), 16(a) to 16(c), 17 and 18 with the appropriate amines. (Compounds are racemic unless noted)

| Example No. | Name | Structure | MS [m/z (M + H)] | HPLC Rt: minute |
|---|---|---|---|---|
| 236 | 2,2-dimethyl-3-phenyl-3-(4-(1-piperidinyl)phenyl)-N-1,3,4-thiadiazol-2-ylpropanamide | 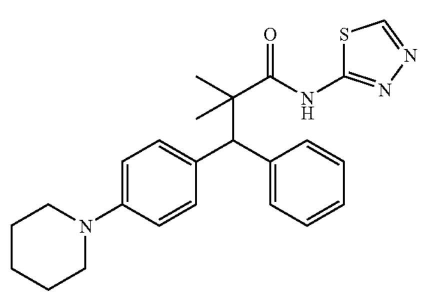 | 421.2 | 2.245 |

| Example No. | Name | Structure | MS [m/z (M + H)] | HPLC Rt: minute |
|---|---|---|---|---|
| 237 | 2,2-dimethyl-3-phenyl-3-(4-(1-pyrrolidinyl)phenyl)-N-1,3,4-thiadiazol-2-ylpropanamide | 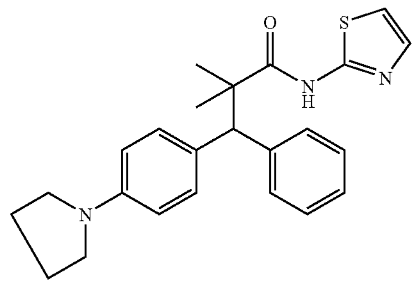 | 407.3 | 3.273 |
| 238 | 1,1-dimethylethyl 4-(4-(2,2-dimethyl-3-oxo-1-phenyl-3-(1,3,4-thiadiazol-2-ylamino)propyl)phenyl)-1-piperazinecarboxylate | 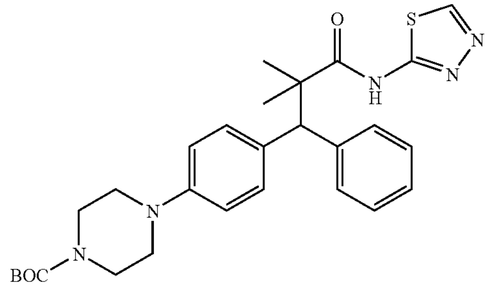 | 423.3 | 3.255 |
| 239 | 2,2-dimethylethyl 4-(4-(2,2-dimethyl-3-oxo-1-phenyl-3-(1,3-thiazol-2-ylamino)propyl)phenyl)-1-piperazinecarboxylate | 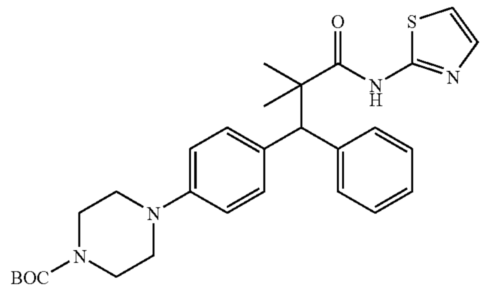 | 521.2 | 3.863 |
| 240 | 2,2-dimethyl-3-(4-(((4-methylphenyl)methyl)amino)phenyl)-3-phenyl-N-1,3,4-thiadiazol-2-ylpropanamide | 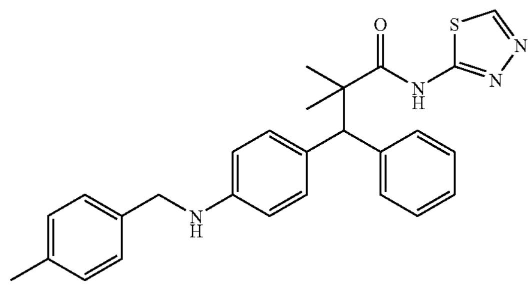 | 457.5 | 3.300 |
| 241 | 3-(4-(4-hydroxy-1-piperidinyl)phenyl)-2,2-dimethyl-3-phenyl-N-1,3,4-thiadiazol-2-ylpropanamide | 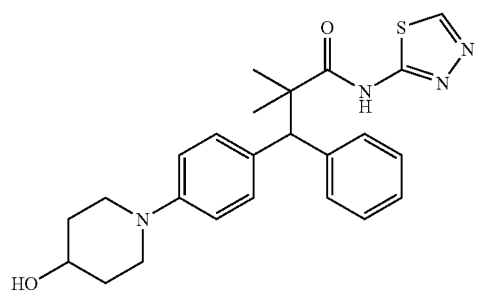 | 437.3 | 2.165 |

-continued
| Example No. | Name | Structure | MS [m/z (M + H)] | HPLC Rt: minute |
|---|---|---|---|---|
| 242 | 3-(4-(4-hydroxy-1-piperidinyl)phenyl)-2,2-dimethyl-3-phenyl-N-1,3-thiazol-2-ylpropanamide | 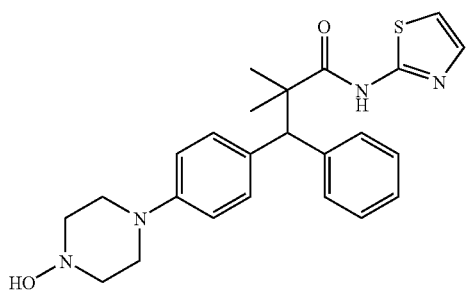 | 436.2 | 2.347 |
| 243 | 3-(4-((4-fluorophenyl)amino)phenyl)-2,2-dimethyl-3-phenyl-N-1,3-thiazol-2-ylpropanamide | 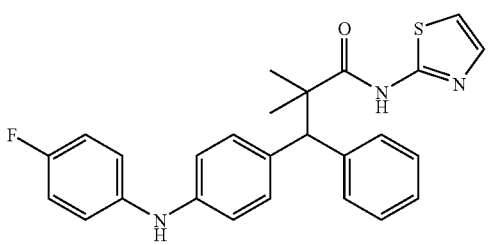 | 446.4 | 3.923 |
| 244 | 3-(3-fluoro-4-(4-morpholinyl)phenyl)-2,2-dimethyl-3-phenyl-N-1,3,4-thiadiazol-2-ylpropanamide | 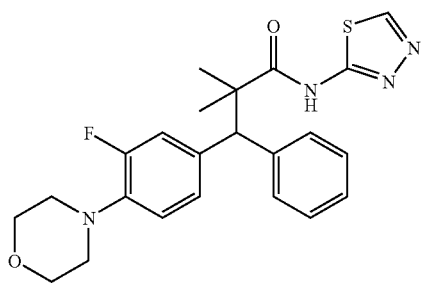 | 441.32 | 3.458 |
| 245 | 2,2-dimethyl-3-(3-(4-morpholinyl)phenyl)-3-phenyl-N-1,3,4-thiadiazol-2-ylpropanamide | 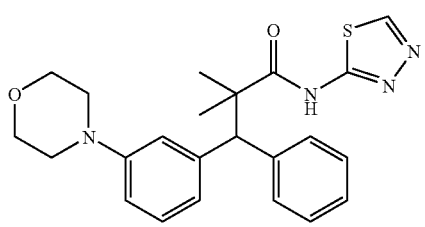 | 423.3 | 3.255 |

-continued

| Example No. | Name | Structure | MS [m/z (M + H)] | HPLC Rt: minute |
|---|---|---|---|---|
| 246 | 3-(4-(acetylamino)phenyl)-2,2-dimethyl-3-phenyl-N-1,3,4-thiadiazol-2-ylpropanamide | 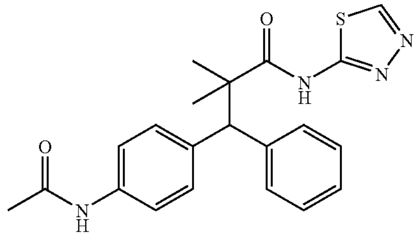 | 395.1 | 2.991 |
| 247 | 3-(4-(acetylamino)phenyl)-2,2-dimethyl-3-phenyl-N-1,3-thiazol-2-ylpropanamide | 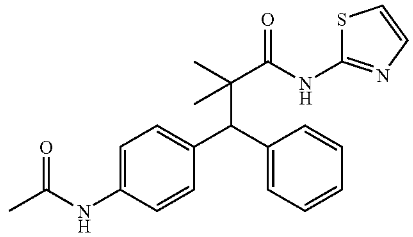 | 394.2 | 3.135 |
| 248 | 1,1-dimethylethyl (4-(2,2-dimethyl-3-oxo-1-phenyl-3-(1,3,4-thiadiazol-2-ylamino)propyl)phenyl)carbamate | 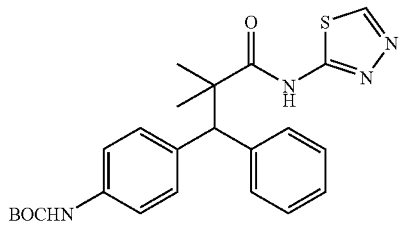 | 453.4 | 3.653 |
| 249 | 2,2-dimethyl-3-(4-(4-morpholinyl)phenyl)-3-phenyl-N-1,3-thiazol-2-ylbutanamide | 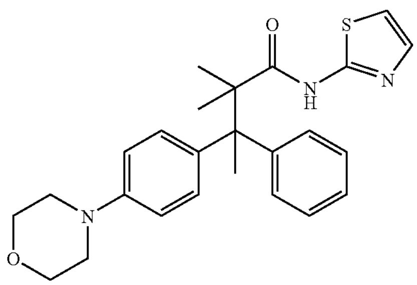 | 458.2 | 3.438 |

Example 250

2,2-Dimethyl-3-phenyl-3-(4-(1-piperazinyl)phenyl)-N-1,3-thiazol-2-ylpropanamide

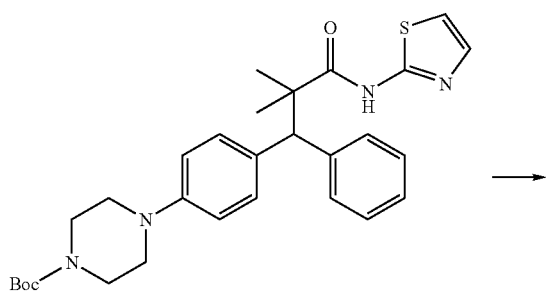

→

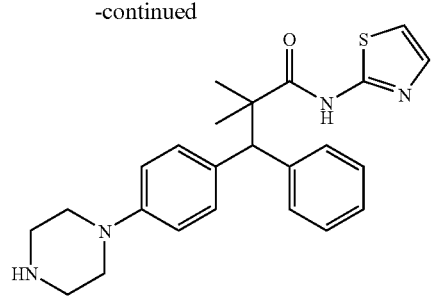

To a solution of the title compound of Example 239 (88.4 mg, 0.169 mmol) in dichloromethane (3 ml) was added trifluoroacetic acid (1 ml) at 0° C. The reaction mixture was allowed to warm to room temperature overnight. The reaction mixture was taken into water and DCM. The organic layer was washed, dried (MgSO$_4$) and concentrated to give the title compound of Example 250. (58 mg, 81.5% yield). LC/MS (m/z) 421.5 [(M+1)$^+$]; HPLC Rt: 2.448 min. $^1$H NMR (400

MHz, MeOD): δ 7.27 (3H, m), 7.13-7.17 (4H, m), 7.07 (1H, m), 6.94 (1H, d, J=3.7 Hz), 6.76 (2H, d, J=8.7 Hz), 4.43 (1H, s), 2.99 (4H, m), 2.86 (4H, m), 1.26 (6H, s). LC/MS (m/z) 251.35 [(M+H)⁺]; HPLC Rt: 3.120 min.

Examples 251 to 252

In a similar manner to Example 250, Examples 251 to 252 were prepared via removal of the BOC-group from the title compounds of Example 238 and 248. (Compounds are racemic unless noted)

following conditions; Column: Chiralpak AD 20×500 mm; 10 um, Mobil Phase: EtOH/MeOH=50:50, Flow rate: 28 mL/min, Detection: UV (254 nm). Analytical HPLC conditions, Column: Chiralpak AD 4.6×250 mm; 10 um, Mobile phase: EtOH/MeOH=50:50, Temperature: ambient, Flow-rate: 1 mL/min, Detection: UV (245 & 220 nm). Retention Time (min) First eluting enantiomer (Example 291), 6.10 (>99.9% ee); Second eluting enantiomer (Example 292), 7.85 (>90% ee).

| Example No. | Name | Structure | MS [m/z (M + H)] | HPLC Rt: minute |
|---|---|---|---|---|
| 251 | 2,2-dimethyl-3-phenyl-3-(4-(1-piperazinyl)phenyl)-N-1,3,4-thiadiazol-2-ylpropanamide | 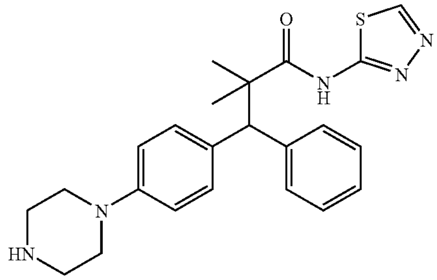 | 422.7 | 2.347 |
| 252 | 3-(4-aminophenyl)-2,2-dimethyl-3-phenyl-N-1,3,4-thiadiazol-2-ylpropanamide | 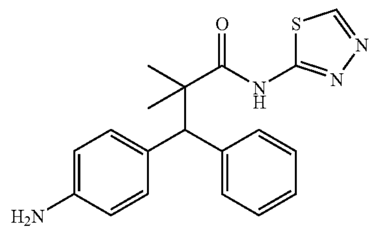 | 353.5 | 2.112 |

Examples 253 to 254

The title compound of Example 229 was resolved into its enantiomers using chiral chromatography/HPLC with the The first peak to elute under the preparative (SFC) conditions described above also eluted first under the aforementioned analytical chiral LC conditions In general, if the absolute stereochemistry of the two enantiomers are not yet defined. Isomer A designates the first eluting enantiomer, and Isomer B the second eluting enantiomer.

| Example No. | Name | Structure | MS [m/z (M + H)] | HPLC Rt: minute |
|---|---|---|---|---|
| 253 | 3-(3-fluorophenyl)-2,2-dimethyl-3-(4-(4-morpholinyl)phenyl)-N-1,3-thiazol-2-ylpropanamide | Isomer A | 440.14 | 3.148 |

| Example No. | Name | Structure | MS [m/z] (M + H)] | HPLC Rt: minute |
|---|---|---|---|---|
| 254 | 3-(3-fluorophenyl)-2,2-dimethyl-3-(4-(4-morpholinyl)phenyl)-N-1,3-thiazol-2-ylpropanamide | Isomer B | 440.21 | 3.125 |

Examples 255 to 256

The title compound of Example 229 was resolved into its enantiomers using chiral chromatography/HPLC with the following conditions; Column: Chiralpak AS 20×500 mm; 10 um, Mobil Phase: EtOH/MeOH=50:50, Flowrate: 28 mL/min, Detection: UV (254 nm). Analytical HPLC conditions, Column: Chiralpak AD 4.6×250 mm; 10 um, Mobile phase: EtOH/MeOH=50:50, Temperature: ambient, Flowrate: 1 mL/min, Detection: UV (245 & 220 nm). Retention Time (min) First eluting enantiomer (Example 293), 4.65 (>99.9% ee); Second eluting enantiomer (Example 292), 8.00 (>99.9% ee).

| Example No. | Name | Structure | MS [m/z] (M + H)] | HPLC Rt: minute |
|---|---|---|---|---|
| 255 | 3-(3-fluroophenyl)-2,2-dimethyl-3-(4-(4-morpholinyl)phenyl)-N-1,3,4-thiadiazol-2-ylpropanamide | Isomer A | 441.4 | 2.991 |
| 256 | 3-(3-fluorophenyl)-2,2-dimethyl-3-(4-(4-morpholinyl)phenyl)-N-1,3,4-thiadiazol-2-ylpropanamide | Isomer B | 441.4 | 2.998 |

Examples 257 to 260

In a similar manner to Example 222, Examples 295-260 were prepared via the amidation reactions of acids of Preparations (19a) and (19b) with the appropriate amines

| Example No. | Name | Structure | MS [m/z (M + H)] | HPLC Rt: minute |
|---|---|---|---|---|
| 257 | 2,2-dimethyl-3-(4-(4-morpholinyl)phenyl)-3-phenyl-N-1,3-thiazol-2-ylpropanamide | R enantiomer | 422.16 | 3.274 |
| 258 | 2,2-dimethyl-3-(4-(4-morpholinyl)phenyl)-3-phenyl-N-1,3-thiazol-2-ylpropanamide | S enantiomer | 422.4 | 3.253 |
| 259 | 2,2-dimethyl-3-(4-(4-morpholinyl)phenyl)-3-phenyl-N-1,3,4-thiadiazol-2-ylpropanamide | R enantiomer | 423.15 | 3.083 |
| 260 | 2,2-dimethyl-3-(4-(4-morpholinyl)phenyl)-3-phenyl-N-1,3,4-thiadiazol-2-ylpropanamide | S enantiomer | 423.10 | 3.110 |

Examples 261 to 293

In a similar manner to Example 222, Examples 261 to 293 were prepared via the amidation reactions of the acids of Preparations (20) to (22) with the appropriate amines (Compounds are racemic unless noted)

| Example No. | Name | Structure | MS [m/z (M + H)] | HPLC Rt: minute |
|---|---|---|---|---|
| 261 | 2,2-dimethyl-3-(4-(methyloxy)phenyl)-3-phenyl-N-1,3-thiazol-2-ylpropanamide | S enantiomer | 367.31 | 3.675 |
| 262 | 2,2-dimethyl-3-(4-(methyloxy)phenyl)-3-phenyl-N-1,3-thiazol-2-ylpropanamide | R enantiomer | 367.29 | 3.660 |
| 263 | ethyl 2-((2,2-dimethyl-3-(4-(methyloxy)phenyl)-3-phenylpropanoyl)amino)-1,3-thiazole-4-carboxylate | S enantiomer | 439.24 | 3.97 |
| 264 | ethyl 2-((2,2-dimethyl-3-(4-(methyloxy)phenyl)-3-phenylpropanoyl)amino)-1,3-thiazole-4-carboxylate | R enantiomer | 439.24 | 3.948 |

-continued

| Example No. | Name | Structure | MS [m/z (M + H)] | HPLC Rt: minute |
|---|---|---|---|---|
| 265 | 2,2-dimethyl-3-(4-(methyloxy)phenyl)-N-(4-methyl-1,3-thiazol-2-yl)-3-phenylpropanamide | S enantiomer | 381.25 | 3.757 |
| 266 | 2,2-dimethyl-3-(4-(methyloxy)phenyl)-N-(4-methyl-1,3-thiazol-2-yl)-3-phenylpropanamide | R enantiomer | 381.25 | 3.750 |
| 267 | (3S)-2,2-dimethyl-3-(4-(methyloxy)phenyl)-N-(5-methyl-1,3-thiazol-2-yl)-3-phenylpropanamide | S enantiomer | 381.19 | 3.777 |
| 268 | (3R)-2,2-dimethyl-3-(4-(methyloxy)phenyl)-N-(5-mehtyl-1,3-thiazol-2-yl)-3-phenylpropanamide | R enantiomer | 381.19 | 3.775 |

-continued

| Example No. | Name | Structure | MS [m/z (M + H)] | HPLC Rt: minute |
|---|---|---|---|---|
| 269 | (3S)-N-cyclopropyl-2,2-dimethyl-3-(4-(methyloxy)phenyl)-3-phenylpropanamide | S enantiomer | 324.22 | 3.392 |
| 270 | (3R)-N-cyclopropyl-2,2-dimethyl-3-(4-(methyloxy)phenyl)-3-phenylpropanamide | R enantiomer | 324.25 | 3.412 |
| 271 | (3S)-N-cyclobutyl-2,2-dimethyl-3-(4-(methyloxy)phenyl)-3-phenylpropanamide | S enantiomer | 338.23 | 3.65 |
| 272 | (3R)-N-cyclobutyl-2,2-dimethyl-3-(4-(methyloxy)phenyl)-3-phenylpropanamide | R enantiomer | 338.23 | 3.608 |
| 273 | (3S)-N-cyclopentyl-2,2-dimethyl-3-(4-(methyloxy)phenyl)-3-phenylpropanamide | S enantiomer | 352.30 | 3.762 |

-continued

| Example No. | Name | Structure | MS [m/z (M + H)] | HPLC Rt: minute |
|---|---|---|---|---|
| 274 | (3R)-N-cyclopentyl-2,2-dimethyl-3-(4-(methyloxy)phenyl)-3-phenylpropanamide | R enantiomer | 356.24 | 3.755 |
| 275 | (3S)-2,2-dimethyl-3-(4-(methyloxy)phenyl-3-phenyl-N-1,3,4-thiadiazol-2-ylpropanamide | S enantiomer | 368.12 | 3.502 |
| 276 | (3R)-2,2-dimethyl-3-(4-(methyloxy)phenyl)-3-phenyl-N-1,3,4-thiadiazol-2-ylpropanamide | R enantiomer | 368.12 | 3.487 |
| 277 | (3S)-2,2-dimethyl-3-(4-(methyloxy)phenyl)-3-phenyl-N-2-pyridinylpropanamide | S enantiomer | 361.18 | 3.142 |
| 278 | (3S)-2,2-dimethyl-3-(4-(methyloxy)phenyl)-3-phenyl-N-4-pyrimidinylpropanamide | S enantiomer | 362.12 | 3.488 |

-continued

| Example No. | Name | Structure | MS [m/z (M + H)] | HPLC Rt: minute |
|---|---|---|---|---|
| 279 | 3-(2-fluoro-4-(methyloxy)phenyl)-2,2-dimethyl-3-phenyl-N-1,3-thiazol-2-ylpropanamide | 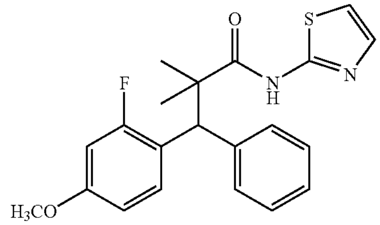 | 385.13 | 3.687 |
| 280 | 3-(2-fluoro-4-(methyloxy)phenyl)-2,2-dimethyl-3-phenyl-N-1,3,4-thiadiazol-2-ylpropanamide | 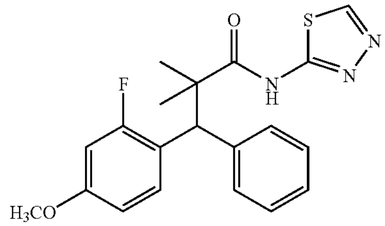 | 386.13 | 3.547 |
| 281 | 3-(3-fluoro-4-(methyloxy)phenyl)-2,2-dimethyl-3-phenyl-N-1,3-thiazol-2-ylpropanamide | 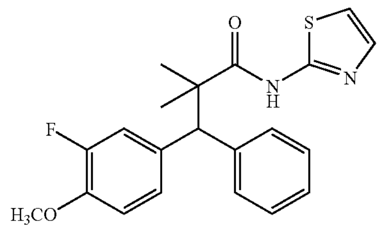 | 385.08 | 3.590 |
| 282 | 3-(3-fluoro-4-(methyloxy)phenyl)-2,2-dimethyl-3-phenyl-N-1,3-thiazol-2-ylpropanamide | Isomer A | 385.07 | 3.633 |
| 283 | 3-(3-fluoro-4-(methyloxy)phenyl)-2,2-dimethyl-3-phenyl-N-1,3-thiazol-2-ylpropanamide | Isomer B | 385.13 | 3.582 |
| 284 | 3-(3-fluoro-4-(methyloxy)phenyl)-2,2-dimethyl-3-phenyl-N-1,3,4-thiadiazol-2-ylpropanamide | Isomer A | 386.01 | 3.458 |

| Example No. | Name | Structure | MS [m/z (M + H)] | HPLC Rt: minute |
|---|---|---|---|---|
| 285 | 3-(3-fluoro-4-(methyloxy)phenyl)-2,2-dimethyl-3-phenyl-N-1,3,4-thiadiazol-2-ylpropanamide | Isomer B | 386.13 | 3.453 |
| 286 | (3R)-3-(3-bromo-4-(methyloxy)phenyl)-2,2-dimethyl-3-phenyl-N-1,3-thiazol-2-ylpropanamide | R enantiomer | 447.05 | 3.835 |
| 287 | (3S)-3-(3-bromo-4-(methyloxy)phenyl)-2,2-dimethyl-3-phenyl-N-1,3,4-thiadiazol-2-ylpropanamide | S enantiomer | 446.18 448.18 | 3.652 |
| 288 | 2,2-dimethyl-3-(4-(methyloxy)phenyl)-N-(4-((4-(methyloxy)phenyl)methyl)-1,3-thiazol-2-yl)-3-phenylpropanamide | 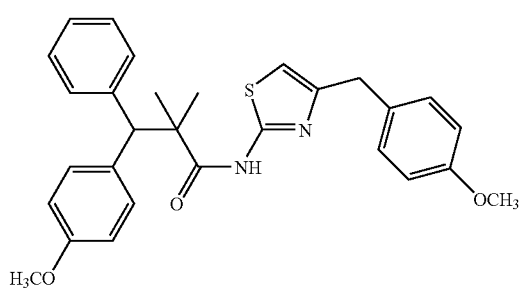 | 487.17 | 4.148 |
| 289 | 2,2-dimethyl-3-(4-(methyloxy)phenyl)-3-phenyl-N-(4-((4-(4-pyridinyl)phenyl)methyl)-1,3-thiazol-2-yl)propanamide | 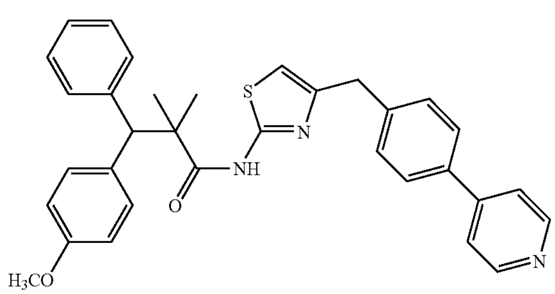 | 534.15 | 3.262 |

| Example No. | Name | Structure | MS [m/z (M + H)] | HPLC Rt: minute |
|---|---|---|---|---|
| 290 | 2,2-dimethyl-3-(4-(methyloxy)phenyl)-3-phenyl-N-(4-((4-(4-pyridinyl)phenyl)methyl)-1,3-thiazol-2-yl)propanamide | S enantiomer | 534.36 | 3.270 |
| 291 | 2,2-dimethyl-3-(4-(methyloxy)phenyl)-3-phenyl-N-(4-((4-(4-pyridinyl)phenyl)methyl)-1,3-thiazol-2-yl)propanamide | R enantiomer | 534.36 | 3.267 |
| 292 | (3R)-3-(3-bromo-4-(methyloxy)phenyl)-2,2-dimethyl-3-phenyl-N-1,3,4-thiadiazol-2-ylpropanamide | R enantiomer | 448.3 | 3.618 |
| 293 | 2,2-dimethyl-3-(3-methyl-4-(methyloxy)phenyl)-3-phenyl-N-1,3,4-thiadiazol-2-ylpropanamide | 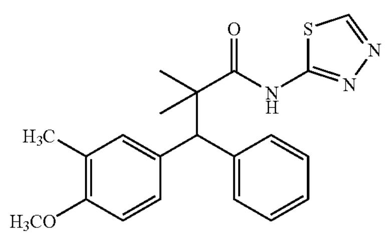 | 382.22 | 3.658 |

Examples 294 to 295

The title compound of Example 293 was resolved into its corresponding enantiomers using chiral supercritical fluid chromatography (SFC). Preparative conditions: Chiralpak AS-H (3×25 cm, 5 um), CO2/MeOH (85/15) @65 ml/min, 220 nm, BPR @100 bars. Analytical HPLC conditions: Column: Chiralpak AS-H (4.6×250 mm, 10 um), Mobile phase: CO2/MeOH (85/15), Temperature: ambient, Flowrate: 2 mL/min, Detection: UV (220 nm). Retention Time (min) First eluting enantiomer, 6.95 (>99.9% ee); Second eluting enantiomer, 8.05 (>99% ee).

In general, if the absolute stereochemistry of the two enantiomers are not yet defined. Isomer A designates the first eluting enantiomer, and Isomer B the second eluting enantiomer.

| Example No. | Name | Structure | MS [m/z (M + H)] | HPLC Rt: minute |
|---|---|---|---|---|
| 294 | 2,2-dimethyl-3-(3-methyl-4-(methyloxy)phenyl)-3-phenyl-N-1,3,4-thiadiazol-2-ylpropanamide | Isomer A | 382.3 | 3.700 |
| 295 | 2,2-dimethyl-3-(3-methyl-4-(methyloxy)phenyl)-3-phenyl-N-1,3,4-thiadiazol-2-ylpropanamide | Isomer B | 382.3 | 3.696 |

Example 296

(3R)-3-(3-Cyano-4-(methyloxy)phenyl)-2,2-dimethyl-3-phenyl-N-1,3-thiazol-2-ylpropanamide

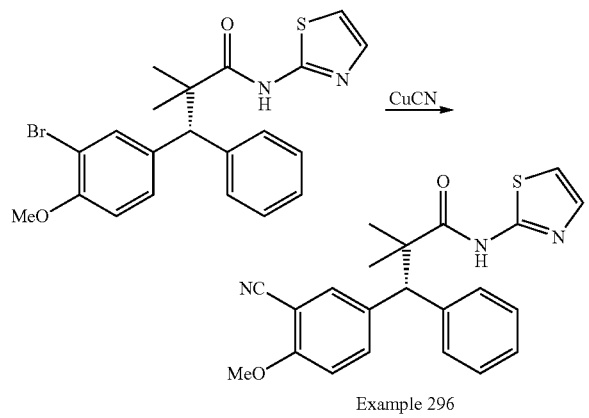

Example 296

An Emry™ process vial was charged with the title compound of Example 292 (23 mg, 0.052 mmol) and copper(I) chloride (47 mg, 0.52 mmol) in DMF. The reaction mixture was sealed and exposed to microwave irradiation for 60 min at 220° C. The reaction was cooled, filtered and purified by prep HPLC (column: YMC, C-18 Ballistic, 30×100 mm; 10-90% aq CH3OH/0.1% TFA, 25 mL/min. flow rate, 220 nm detection wavelength, same for compounds hereafter unless noted) to give the TFA salt of the title compound of Example 296 as a white solid. (21 mg, 80% yield). LC/MS (m/z 392.22 (M+H)$^+$); HPLC Rt: 3.443 min. $^1$H NMR (400 MHz, CDCl$_3$): δ 7.51 (2H, m), 7.24 (m, 4H), 7.19 (m, 1H), 7.03 (1H, d, J=4.1 Hz), 6.85) 1H, d, J=8.6 Hz), 4.71 (1H, s), 3.86 (3H, s), 1.40 (6H, s). LC/MS (m/z) 392.2 [(M+H)$^+$]; HPLC Rt: 3.443 min.

Examples 297 to 324

In a similar manner to the Example 222, Examples 297 to 324 were prepared via the amidation reactions of the formula of acids of 2 and 23 or appropriate acids prepared from the corresponding ketones according to the procedure described in Preparation 2 or appropriate acids prepared from the corresponding aldehydes according to the procedure described in Preparation 14, with appropriate amines (Compounds are racemic unless noted)

| Example No. | Name | Structure | MS [m/z (M + H)] | HPLC Rt: minute |
|---|---|---|---|---|
| 297 | 2,2-dimethyl-N-(4-((4-(methyloxy)phenyl)methyl)-1,3-thiazol-2-yl)-3,3-diphenylpropanamide | 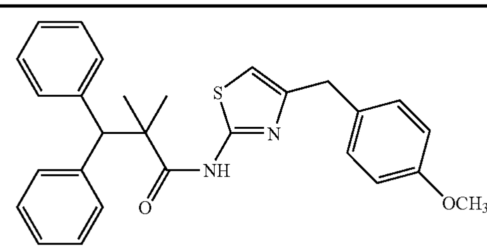 | 457.2 | 4.152 |

| Example No. | Name | Structure | MS [m/z (M + H)] | HPLC Rt: minute |
|---|---|---|---|---|
| 298 | 2,2-dimethyl-3-(3-(methyloxy)phenyl)-N-(4-((4-(methyloxy)phenyl)methyl)-1,3-thiazol-2-yl)-3-phenylpropanamide | 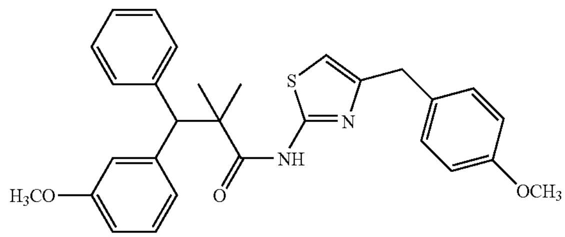 | 487.2 | 4.160 |
| 299 | 2,2-dimethyl-3,3-diphenyl-N-(4-((4-(4-pyridinyl)phenyl)methyl)-1,3-thiazol-2-yl)propanamide | 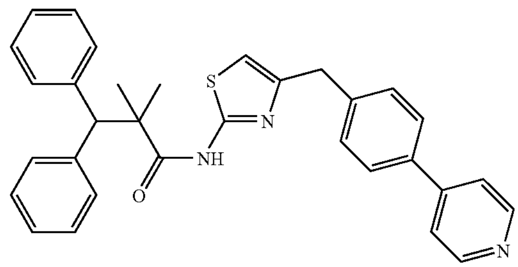 | 504..4 | 3.267 |
| 300 | 3-(4-bromophenyl)-2,2-dimethyl-3-phenyl-N-(4-((4-(4-pyridinyl)phenyl)methyl)-1,3-thiazol-2-yl)propanamide | 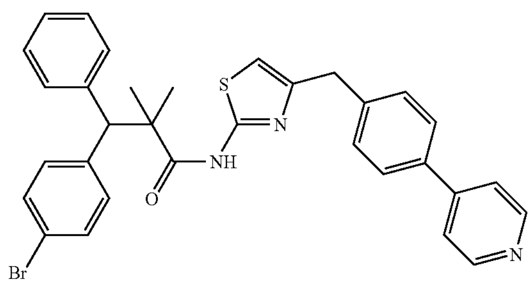 | 582.20 584.22 | 3.585 |
| 301 | 3-(4-chlorophenyl)-2,2-dimethyl-3-phenyl-N-(4-((4-(4-pyridinyl)phenyl)methyl)-1,3-thiazol-2-yl)propanamide | 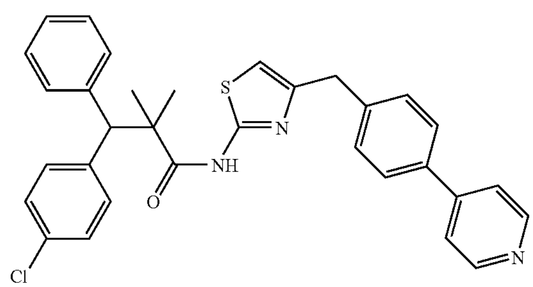 | 538.14 540.14 | 3.533 |
| 302 | 3-(4-fluorophenyl)-2,2-dimethyl-3-phenyl-N-(4-((4-(4-pyridinyl)phenyl)methyl)-1,3-thiazol-2-yl)propanamide | 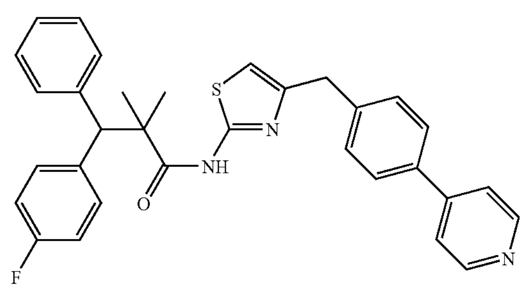 | 522.4 | 3.318 |

-continued

| Example No. | Name | Structure | MS [m/z (M + H)] | HPLC Rt: minute |
|---|---|---|---|---|
| 303 | 3-(4-(1,1-dimethylethyl)phenyl)-2,2-dimethyl-3-phenyl-N-(4-((4-(4-pyridinyl)phenyl)methyl)-1,3-thiazol-2-yl)propanamide | 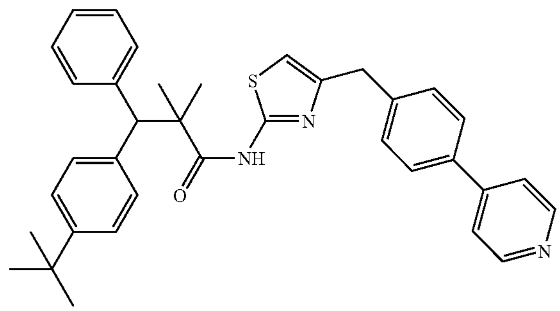 | 560.5 | 3.798 |
| 304 | 2,2-dimethyl-3,3-bis(4-(methyloxy)phenyl)-N-(4-((4-(4-pyridinyl)phenyl)methyl)-1,3-thiazol-2-yl)propanamide | 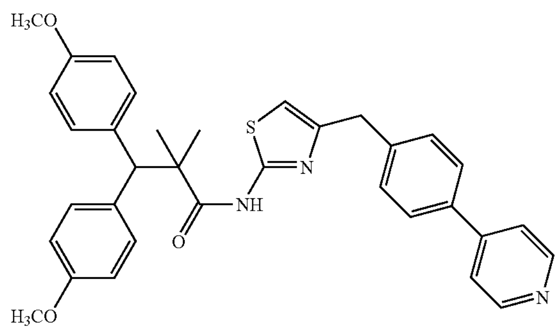 | 564.4 | 3.243 |
| 305 | 2,2-dimethyl-3-(3-(methyloxy)phenyl)-3-phenyl-N-(4-((4-(4-pyridinyl)phenyl)methyl)-1,3-thiazol-2-yl)propanamide | 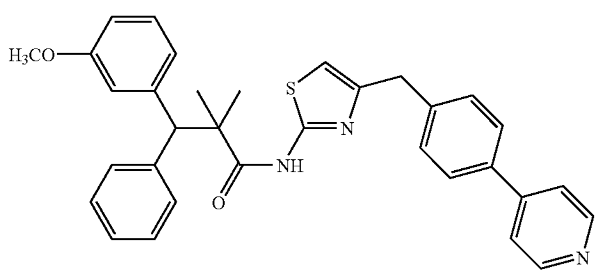 | 534.2 | 3.443 |
| 306 | 3-(4-chlorophenyl)-2,2-dimethyl-3-phenyl-N-1,3-thiazol-2-ylpropanamide | 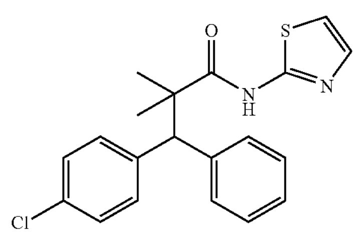 | 371.1 | 3.902 |
| 307 | 3-(4-fluorophenyl)-2,2-dimethyl-3-phenyl-N-1,3-thiazol-2-ylpropanamide | 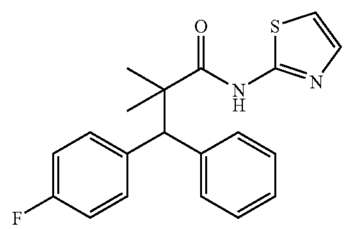 | 355.3 | 3.743 |

-continued

| Example No. | Name | Structure | MS [m/z (M + H)] | HPLC Rt: minute |
|---|---|---|---|---|
| 308 | 3-(4-fluorophenyl)-2,2-dimethyl-3-phenyl-N-1,3-thiazol-2-ylpropanamide | Isomer A | 355.1 | 3.712 |
| 309 | 3-(4-fluorophenyl)-2,2-dimethyl-3-phenyl-N-1,3-thiazol-2-ylpropanamide | Isomer B | 355.2 | 3.710 |
| 310 | 3-(4-cyanophenyl)-2,2-dimethyl-3-phenyl-N-1,3-thiazol-2-ylpropanamide | 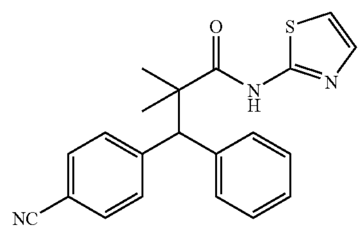 | 362.1 | 3.464 |
| 311 | 3-(3-bromophenyl)-2,2-dimethyl-3-phenyl-N-1,3-thiazol-2-ylpropanamide | 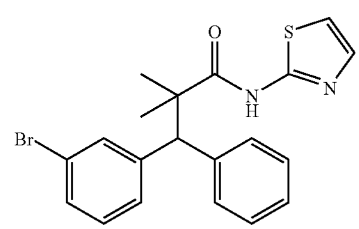 | 415.0 416.9 | 3.972 |
| 312 | 3-(3-bromophenyl)-2,2-dimethyl-3-phenyl-N-1,3-thiadiazol-2-ylpropanamide | 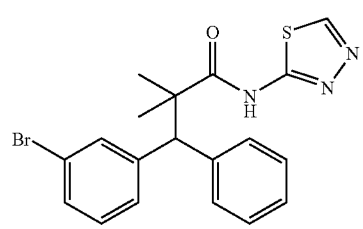 | 416.0 417.97 | 3832 |
| 313 | 3-(3-cyanophenyl)-2,2-dimethyl-3-phenyl-N-1,3-thiazol-2-ylpropanamide | 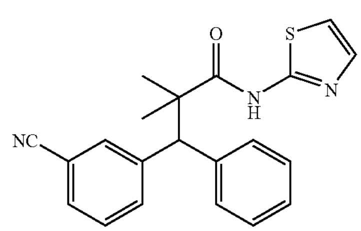 | 362.1 | 3.408 |

-continued

| Example No. | Name | Structure | MS [m/z (M + H)] | HPLC Rt: minute |
|---|---|---|---|---|
| 314 | 3-(4-bromo-3-fluorophenyl)-2,2-dimethyl-3-phenyl-N-1,3-thiazol-2-ylpropanamide | 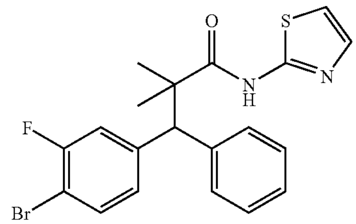 | 431.06 433.06 | 3.940 |
| 315 | 3-(4-bromo-3-fluorophenyl)-2,2-dimethyl-3-phenyl-N-1,3,4-thiadiazol-2-ylpropanamide | 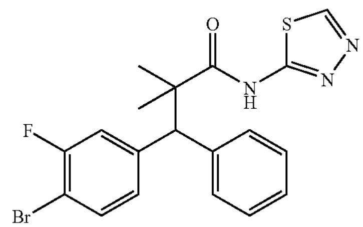 | 434.24 436.00 | 3.831 |
| 316 | 2,2-dimethyl-3,3-diphenyl-N-1,3-thiazol-2-ylbutanamide | 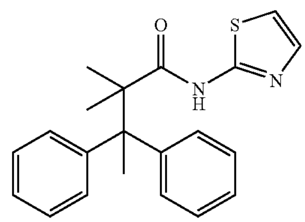 | 351.2 | 3.948 |
| 317 | 3-(4-bromophenyl)-2,2-dimethyl-3-phenyl-N-1,3-thiazol-2-ylpropanamide | 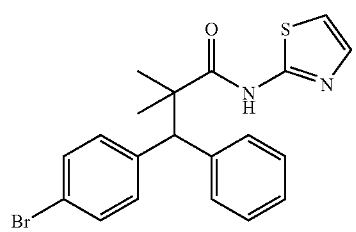 | 415.9 | 3.962 |
| 318 | 3-(4-bromophenyl)-2,2-dimethyl-3-phenyl-N-1,3,4-thiadiazol-2-ylpropanamide | 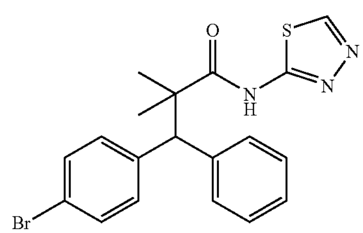 | 416.02 418.02 | 3.847 |
| 319 | 2,2-dimethyl-3-phenyl-3-(4-(phenylmethyl)phenyl)-N-1,3-thiazol-2-ylpropanamide | 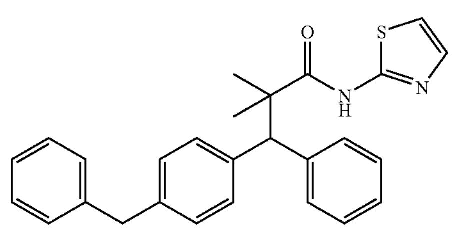 | 427.4 | 3.961 |

-continued

| Example No. | Name | Structure | MS [m/z (M + H)] | HPLC Rt: minute |
|---|---|---|---|---|
| 320 | 2,2-dimethyl-3-phenyl-3-(4-(phenylmethyl)phenyl)-N-1,3,4-thiadiazol-2-ylpropanamide | 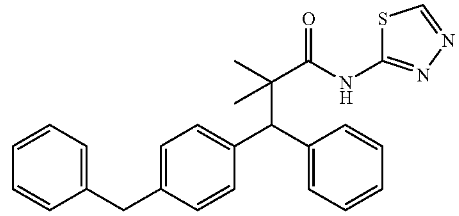 | 428.4 | 3.53 |
| 321 | 2,2-dimethyl-3-phenyl-3-(4-(phenyloxy)phenyl)-N-1,3-thiazol-2-ylpropanamide | 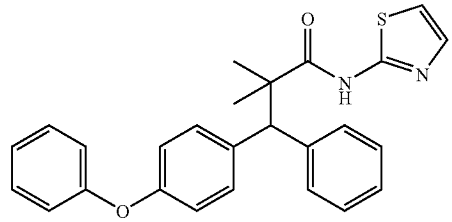 | 429.2 | 3.838 |
| 322 | 2,2-dimethyl-3-phenyl-3-(4-(phenyloxy)phenyl)-N-1,3,4-thiadiazol-2-ylpropanamide | 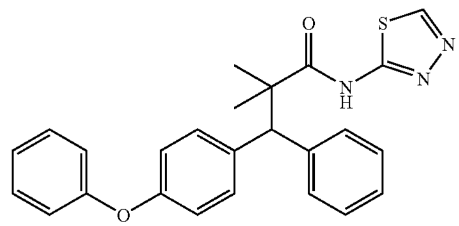 | 430.4 | 3.773 |
| 323 | 3-(4-bromophenyl)-2,2-dimethyl-3-phenyl-N-1,3,4-thiadiazol-2-ylpropanamide | Isomer A | 416.3 418.3 | 3.621 |
| 324 | 3-(4-bromophenyl)-2,2-dimethyl-3-phenyl-N-1,3,4-thiadiazol-2-ylpropanamide | Isomer B | 416.3 418.3 | 3.565 |

Examples 325 to 358

In a similar manner to Example 285, Examples 325 to 358 were prepared from the corresponding methoxy-phenyl analogs.

(Compounds with given absolute configuration are drawn with stereo bond. Chiral compounds with undefined absolute stereochemistry are noted as Isomer A or Isomer B. Unmarked compounds with no stereo bond are racemic.)

| Example No. | Name | Structure | MS [m/z (M + H)] | HPLC Rt: minute |
|---|---|---|---|---|
| 325 | (3S)-3-(4-hydroxyphenyl)-2,2-dimethyl-3-phenyl-N-1,3-thiazol-2-ylpropanamide | 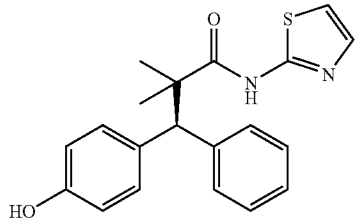 | 353.3 | 3.158 |
| 326 | (3R)-3-(4-hydroxyphenyl)-2,2-dimethyl-3-phenyl-N-1,3-thiazol-2-ylpropanamide | 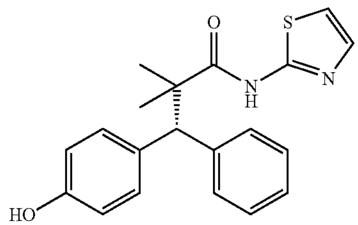 | 353.3 | 3.155 |
| 327 | 3-(3-hydroxyphenyl)-2,2-dimethyl-3-phenyl-N-1,3-thiazol-2-ylpropanamide | 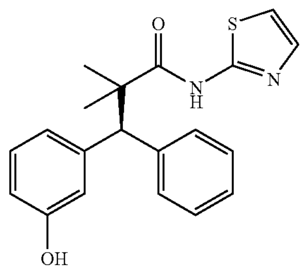 | 353.2 | 3.228 |
| 328 | 3-(3-hydroxyphenyl)-2,2-dimethyl-3-phenyl-N-1,3-thiazol-2-ylpropanamide | 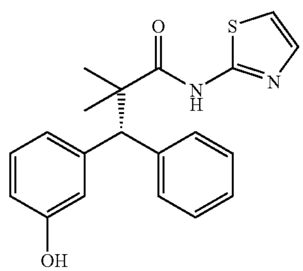 | 353.2 | 3.223 |
| 329 | (3S)-3-(4-hydroxyphenyl)-2,2-dimethyl-N-(4-methyl-1,3-thiazol-2-yl)-3-phenylpropanamide | 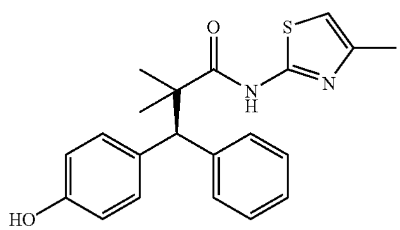 | 367.2 | 3.347 |

-continued

| Example No. | Name | Structure | MS [m/z (M + H)] | HPLC Rt: minute |
|---|---|---|---|---|
| 330 | (3R)-3-(4-hydroxyphenyl)-2,2-dimethyl-N-(4-methyl-1,3-thiazol-2-yl)-3-phenylpropanamide | 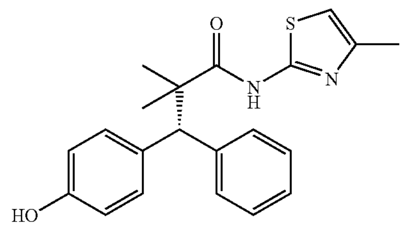 | 367.2 | 3.355 |
| 331 | (3S)-3-(4-hydroxyphenyl)-2,2-dimethyl-N-(5-methyl-1,3-thiazol-2-yl)-3-phenylpropanamide | 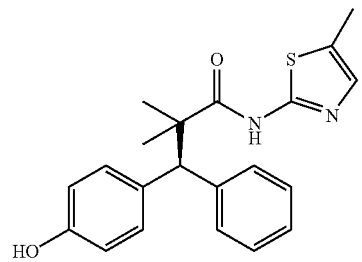 | 367.2 | 3.353 |
| 332 | (3R)-3-(4-hydroxyphenyl)-2,2-dimethyl-N-(5-methyl-1,3-thiazol-2-yl)-3-phenylpropanamide | 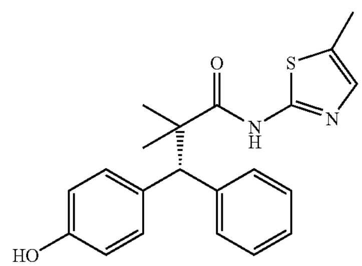 | 367.2 | 3.345 |
| 333 | (3S)-N-cyclobutyl-3-(4-hydroxyphenyl)-2,2-dimethyl-3-phenylpropanamide | 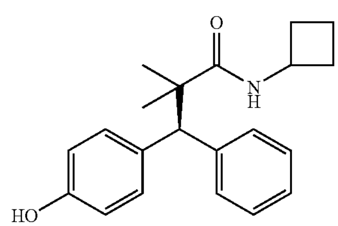 | 324.2 | 3.142 |
| 334 | (3R)-N-cyclobutyl-3-(4-hydroxyphenyl)-2,2-dimethyl-3-phenylpropanamide | 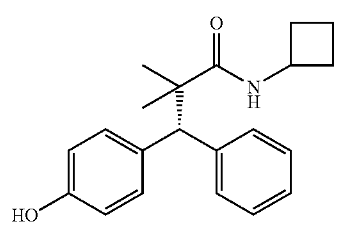 | 324.2 | 3.147 |
| 335 | (3S)-N-cyclopentyl-3-(4-hydroxyphenyl)-2,2-dimethyl-3-phenylpropanamide | 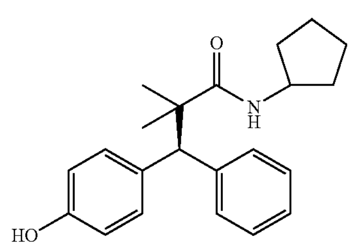 | 338.2 | 3.320 |

-continued

| Example No. | Name | Structure | MS [m/z (M + H)] | HPLC Rt: minute |
|---|---|---|---|---|
| 336 | (3R)-N-cyclopentyl-3-(4-hydroxyphenyl)-2,2-dimethyl-3-phenylpropanamide | 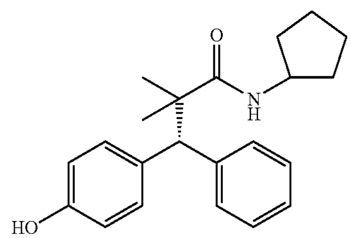 | 338.2 | 3.357 |
| 337 | 4-((1S)-2,2-dimethyl-3-(4-morpholinyl)-3-oxo-1-phenylpropyl)phenol | 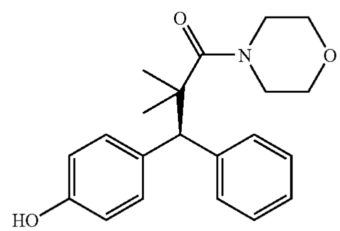 | 340.2 | 2.940 |
| 338 | ethyl 2-(((3S)-3-(4-hydroxyphenyl)-2,2-dimethyl-3-phenylpropanoyl)amino)-1,3-thiazole-4-carboxylate | 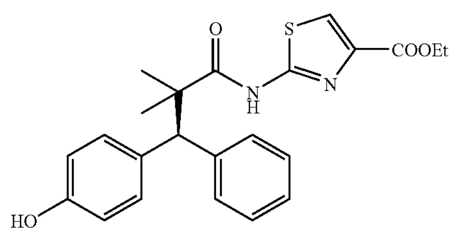 | 425.0 | 3.573 |
| 339 | (3S)-3-(4-hydroxyphenyl)-2,2-dimethyl-3-phenyl-N-1,3,4-thiadiazol-2-ylpropanamide | 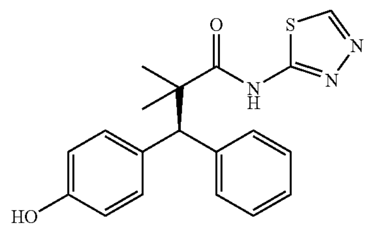 | 354.1 | 3.032. |
| 340 | (3R)-3-(4-hydroxyphenyl)-2,2-dimethyl-3-phenyl-N-1,3,4-thiadiazol-2-ylpropanamide | 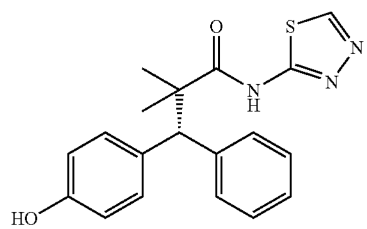 | 354.1 | 3.030 |
| 341 | (3S)-3-(4-hydroxyphenyl)-2,2-dimethyl-3-phenyl-N-2-pyridinylpropanamide | 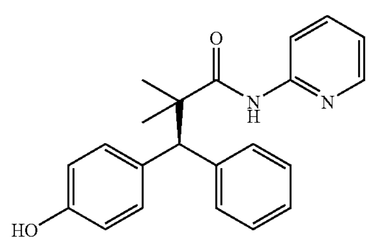 | 347.3 | 2.527 |

-continued

| Example No. | Name | Structure | MS [m/z (M + H)] | HPLC Rt: minute |
|---|---|---|---|---|
| 342 | (3S)-3-(4-hydroxyphenyl)-2,2-dimethyl-3-phenyl-N-1,2,4-thiadiazol-5-ylpropanamide | 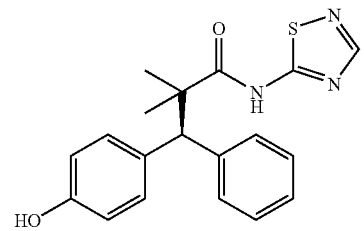 | 354.1 | 3.233 |
| 343 | 3-(2-fluoro-4-hydroxyphenyl)-2,2-dimethyl-3-phenyl-N-1,3-thiazol-2-ylpropanamide | 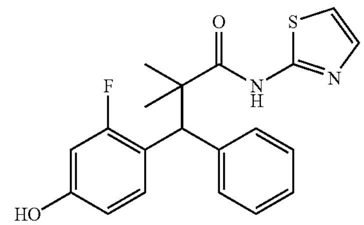 | 371.1 | 3.275 |
| 344 | 3-(2-fluoro-4-hydroxyphenyl)-2,2-dimethyl-3-phenyl-N-1,3,4-thiadiazol-2-ylpropanamide | 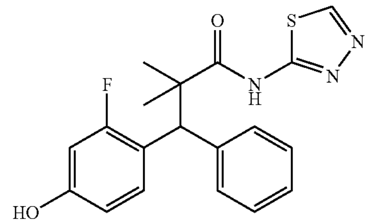 | 372.1 | 3.143 |
| 345 | 3-(3-fluoro-4-hydroxyphenyl)-2,2-dimethyl-3-phenyl-N-1,3-thiazol-2-ylpropanamide | 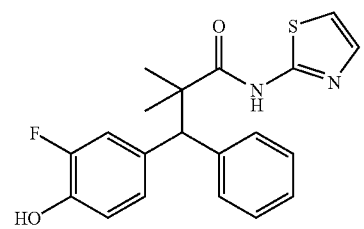 | 371.1 | 3.250 |
| 346 | 3-(3-fluoro-4-hydroxyphenyl)-2,2-dimethyl-3-phenyl-N-1,3-thiazol-2-ylpropanamide | Isomer A | 371.1 | 3.288 |
| 347 | 3-(3-fluoro-4-hydroxyphenyl)-2,2-dimethyl-3-phenyl-N-1,3-thiazol-2-ylpropanamide | Isomer B | 371.1 | 3.255 |

-continued

| Example No. | Name | Structure | MS [m/z (M + H)] | HPLC Rt: minute |
|---|---|---|---|---|
| 348 | 3-(3-fluoro-4-hydroxyphenyl)-2,2-dimethyl-3-phenyl-N-1,3,4-thiadiazol-2-ylpropanamide | Isomer A | 372.1 | 3.060 |
| 349 | (3R)-3-(3-bromo-4-hydroxyphenyl)-2,2-dimethyl-3-phenyl-N-1,3-thiazol-2-ylpropanamide | Isomer B | 433.0 | 3.462 |
| 350 | (3S)-3-(3-bromo-4-hydroxyphenyl)-2,2-dimethyl-3-phenyl-N-1,3-thiazol-2-ylpropanamide | S enantiomer | 431.16 433.16 | 3.428 |
| 351 | (3S)-3-(3-bromo-4-hydroxyphenyl)-2,2-dimethyl-3-phenyl-N-1,3,4-thiadiazol-2-ylpropanamide | S enantiomer | 432.15 434.15 | 3.272 |
| 352 | 3-(4-hydroxyphenyl)-2,2-dimethyl-3-phenyl-N-(4-((4-(4-pyridinyl)phenyl)methyl)-1,3-thiazol-2-yl)propanamide | 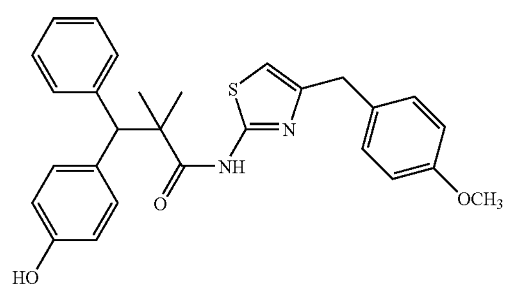 | 473.2 | 3.835 |

-continued

| Example No. | Name | Structure | MS [m/z (M + H)] | HPLC Rt: minute |
|---|---|---|---|---|
| 353 | 3-(4-hydroxyphenyl)-2,2-dimethyl-3-phenyl-N-(4-((4-(4-pyridinyl)phenyl)methyl)-1,3-thiazol-2-yl)propanamide | 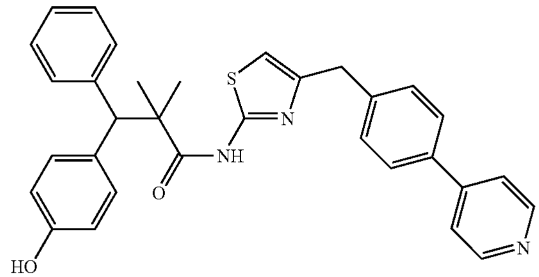 | 520.1 | 2.942 |
| 354 | 3-(4-hydroxyphenyl)-2,2-dimethyl-3-phenyl-N-(4-((4-(4-pyridinyl)phenyl)methyl)-1,3-thiazol-2-yl)propanamide | S enantiomer | 520.3 | 2.970 |
| 355 | 3,3-bis(4-hydroxyphenyl)-2,2-dimethyl-N-(4-((4-(4-pyridinyl)phenyl)methyl)-1,3-thiazol-2-yl)propanamide | R enantiomer | 520.3 | 2.988 |
| 356 | 3-(3-hydroxyphenyl)-2,2-dimethyl-3-phenyl-N-(4-((4-(4-pyridinyl)phenyl)methyl)-1,3-thiazol-2-yl)propanamide | 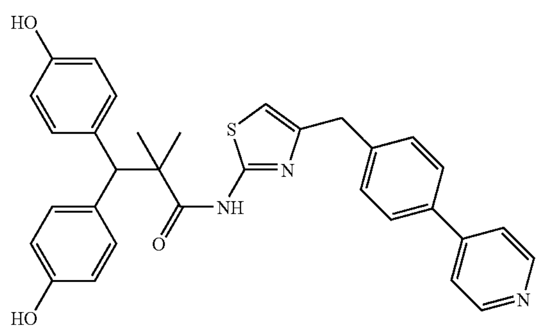 | 536.4 | 2.728 |
| 357 | (3R)-3-(3-cyano-4-hydroxyphenyl)-2,2-dimethyl-3-phenyl-N-1,3-thiazol-2-ylpropanamide | 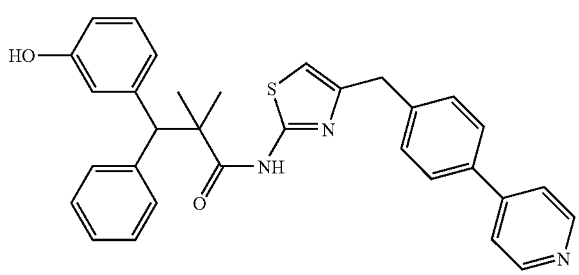 | 520.20 | 3.028 |

| Example No. | Name | Structure | MS [m/z (M + H)] | HPLC Rt: minute |
|---|---|---|---|---|
| 358 | (3S)-3-(4-hydroxyphenyl)-2,2-dimethyl-3-phenyl-N-1,3-thiazol-2-ylpropanamide | 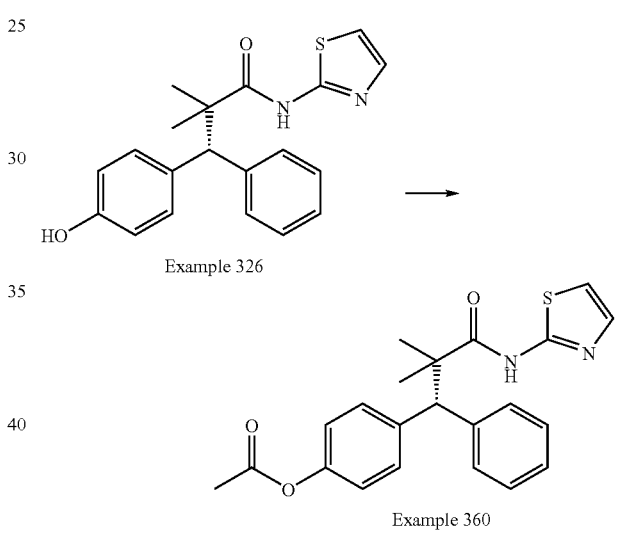<br>R enantiomer | 378.30 | 3.205 |

Example 359

(3S)-3-(3-Cyano-4-hydroxyphenyl)-2,2-dimethyl-3-phenyl-N-1,3-thiazol-2-ylpropanamide

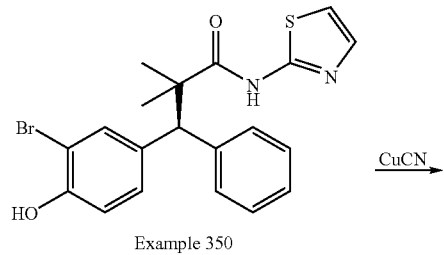

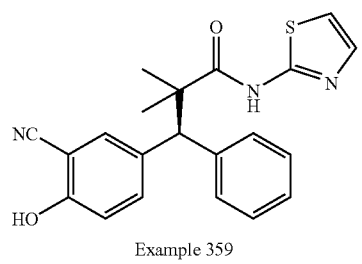

In a similar manner to Example 296, Example 359 was prepared via the reaction of the title compound of Example 350 and copper (I) chloride. LC/MS (m/z) 378.27 [(M+1)$^+$]; HPLC Rt: 3.195 min. 1H NMR (400 MHz, CDCl$_3$) δ ppm 7.47-7.37 (3H, m) 7.21-7.14 (5H, m) 6.96 (1H, d, J=3.67) 6.80 (1H, d, J=8.44 Hz) 4.62 (1H, s) 1.35 (6H, d, J=3.88 Hz)

Example 360

4-((1R)-2,2-Dimethyl-3-oxo-1-phenyl-3-(1,3-thiazol-2-ylamino)propyl)phenyl acetate To a solution of the title compound of Example 326 (20 mg, 0.0567 mmol) in DCM (1 ml) was added diisopropylethyl amine (0.011 ml, 0.062 mmol) followed by acetic anhydride ('23 mg, 0.227 mmol). The reaction mixture was stirred at room temperature. After 2 h, the reaction mixture was taken into water and ethyl acetate. The organic extract was washed (brine), dried (MgSO$_4$) and concentrated. The crude product was purified by silica gel flash chromatography using 30% ethyl acetate in hexanes to give the title compound of Example 360 as a white solid (20 mg, 89% yield). LC/MS (m/z) 395.27 [(M+1)$^+$]; HPLC Rt: 3.276 min. 1H NMR (400 MHz, MeOD) δ ppm 7.26-7.31 (5H, m) 7.16-7.12 (2H, m) 7.07-7.09 (1H, m) 6.94 (1H, d, J=3.56 Hz) 6.89 (2H, d, J=8.59 Hz) 4.55 (1H, s) 2.13 (3H, s) 1.28 (6H, s).

Examples 361 to 367

In a similar manner to Example 360, Examples 361 to 367 were prepared from the corresponding phenols with acetic anhydride or appropriate acids according to the procedure described in Example 222.

(The absolute stereochemistry of compounds are specified in the structures)

| Example No. | Name | Structure | MS [m/z (M + H)] | HPLC Rt: minute |
|---|---|---|---|---|
| 361 | 4-((1S)-2,2-dimethyl-3-oxo-1-phenyl-3-(1,3-thiazol-2-ylamino)propyl)phenyl acetate | S enantiomer | 395.27 | 3.265 |
| 362 | 4-((1S)-2,2-dimethyl-3-oxo-1-phenyl-3-(1,3-thiazol-2-ylamino)propyl)phenyl 2-furancarboxylate | S enantiomer | 447.28 | 3.496 |
| 363 | 4-((1R)-2,2-dimethyl-3-oxo-1-phenyl-3-(1,3-thiazol-2-ylamino)propyl)phenyl 2-furancarboxylate | R enantiomer | 447.24 | 3.485 |
| 364 | 4-((1S)-2,2-dimethyl-3-oxo-1-phenyl-3-(1,3-thiazol-2-ylamino)propyl)phenyl 3-furancarboxylate | S enantiomer | 447.31 | 3.536 |

| Example No. | Name | Structure | MS [m/z (M+H)] | HPLC Rt: minute |
|---|---|---|---|---|
| 365 | 4-((1R)-2,2-dimethyl-3-oxo-1-phenyl-3-(1,3-thiazol-2-ylamino)propyl)phenyl 3-furancarboxylate | R enantiomer | 447.24 | 3.565 |
| 366 | 4-((1S)-2,2-dimethyl-3-oxo-1-phenyl-3-(1,3-thiazol-2-ylamino)propyl)phenyl tetrahydro-2-furancarboxylate | S enantiomer | 451.33 | 3.290 |
| 367 | 4-((1R)-2,2-dimethyl-3-oxo-1-phenyl-3-(1,3-thiazol-2-ylamino)propyl)phenyl tetrahydro-2-furancarboxylate | R enantiomer | 451.29 | 3.301 |

Example 368

3-(4-Acetylphenyl)-2,2-dimethyl-3-phenyl-N-1,3-thiazol-2-ylpropanamide

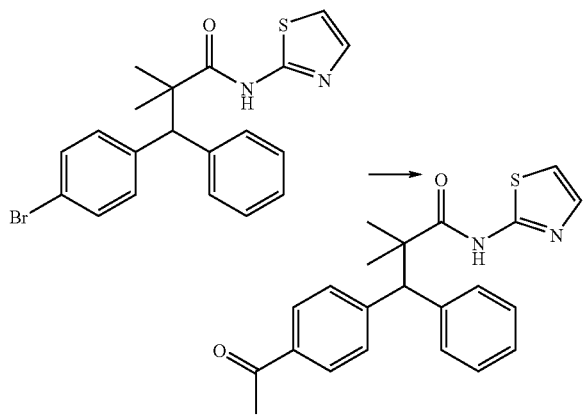

Example 368

A solution of the title compound of Example 317 (200 mg, 0.482 mmol) and tetrakis(triphenylphosphine)palladium(0) (111 mg, 0.09 mmol) in dioxane (2 ml) was degassed by bubbling nitrogen through for 15 min followed by addition of tributyl(1-ethoxyvinyl)stannane (1.6 ml, 4.82 mmol). The solution was degassed for 5 min. before it was sealed and heated at 110° C. for 16 h. The reaction mixture was quenched with 4 ml of 6 N HCl and heated at 80° C. for 30 min. After cooling to room temperature, the reaction solution was adjusted to basic with 10% aqueous $Na_2CO_3$ and extracted with ethyl acetate. The organic extract was washed (brine), dried ($MgSO_4$) and concentrated. The crude product was purified by silica gel flash chromatography using 0 to 70% ethyl acetate in hexanes to afford the title compound of Example 368 as a white solid (135 mg, 74% yield). LC/MS (m/z) 379.15 [(M+1)$^+$]; HPLC Rt: 3.240 min. 1H NMR (400 MHz, MeOD) δ ppm 7.78 (2H, dd, J=7.60, 1.66 Hz) 7.42 (2H, d, J=8.41 Hz) 7.29-7.27 (3H, m) 7.18-7.16 (2H, m) 7.14-7.1 (1H, m) 6.94 (1H, d, J=3.58 Hz) 4.63 (1H, s) 2.45 (3H, s) 1.30 (6H, d, J=6.41 Hz).

Examples 369 to 370

In a similar manner to Example 368, Examples 369 to 370 were prepared via the Pd-catalyzed coupling reactions of the corresponding bromo-amides with tributyl(1-ethoxyvinyl)stannane. (Compounds are racemic unless noted)

| Example No. | Name | Structure | MS [m/z (M + H)] | HPLC Rt: minute |
|---|---|---|---|---|
| 369 | 3-(4-acetylphenyl)-2,2-dimethyl-3-phenyl-N-1,3,4-thiadiazol-2-ylpropanamide | 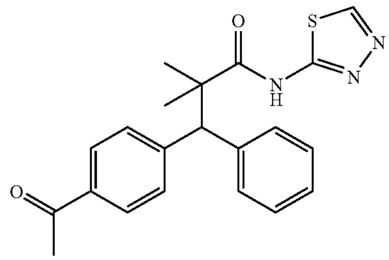 | 380.13 | 3.193 |
| 370 | 3-(3-acetylphenyl)-2,2-dimethyl-3-phenyl-N-1,3-thiazol-2-ylpropanamide | 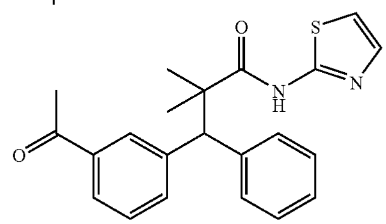 | 379.13 | 3.267 |

Example 371
3-(4-(1-Hydroxyethyl)phenyl)-2,2-dimethyl-3-phenyl-N-1,3-thiazol-2-ylpropanamide

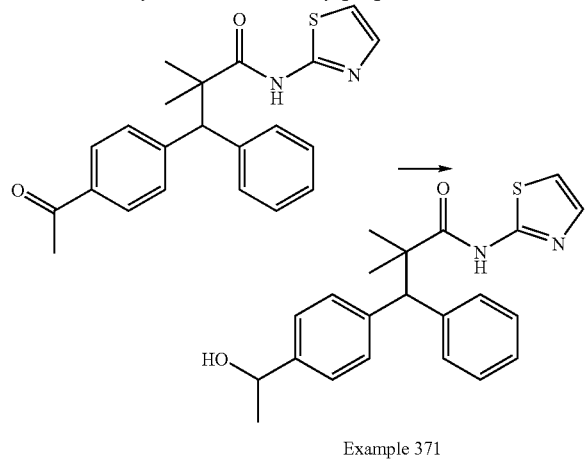

Example 371

To a solution of the title compound of Example 368 (20 mg, 0.053 mmol) in ethanol (1 ml) was added sodium borohydride (2 mg, 0.053 mmol) at ° C. The reaction mixture was stirred for 2 h. It was diluted with DCM and saturated aqueous NaHCO$_3$. After separation, the organic extract was washed (brine), dried (MgSO$_4$) and concentrated. The crude product was purified by silica gel flash chromatography using 0 to 50% ethyl acetate in heptane to afford the title compound of Example 371 as a white solid (18 mg, 89% yield). LC/MS (m/z) 381.19 [(M+1)$^+$]; HPLC Rt: 3.246 min. 1H NMR (400 MHz, MeOD) δ ppm 7.36-7.40 (5H, m) 7.28-7.23 (4H, m) 7.20-7.16 (1H, m) 7.06 (1H, s) 4.79-4.75 (1H, m) 4.64 (1H, s) 1.4-1.39 (9H, m).

Examples 372 to 373

In a similar manner to Example 371, Examples 372 and 373 were prepared via the sodium borohydride reduction of Examples 369 and 370 respectively. (Compounds are racemic unless noted)

| Example No. | Name | Structure | MS [m/z (M + H)] | HPLC Rt: minute |
|---|---|---|---|---|
| 372 | 3-(4-hydroxyethyl)phenyl)-2,2-dimethyl-3-phenyl-N-1,3,4-thiadiazol-2-ylpropanamide | 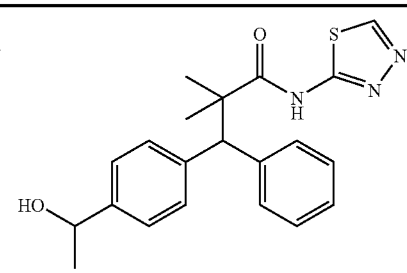 | 382.17 | 3.128 |

| Example No. | Name | Structure | MS [m/z (M + H)] | HPLC Rt: minute |
|---|---|---|---|---|
| 373 | 3-(3-(1-hydroxyethyl)phenyl)-2,2-dimethyl-3-phenyl-N-1,3-thiazol-2-ylpropanamide | 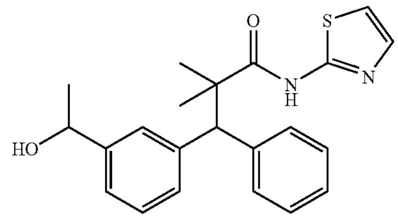 | 381.13 | 3.275 |

Example 374

2,2-Dimethyl-3-(4'-(methyloxy)-4-biphenylyl)-3-phenyl-N-1,3-thiazol-2-ylpropanamide

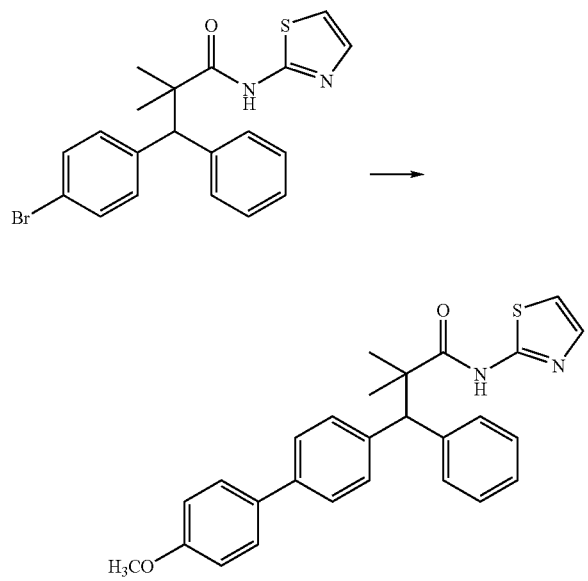

Example 412

An Emry™ process vial was charged with 3-(4-bromophenyl)-2,2-dimethyl-3-phenyl-N-thiazol-2-yl-propionamide (70 mg, 0.168 mmol) and 4-methoxy-phenylboronic acid (77 mg, 0.50 mmol), tetrakis(triphenylphosphine)palladium(0) (20 mg, 0.017 mmol), 2.0 mL of 2M $K_2CO_3$, and 1.5 mL of DMF. The reaction mixture was degassed by bubbling nitrogen through for 15 min, then sealed and exposed to microwave irradiation for 30 min at 150° C. The reaction mixture was cooled, filtered, and diluted with ethyl acetate. The organic solution was washed, dried and concentrated. The crude product was purified by preparative HPLC to give the title compound of Example 374 as a white solid (30 mg, 40%). LC/MS (m/z) 444.37 [(M+H)$^+$]; HPLC Rt: 3.770 min. 1H NMR (400 MHz, MeOD) δ ppm 7.34-7.54 (9H, m) 7.23 (2H, t, J=7.38 Hz) 7.16 (1H, t, J=7.12 Hz) 7.02 (1H, d, J=3.56 Hz) 6.93 (2H, d, J=8.65 Hz) 4.63 (1H, s) 3.78 (3H, s) 1.40 (6H, s).

Examples 375 to 385

In a similar manner to Example 374, Examples 375 to 385 were prepared via the Pd-catalyzed coupling reactions of the corresponding bromo-amides with arylboronic acids. (Compounds are racemic unless noted)

| Example No. | Name | Structure | MS [m/z (M + H)] | HPLC Rt: minute |
|---|---|---|---|---|
| 375 | 2,2-dimethyl-3-phenyl-3-(4-(4-pyridinyl)phenyl)-N-1,3-thiazol-2-ylpropanamide | 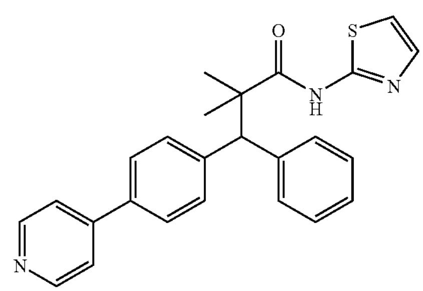 | 414.39 | 2.470 |

-continued

| Example No. | Name | Structure | MS [m/z (M + H)] | HPLC Rt: minute |
|---|---|---|---|---|
| 376 | 3-(4-(3-furanyl)phenyl)-2,2-dimethyl-3-phenyl-N-1,3-thiazol-2-ylpropanamide | 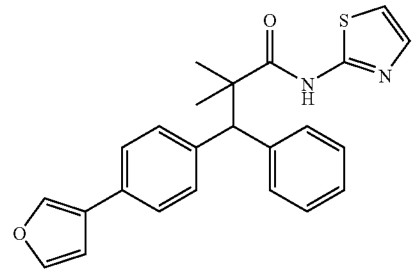 | 403.36 | 3.870 |
| 377 | 2,2-dimethyl-3-(4'-(methyloxy)-4-biphenylyl)-3-phenyl-N-1,3,4-thiadiazol-2-ylpropanamide | Isomer A | 444.43 | 3.775 |
| 378 | 2,2-dimethyl-3-(4'-(methyloxy)-4-biphenylyl)-3-phenyl-N-1,3,4-thiadiazol-2-ylpropanamide | Isomer B | 485.37 | 3.770 |
| 379 | 4'-(2,2-dimethyl-3-oxo-1-phenyl-3-(1,3,4-thiadiazol-2-ylamino)propyl)-N,N-dimethyl-4-biphenylcarboxamide | Isomer A | 485.39 | 3.376 |

-continued

| Example No. | Name | Structure | MS [m/z] (M + H)] | HPLC Rt: minute |
|---|---|---|---|---|
| 380 | 4'-(2,2-dimethyl-3-oxo-1-phenyl-3-(1,3,4-thiadiazol-2-ylamino)propyl)-N,N-dimethyl-4-biphenylcarboxamide | Isomer B | 485.39 | 3.376 |
| 381 | 4'-(2,2-dimethyl-3-oxo-1-phenyl-3-(1,3-thiazol-2-ylamino)propyl)-N,N-dimethyl-4-biphenylcarboxamide | 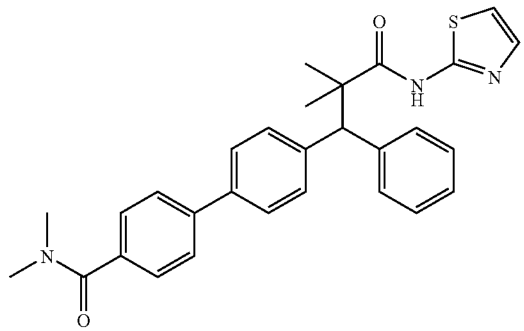 | 484.21 | 3.485 |
| 382 | 2,2-dimethyl-3-(4'-((1-methylethyl)oxy)-4-biphenylyl)-3-phenyl-N-1,3,4-thiadiazol-2-ylpropanamide | 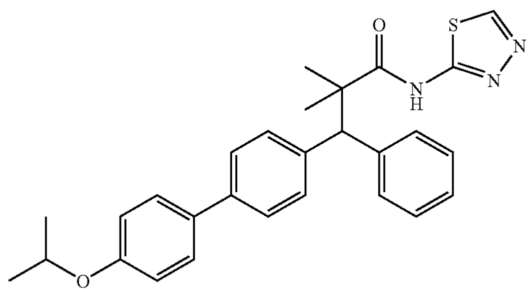 | 472.2 | 4.148 |
| 383 | 2,2-dimethyl-3-(4'-(2-methylpropyl)-4-biphenylyl)-3-phenyl-N-1,3,4-thiadiazol-2-ylpropanamide | 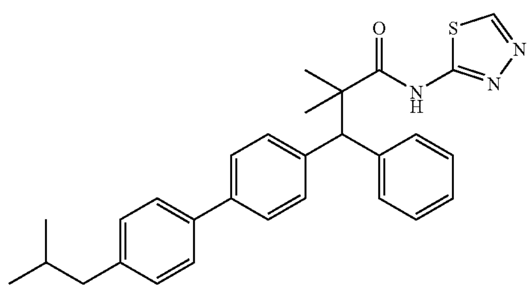 | 470.4 | 4.4466 |
| 384 | 2,2-dimethyl-3-phenyl-3-(4'-propyl-4-biphenylyl)-N-1,3,4-thiadiazol-2-ylpropanamide | 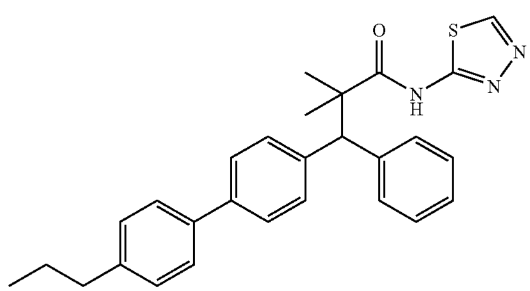 | 456.4 | 4.370 |

| Example No. | Name | Structure | MS [m/z (M + H)] | HPLC Rt: minute |
|---|---|---|---|---|
| 385 | 3-(3'-fluoro-4'-((1-methylethyl)oxy)-4-biphenylyl)-2,2-dimethyl-3-phenyl-N-1,3,4-thiadiazol-2-ylpropanamide | 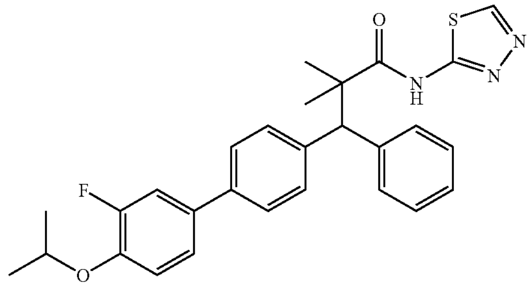 | 490.5 | 4.128 |

Examples 386 to 390

In a similar manner to Example 222, Examples 386 to 390 were prepared via the amidation reactions of acids of Preparation (24) and appropriate amines. (Compounds are racemic unless noted)

| Example No. | Name | Structure | MS [m/z (M + H)] | HPLC Rt: minute |
|---|---|---|---|---|
| 386 | 3-(4-bromophenyl)-2,2,5-trimethyl-N-1,3-thiazol-2-ylhexanamide | 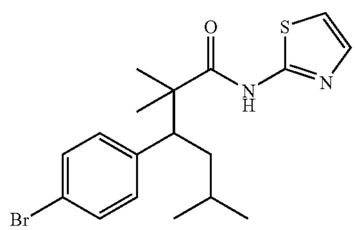 | 395.28 397.28 | 3.873 |
| 387 | 3-(4-bromophenyl)-2,2,5-trimethyl-N-1,3,4-thiadiazol-2-ylhexanamide | 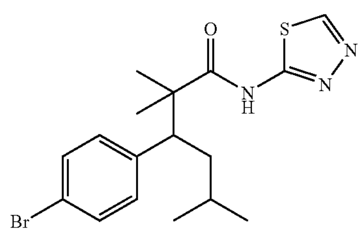 | 396.27 398.27 | 3.751 |
| 388 | 2,2,5-trimethyl-N-(5-methyl-1,3,4-thiadiazol-2-yl)-3-(4-(4-morpholinyl)phenyl)hexanamide | 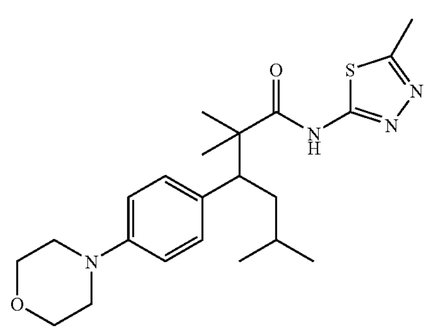 | 47.36 | 3.538 |

-continued

| Example No. | Name | Structure | MS [m/z (M + H)] | HPLC Rt: minute |
|---|---|---|---|---|
| 389 | 2,2,5-trimethyl-3-(4-(4-morpholinyl)phenyl)-N-1,3-thiazol-2-ylhexanamide | 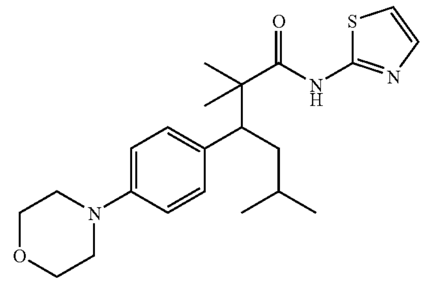 | 402.37 | 3.511 |
| 390 | 2,2,5-trimethyl-3-(4-(4-morpholinyl)phenyl)-N-1,3,4-thiadiazol-2-ylhexanamide | 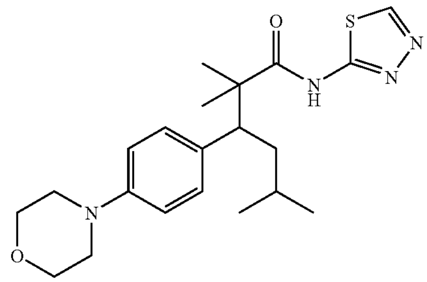 | 403.34 | 3.338 |

Examples 390 to 400

In a similar manner to Example 374, Examples 391 to 400 were prepared via the Pd-catalyzed coupling reactions of the title compounds of Example 386 or 387 with appropriate arylboronic acids. (Compounds are racemic unless noted otherwise)

| Example No. | Name | Structure | MS [m/z (M + H)] | HPLC Rt: minute |
|---|---|---|---|---|
| 391 | 2,2,5-trimethyl-3-(4'-(methyloxy)-4-biphenylyl)-N-1,3-thiazol-2-ylhexanamide | 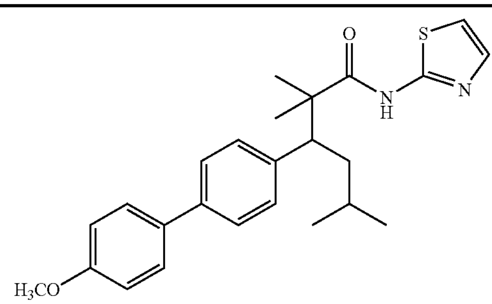 | 428.42 | 4.010 |
| 392 | 4'-(1-(1,1-dimethyl-2-oxo-2-(1,3-thiazol-2-ylamino)ethyl)-3-methylbutyl)-N,N-dimethyl-4-biphenylcarboxamide | 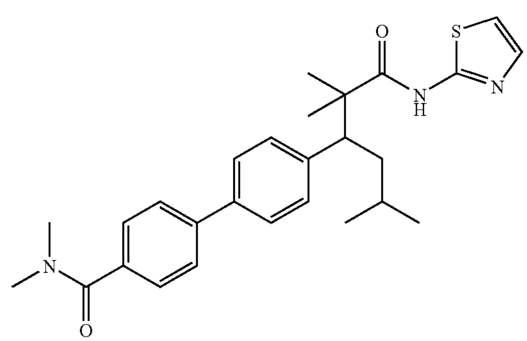 | 464.44 | 3.650 |

-continued

| Example No. | Name | Structure | MS [m/z (M + H)] | HPLC Rt: minute |
|---|---|---|---|---|
| 393 | 4'-(1-(1,1-dimethyl-2-oxo-2-(1,3,4-thiadiazol-2-ylamino)ethyl)-3-methylbutyl)-N,N-dimethyl-4-biphenylcarboxamide | 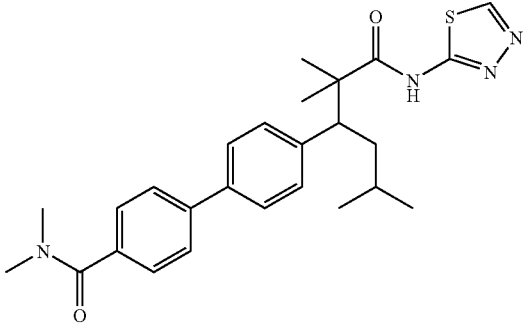 | 465.44 | 3.588 |
| 394 | 2,2,5-trimethyl-3-(4'-(methyloxy)-4-biphenylyl)-N-1,3,4-thiadiazol-2-ylhexanamide | 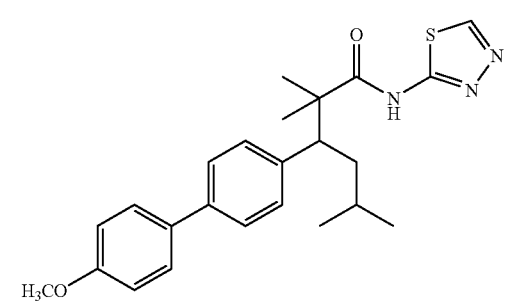 | 424.42 | 3.963 |
| 395 | 2,2,5-trimethyl-3-(4'-((1-methylethyl)oxy)-4-biphenylyl)-N-1,3,4-thiadiazol-2-ylhexanamide | 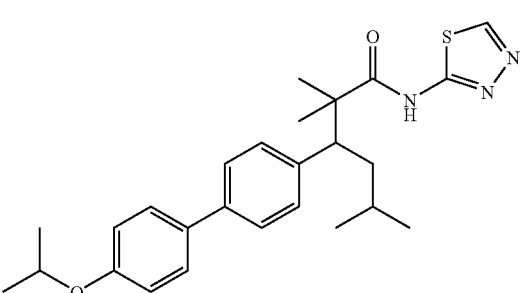 | 452.43 | 4.101 |
| 396 | 2,2,5-trimethyl-3-(4'-(2-methylpropyl)-4-biphenylyl)-N-1,3-thiazol-2-ylhexanamide | 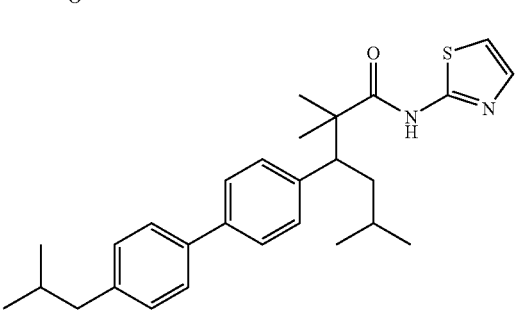 | 449.48 | 4.416 |
| 397 | 2,2,5-trimethyl-3-(4'-(2-methylpropyl)-4-biphenylyl)-N-1,3,4-thiadiazol-2-ylhexanamide | 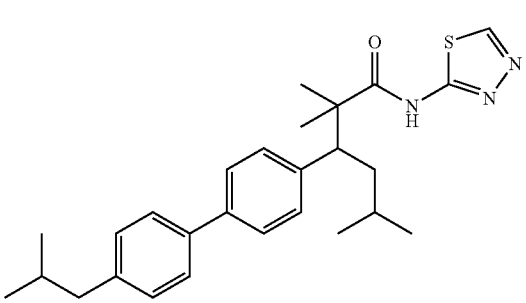 | 450.44 | 4.343 |

| Example No. | Name | Structure | MS [m/z (M + H)] | HPLC Rt: minute |
|---|---|---|---|---|
| 398 | 2,2,5-trimethyl-3-(4'-propyl-4-biphenylyl)-N-1,3-thiazol-2-ylhexanamide | 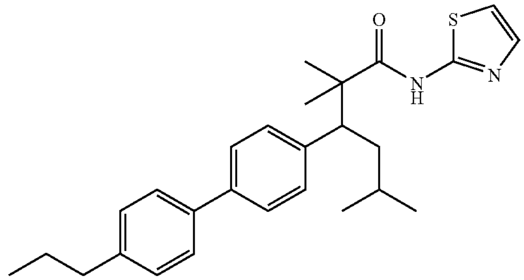 | 435.43 | 4.343 |
| 399 | 2,2,5-trimethyl-3-(4'-propyl-4-biphenylyl)-N-1,3,4-thiadiazol-2-ylhexanamide | 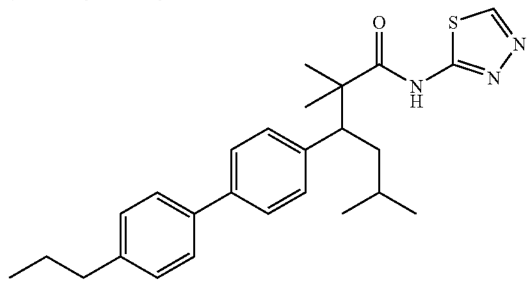 | 436.43 | 4.268 |
| 400 | 2,2,5-trimethyl-3-(4'-((1-methylethyl)oxy)-4-biphenylyl)-N-1,3-thiazol-2-ylhexanamide | 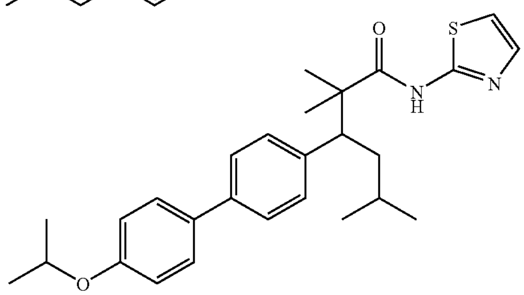 | 451.44 | 4.191 |

Examples 401 to 426

In a similar manner to Example 374, Examples 401 to 426 were prepared via the Pd-catalyzed coupling reactions of the title compound of Example 318 with arylboronic acids. (Compounds are racemic unless noted)

| Example No. | Name | R | HPLC Rt: minute | MS m/z [(M + H)+] |
|---|---|---|---|---|
| 401 | 2,2-dimethyl-3-(4'-(4-morpholinylcarbonyl)-4-biphenylyl)-3-phenyl-N-1,3,4-thiadiazol-2-ylpropanamide | | 3.455 | 527.42 |
| 402 | 3-(4-biphenylyl)-2,2-dimethyl-3-phenyl-N-1,3,4-thiadiazol-2-ylpropanamide | Ph | 4.001 | 414.50 |

-continued

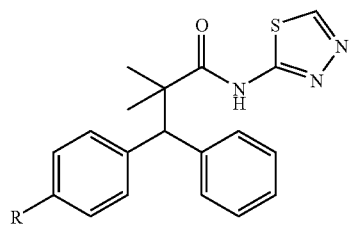

| Example No. | Name | R | HPLC Rt: minute | MS m/z [(M + H)+] |
|---|---|---|---|---|
| 403 | 3-(4'-chloro-4-biphenylyl)-2,2-dimethyl-3-phenyl-N-1,3,4-thiadiazol-2-ylpropanamide | | 4.190 | 448.44 |
| 404 | 2,2-dimethyl-3-phenyl-3-(1,1':4',1''-terphenyl-4-yl)-N-1,3,4-thiadiazol-2-ylpropanamide | | 4.371 | 490.50 |
| 405 | 2,2-dimethyl-3-phenyl-N-1,3,4-thiadiazol-2-yl-3-(4'-(trifluoromethoxy)-4-biphenylyl)propanamide | | 4.191 | 498.44 |
| 406 | 3-(4'-acetyl-4-biphenylyl)-2,2-dimethyl-3-phenyl-N-1,3,4-thiadiazol-2-ylpropanamide | | 3.753 | 456.50 |
| 407 | 3-(4'-ethyl-4-biphenylyl)-2,2-dimethyl-3-phenyl-N-1,3,4-thiadiazol-2-ylpropanamide | | 4.251 | 442.57 |
| 408 | 3-(4'-(methoxymethyl)-4-biphenylyl)-2,2-dimethyl-3-phenyl-N-1,3,4-thiadiazol-2-ylpropanamide | | 3.890 | 458.54 |
| 409 | 3-(3'-chloro-4-biphenylyl)-2,2-dimethyl-3-phenyl-N-1,3,4-thiadiazol-2-ylpropanamide | | 4.181 | 448.48 |
| 410 | 3-(3'-methoxy-4-biphenylyl)-2,2-dimethyl-3-phenyl-N-1,3,4-thiadiazol-2-ylpropanamide | | 3.975 | 444.55 |
| 411 | 3-(2'-methoxy-4-biphenylyl)-2,2-dimethyl-3-phenyl-N-1,3,4-thiadiazol-2-ylpropanamide | | 3.916 | 444.54 |
| 412 | 3-(4'-hydroxy-4-biphenylyl)-2,2-dimethyl-3-phenyl-N-1,3,4-thiadiazol-2-ylpropanamide | | 3.545 | 430.57 |

-continued

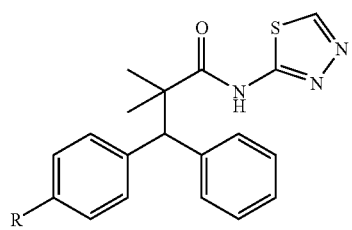

| Example No. | Name | R | HPLC Rt: minute | MS m/z [(M + H)+] |
|---|---|---|---|---|
| 413 | 3-(3'-acetyl-4-biphenylyl)-2,2-dimethyl-3-phenyl-N-1,3,4-thiadiazol-2-ylpropanamide | 3-acetylphenyl | 3.755 | 456.50 |
| 414 | 3-(4'-acetamido-4-biphenylyl)-2,2-dimethyl-3-phenyl-N-1,3,4-thiadiazol-2-ylpropanamide | 4-acetamidophenyl | 3.533 | 471.54 |
| 415 | 3-(4-(2,3-dihydro-1-benzofuran-5-yl)phenyl)-2,2-dimethyl-3-phenyl-N-1,3,4-thiadiazol-2-ylpropanamide | 2,3-dihydrobenzofuran-5-yl | 3.968 | 456.49 |
| 416 | 3-(4'-butoxy-4-biphenylyl)-2,2-dimethyl-3-phenyl-N-1,3,4-thiadiazol-2-ylpropanamide | 4-BuO-phenyl | 4.348 | 486.55 |
| 417 | 3-(4'-tert-butyl-4-biphenylyl)-2,2-dimethyl-3-phenyl-N-1,3,4-thiadiazol-2-ylpropanamide | 4-t-Bu-phenyl | 4.401 | 470.56 |
| 418 | 3-(4'-butyl-4-biphenylyl)-2,2-dimethyl-3-phenyl-N-1,3,4-thiadiazol-2-ylpropanamide | 4-n-Bu-phenyl | 4.518 | 470.52 |
| 419 | 3-(4'-ethoxy-4-biphenylyl)-2,2-dimethyl-3-phenyl-N-1,3,4-thiadiazol-2-ylpropanamide | 4-EtO-phenyl | 4.076 | 458.55 |
| 420 | 3-(3'-fluoro-4'-methoxy-4-biphenylyl)-2,2-dimethyl-3-phenyl-N-1,3,4-thiadiazol-2-ylpropanamide | 3-fluoro-4-methoxyphenyl | 3.935 | 462.47 |
| 421 | 3-(4'-(hydroxymethyl)-4-biphenylyl)-2,2-dimethyl-3-phenyl-N-1,3,4-thiadiazol-2-ylpropanamide | 4-HOCH2-phenyl | 3.545 | 444.55 |
| 422 | 3-(4'-isopropyl-4-biphenylyl)-2,2-dimethyl-3-phenyl-N-1,3,4-thiadiazol-2-ylpropanamide | 4-i-Pr-phenyl | 4.330 | 456.56 |

-continued

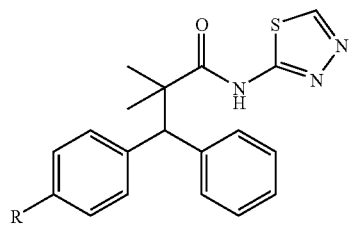

| Example No. | Name | R | HPLC Rt: minute | MS m/z [(M + H)+] |
|---|---|---|---|---|
| 423 | 3-(3'-isopropyl-4-biphenylyl)-2,2-dimethyl-3-phenyl-N-1,3,4-thiadiazol-2-ylpropanamide | i-Pr-substituted phenyl | 4.325 | 456.57 |
| 424 | N-tert-butyl-4'-(2,2-dimethyl-3-oxo-1-phenyl-3-(1,3,4-thiadiazol-2-ylamino)propyl)-4-biphenylcarboxamide | t-Bu-HN-C(O)-phenyl | 3.818 | 513.53 |
| 425 | N-cyclopropyl-4'-(2,2-dimethyl-3-oxo-1-phenyl-3-(1,3,4-thiadiazol-2-ylamino)propyl)-4-biphenylcarboxamide | cyclopropyl-HN-C(O)-phenyl | 3.568 | 497.46 |
| 426 | 2,2-dimethyl-3-(4'-((4-methyl-1-piperazinyl)carbonyl)-4-biphenylyl)-3-phenyl-N-1,3,4-thiadiazol-2-ylpropanamide | N-methylpiperazinyl-C(O)-phenyl | 2.813 | 540.44 |

Examples 427 to 445

In a similar manner to Example 374, Examples 427 to 445 were prepared via the Pd-catalyzed coupling reactions of the title compound of Example 387 with appropriate arylboronic acids. (Compounds are racemic unless noted otherwise)

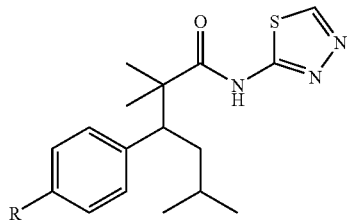

| Example No. | Name | R | HPLC Rt: minute | MS m/z [(M + H)+] |
|---|---|---|---|---|
| 427 | 2,2,5-trimethyl-3-(4'-(4-morpholinylcarbonyl)-4-biphenylyl)-N-1,3,4-thiadiazol-2-ylhexanamide | morpholinyl-C(O)-phenyl | 2.813 | 5077.32 |

-continued

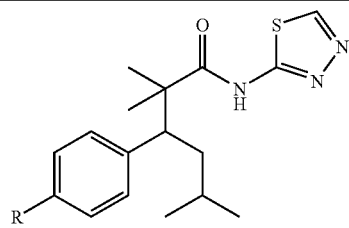

| Example No. | Name | R | HPLC Rt: minute | MS m/z [(M + H)+] |
|---|---|---|---|---|
| 428 | 3-(4'-(methoxymethyl)-4-biphenylyl)-2,2,5-trimethyl-N-1,3,4-thiadiazol-2-ylhexanamide | 4-(H₃COCH₂)-phenyl | 3.470 | 438.36 |
| 429 | N-cyclopropyl-4'-(1-(1,1-dimethyl-2-oxo-2-(1,3,4-thiadiazol-2-ylamino)ethyl)-3-methylbutyl)-4-biphenylcarboxamide | 4-(cyclopropyl-NHC(O))-phenyl | 2.897 | 477.33 |
| 430 | 3-(4'-ethoxy-4-biphenylyl)-2,2,5-trimethyl-N-1,3,4-thiadiazol-2-ylhexanamide | 4-EtO-phenyl | 3.728 | 438.34 |
| 431 | 3-(4-biphenylyl)-2,2,5-trimethyl-N-1,3,4-thiadiazol-2-ylhexanamide | Ph | 3.582 | 394.38 |
| 432 | 3-(4'-chloro-4-biphenylyl)-2,2,5-trimethyl-N-1,3,4-thiadiazol-2-ylhexanamide | 4-Cl-phenyl | 3.84 | 428.34 |
| 433 | 2,2,5-trimethyl-3-(1,1':4',1''-terphenyl-4-yl)-N-1,3,4-thiadiazol-2-ylhexanamide | 4-Ph-phenyl | 4.078 | 470.36 |
| 434 | 3-(3'-chloro-4-biphenylyl)-2,2,5-trimethyl-N-1,3,4-thiadiazol-2-ylhexanamide | 3-Cl-phenyl | 3.835 | 428.30 |
| 435 | 3-(2'-methoxy-4-biphenylyl)-2,2,5-trimethyl-N-1,3,4-thiadiazol-2-ylhexanamide | 2-MeO-phenyl | 3.507 | 424.36 |
| 436 | 3-(4'-hydroxy-4-biphenylyl)-2,2,5-trimethyl-N-1,3,4-thiadiazol-2-ylhexanamide | 4-HO-phenyl | 2.932 | 410.36 |
| 437 | 2,2,5-trimethyl-N-1,3,4-thiadiazol-2-yl-3-(4'-(trifluoromethoxy)-4-biphenylyl)hexanamide | 4-F₃CO-phenyl | 3.891 | 478.28 |
| 438 | 3-(4'-acetyl-4-biphenylyl)-2,2,5-trimethyl-N-1,3,4-thiadiazol-2-ylhexanamide | 4-acetyl-phenyl | 3.280 | 436.37 |

-continued

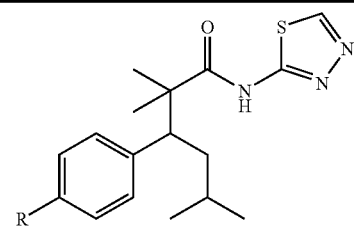

| Example No. | Name | R | HPLC Rt: minute | MS m/z [(M + H)+] |
|---|---|---|---|---|
| 439 | 3-(3'-acetyl-4-biphenylyl)-2,2,5-trimethyl-N-1,3,4-thiadiazol-2-ylhexanamide | | 3.302 | 436.34 |
| 440 | 3-(4'-acetamido-4-biphenylyl)-2,2,5-trimethyl-N-1,3,4-thiadiazol-2-ylhexanamide | | 2.830 | 451.35 |
| 441 | 3-(4-(2,3-dihydro-1-benzofuran-5-yl)phenyl)-2,2,5-trimethyl-N-1,3,4-thiadiazol-2-ylhexanamide | | 3.498 | 436.35 |
| 442 | 3-(4'-butoxy-4-biphenylyl)-2,2,5-trimethyl-N-1,3,4-thiadiazol-2-ylhexanamide | | 3.925 | 466.32 |
| 443 | 3-(3'-fluoro-4'-methoxy-4-biphenylyl)-2,2,5-trimethyl-N-1,3,4-thiadiazol-2-ylhexanamide | | 3.490 | 442.32 |
| 444 | N-tert-butyl-4'-(1-(1,1-dimethyl-2-oxo-2-(1,3,4-thiadiazol-2-ylamino)ethyl)-3-methylbutyl)-4-biphenylcarboxamide | | 3.333 | 493.34 |
| 445 | 3-(4'-(hydroxymethyl)-4-biphenylyl)-2,2,5-trimethyl-N-1,3,4-thiadiazol-2-ylhexanamide | | 2.863 | 424.34 |

Biological Activity Data

The AP-1 activity of Examples 1 to 442 is given where the AP-1 EC$_{50}$ is less than 1 uM. Accompanying AP-1 maximum inhibition values are also given. Where the AP-1 EC50 is greater than 1 uM and/or the maximal inhibition is less than 20%, the glucocorticoid receptor (GR) binding affinity is given (Ki or RBA). The data presented below were obtained using the assays referred to in the table below and described herein in the ASSAY section supra.

| Example No. | GR % RBA | GR (Ki, nM) (GR Binding Assay (I)$^a$) | GR (Ki, nM) (GR Binding Assay (II)$^b$) | AP-1 EC$_{50}$, nM (Cellular Transrepression Assay) | AP-1 Max % inh (Cellular Transrepression Assay) |
|---|---|---|---|---|---|
| 1 | 103.8 | | | | |
| 2 | | | | | |

-continued

| Example No. | GR % RBA | GR (Ki, nM) (GR Binding Assay (I)[a]) | GR (Ki, nM) (GR Binding Assay (II)[b]) | AP-1 EC$_{50}$, nM (Cellular Transrepression Assay) | AP-1 Max % inh (Cellular Transrepression Assay) |
|---|---|---|---|---|---|
| 3 | 94.4 | | | | |
| 4 | 97.5 | | | | |
| 5 | 89.6 | | | | |
| 6 | 95.9 | | | | |
| 7 | 94.2 | | | | |
| 8 | 95.8 | | | | |
| 9 | 97.9 | | | | |
| 10 | 90.4 | | | | |
| 11 | 91.3 | | | | |
| 12 | 95.1 | | | | |
| 13 | 92.8 | | | | |
| 14 | 97.6 | | | | |
| 15 | 89.8 | | | | |
| 16 | 97.5 | | | | |
| 17 | 84.9 | | | | |
| 18 | 97.1 | | | | |
| 19 | 93.1 | | | | |
| 20 | 87.3 | | | | |
| 21 | 97.0 | | | | |
| 22 | 56.2 | | | | |
| 23 | 99.0 | | | | |
| 24 | 92.9 | | | | |
| 25 | 56.3 | | | | |
| 26 | 63.3 | | | | |
| 27 | 73.6 | | | | |
| 28 | 69.4 | | | | |
| 29 | 92.4 | | | | |
| 30 | 75.6 | | | | |
| 31 | 92.8 | | | | |
| 32 | 100.3 | | 2.90 | | |
| 33 | | | | | |
| 34 | 95.7 | | | | |
| 35 | 102.8 | | | | |
| 36 | 89.6 | | | | |
| 37 | 90.4 | | | | |
| 38 | 95.2 | | | | |
| 39 | 79.0 | | | | |
| 40 | 92.4 | | | | |
| 41 | | | | | |
| 42 | 87.2 | | | | |
| 43 | 89.4 | | | | |
| 44 | 87.2 | | | | |
| 45 | 91.7 | | | | |
| 46 | | | | | 22.86 |
| 47 | 90.0 | | | | |
| 48 | 56.7 | | | | |
| 49 | | | | | 20.10 |
| 50 | 94.5 | | | | |
| 51 | 74.0 | | | | |
| 52 | 81.7 | | | | |
| 53 | 81.7 | | | | |
| 54 | 75.7 | | | | |
| 55 | 58.1 | | | | |
| 56 | 83.2 | | | | |
| 57 | 68.7 | | | | |
| 58 | 89.9 | | | | |
| 59 | 80.6 | | | | |
| 60 | 75.7 | | | | |
| 61 | 64.3 | | | | |
| 62 | 90.2 | | | | |
| 63 | 63.7 | | | | |
| 64 | 88.2 | | | | |
| 65 | 89.3 | | | | |
| 66 | 54.1 | | | | |
| 67 | 68.5 | | | | |
| 68 | 62.1 | | | | |
| 69 | 97.9 | | 67.20 | | |
| 70 | 88.6 | | | | |
| 71 | 91.4 | | | | |
| 72 | 74.1 | | | | |
| 73 | 88.4 | | | | |
| 74 | | | | | 28.12 |
| 75 | 35.2 | | | | |
| 76 | 89.4 | | | | |
| 77 | 64.9 | | | | |

-continued

| Example No. | GR % RBA | GR (Ki, nM) (GR Binding Assay (I)[a]) | GR (Ki, nM) (GR Binding Assay (II)[b]) | AP-1 EC$_{50}$, nM (Cellular Transrepression Assay) | AP-1 Max % inh (Cellular Transrepression Assay) |
|---|---|---|---|---|---|
| 78 | 79.8 | | | | |
| 79 | 68.5 | | | | |
| 80 | 96.9 | | | | |
| 81 | | | | | 23.14 |
| 82 | | | | | 25.88 |
| 83 | 92.0 | | | | |
| 84 | | | | | 30.84 |
| 85 | 81.0 | | | | |
| 86 | 57.6 | | | | |
| 87 | 71.2 | | | | |
| 88 | 71.1 | | | | |
| 89 | 90.2 | | | | |
| 90 | 84.7 | | | | |
| 91 | | | | | 23.18 |
| 92 | 97.3 | | | | |
| 93 | 95.9 | | | | 28.13 |
| 94 | | | | | 35.37 |
| 95 | | | | | 36.21 |
| 96 | 79.1 | | | | 37.09 |
| 97 | | | | | 26.54 |
| 98 | 91.6 | | | | |
| 99 | 91.1 | | | | |
| 100 | | | | | 29.99 |
| 101 | | | | | 26.95 |
| 102 | 86.3 | | | | |
| 103 | 100.7 | | 5.70 | | |
| 104 | | | | | 27.29 |
| 105 | | | | | 22.15 |
| 106 | | | | | 35.89 |
| 107 | | | | | 38.40 |
| 108 | 70.0 | | | | |
| 109 | | | | | 22.57 |
| 110 | 89.7 | | | | |
| 111 | 86.3 | | | | |
| 112 | | | | | 20.86 |
| 113 | 89.5 | | | | |
| 114 | 81.8 | | | | |
| 115 | 14.2 | | | | |
| 116 | 97.1 | | | | |
| 117 | 90.4 | | | | |
| 118 | 91.8 | | | | |
| 119 | 88.3 | | | | |
| 120 | 87.2 | | | | |
| 121 | 80.3 | | | | |
| 122 | 62.5 | | | | |
| 123 | 79.9 | | | | |
| 124 | 81.5 | | | | |
| 125 | 70.8 | | | | |
| 126 | 86.9 | | | | |
| 127 | 81.8 | | | | |
| 128 | 96.6 | | | | |
| 129 | 90.1 | | | | |
| 130 | 88.0 | | | | |
| 131 | 72.4 | | | | |
| 132 | 86.3 | | | | |
| 133 | 61.7 | | | | |
| 134 | 86.8 | | | | |
| 135 | 80.8 | | | | |
| 136 | 48.8 | | | | |
| 137 | 78.7 | | | | |
| 138 | 69.1 | | | | |
| 139 | 80.2 | | | | |
| 140 | 100.4 | | | | |
| 141 | 83.4 | | | | |
| 142 | 73.3 | | | | |
| 143 | 66.5 | | | | |
| 144 | 35.8 | | | | |
| 145 | 26.0 | | | | |
| 146 | 69.2 | | | | |
| 147 | 61.5 | | | | |
| 148 | 53.6 | | | | |
| 149 | 63.8 | | | | |
| 150 | 82.7 | | | | |
| 151 | 89.1 | 1154.00 | | | |
| 152 | 67.7 | | | | |

| Example No. | GR % RBA | GR (Ki, nM) (GR Binding Assay (I)[a]) | GR (Ki, nM) (GR Binding Assay (II)[b]) | AP-1 EC$_{50}$, nM (Cellular Transrepression Assay) | AP-1 Max % inh (Cellular Transrepression Assay) |
|---|---|---|---|---|---|
| 153 | 98.9 | 23.22 | | | |
| 154 | 84.9 | | | | |
| 155 | 87.7 | | | | |
| 156 | 95.8 | 36.88 | | | |
| 157 | 84.1 | | | | |
| 158 | 85.4 | | | | |
| 159 | 95.3 | 101.10 | | | |
| 160 | 68.3 | | | | |
| 161 | 62.2 | | | | |
| 162 | | | | | 22.84 |
| 163 | 82.4 | | | | |
| 164 | | | | 809.67 | 75.24 |
| 165 | 66.4 | | | | |
| 166 | 88.4 | | | 950.29 | 62.29 |
| 167 | 83.1 | | | | |
| 168 | | | | | 22.99 |
| 169 | 75.2 | | | | |
| 170 | | | | | 27.02 |
| 171 | 73.6 | | | | |
| 172 | 82.2 | | | | |
| 173 | 86.7 | | | | |
| 174 | 87.9 | | | | |
| 175 | 88.4 | | | | |
| 176 | 98.4 | 53.99 | | | |
| 177 | 82.5 | | | | |
| 178 | 87.1 | | | | |
| 179 | | | | | |
| 180 | 58.2 | | | | |
| 181 | | | | | 28.93 |
| 182 | 94.0 | | | | |
| 183 | | | | | 65.31 |
| 184 | | | | | 57.48 |
| 185 | 93.9 | | | | |
| 186 | | | | | 20.51 |
| 187 | | | | | |
| 188 | 94.0 | | | | |
| 189 | 88.2 | | | | |
| 190 | 97.2 | | | | |
| 191 | 83.6 | | | | |
| 192 | 73.8 | | | | |
| 193 | 97.5 | | | | |
| 194 | | | | | 25.40 |
| 195 | 97.5 | | | | |
| 196 | 95.3 | | | | |
| 197 | | | | | 36.33 |
| 198 | | | | | 25.81 |
| 199 | | | | | 31.15 |
| 200 | 88.7 | | | | |
| 201 | 96.7 | | | | |
| 202 | 92.7 | | | | |
| 203 | | | | | 35.13 |
| 204 | 94.7 | | | | |
| 205 | 94.5 | | | | |
| 206 | | | | | 37.72 |
| 207 | 98.6 | | | | |
| 208 | 94.4 | | | | |
| 209 | | | | 86.48 | 46.88 |
| 210 | 99.3 | | | | |
| 211 | 99.8 | | | | |
| 212 | 98.1 | | | | |
| 213 | 96.4 | | | | |
| 214 | 98.1 | | | | |
| 215 | 93.9 | | | | |
| 216 | 98.6 | | | | |
| 217 | | | | 516.00 | 35.03 |
| 218 | | | | | 38.04 |
| 219 | 97.5 | | | | |
| 220 | | | | | 36.22 |
| 221 | 91.8 | | | | |
| 222 | | | 12.60 | | |
| 223 | | | | 88.11 | 70.83 |
| 224 | | | | 161.00 | 33.79 |
| 225 | | | | 114.20 | 34.28 |
| 226 | | | 9.40 | | |
| 227 | | | | 666.30 | 43.71 |

-continued

| Example No. | GR % RBA | GR (Ki, nM) (GR Binding Assay (I)[a]) | GR (Ki, nM) (GR Binding Assay (II)[b]) | AP-1 EC$_{50}$, nM (Cellular Transrepression Assay) | AP-1 Max % inh (Cellular Transrepression Assay) |
|---|---|---|---|---|---|
| 228 | | | | 33.54 | 36.94 |
| 229 | | | | 18.64 | 44.17 |
| 230 | | | | | |
| 231 | | | 18.20 | | |
| 232 | | | 14.50 | | |
| 233 | | | 13.20 | | |
| 234 | | | | 572.80 | 38.96 |
| 235 | | 5.19 | 13.60 | | |
| 236 | | | | 150.80 | 38.52 |
| 237 | | | 13.60 | | |
| 238 | | | 408.30 | | |
| 239 | | | 324.10 | | |
| 240 | | | 18.60 | | |
| 241 | | | 31.30 | | |
| 242 | | | 9.60 | | |
| 243 | | | 29.10 | | |
| 244 | | | 17.85 | | |
| 245 | | | 2308.00 | | |
| 246 | | | 1503.00 | | |
| 247 | | | 413.00 | | |
| 248 | | | 306.50 | | |
| 249 | | | 180.70 | | |
| 250 | | | 348.00 | | |
| 251 | | | 635.70 | | |
| 252 | | | 60.50 | | |
| 253 | | | | 37.03 | 27.88 |
| 254 | | 104.10 | 25.80 | | |
| 255 | | | | 10.17 | 43.01 |
| 256 | | 125.00 | 121.00 | | |
| 257 | | | 71.40 | | |
| 258 | | | | 10.48 | 42.67 |
| 259 | | | 189.70 | | |
| 260 | | | | 4.06 | 35.64 |
| 261 | 97.8 | | 1.10 | | |
| 262 | 96.9 | | 8.30 | | |
| 263 | | | 129.90 | | |
| 264 | | | | 772.20 | 58.61 |
| 265 | | | 193.00 | | |
| 266 | | | 314.90 | | |
| 267 | | | 111.00 | | |
| 268 | | | 302.20 | | |
| 269 | | | 1298.00 | | |
| 270 | | | 2001.00 | | |
| 271 | | | 770.00 | | |
| 272 | | | 1160.00 | | |
| 273 | | | 987.30 | | |
| 274 | | | 1531.00 | | |
| 275 | | | 51.90 | | |
| 276 | | | | 190.10 | 34.03 |
| 277 | | | 2669.00 | | |
| 278 | | | 1851.00 | | |
| 279 | | | 74.70 | | |
| 280 | | | 100.20 | | |
| 281 | | | 15.50 | | |
| 282 | | | 29.50 | | |
| 283 | | | 9.20 | | |
| 284 | | | 26.90 | | |
| 285 | | | 13.80 | | |
| 286 | | | 46.70 | | |
| 287 | | | 14.70 | | |
| 288 | | | | 215.70 | 62.17 |
| 289 | | | | 18.54 | 71.62 |
| 290 | | | | 9.65 | 72.60 |
| 291 | | | | 10.30 | 74.29 |
| 292 | | 24.50 | | | |
| 293 | | 9.85 | | | |
| 294 | | 9.22 | | | |
| 295 | | 13.85 | | | |
| 296 | | | 45.70 | | |
| 297 | | | | 261.50 | 77.31 |
| 298 | | | | 417.00 | 78.66 |
| 299 | | | | 13.26 | 69.29 |
| 300 | | | | 9.97 | 73.69 |
| 301 | | | | 10.22 | 73.70 |
| 302 | | | | 33.29 | 76.78 |

-continued

| Example No. | GR % RBA | GR (Ki, nM) (GR Binding Assay (I)[a]) | GR (Ki, nM) (GR Binding Assay (II)[b]) | AP-1 EC$_{50}$, nM (Cellular Transrepression Assay) | AP-1 Max % inh (Cellular Transrepression Assay) |
|---|---|---|---|---|---|
| 303 | | | | 16.55 | 75.66 |
| 304 | | | | 19.89 | 74.55 |
| 305 | | | | 22.49 | 84.24 |
| 306 | | | 26.30 | | |
| 307 | | | 15.50 | | |
| 308 | | | 34.95 | | |
| 309 | | | 76.40 | | |
| 310 | | | 26.60 | | |
| 311 | | | 17.50 | | |
| 312 | | | 19.90 | | |
| 313 | | | 57.60 | | |
| 314 | | | 13.20 | | |
| 315 | | | 10.90 | | |
| 316 | | | 472.20 | | |
| 317 | | | 23.20 | | |
| 318 | | | 12.80 | | |
| 319 | | 386.30 | | | |
| 320 | | 187.30 | | | |
| 321 | | 5.68 | | | |
| 322 | | 5.17 | | | |
| 323 | | 5.07 | | | |
| 324 | | 9.36 | | | |
| 325 | | | | 53.86 | 57.78 |
| 326 | | 18.70 | 12.90 | | |
| 327 | | | 90.90 | | |
| 328 | | | 17.80 | | |
| 329 | | | 16.80 | | |
| 330 | | | 168.90 | | |
| 331 | | | 18.80 | | |
| 332 | | | 204.50 | | |
| 333 | | | 392.20 | | |
| 334 | | | 395.30 | | |
| 335 | | | | 9.32 | 21.18 |
| 336 | | | 504.40 | | |
| 337 | | | 2092.00 | | |
| 338 | | | 11.80 | | |
| 339 | | | | 30.48 | 60.83 |
| 340 | | | | 90.34 | 57.04 |
| 341 | | | 175.00 | | |
| 342 | | | 8.10 | | |
| 343 | | | 20.70 | | |
| 344 | | | 43.20 | | |
| 345 | | | | 35.24 | 68.07 |
| 346 | | | 16.00 | | |
| 347 | | | | 10.83 | 55.26 |
| 348 | | | | 120.30 | 53.97 |
| 349 | | | 12.50 | | |
| 350 | | | | 14.99 | 81.84 |
| 351 | | | | 16.35 | 65.98 |
| 352 | | | | 118.20 | 61.73 |
| 353 | | | | 100.40 | 77.76 |
| 354 | | | | 158.30 | 71.82 |
| 355 | | | | 64.60 | 63.05 |
| 356 | | | | 735.90 | 61.08 |
| 357 | | | | 143.90 | 73.69 |
| 358 | | | 22.90 | | |
| 359 | | | | 278.20 | 65.18 |
| 360 | | | 21.70 | | |
| 361 | | | | 13.32 | 36.44 |
| 362 | | | | 16.62 | 33.37 |
| 363 | | | 47.00 | | |
| 364 | | | | 183.60 | 39.10 |
| 365 | | | 31.90 | | |
| 366 | | | | 20.03 | 32.56 |
| 367 | | | 26.90 | | |
| 368 | | | 19.20 | | |
| 369 | | | | 818.60 | 34.87 |
| 370 | | | 60.90 | | |
| 371 | | | 38.10 | | |
| 372 | | | 96.10 | | |
| 373 | | | 319.50 | | |
| 374 | | | | 120.80 | 39.69 |
| 375 | | | 11.00 | | |
| 376 | | | 15.80 | | |
| 377 | | 1.81 | | | |

-continued

| Example No. | GR % RBA | GR (Ki, nM) (GR Binding Assay (I)$^a$) | GR (Ki, nM) (GR Binding Assay (II)$^b$) | AP-1 EC$_{50}$, nM (Cellular Transrepression Assay) | AP-1 Max % inh (Cellular Transrepression Assay) |
|---|---|---|---|---|---|
| 378 | | | | 894.30 | 26.23 |
| 379 | | 1.24 | | | |
| 380 | | 24.25 | | | |
| 381 | | 3.53 | | | |
| 382 | | | | 28.07 | 40.09 |
| 383 | | 9.18 | | | |
| 384 | | 6.43 | | | |
| 385 | | 13.77 | | | |
| 386 | | 20.56 | | | |
| 387 | | 17.15 | | | |
| 388 | | 14.01 | | | |
| 389 | | 4.65 | | | |
| 390 | | 5.41 | | | |
| 391 | | 11.06 | | | |
| 392 | | 6.83 | | | |
| 393 | | 3.68 | | | |
| 394 | | 9.28 | | | |
| 395 | | | | 13.43 | 32.48 |
| 396 | | | | 226.60 | 31.51 |
| 397 | | 12.07 | | | |
| 398 | | | | 69.95 | 28.25 |
| 399 | | 7.10 | | | |
| 400 | | | | 267.00 | 46.09 |
| 401 | | | | 13.35 | 46.99 |
| 402 | | | | 7.90 | 26.49 |
| 403 | | | | 3.03 | 24.85 |
| 404 | | | | 9.57 | 21.85 |
| 405 | | | | 24.55 | 35.17 |
| 406 | | | | 39.02 | 29.39 |
| 407 | | | | 14.88 | 37.46 |
| 408 | | | | 39.83 | 24.92 |
| 409 | | 25.45 | | | |
| 410 | | 4.45 | | | |
| 411 | | 154.40 | | | |
| 412 | | 16.50 | | | |
| 413 | | 109.90 | | | |
| 414 | | 9.27 | | | |
| 415 | | 6.08 | | | |
| 416 | | 42.46 | | | |
| 417 | | 52.86 | | | |
| 418 | | 26.52 | | | |
| 419 | | 5.53 | | | |
| 420 | | 13.33 | | | |
| 421 | | 5.72 | | | |
| 422 | | | | 2.70 | 33.66 |
| 423 | | | | 6.07 | 34.80 |
| 424 | | | | 14.49 | 26.37 |
| 425 | | | | 3.63 | 28.72 |
| 426 | | 3.68 | | | |
| 427 | | 9.28 | | | |
| 428 | | 17.94 | | | |
| 429 | | 31.02 | | | |
| 430 | | 4.87 | | | |
| 431 | | 52.77 | | | |
| 432 | | 183.90 | | | |
| 433 | | 12.43 | | | |
| 434 | | 19.44 | | | |
| 435 | | 10.72 | | | |
| 436 | | 104.70 | | | |
| 437 | | 5.33 | | | |
| 438 | | 12.05 | | | |
| 439 | | 20.25 | | | |
| 440 | | 21.40 | | | |
| 441 | | 103.80 | | | |
| 442 | | | | 11.67 | 22.72 |

*% RBA = % Relative Binding Affinity to dexamethasone

What is claimed is:

1. A compound according to formula (I),

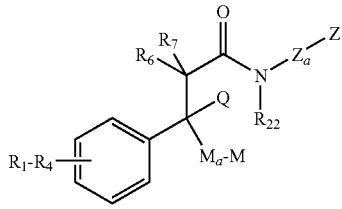

(I)

or an enantiomer, diastereomer, or a pharmaceutically-acceptable salt thereof, wherein:

M is aryl;

$M_a$ is a linker between C and M and is a bond;

Q is selected from the group consisting of hydrogen, $C_1$-$C_4$ alkyl, and substituted $C_1$-$C_4$ alkyl;

Z is selected from the group consisting of cycloalkyl, heterocyclo, aryl, and heteroaryl;

$Z_a$ is a linker between N and Z and is a bond;

$R_1$, $R_2$, $R_3$, and $R_4$ at each occurrence are independently selected from the group consisting of hydrogen, halogen, alkyl, substituted alkyl, alkenyl, substituted alkenyl, alkynyl, substituted alkynyl, nitro, cyano, —$OR_{10}$—$SR_{10}$—$NR_{10}R_{11}$, —C(=O)$R_{10}$, —$CO_2R_{10}$, —C(=O)$NR_{10}R_{11}$, —O—C(=O)$R_{10}$, —$NR_{10}$C(=O)$NR_{10}R_{11}$, —$NR_{10}$C(=O)$R_{11}$, —$NR_{10}$C(=O)$OR_{11}$, —$NR_{10}$C(S)$OR_{11}$, —S(=O)$_p$$R_{12}$, —$NR_{10}SO_pR_{12}$, —$SO_pNR_{10}R_{11}$, cycloalkyl, heterocyclo, aryl, and heteroaryl;

$R_6$ is selected from the group consisting of alkyl, substituted alkyl, alkenyl, substituted alkenyl, alkynyl, substituted alkynyl, —C(=O)$R_{17}$, —$CO_2R_{17}$, —C(=O)$NR_{16}R_{17}$, cycloalkyl, heterocyclo, and heteroaryl, provided that the point of attachment occurs at a carbon atom on the heterocyclo or heteroaryl;

$R_7$ is selected from the group consisting of halogen, alkyl, substituted alkyl, alkenyl, substituted alkenyl, alkynyl, substituted alkynyl, nitro, —$OR_{19}$, —$SR_{19}$, —$NR_{19}R_{20}$, —C(=O)$R_{19}$, —$CO_2R_{19}$, —C(=O)$NR_{19}R_{20}$, —O—C(=O)$R_{19}$, —$NR_{19}$C(=O)$R_{20}$, —$NR_{19}$C(=O)$OR_{20}$, —$NR_{19}$C(=S)$OR_{20}$, —S(=O)$_p$$R_{21}$, —$NR_{19}SO_2R_{21}$, —$SO_2NR_{19}R_{20}$, cycloalkyl, heterocyclo, aryl, and heteroaryl, provided that if $R_7$ is OH then $R_6$ is selected from a group other than unsubstituted or substituted alkyl;

or $R_6$ and $R_7$ are taken together with the carbon to which they are attached to form a cycloalkyl, or heterocyclo group;

$R_{10}$, $R_{11}$, $R_{16}$, $R_{17}$, $R_{19}$, and $R_{20}$ at each occurrence are independently selected from the group consisting of
(i) hydrogen, alkyl, substituted alkyl, alkenyl, substituted alkenyl, alkynyl, substituted alkynyl, cycloalkyl, aryl, heteroaryl, and heterocyclo; or
(ii) $R_{10}$ is taken together with $R_{11}$, and/or $R_{16}$ is taken together with $R_{17}$; and/or $R_{19}$ is taken together with $R_{20}$ to form a 4- to 7-membered heteroaryl ring, or a 4- to 7-membered heterocyclo ring;

$R_{12}$ and $R_{21}$ are independently selected from the group consisting of alkyl, substituted alkyl, alkenyl, substituted alkenyl, alkynyl, substituted alkynyl, cycloalkyl, aryl, heteroaryl, and heterocyclo;

$R_{22}$ is hydrogen; and p is 1 or 2.

2. The compound as defined in claim 1, or an enantiomer, diastereomer, or a pharmaceutically-acceptable salt thereof, wherein:

$R_1$, $R_2$, $R_3$, and $R_4$ are independently selected from the group consisting of (i) hydrogen, halogen, cyano, $CF_3$, $C_{1-6}$alkyl, CH(OH)$R_{10}$, $C_{2-4}$alkenyl, $C_{2-4}$alkynyl, $OR_{10}$, $CO_2R_{10}$, $SR_{10}$, $SO_2R_{12}$, C(O)$R_{10}$, C(O)$NR_{10}R_{11}$, $SO_2NR_{10}R_{11}$, NHC(O)$R_{11}$, NHC(O)$NR_{10}R_{11}$, NHC(O)$_2R_{11}$, NHS(O)$_2R_{12}$, and $NR_{10}R_{11}$; and/or (ii) $C_{0-3}$alkylene substituted by an optionally substituted group selected from the group consisting of phenyl and a 5- to 7-membered heterocyclo or heteroaryl;

$R_{10}$ and $R_{11}$ at each occurrence are independently selected from the group consisting of (i) hydrogen, substituted $C_{1-6}$alkyl, and $C_{1-6}$alkyl; and/or (ii) $C_{0-3}$alkylene substituted by an optionally substituted group selected from the group consisting of $C_{3-7}$cycloalkyl, phenyl, naphthyl, and a 5- to 7-membered heterocyclo or a 5- to 7-membered heteroaryl; and/or (iii) $R_{10}$ is taken together with $R_{11}$ and the nitrogen atom to which they are both attached to form an optionally substituted 5- to 6-membered heteroaryl or 5- to 6-membered heterocyclo; and $R_{12}$ at each occurrence is selected from the group consisting of $C_{1-6}$alkyl and $C_{0-3}$alkylene substituted by an optionally substituted group selected from the group consisting of $C_{3-7}$cycloalkyl, heterocyclo, aryl, and heteroaryl.

3. The compound as defined in claim 1, or an enantiomer, diastereomer, or a pharmaceutically-acceptable salt thereof, wherein:

Q is hydrogen or alkyl;

M is aryl, alkylaryl, or haloaryl; and $R_6$ is selected from the group consisting of $C_{1-4}$alkyl, $C_{1-4}$substituted alkyl, and $C_{3-7}$cycloalkyl;

$R_7$ is selected from the group consisting of $C_{1-4}$alkyl, $C_{1-4}$substituted alkyl, $C_{1-4}$alkoxy, and $C_{3-7}$cycloalkyl;

or $R_6$ and $R_7$ are taken together with the carbon to which they are attached to form a $C_{3-7}$cycloalkyl group.

4. The compound as defined in claim 1, or an enantiomer, diastereomer, or a pharmaceutically-acceptable salt thereof, wherein:

$M_a$ is a bond;

M is aryl; and

Q is hydrogen or $C_{1-4}$alkyl.

5. The compound as defined in claim 1, or an enantiomer, diastereomer, or a pharmaceutically-acceptable salt thereof, wherein:

$Z_a$ is a bond;

Z is $C_{3-6}$cycloalkyl, a 5- to 7-membered heterocyclo or a 5- to 7-membered heteroaryl, each group substituted with one to three groups, —$R'''$, $R''$, and/or $R°$;

$R'''$, $R''$, and $R°$ are independently selected from the group consisting of
(i) hydrogen, halogen, alkyl, substituted alkyl, alkenyl, substituted alkenyl, alkynyl, substituted alkynyl, nitro, cyano, $OR_{23}$, $SR_{23}$, —C(=NOR$_{23}$)CO$_2R_{24}$, $NR_{23}R_{24}$, —CO$_rR_{23}$, C(=O)$NR_{23}R_{24}$, —O—C(=O)$R_{23}$, $NR_{23}$C(=O)$R_{24}$, $NR_{23}$C(=O)$OR_{24}$, $NR_{23}$C(=S)$OR_{24}$, S(O)$_rR_{25}$, $NR_{23}SO_rR_{25}$, SO$_rNR_{23}R_{24}$, cycloalkyl, heterocyclo, aryl, and heteroaryl; or
(ii) two of $R'''$, $R''$, and/or $R°$ located on adjacent atoms together with the atoms to which they are attached may combine to form an optionally substituted fused cycloalkyl, aryl, heteroaryl, and heterocyclo ring;

$R_{23a}$, $R_{23}$ and $R_{24}$ at each occurrence are independently selected from the group consisting of (i) hydrogen, alkyl, substituted alkyl, —C(=O)alkyl, —CO₂(alkyl), alkenyl, substituted alkenyl, alkynyl, substituted alkynyl, amino, substituted amino, aryl, heteroaryl, heterocyclo, and cycloalkyl; or (ii) $R_{23}$ and $R_{24}$ together with the atom(s) to which they are attached form a heteroaryl or heterocyclo ring;

$R_{25}$ is selected from the group consisting of alkyl, substituted alkyl, alkenyl, substituted alkenyl, alkynyl, substituted alkynyl, alkoxy, amino, substituted amino, heteroaryl, heterocyclo, cycloalkyl, and aryl; and t is 1 or 2.

6. A compound as defined in claim 5, or an enantiomer, diastereomer, or a pharmaceutically-acceptable salt thereof, wherein:

Z is selected from the group consisting of thiazolyl, benzothiazolyl, tetrahydrobenzothiazolyl, pyridyl, pyrimidinyl, pyrazinyl, imidazolyl, oxazolyl, pyrazolyl, thiadiazolyl, cyclopropyl, cyclobutyl, cyclopentyl, and morpholinyl, each group substituted by one to two groups, $R'''$ and/or $R''$;

$R'''$ and $R''$ are independently selected from the group consisting of hydrogen, halogen, nitro, cyano, alkyl, substituted alkyl, haloalkyl, thioalkyl, —NR₂₃R₂₄, —CO₂R₂₃, —C(=O)R₂₃, —C(O)N(R₂₃)(R₂₄), —C(=NOR₂₃ₐ)CO₂R₂₄, OR₂₃; SR₂₃, cycloalkyl, aryl, heterocyclo and heteroaryl;

or $R'''$ and $R''$ together with the atoms to which they are attached combine to form an optionally substituted fused 5- or 6-membered cycloalkyl, aryl, heteroaryl, or heterocyclo ring.

7. A compound according to formula (Ia),

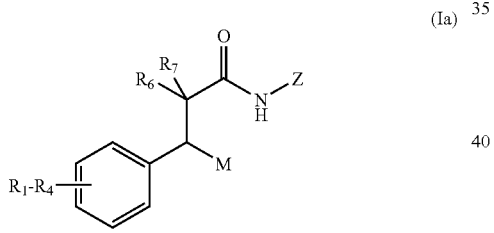

(Ia)

or an enantiomer, diastereomer, or a pharmaceutically-acceptable salt thereof, wherein:

M is

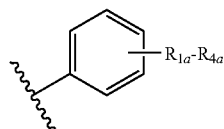

Z is selected from the group consisting of thiazolyl, benzothiazolyl, tetrahydrobenzothiazolyl, pyridyl, pyrimidinyl, pyrazinyl, imidazolyl, oxazolyl, pyrazolyl, thiadiazolyl, and morpholinyl, each group substituted by one to two groups, $R'''$ and/or $R''$;

$R'''$ and $R''$ are independently selected from the group consisting of hydrogen, halogen, nitro, cyano, alkyl, substituted alkyl, haloalkyl, thioalkyl, —NR₂₃R₂₄, —CO₂R₂₃, —C(=O)R₂₃, —C(O)N(R₂₃)(R₂₄), —C(NOR₂₃ₐ)CO₂R₂₄, OR₂₃; SR₂₃, cycloalkyl, aryl, heterocycle and heteroaryl;

or $R'''$ and $R''$ together with the atoms to which they are attached combine to form an optionally substituted fused 5- or 6-membered cycloalkyl, aryl, heteroaryl, or heterocyclo ring;

$R_1$, $R_2$, $R_3$, $R_4$, $R_{1a}$, $R_{2a}$, $R_{3a}$, and/or $R_{4a}$ are independently selected from the group consisting of (i) hydrogen, halogen, cyano, $CF_3$, $C_{1-6}$alkyl, $CH(OH)R_{10}$, $C_{2-4}$alkenyl, $C_{2-4}$alkynyl, $OR_{10}$, $CO_2R_{10}$, $SR_{10}$, $SO_pR_{12}$, $C(O)R_{10}$, $C(O)NR_{10}R_{11}$, $SO_pNR_{10}R_{11}$, $NHC(O)R_{11}$, $NHC(O)NR_{10}R_{11}$, $NHC(O)_2R_{11}$, $NHS(O)_pR_{12}$, and $NR_{10}R_{11}$; and/or (ii) $C_{0-3}$alkylene substituted by an optionally substituted group selected from phenyl and a 5- to 7-membered heterocyclo or 5- to 7-membered heteroaryl;

$R_6$ is selected from the group consisting of $C_{1-4}$alkyl, $C_{1-4}$substituted alkyl, and $C_{3-7}$cycloalkyl;

$R_7$ is selected from the group consisting of $C_{1-4}$alkyl, $C_{1-4}$substituted alkyl, nitro, cyano, $C_{1-4}$alkoxy, and $C_{3-7}$cycloalkyl;

or $R_6$ and $R_7$ are taken together with the carbon to which they are attached to form a $C_{3-7}$cycloalkyl group;

$R_{10}$ and $R_{11}$ at each occurrence are independently selected from the group consisting of (i) hydrogen, substituted $C_{1-6}$alkyl, and $C_{1-6}$alkyl; and/or (ii) $C_{0-3}$alkylene substituted by an optionally substituted group selected from $C_{3-7}$cycloalkyl, phenyl, naphthyl, a 5- to 7-membered heterocyclo and a 5- to 7-membered heteroaryl; and/or (iii) $R_{10}$ is taken together with $R_{11}$ and the nitrogen atom to which they are both attached to form an optionally substituted 5- to 6-membered heteroaryl or 5- to 6-membered heterocyclo;

$R_{12}$ at each occurrence is selected from the group consisting of $C_{1-6}$alkyl and $C_{0-3}$alkylene substituted by an optionally substituted group selected from $C_{3-7}$cycloalkyl, heterocyclo, aryl, and heteroaryl;

$R_{23a}$, $R_{23}$, and $R_{24}$ at each occurrence are independently selected from the group consisting of (i) hydrogen, alkyl, substituted alkyl, —C(=O)alkyl, —CO₂(alkyl), alkenyl, substituted alkenyl, alkynyl, substituted alkynyl, amino, substituted amino, aryl, heteroaryl, heterocyclo, and cycloalkyl, or (ii) $R_{23}$ and $R_{24}$ are combined with the nitrogen atom to which they are both attached to form a heteroaryl or heterocyclo ring; and t and p at each occurrence are independently 1 or 2.

8. The compound as defined in claim 7, or an enantiomer, diastereomer, or a pharmaceutically-acceptable salt thereof, wherein:

$R_1$, $R_2$, $R_3$, and $R_4$, are independently selected from the group consisting of (i) hydrogen, methyl, ethyl, t-butyl, fluoro, chloro, bromo, hydroxy, cyano, $CF_3$, $CH(OH)C_{1-4}$alkyl, $CH_2OH$, $C_{2-4}$ alkenyl, $C_{1-4}$-alkoxy, $C_{2-4}$alkynyl, $CO_2Me$, $C(O)N(C_{1-4}$alkyl)$_2$, $SO_2NR_{10}R_{11}$, $NH_2$, and $NHC(O)_{1-2}C_{1-4}$alkyl; and/or (ii) $NH(CH_2)_{0-1}C(O)$phenyl, —$CO_2$furyl, —$CO_2$tetrahydrofuryl, phenoxy, —$(CH_2)_{0-2}$-phenyl, —$NH(CH_2)_{0-1}C(O)$phenyl, morpholinyl, pyrrolidinyl, piperazinyl, pyridinyl, and furyl, wherein the ring of said group is substituted by one to two groups selected from the group consisting of hydrogen, —C(O)-4-morpholinyl, —C(O)N(C$_{1-4}$alkyl)$_2$, —C(O)NH(C$_{1-4}$alkyl)NH$_2$, $C_{1-4}$-alkoxy, halogen, $C_{1-6}$alkyl, BOC, hydroxy, $OCF_3$, $C(O)(C_{1-4}$alkyl), $CH_2OH$, $C(O)$-4-methyl-1-piperazinyl, and $CH_2O(C_{1-4}$alkyl); and $R_{1a}$, $R_{2a}$, $R_{3a}$, and/or $R_{4a}$ are independently selected from the group consisting of hydrogen, halogen, hydroxy, $C_{1-4}$alkoxy, $C_{1-6}$alkyl, and cyano.

9. A compound according to claim 7, or an enantiomer, diastereomer, or a pharmaceutically-acceptable salt thereof, wherein
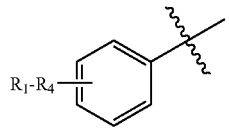
is selected from the group consisting of
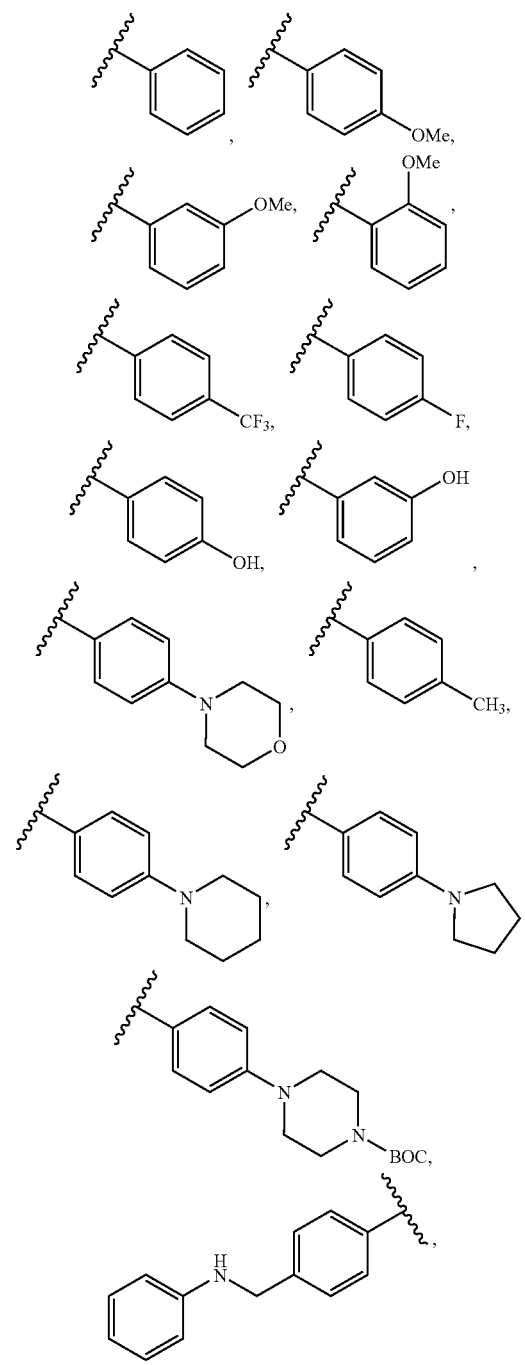
-continued
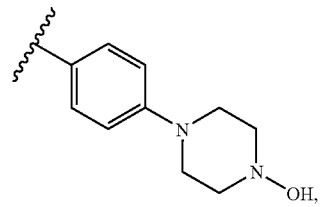
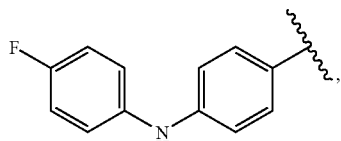
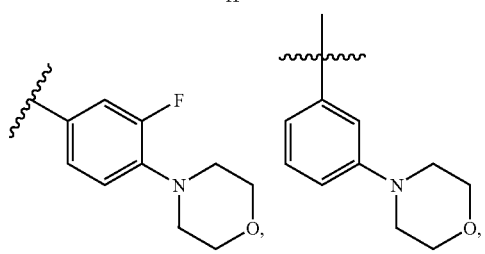
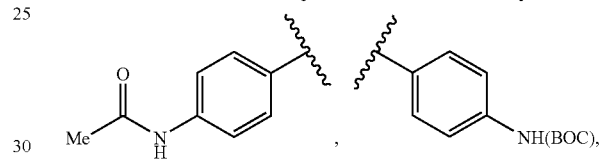
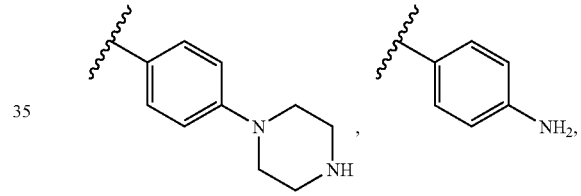
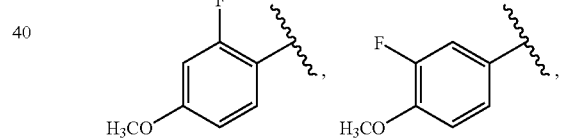
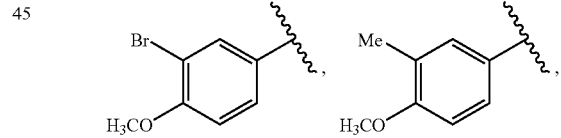
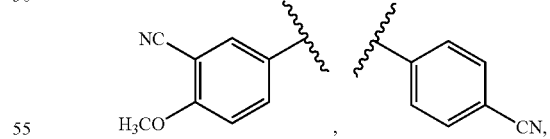
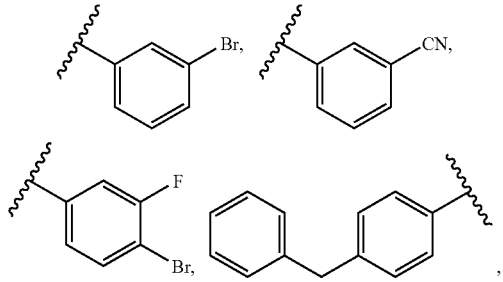

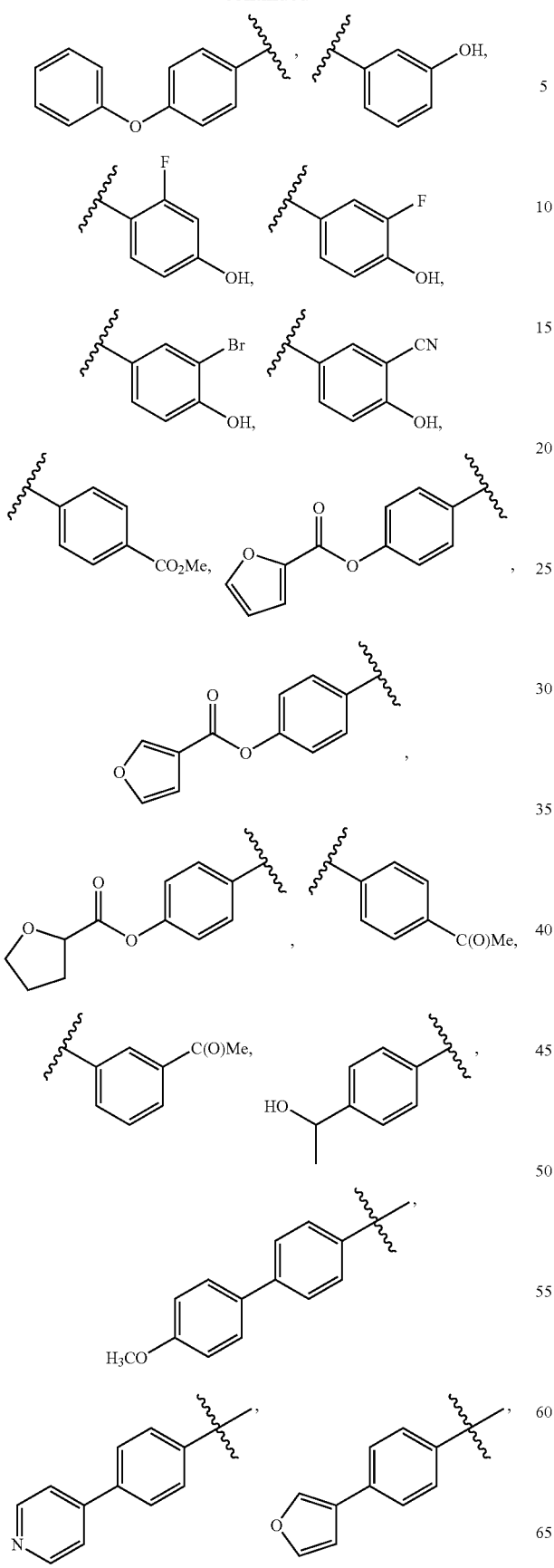
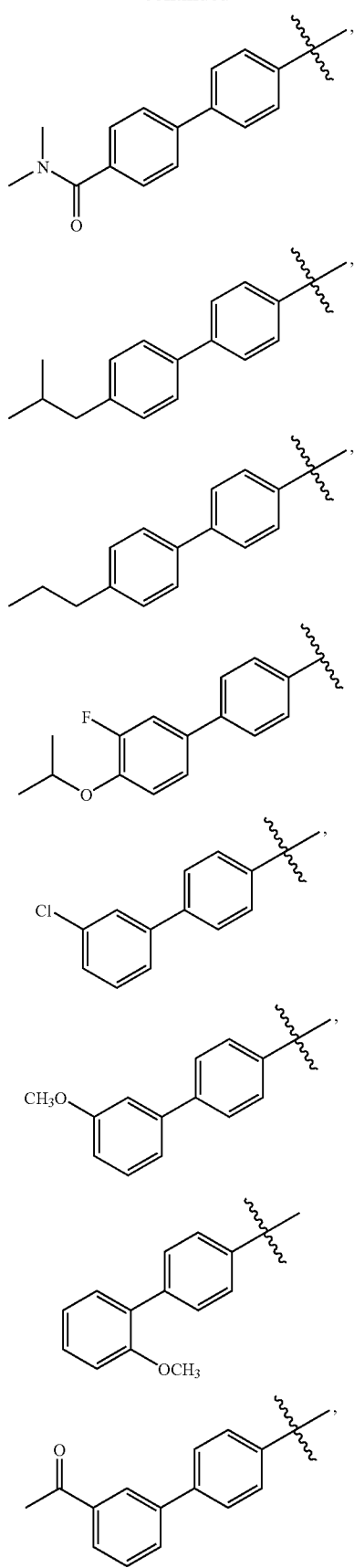

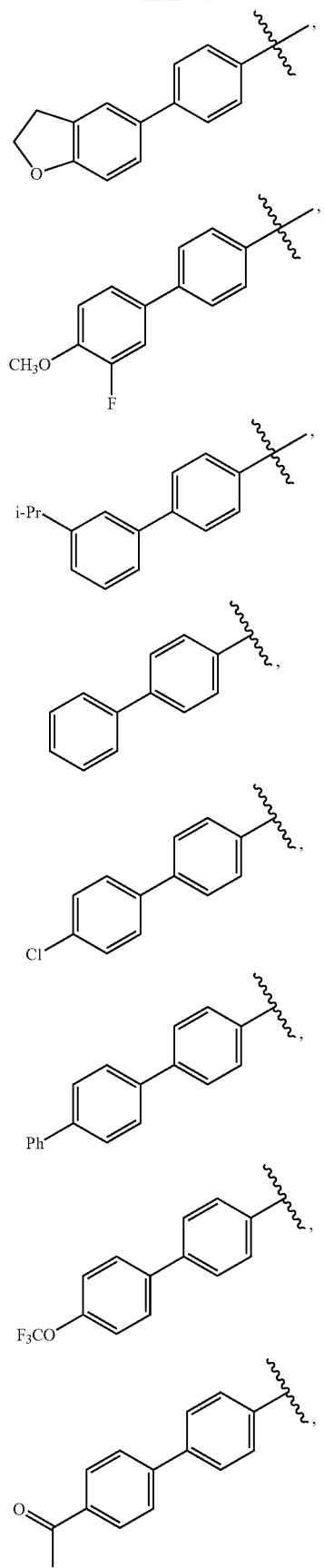
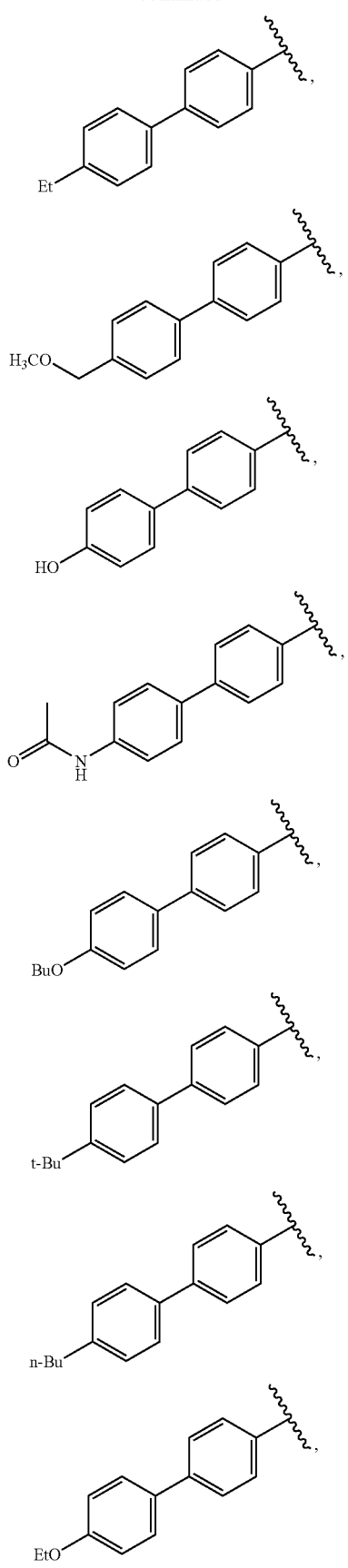

-continued

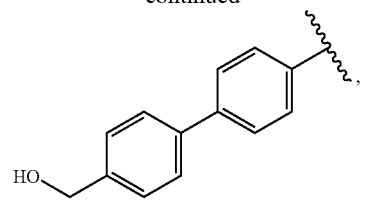

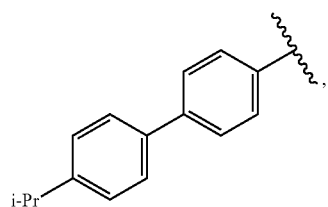

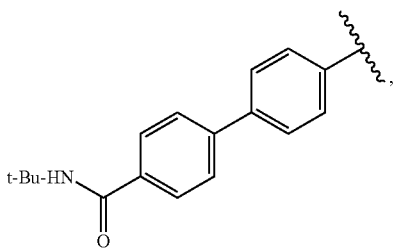

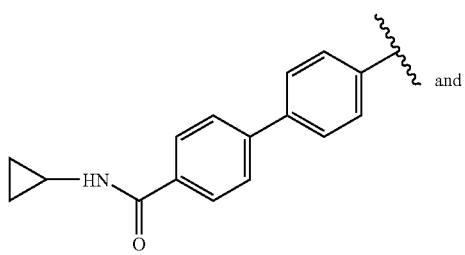 and

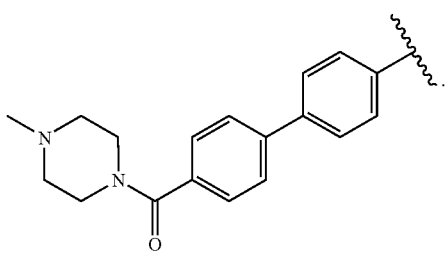

10. A compound according to claim 7, or an enantiomer, diastereomer, or a pharmaceutically-acceptable salt thereof, wherein $R_6$ and $R_7$ are each selected independently from $C_{1-4}$-alkyl.

11. A compound as defined in claim 7, or an enantiomer, diastereomer, or a pharmaceutically-acceptable salt thereof, wherein:

Z is selected from the group consisting of

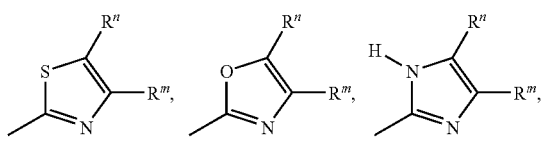

-continued

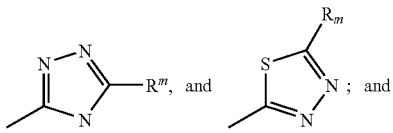

$R^m$ and $R^n$ are independently selected from the group consisting of (i) hydrogen, fluoro, chloro, bromo, $C_{1-4}$alkyl, trifluoroalkyl, nitro, $-(CH_2)_{0-2}CO_2R_{23}$, $-C(=NOR_{23a})CO_2R_{24}$, and $C_{1-4}$alkoxy, or (ii) $C_{0-3}$alkylene substituted by an optionally substituted ring selected from phenyl, naphthyl, a 5- to 7-membered heterocyclo, 5- to 7-membered heteroaryl, a 7- to 11-membered bicyclic heterocyclo ring, and a 7- to 11-membered bicyclic heteroaryl ring.

12. A compound according to claim 11, or an enantiomer, diastereomer, or a pharmaceutically-acceptable salt thereof, wherein:

Z is selected from the group consisting of

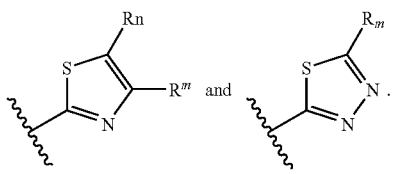

13. A pharmaceutical composition comprising a compound according to claim 1 and a pharmaceutically acceptable carrier therefor.

14. A pharmaceutical combination comprising a compound as defined in claim 1 and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

15. The compound as defined in claim 7 wherein M is
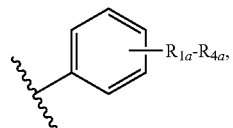
Z is
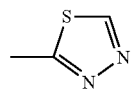
and
R$_1$-R$_4$ is optionally substituted phenyl.
16. The compound is defined as claim 15 of the structure
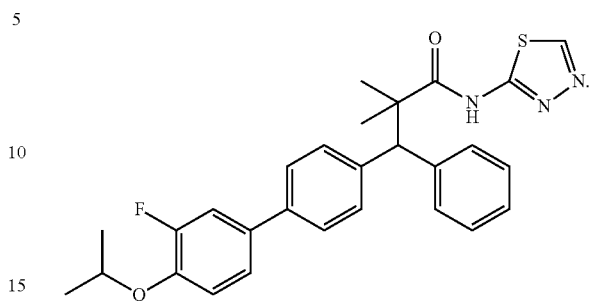
* * * * *

UNITED STATES PATENT AND TRADEMARK OFFICE
CERTIFICATE OF CORRECTION

PATENT NO. : 7,968,577 B2
APPLICATION NO. : 12/513187
DATED : June 28, 2011
INVENTOR(S) : Bingwei Vera Yang et al.

It is certified that error appears in the above-identified patent and that said Letters Patent is hereby corrected as shown below:

On the Title Page:

Item (54), line 1, and Col. 1, line 5 change "MODULATORS OF GLUCOCORTICOID" to -- MODULATORS OF THE GLUCOCORTICOID --.

Item (65), References Cited, under "FOREIGN PATENT DOCUMENTS":
Column 2, change "WO2008/057867" to -- WO 2008/057857 --.

Column 1, line 1, change "MODULATORS OF GLUCOCORTICOID" to -- MODULATORS OF THE GLUCOCORTICOID --.

Claim 1:

Column 287, line 28, change "—$OR_{10}$—$SR_{10}$—$NR_{10}R_{11}$" to -- —$OR_{10}$, —$SR_{10}$, —$NR_{10}R_{11}$ --.

Claim 5:

Column 288, line 59, change "$S(O)_tR_{25}$" to -- $S(=O)_tR_{25}$ --.

Claim 7:

Column 289, line 66, change "—$C(NOR_{23a})CO_2R_{24}$" to -- —$C(=NOR_{23a})CO_2R_{24}$ --.

Claim 8:

Column 290, line 52, change "$C_{1-4}$-alkoxy" to -- $C_{1-4}$alkoxy --.

Column 290, line 56, change "—$(CH_2)_{0-2}$-phenyl" to -- —$(CH_2)_{0-2}$phenyl --.

Signed and Sealed this
Twenty-second Day of November, 2011

David J. Kappos
*Director of the United States Patent and Trademark Office*

Page 1 of 2

Column 290, line 61, change "—C(O)NH(C$_{1-4}$alkyl)NH$_2$" to -- —C(O)NH(C$_{1-4}$alkyl),NH$_2$ --.

Column 290, line 61, change "C$_{1-4}$-alkoxy" to -- C$_{1-4}$alkoxy --.

Column 297, line 54, change "C$_{1-4}$-alkyl" to -- C$_{1-4}$alkyl --.